(12) United States Patent
Park et al.

(10) Patent No.: US 11,963,445 B2
(45) Date of Patent: Apr. 16, 2024

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Ji Hyun Park, Cheonan-si (KR); Se Hoon Lee, Cheonan-si (KR); Jae Wan Jang, Cheonan-si (KR); Hyung Dong Lee, Cheonan-si (KR); Yun Suk Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/446,879

(22) Filed: Aug. 9, 2023

(65) Prior Publication Data
US 2024/0049598 A1 Feb. 8, 2024

Related U.S. Application Data

(63) Continuation-in-part of application No. 18/180,625, filed on Mar. 8, 2023, which is a continuation-in-part
(Continued)

(30) Foreign Application Priority Data

Oct. 26, 2020 (KR) .................. 10-2020-0139441

(51) Int. Cl.
*H10K 85/60* (2023.01)
*C07D 251/24* (2006.01)
(Continued)

(52) U.S. Cl.
CPC ....... *H10K 85/6574* (2023.02); *C07D 251/24* (2013.01); *C09K 11/06* (2013.01);
(Continued)

(58) Field of Classification Search
CPC .................. C07D 251/24; C07B 2200/05; H10K 85/654; H10K 85/6572; H10K 85/6574; H10K 85/6576; C09K 11/06
See application file for complete search history.

(56) References Cited

U.S. PATENT DOCUMENTS

2014/0367654 A1 12/2014 Kim et al.
2015/0303379 A1 10/2015 Lee et al.
(Continued)

FOREIGN PATENT DOCUMENTS

CN 112552251 A * 3/2021
KR 10-2009-0079134 A 7/2009
(Continued)

OTHER PUBLICATIONS

Machine-generated English-language translation of CN-112552251-A.*
(Continued)

*Primary Examiner* — Vu A Nguyen
(74) *Attorney, Agent, or Firm* — Vorys, Sater, Seymour and Pease LLP; Mih Suhn Koh

(57) ABSTRACT

Provided are a compound capable of improving the light-emitting efficiency, stability, and lifespan of an element; an organic electronic element using same; and an electronic device thereof.

14 Claims, 2 Drawing Sheets

Related U.S. Application Data of application No. 17/212,886, filed on Mar. 25, 2021, now Pat. No. 11,678,577, which is a continuation of application No. 17/096,790, filed on Nov. 12, 2020, now Pat. No. 11,063,226.

(51) Int. Cl.
*C09K 11/06* (2006.01)
*H10K 50/11* (2023.01)
*H10K 50/15* (2023.01)
*H10K 50/16* (2023.01)
*H10K 50/18* (2023.01)
*H10K 101/00* (2023.01)
*H10K 101/10* (2023.01)

(52) U.S. Cl.
CPC ......... *H10K 85/626* (2023.02); *H10K 85/631* (2023.02); *H10K 85/653* (2023.02); *H10K 85/654* (2023.02); *H10K 85/6572* (2023.02); *H10K 85/6576* (2023.02); *C07B 2200/05* (2013.01); *C09K 2211/1018* (2013.01); *H10K 50/11* (2023.02); *H10K 50/15* (2023.02); *H10K 50/16* (2023.02); *H10K 50/18* (2023.02); *H10K 2101/10* (2023.02); *H10K 2101/90* (2023.02)

(56) References Cited

U.S. PATENT DOCUMENTS

| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

FOREIGN PATENT DOCUMENTS

| KR | 10-2016-0111780 A | 9/2016 |
| WO | 2017/171420 A1 | 10/2017 |
| WO | 2019/124902 A1 | 6/2019 |

OTHER PUBLICATIONS

SciFinder Search, 4 pages, Apr. 7, 2021.
STN Search, 351 pages, Apr. 7, 2021.

* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

That is, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic element has not yet been sufficiently made. Therefore, the development of new materials is continuously required, and in particular, the development of a host material for the emitting layer is urgently required.

DETAILED DESCRIPTION OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

The present invention provides a compound represented by Formula 1.

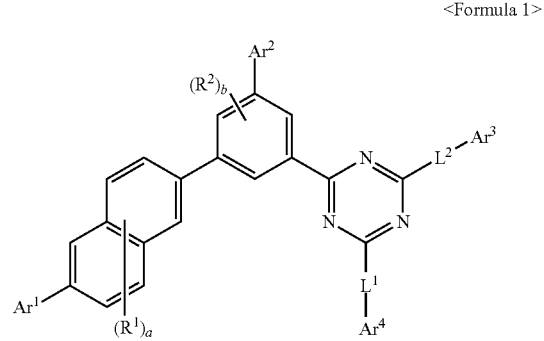

<Formula 1>

In another aspect, the present invention provides an organic electric element and an electronic device comprising the compound represented by Formula 1.

Effects of the Invention

By using the compound according to the present invention, high luminous efficiency, low driving voltage and high heat resistance of the element can be achieved, and color purity and lifespan of the element can be greatly improved.

Figure 1:
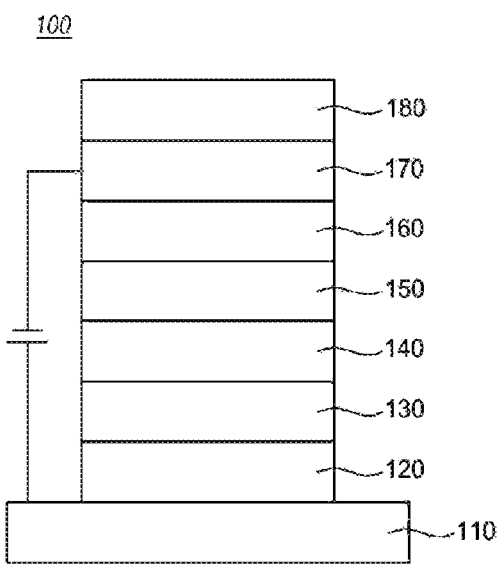
FIG. 1 to FIG. 3 are each an exemplary view of an organic electroluminescent device according to the present invention.

| 100, 200, 300: organic electronic element | 110: the first electrode |
|---|---|
| 120 hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack |

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected, coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an alkyl group bonded to oxygen radical, but is not limited thereto, and has 1 to 60 carbon atoms.

Unless otherwise stated, the term "aryloxyl group" or "aryloxy group", as used herein, means an aryl group bonded to oxygen radical, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including $SO_2$ instead of carbon consisting of cycle. For example, "heterocyclic group" includes the following compound.

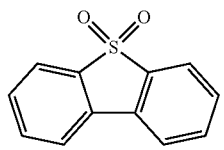 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

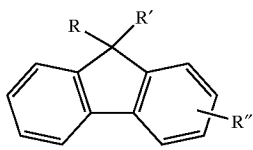

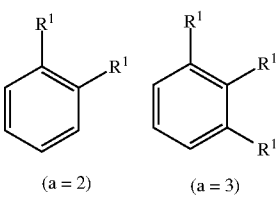

(a = 2)   (a = 3)

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

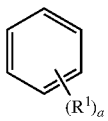

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

Reorganization energy refers to the energy lost due to the change in molecular structure arrangement during the movement of charges (electrons, holes). It depends on the molecular geometry, and has a characteristic that the value becomes smaller as the difference between the PES (Potential Energy Surface) in the neutral state and the PES in the charged state is small. The RE value can be obtained by the following formula.

$$RE_{hole}: \lambda^+ = (E_{NOCE} - E_{COCE}) + (E_{CONE} - E_{NONE})$$

$$RE_{elec}: \lambda^- = (E_{NOAE} - E_{AOAE}) + (E_{AONE} - E_{NONE})$$

Each factor is described as NONE: Neutral geometry of Neutral molecules (=NO opt.), NOAE: Anion geometry of Neutral molecules, NOCE: Cation geometry of Neutral molecules, AONE: Neutral geometry of Anion molecules, AOAE: Anion geometry of Anion molecules (=AO opt.), CONE: Neutral geometry of Cation molecules, COCE: Cation geometry of Cation molecules (=CO opt.)

The value of Reorganization Energy is inversely proportional to mobility, and under the condition that they have the same r and T values, RE value of each material directly affects the mobility. The relation between RE value and mobility is expressed as follows.

$$\mu = k \frac{r^2}{2k_B T/e}$$

$$k = \left(\frac{4\pi^2}{h}\right) \frac{t^2}{\sqrt{4\pi \lambda k_B T}} \exp\left[-\frac{\lambda}{4k_B T}\right]$$

Each factor is described as λ: Reorganization energy/μ: mobility/r: dimer displacement/t: intermolecular charge transfer matrix element. From the above equation, it can be seen that the lower RE value, the faster the mobility.

Reorganization energy value requires a simulation tool that can calculate the potential energy according to the molecular structure, we used Gaussian09 (hereinafter G09) and Jaguar module of Schrodinger Materials Science (hereinafter JG). Both G09 and JG are tools to analyze the properties of molecules through quantum mechanical (QM) calculations, and have the function of optimizing the molecular structure or calculating the energy for a given molecular structure (single-point energy).

The process of performing QM calculations in molecular structures requires large computational resources, and our company uses 2 cluster servers for these calculations. Each cluster server consists of 4 node workstations and 1 master workstation, each node performed molecular QM calculations by Parallel computing through symmetric multi-processing (SMP) using a CPU with more than 36 cores.

Using G09, the optimized molecular structure and its potential energy (NONE/COCE) in the neutral/charged state required for rearrangement energy were calculated. The charge state potential energy (NOCE) of the structure optimized for the neutral state and the neutral state potential energy (CONE) of the structure optimized for the charge state were calculated by changing only the charges to the 2 optimized structures. After that, the rearrangement energy was calculated according to the following relation.

$$RE_{charge}: \lambda=(E_{NOCE}-E_{COCE})+(E_{CONE}-E_{NONE})$$

Because Schrödinger provides a function to automatically perform such a calculation process, the potential energy according to each state was sequentially calculated through the JG module by providing the molecular structure (NO) of the basic state, and the RE value was calculated.

Hereinafter, a compound according to an aspect of the present invention and an organic electric element including the same will be described.

The present invention provides a compound represented by Formula 1.

<Formula 1>

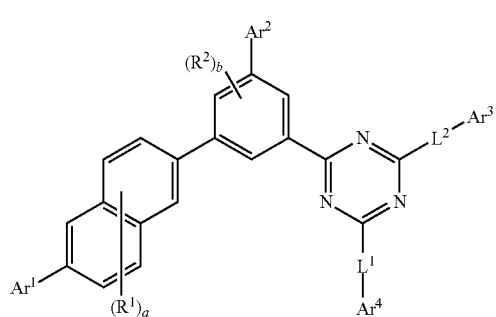

Wherein:

$Ar^1$ is a substituent represented by Formula 1-A; or a substituent represented by Formula 1-B;

<Formula 1-A>

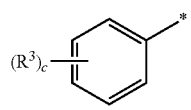

<Formula 1-B>

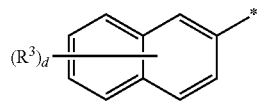

$Ar^2$ is a substituent represented by Formula 1-C; or a substituent represented by Formula 1-D;

<Formula 1-C>

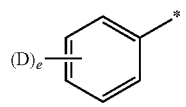

<Formula 1-D>

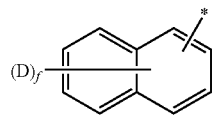

$Ar^3$ and $Ar^4$ are each independently an $C_6$-$C_{60}$ aryl group; or a $C_2$-$C_{60}$ heterocyclic group including at least one heteroatom of O, N, S, Si or P;

When $Ar^3$ and $Ar^4$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, chryssen, etc, When $Ar^3$ and $Ar^4$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., $R^1$ and $R^2$ are each the same or different, and each independently selected from the group consisting of a hydrogen; or deuterium;

$L^1$ and $L^2$ are each independently a single bond; a $C_6$-$C_{60}$ arylene group; a $C_2$-$C_{60}$ heterocyclic group including at least one heteroatom of O, N, S, Si or P;

When $L^1$ and $L^2$ are an arylene group, it may be preferably a $C_6$-$C_{30}$ arylene group, more preferably a $C_6$-$C_{25}$ arylene group, for example, phenylene, biphenylene, naphthylene, terphenylene, anthracenylene etc., When $L^1$ and $L^2$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., a is an integer of 0 to 6, b is an integer of 0 to 3, In Formula 1-A to 1-D, $R^3$ is each the same or different, and each independently a hydrogen; or deuterium;

D means deuterium, c is an integer of 0 to 5, d is an integer of 0 to 7, e is an integer of 1 to 5, f is an integer of 1 to 7,

* means a position to be boned, wherein the aryl group, arylene group and heterocyclic group may be substituted with one or more substituents selected from the group consisting of deuterium; $C_6$-$C_{20}$ aryl group; and $C_6$-$C_{20}$ aryl group substituted with deuterium;

Also, Formula 1 is represented by any one of Formulas 1-1 to 1-4.

<Formula 1-1>

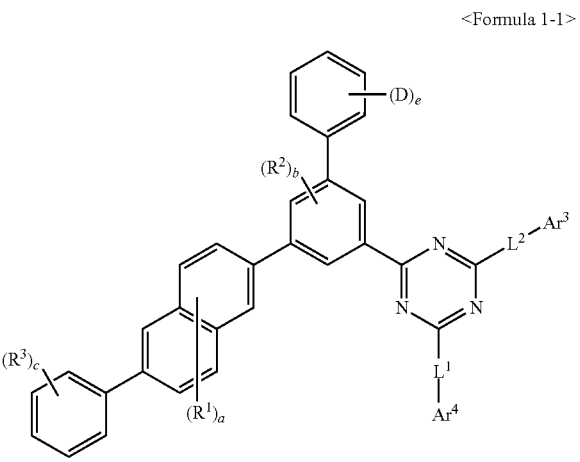

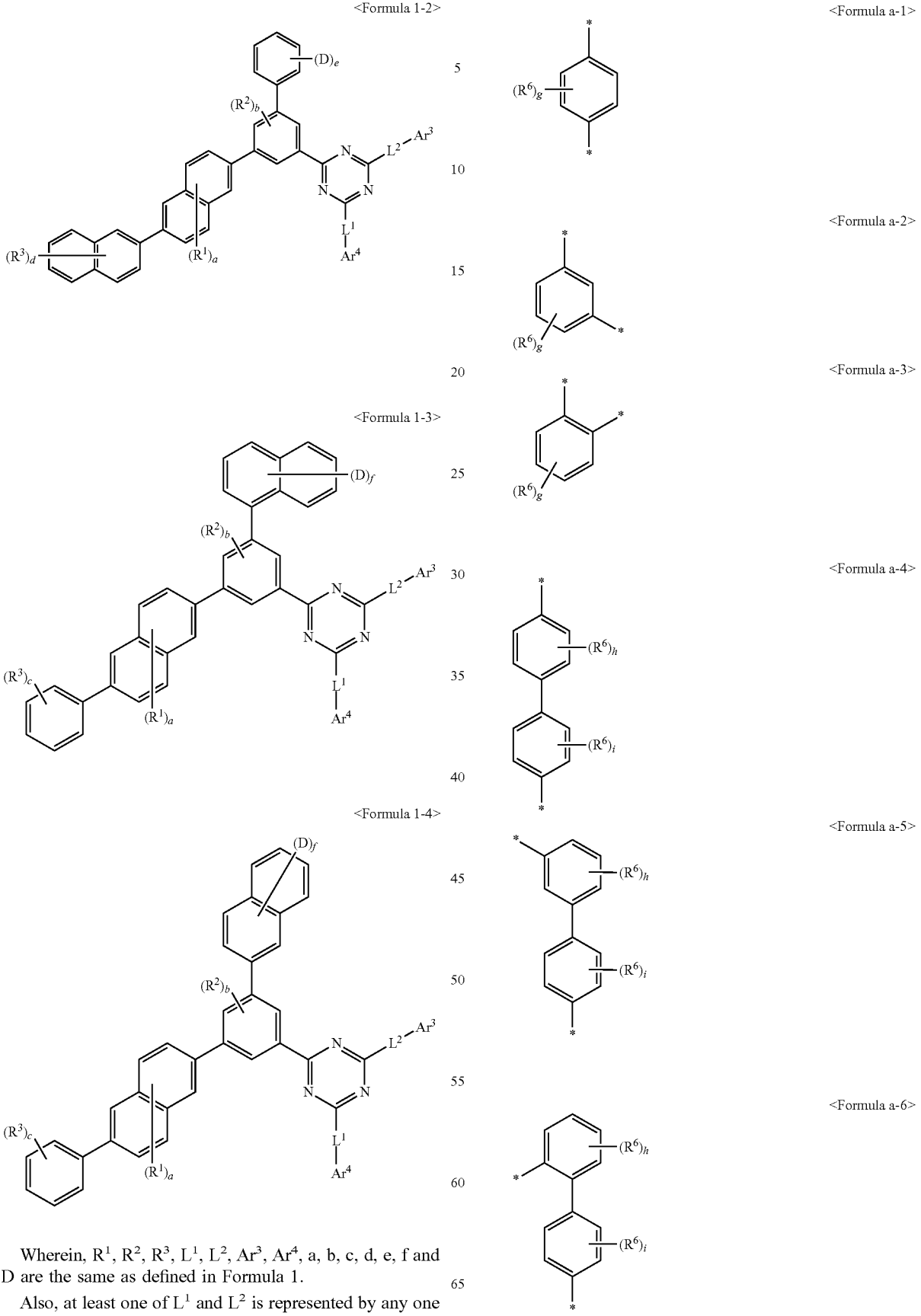
Wherein, $R^1$, $R^2$, $R^3$, $L^1$, $L^2$, $Ar^3$, $Ar^4$, a, b, c, d, e, f and D are the same as defined in Formula 1.
Also, at least one of $L^1$ and $L^2$ is represented by any one of the following Formula a-1 to Formula a-20.

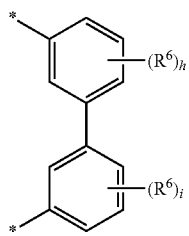
<Formula a-7>
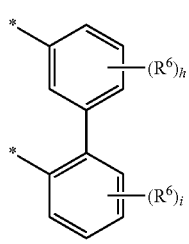
<Formula a-8>
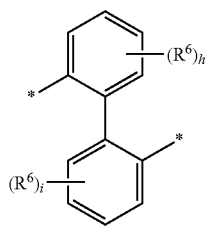
<Formula a-9>
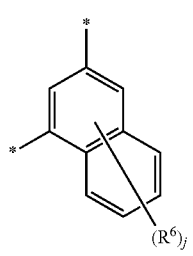
<Formula a-10>
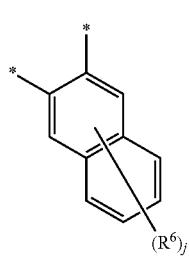
<Formula a-11>
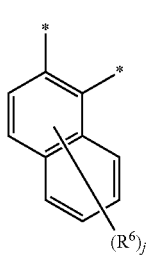
<Formula a-12>
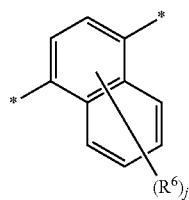
<Formula a-13>
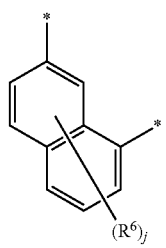
<Formula a-14>
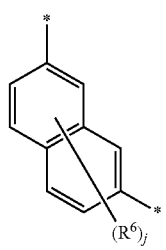
<Formula a-15>
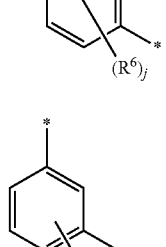
<Formula a-16>
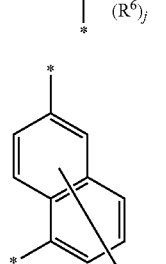
<Formula a-17>
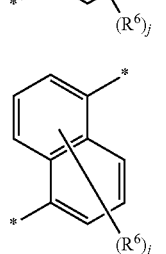
<Formula a-18>
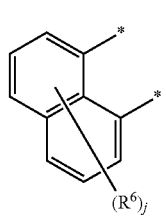
<Formula a-19>

<Formula a-20>

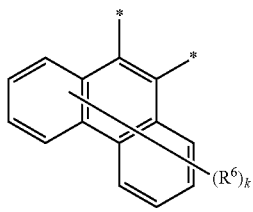

Wherein:

R⁶ is each the same or different, and each independently deuterium; $C_6$-$C_{20}$ aryl group; and $C_6$-$C_{20}$ aryl group substituted with deuterium;

g, h and i are each independently an integer of 0 to 4, j is an integer of 0 to 6, k is an integer of 0 to 8,

* means a moiety bonded to triazine or $Ar^3$ or $Ar^4$.

Also, at least one of $Ar^3$ and $Ar^4$ is represented by any one of the following Formula b-1 to Formula b-12.

<Formula b-1>

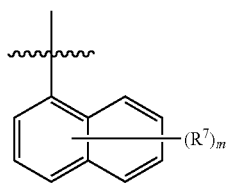

<Formula b-2>

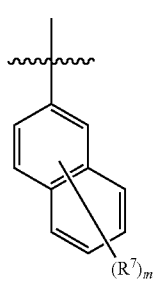

<Formula b-3>

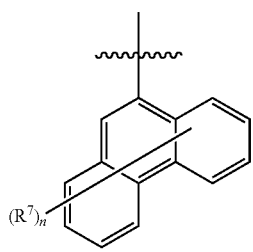

<Formula b-4>

<Formula b-5>

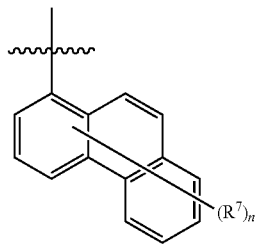

<Formula b-6>

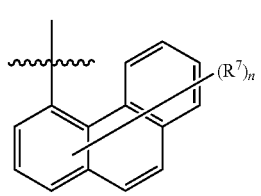

<Formula b-7>

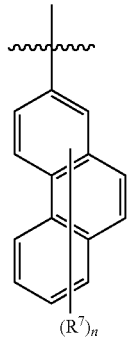

<Formula b-8>

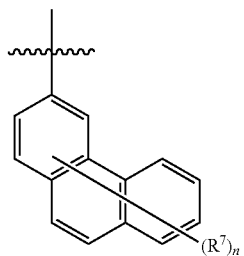

<Formula b-9>

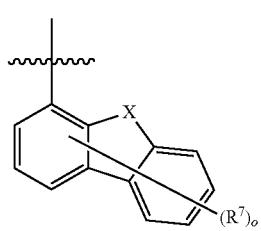

<Formula b-10>

-continued

<Formula b-11>

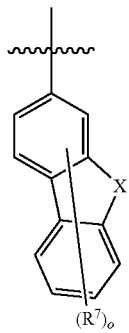

<Formula b-12>

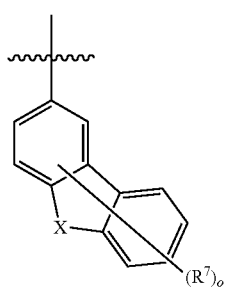

Wherein:

X is NR⁸, O or S, $R^7$ is each the same or different, and each independently deuterium; $C_6$-$C_{20}$ aryl group; and $C_6$-$C_{20}$ aryl group substituted with deuterium;

$R^8$ is an $C_6$-$C_{60}$ aryl group; or a $C_2$-$C_{60}$ heterocyclic group including at least one heteroatom of O, N, S, Si or P;

When $R^8$ is an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, chryssen, etc, When $R^8$ is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., l is an integer of 0 to 5, m and o are each independently an integer of 0 to 7, n is an integer of 0 to 9, ⌇⌇⌇ means a part that binds to $L^1$ or $L^2$.

Specifically, the compound represented by Formula 1 may be any one of the following compounds P-1 to P-76, but is not limited thereto.

P-1

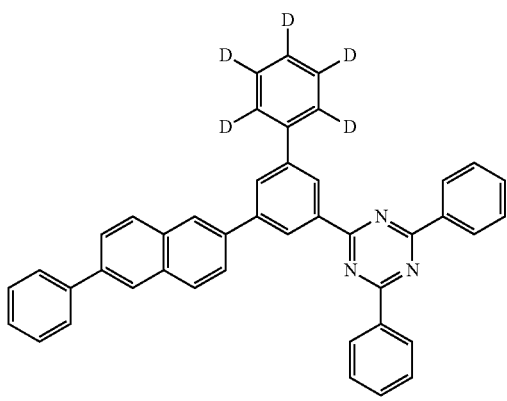

P-2

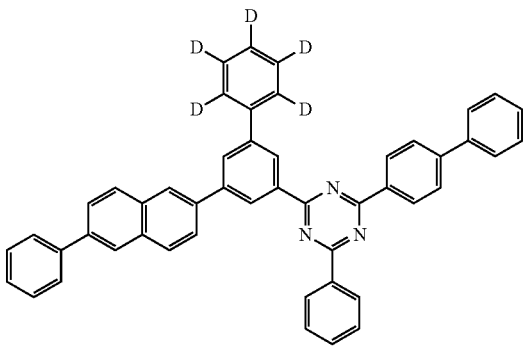

P-3

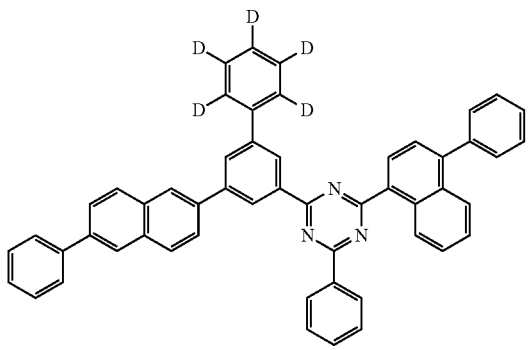

P-4

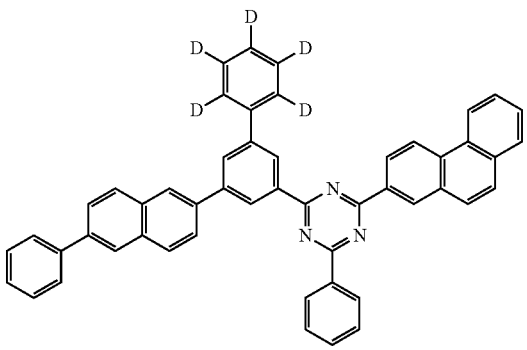

P-5
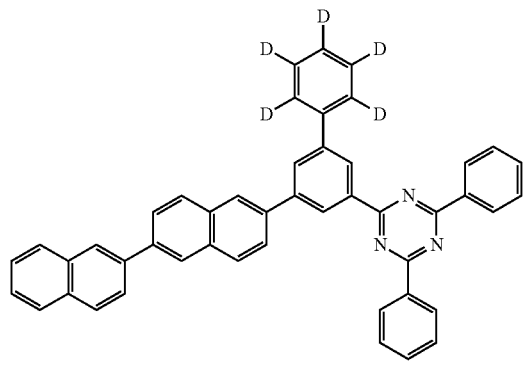
P-6
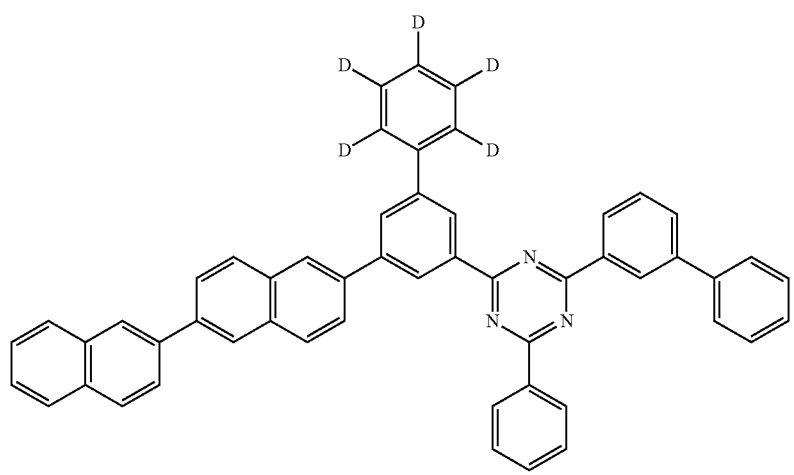
P-7
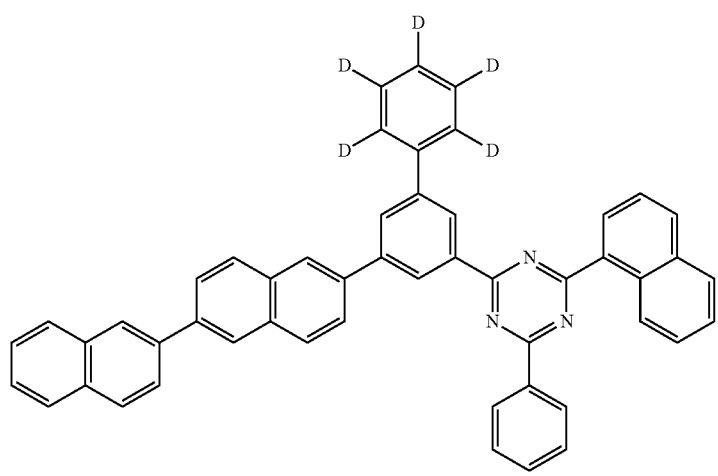

-continued
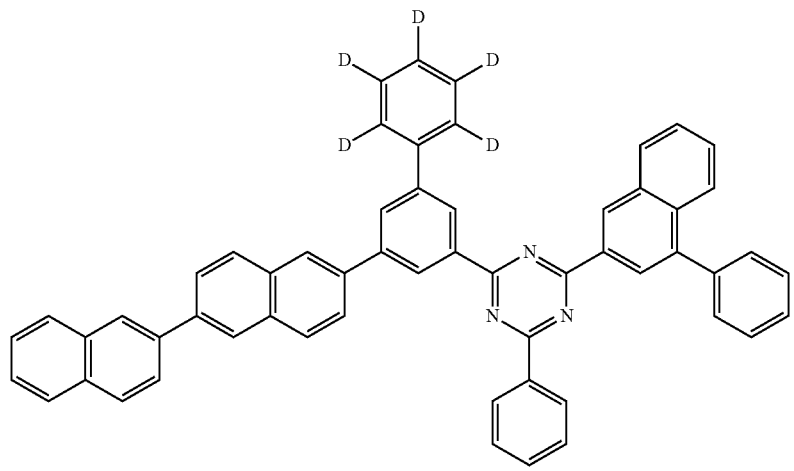
P-8
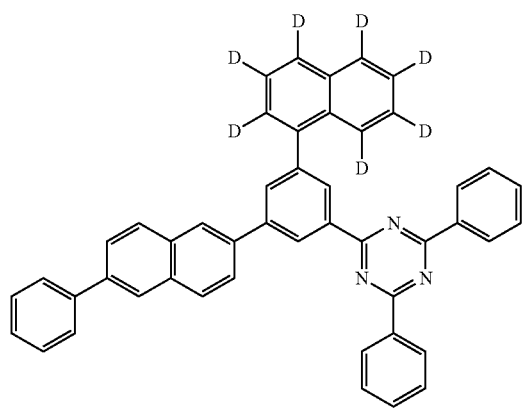
P-9
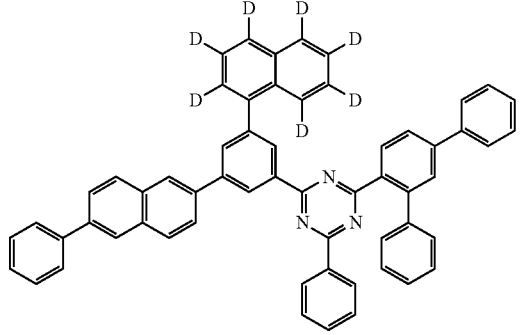
P-10
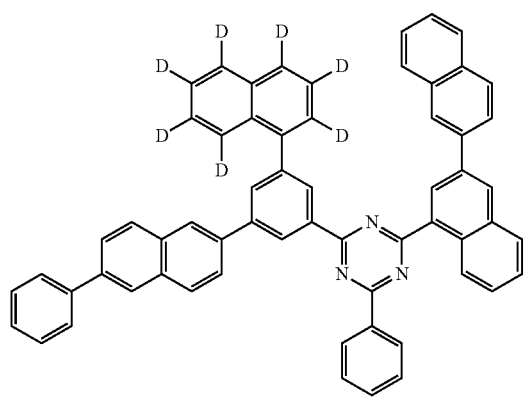
P-11
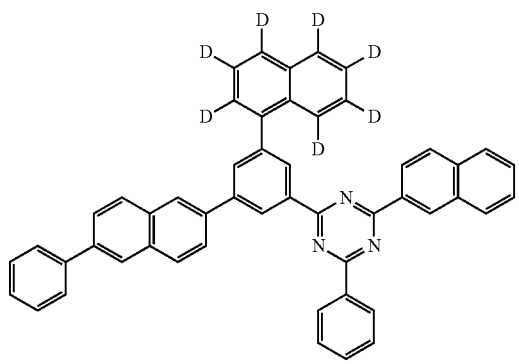
P-12

-continued
P-13
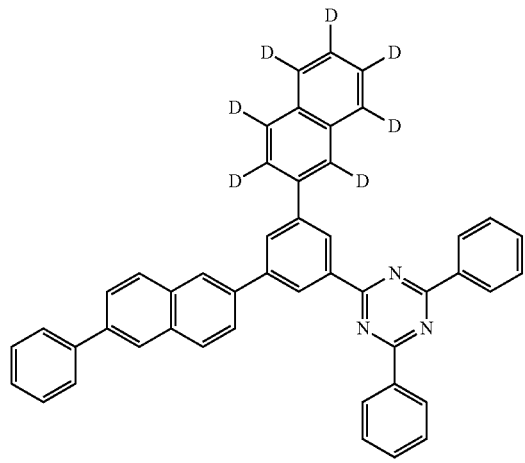
P-14
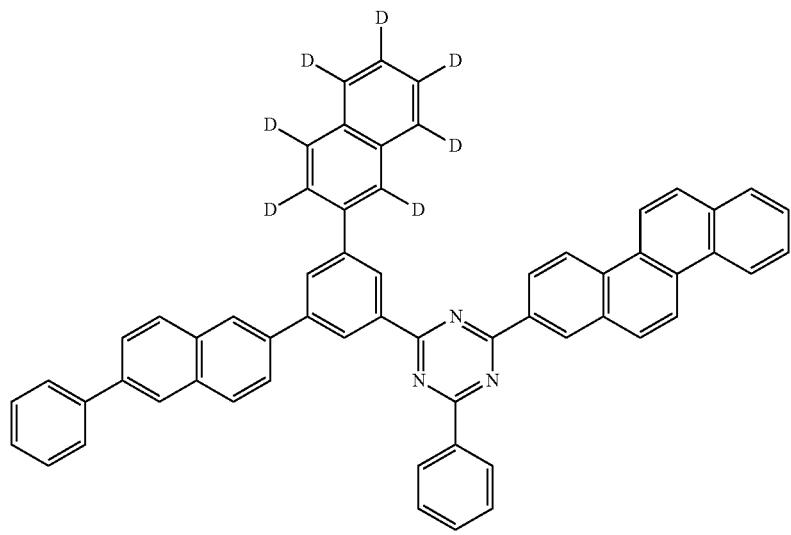
P-15
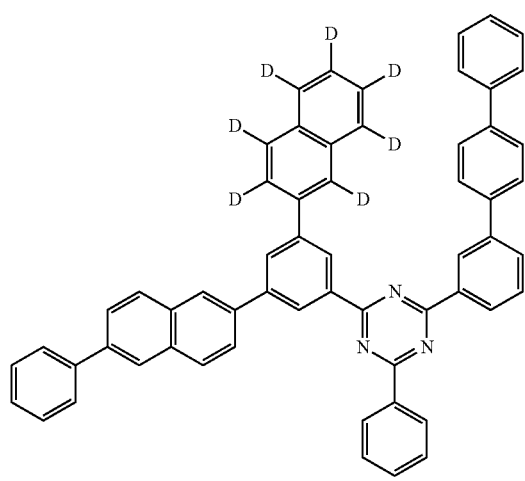
P-16
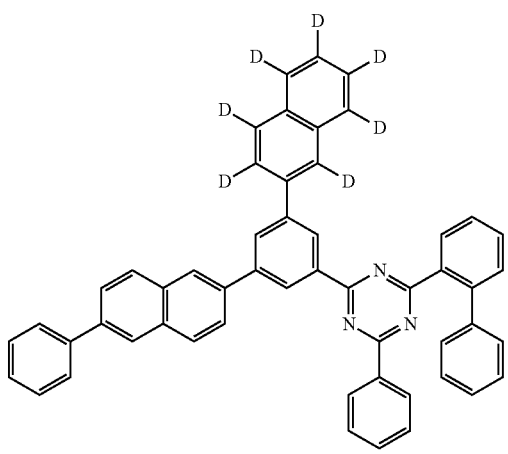

-continued
P-17
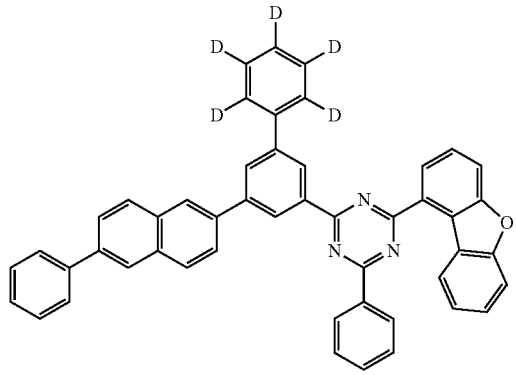
P-18
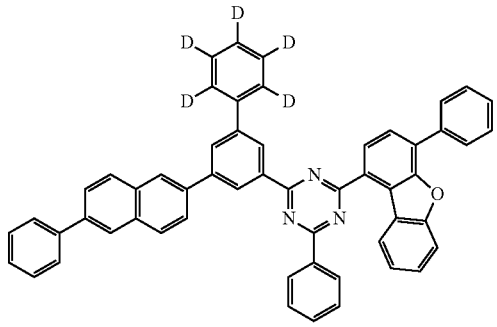
P-19
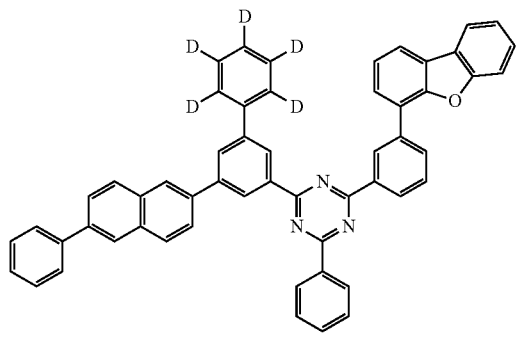
P-20
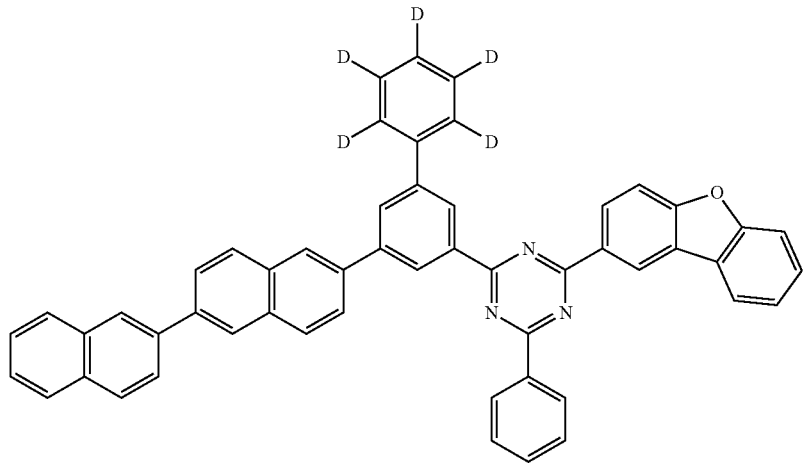
P-21
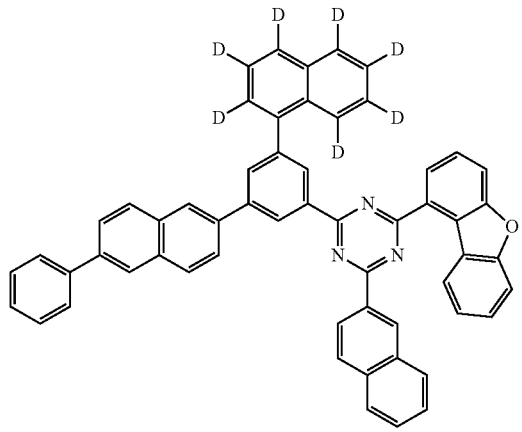
P-22
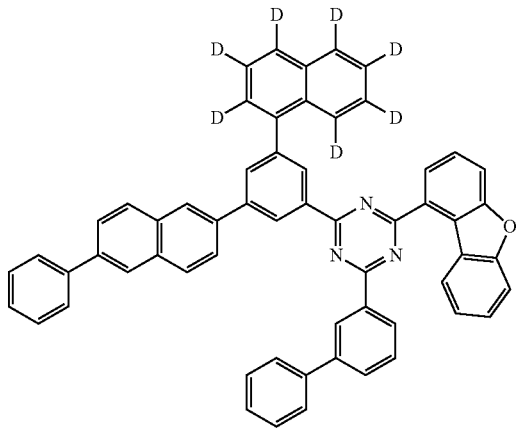

-continued
P-23
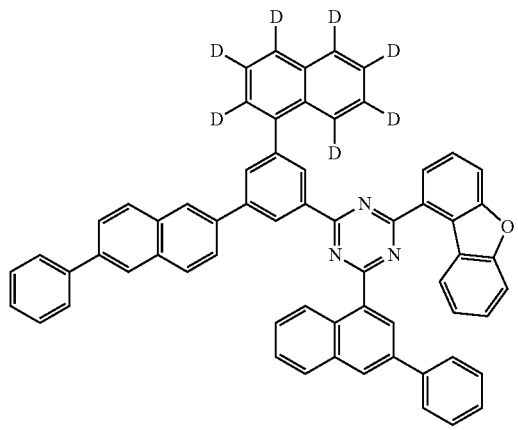
P-24
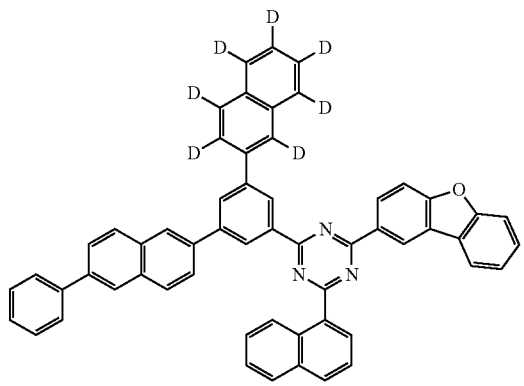
P-25
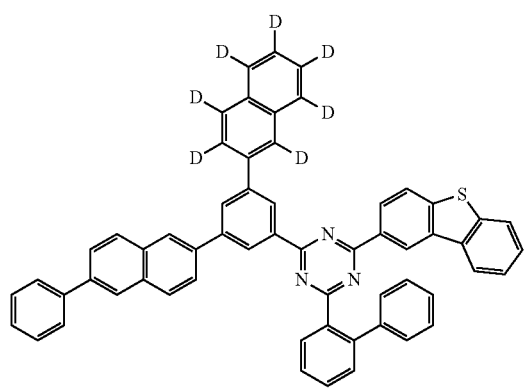
P-26
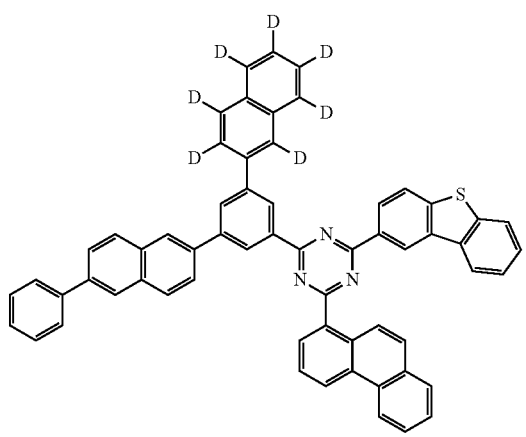
P-27
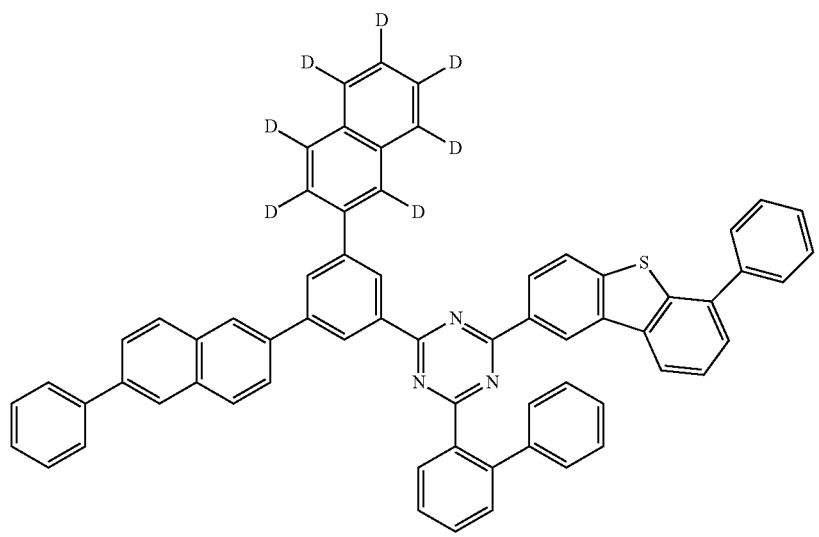

-continued
P-28
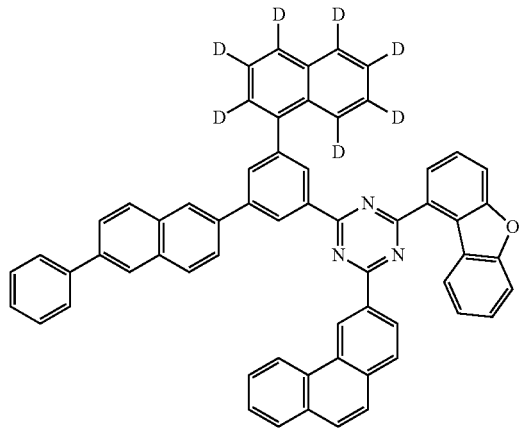
P-29
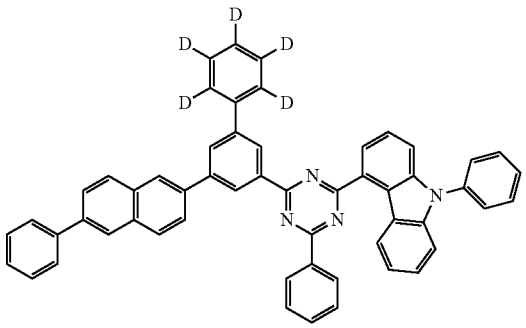
P-30
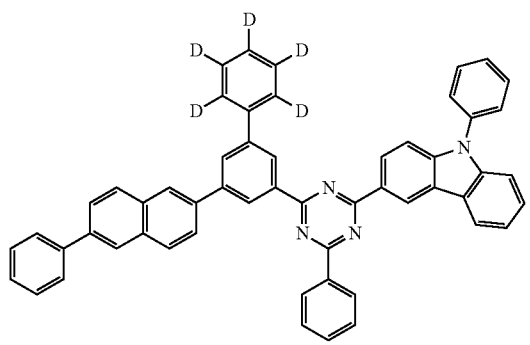
P-31
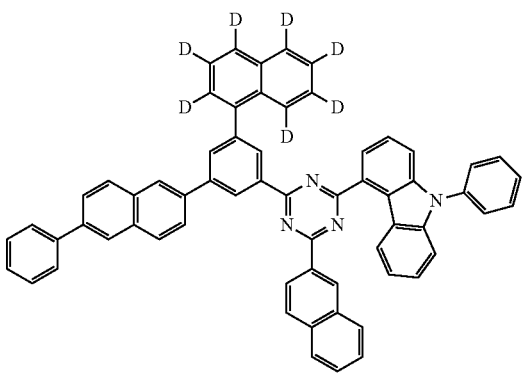
P-32
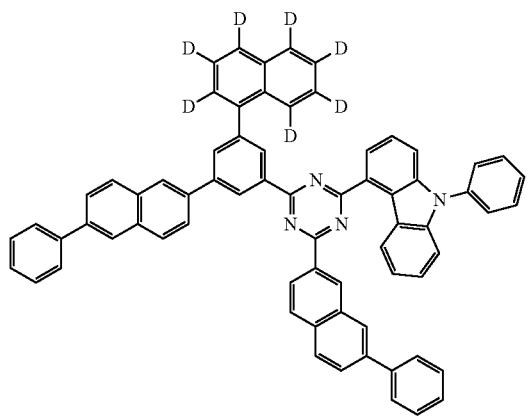

-continued
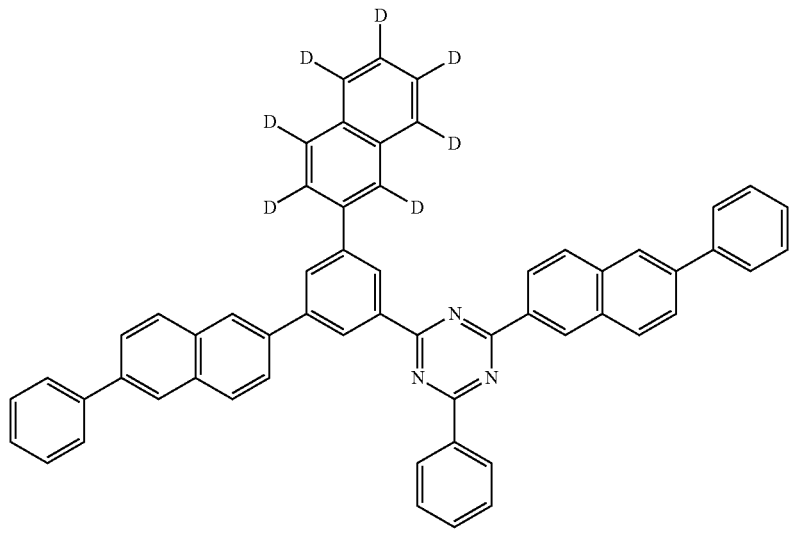
P-33
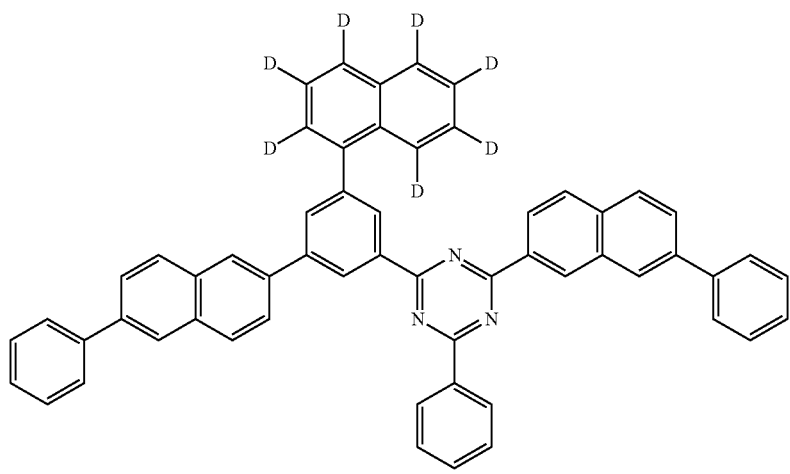
P-34
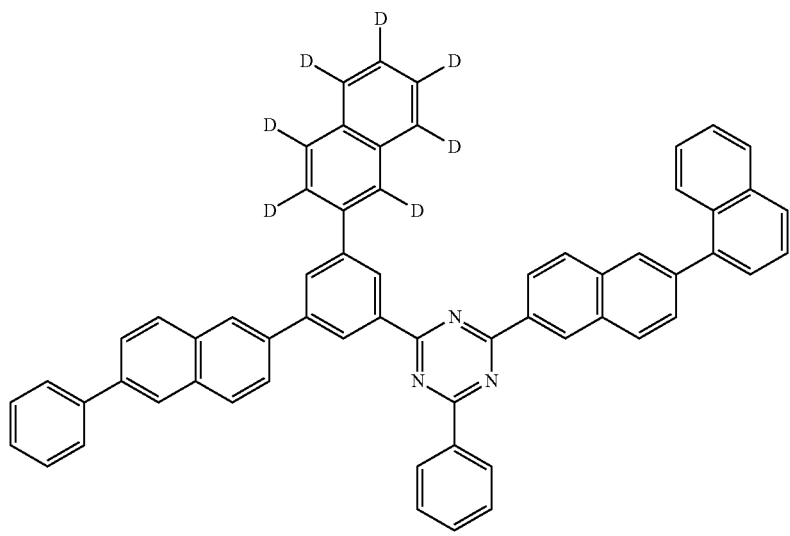
P-35

-continued
P-36
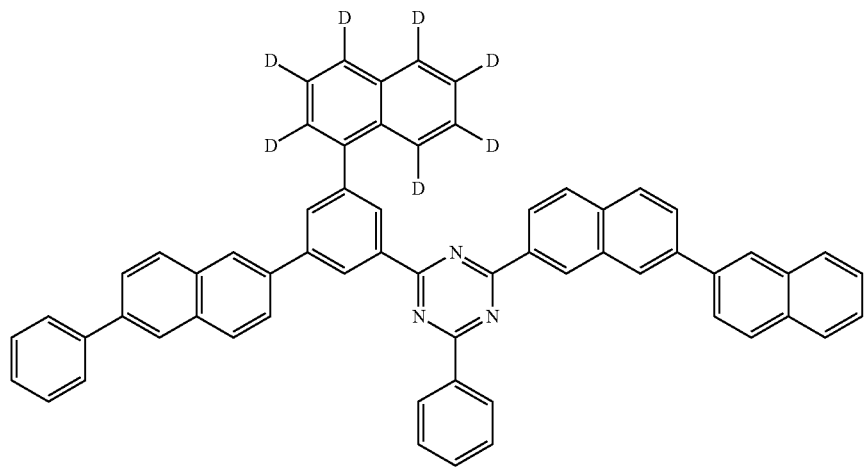
P-37
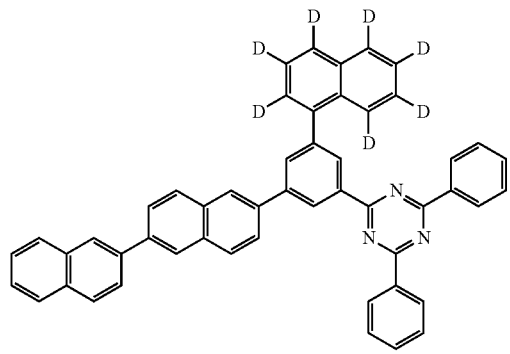
P-38
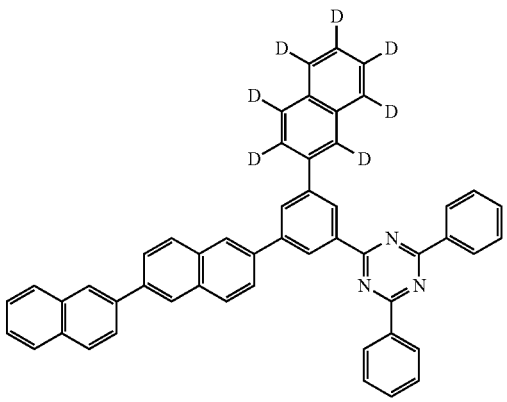
P-39
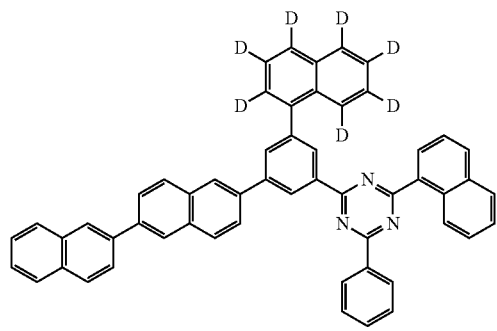
P-40
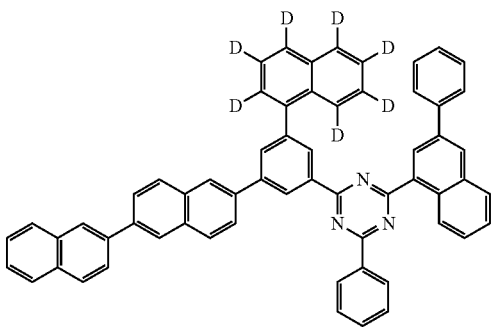
P-41
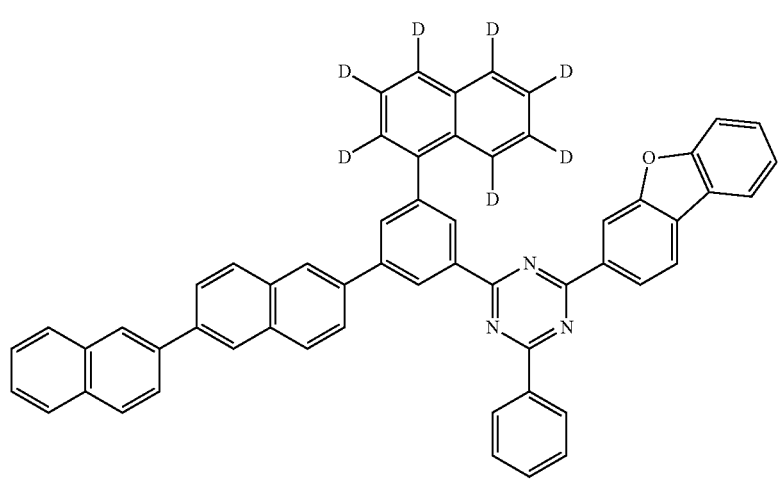

P-42
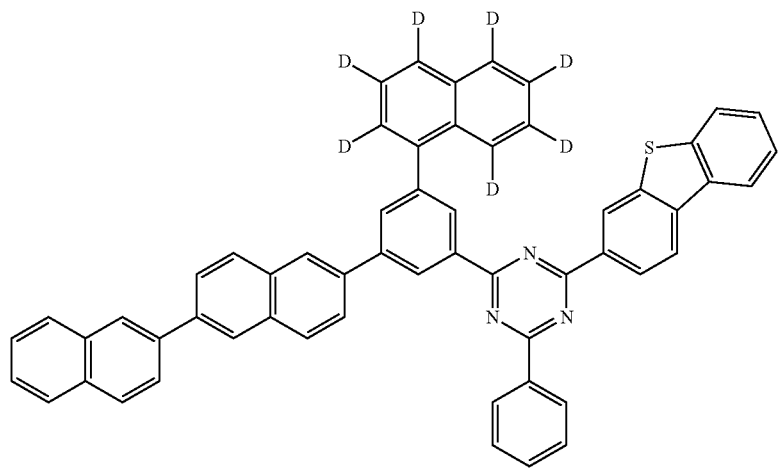
P-43
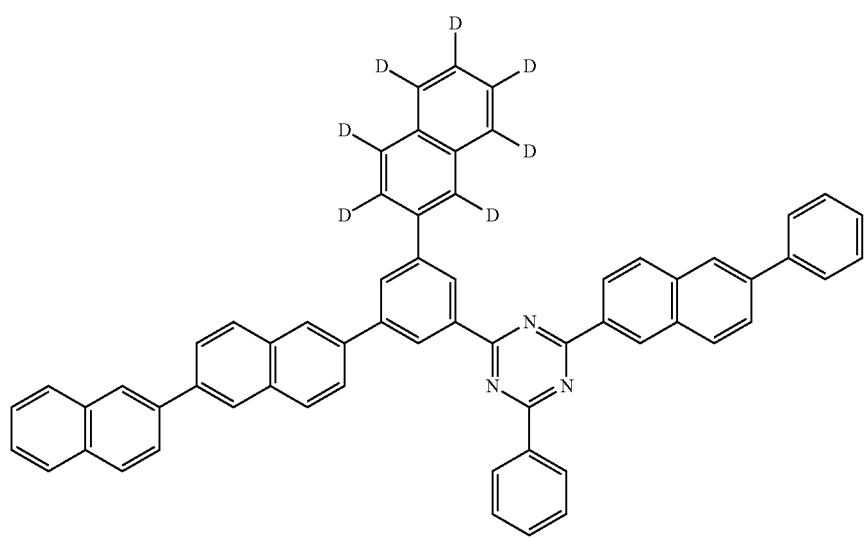
P-44         P-45
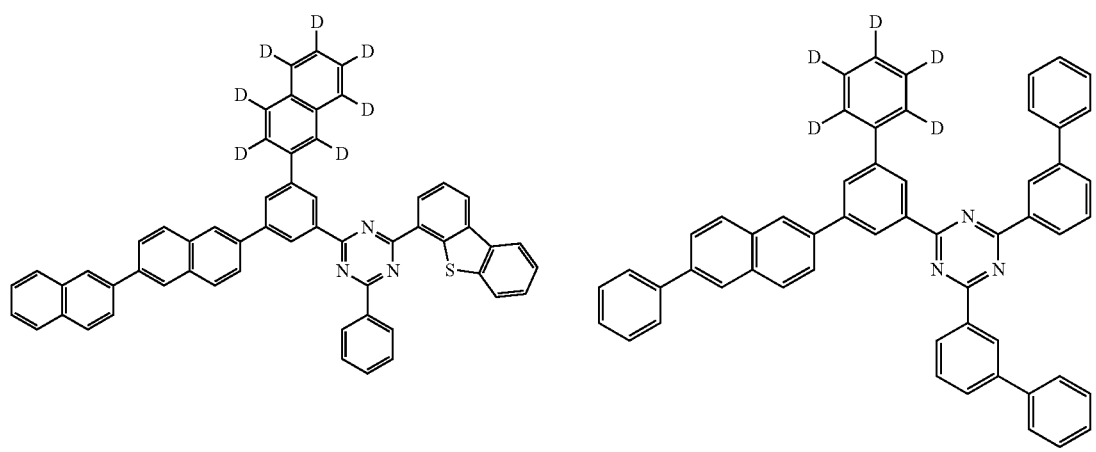

-continued
P-46
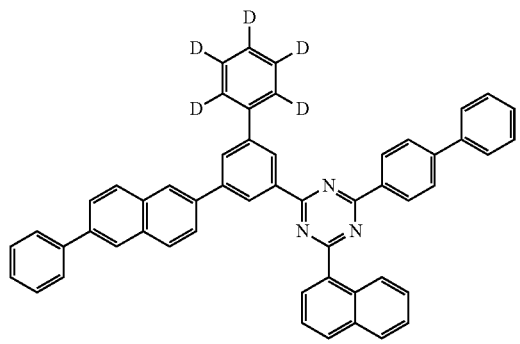
P-47
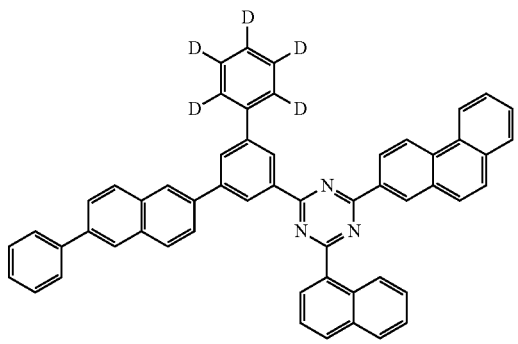
P-48
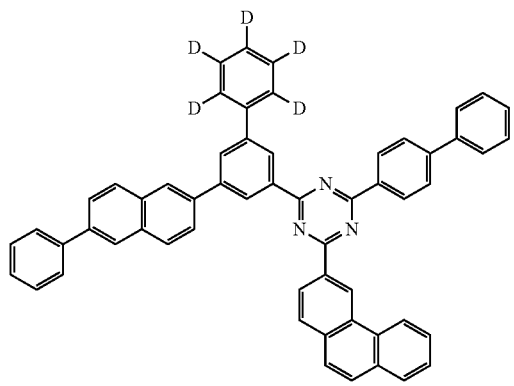
P-49
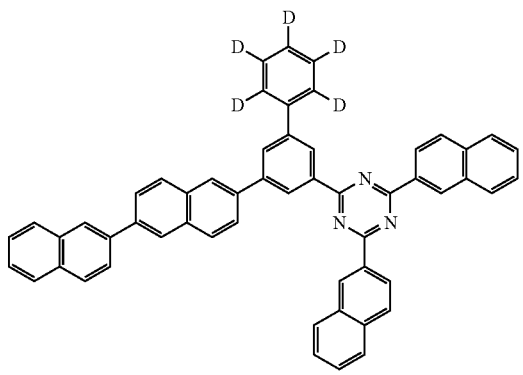
P-50
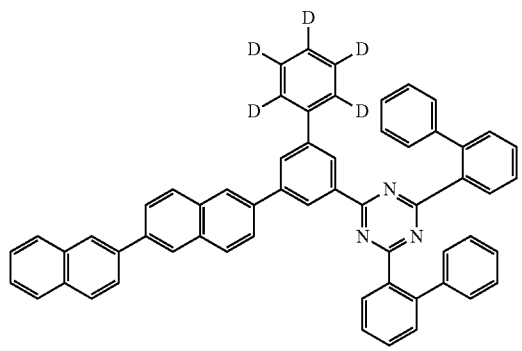
P-51
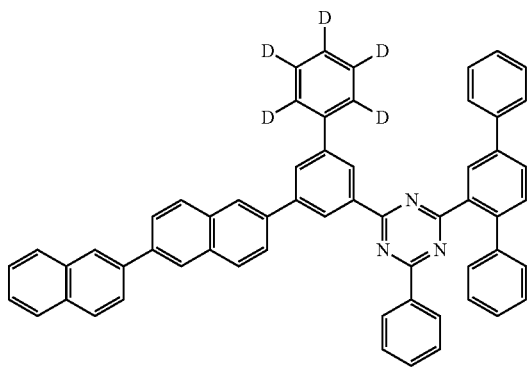
P-52
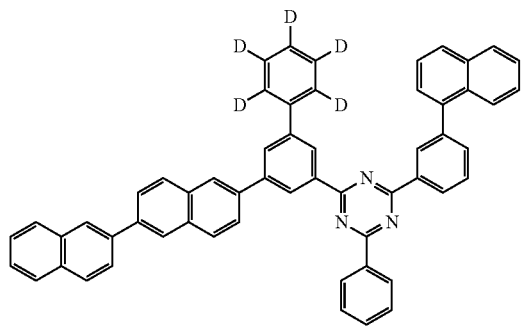
P-53
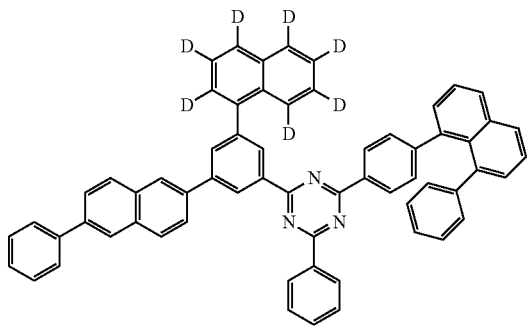

-continued
P-54
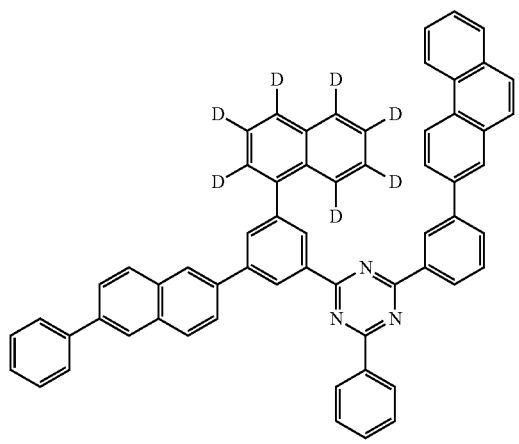
P-55
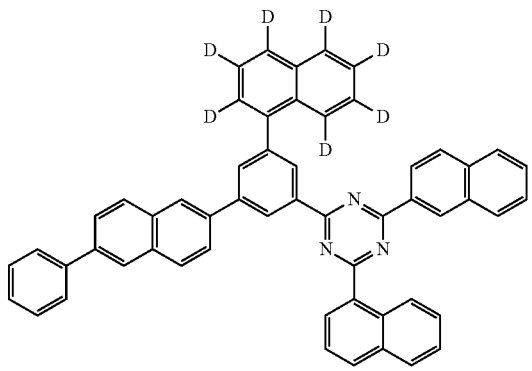
P-56
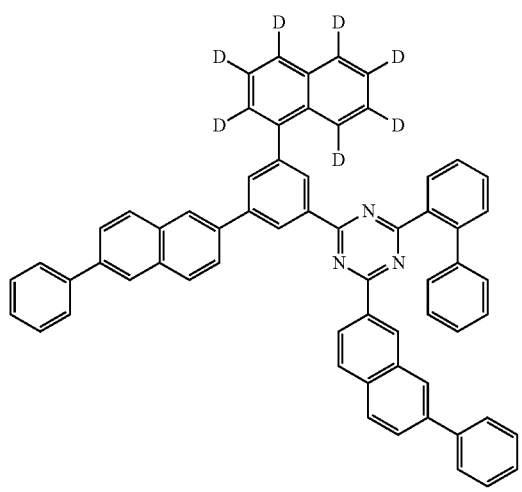
P-57
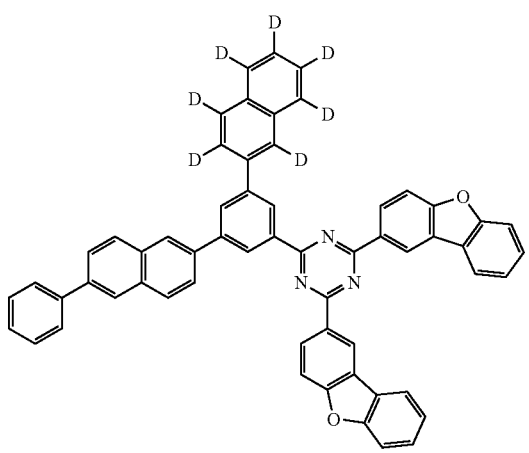
P-58
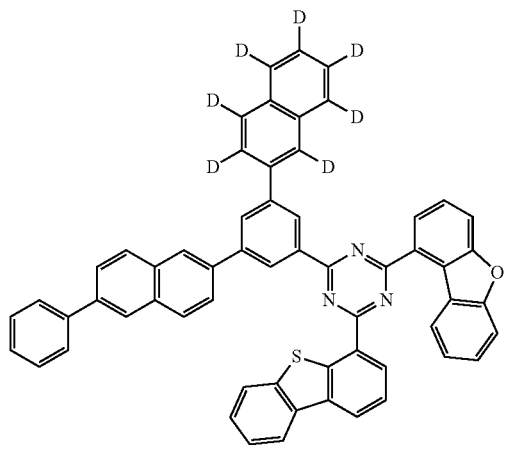
P-59
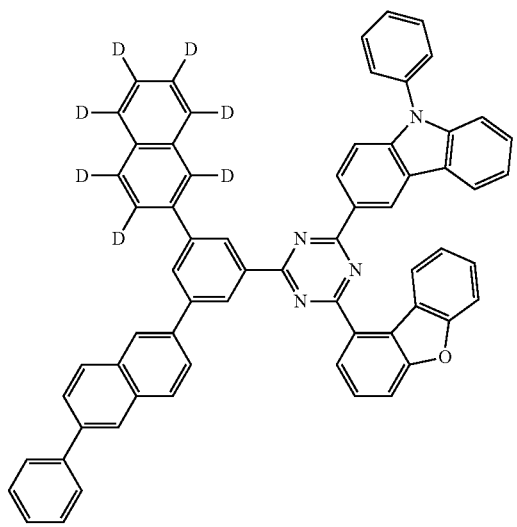

-continued
P-60
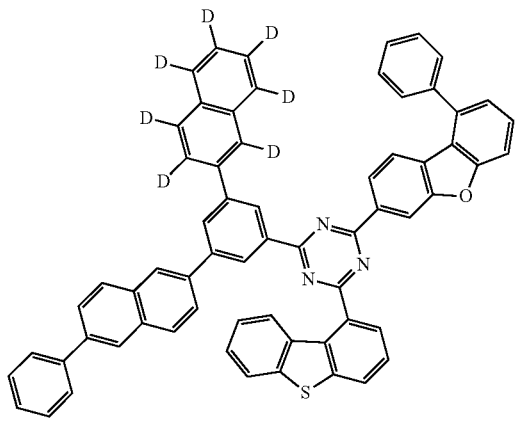
P-61
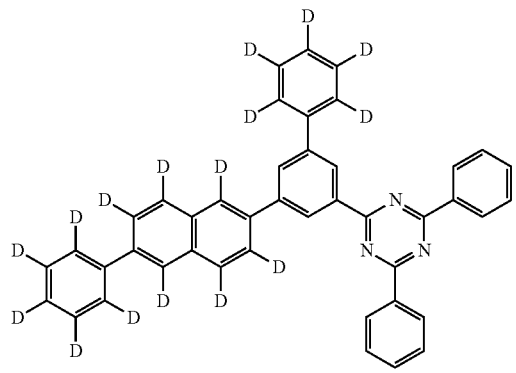
P-62
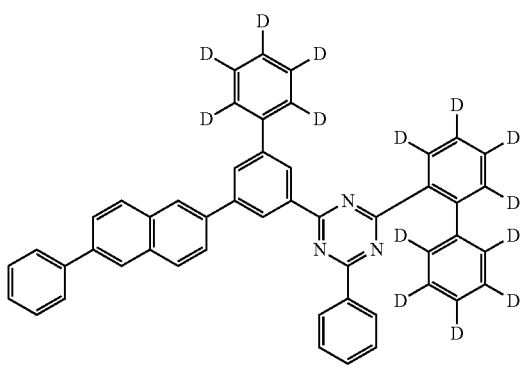
P-63
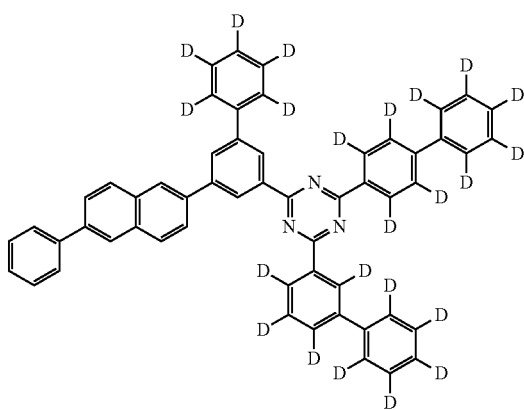
P-64
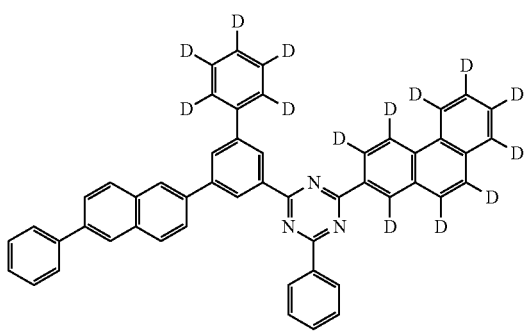
P-65
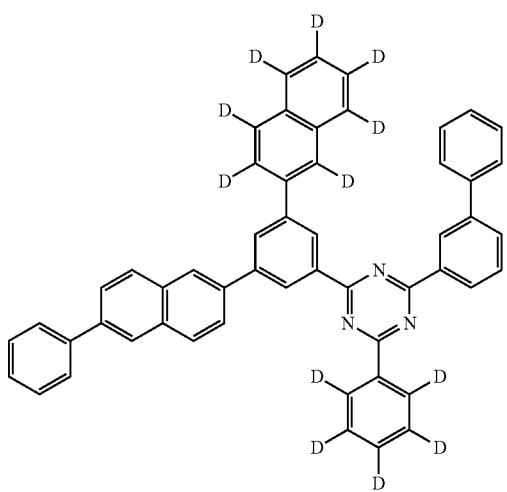

-continued
P-66
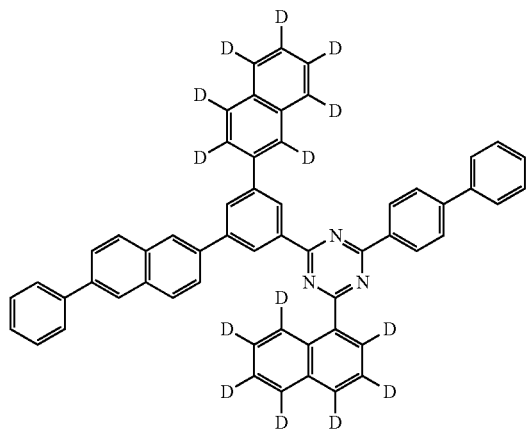
P-67
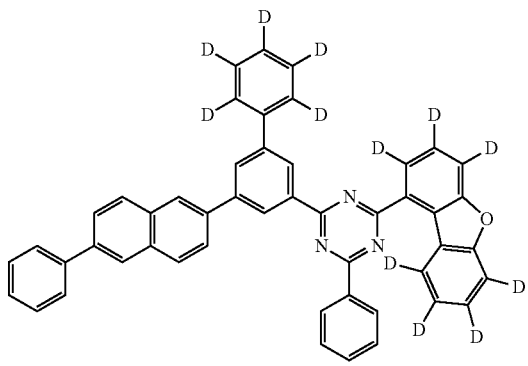
P-68
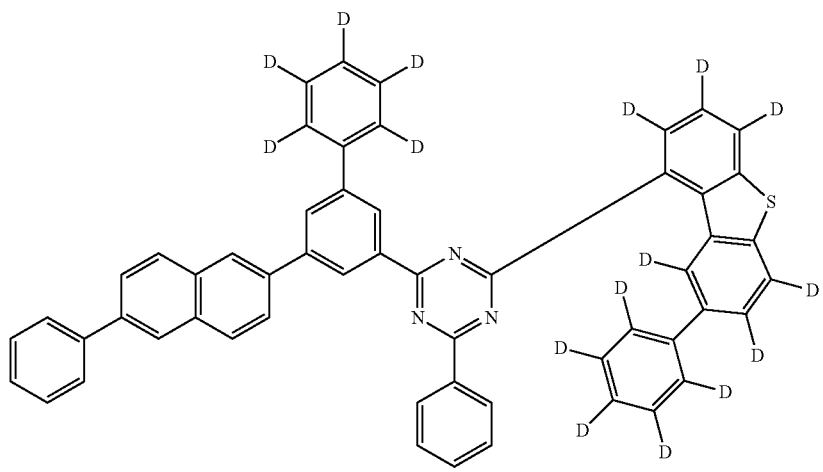
P-69
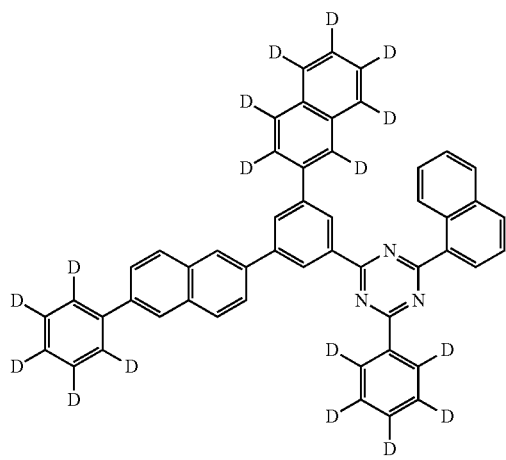
P-70
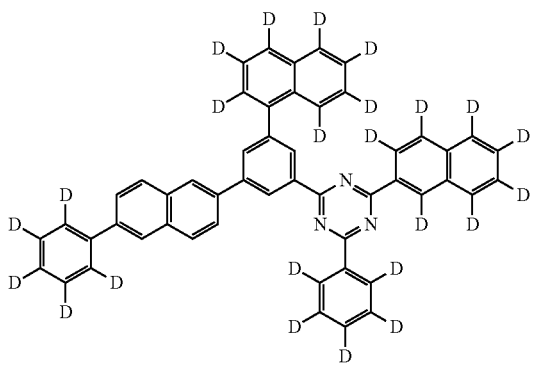

P-71
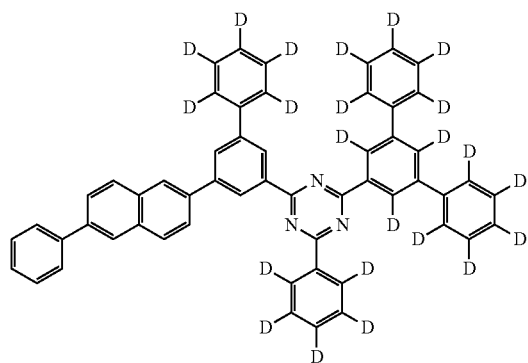
P-72
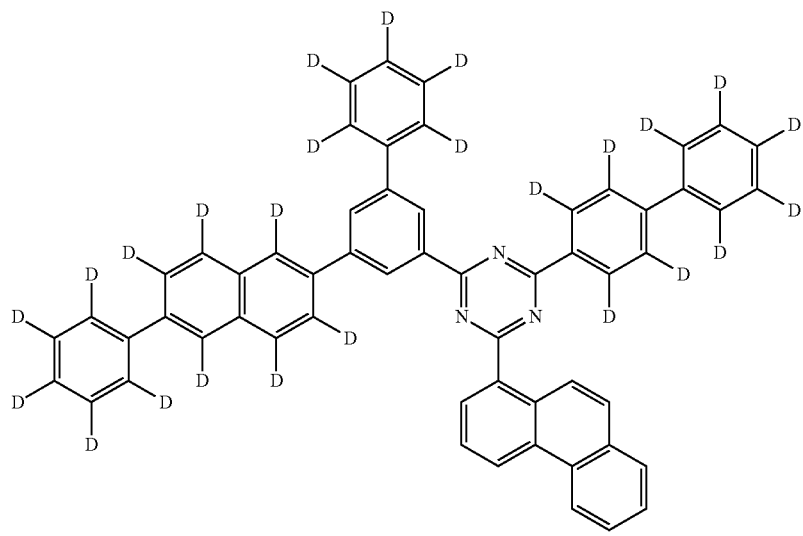
P-73
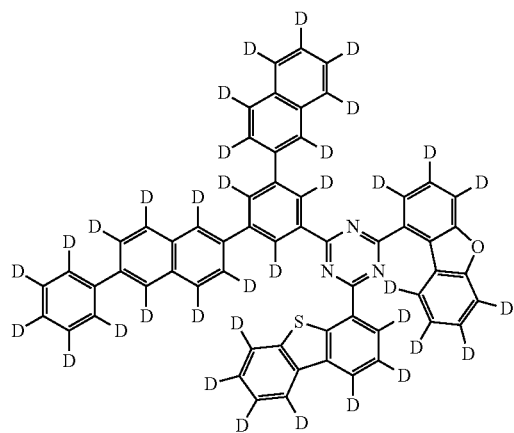

P-74
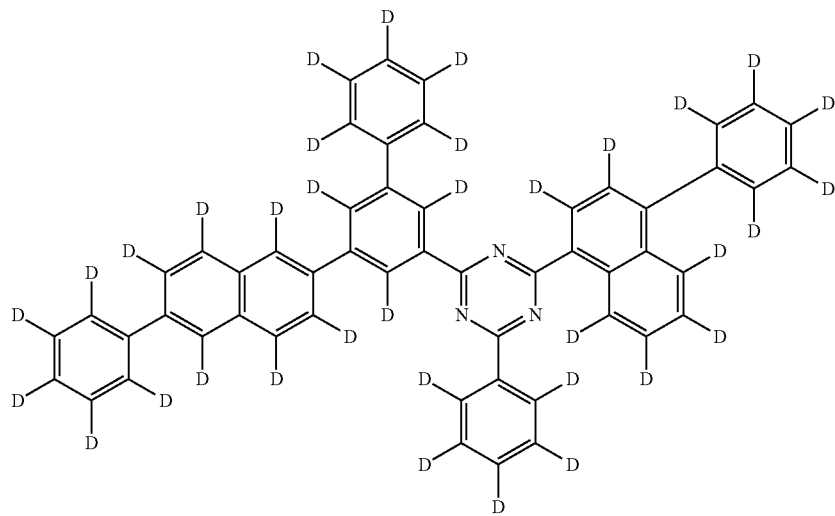
P-75
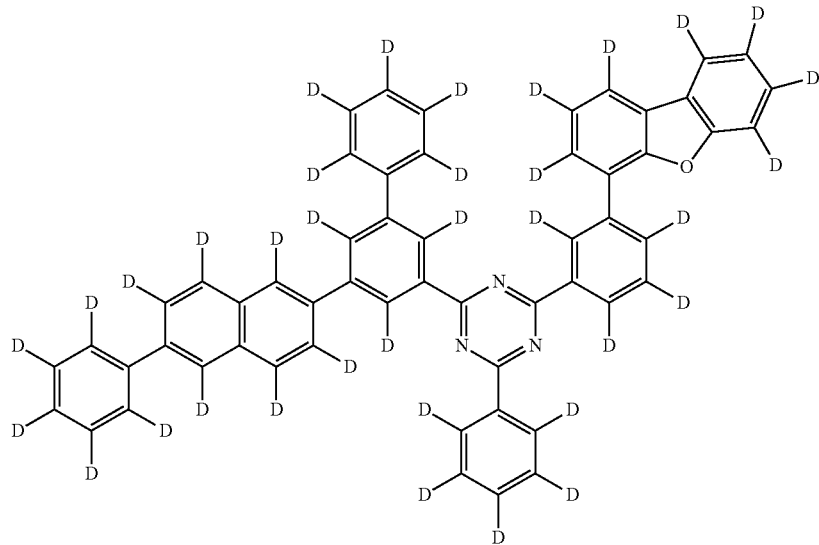
P-76
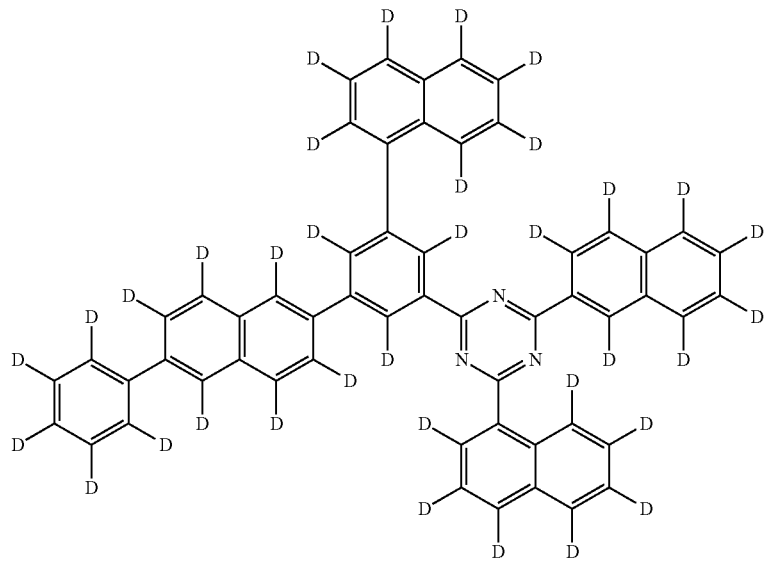

In another aspect, the present invention provides an organic electronic element comprising a first electrode; a second electrode; and an organic material layer formed between the first electrode and the second electrode, wherein the organic material layer comprises an emitting layer, wherein the emitting layer is a phosphorescent emitting layer, and comprises a first host compound represented by Formula 1 and a second host compound represented by Formula 3 or Formula 4.

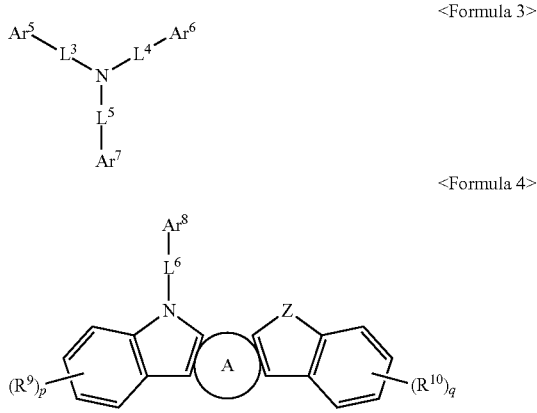

<Formula 3>

<Formula 4>

Wherein:

$L^3$, $L^4$, $L^5$ and $L^6$ are each independently selected from the group consisting of a single bond; a $C_6$-$C_{60}$ arylene group; fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

When $L^3$, $L^4$, $L^5$ and $L^6$ are an arylene group, it may be preferably a $C_6$-$C_{30}$ arylene group, more preferably a $C_6$-$C_{25}$ arylene group, for example, phenylene, biphenylene, naphthylene, terphenyl, anthracenylene, etc., When $L^3$, $L^4$, $L^5$ and $L^6$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., When $L^3$, $L^4$, $L^5$ and $L^6$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring, $Ar^5$, $Ar^6$ and $Ar^7$ are each independently selected from the group consisting of an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

When $Ar^5$, $Ar^6$ and $Ar^7$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, When $Ar^5$, $Ar^6$ and $Ar^7$ are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., When $Ar^5$, $Ar^6$ and $Ar^7$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

$Ar^8$ is each independently selected from the group consisting of an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-$NR^bR^c$;

When $Ar^8$ is aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, When $Ar^8$ is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., When $Ar^8$ is a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

Z is O, S, CR'R" or $NR^a$,

Ring A is an $C_6$-$C_{20}$ aryl group, $R^9$ and $R^{10}$ are each independently the same or different, and each independently selected from the group consisting of a hydrogen; deuterium; halogen; cyano group; nitro group; an $C_6$-$C_{60}$ aryl group; fluorenyl group; a $C_2$-$C_{06}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or a plurality of adjacent $R^9$s or a plurality of $R^{10}$s may be bonded to each other to form a ring, When $R^9$ and $R^{10}$ are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, When $R^9$ and $R^{10}$ are a heterocyclic group, it may be preferably a $C_2$~$C_{30}$ heterocyclic group, and more preferably a $C_2$~$C_{24}$ heterocyclic group, for example, pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine etc., When $R^9$ and $R^{10}$ are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When $R^9$ and $R^{10}$ are an alkyl group, it may be preferably a $C_1$-$C_{30}$ alkyl group, and more preferably a $C_1$-$C_{24}$ alkyl group.

When $R^9$ and $R^{10}$ are alkoxyl groups, they may be preferably $C_1$~$C_{30}$ alkoxyl groups, and more preferably $C_1$~$C_{24}$ alkoxyl groups, When $R^9$ and $R^{10}$ are an aryloxy group, it may be preferably an $C_6$~$C_{30}$ aryloxy group, and more preferably an $C_6$~$C_{24}$ aryloxy, p and q are each independently an interger 0 to 4, L' is each independently selected from the group consisting of a single bond; a $C_6$-$C_{60}$ arylene group; fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

When L' is an arylene group, it may be preferably a $C_6$-$C_{30}$ arylene group, more preferably a $C_6$-$C_{25}$ arylene group, for example, phenylene, biphenylene, naphthylene, terphenylene, anthracenylene etc., When L' is a heterocyclic group, it may be preferably a $C_2$~$C_{30}$ heterocyclic group, and more preferably a $C_2$~$C_{20}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene, etc., When L' is aliphatic groups, they may be preferably $C_3$-$C_{30}$ aliphatic groups, more preferably $C_3$-$C_{24}$ aliphatic groups.

$R^b$ and $R^c$ are each independently selected from the group consisting of an $C_6$-$C_{60}$ aryl group; fluorenyl group; a $C_2$-$C_{60}$ heterocyclic group including at least one heteroatom of O, N, S, Si or P; a $C_3$-$C_{60}$ aliphatic ring;

When $R^b$ and $R^c$ are aliphatic groups, they may be preferably $C_3$-$C_{30}$ aliphatic groups, more preferably $C_3$-$C_{24}$ aliphatic groups.

When $R^b$ and $R^c$ are a heterocyclic group, it may be preferably a $C_2$~$C_{30}$ heterocyclic group, and more preferably a $C_2$~$C_{20}$ heterocyclic group, for example, pyridine, pyrimidine, quinoline, quinazoline, quinoxaline, dibenzofuran, dibenzothiophene, naphthobenzothiophene, naphthobenzofuran, benzofuran, benzothiophene, etc., R' and R" are each independently selected from the group consisting of a hydrogen; deuterium; an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or R' and R" may be bonded to each other to form a ring, When R' and R" are an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, When R' and R" are a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., When R' and R" are a fused ring group, it may be preferably a fused ring group of a $C_3$-$C_{30}$ aliphatic ring and a $C_6$-$C_{30}$ aromatic ring, more preferably a fused ring group of a $C_3$-$C_{24}$ aliphatic ring and a $C_6$-$C_{24}$ aromatic ring.

When R' and R" are an alkyl group, it may be preferably a $C_1$-$C_{30}$ alkyl group, and more preferably a $C_1$-$C_{24}$ alkyl group.

When R' and R" are alkoxyl groups, it may be preferably $C_1$~$C_{24}$ alkoxyl groups, When R' and R" are an aryloxy group, it may be preferably an $C_6$~$C_{24}$ aryloxy, $R^a$ is an $C_6$-$C_{60}$ aryl group; or a $C_2$-$C_{60}$ heterocyclic group including at least one heteroatom of O, N, S, Si or P;

When $R^a$ is an aryl group, it may be preferably a $C_6$-$C_{30}$ aryl group, and more preferably a $C_6$-$C_{25}$ aryl group, for example, it may be phenyl, biphenyl, terphenyl, naphthalene, phenanthrene, etc, When $R^a$ is a heterocyclic group, it may be preferably a $C_2$-$C_{30}$ heterocyclic group, and more preferably a $C_2$-$C_{24}$ heterocyclic group, for example, it may be pyrazine, thiophene, pyridine, pyrimidoindole, 5-phenyl-5H-pyrimido[5,4-b]indole, quinazoline, benzoquinazoline, carbazole, dibenzoquinazoline, dibenzofuran, dibenzothiophene, benzothienopyrimidine, benzofuropyrimidine, phenothiazine, phenylphenothiazine, etc., wherein the aryl group, arylene group, heterocyclic group, fluorenyl group, fluorenylene group, aliphatic ring group, fused ring group, alkyl group, alkenyl group, alkynyl group, alkoxyl group, and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Formula 3 is represented by any one of Formulas 3-1 to 3-3.

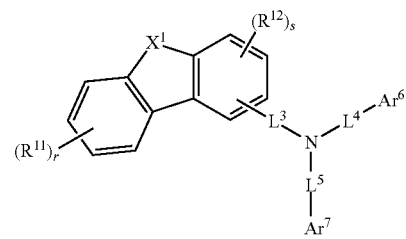

<Formula 3-1>

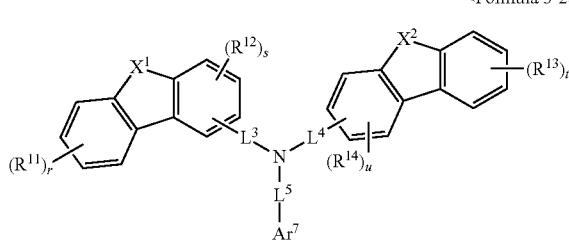

<Formula 3-2>

<Formula 3-3>

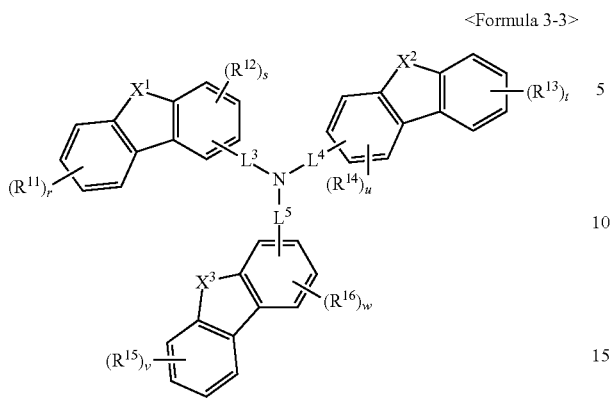

<Formula 4-3>

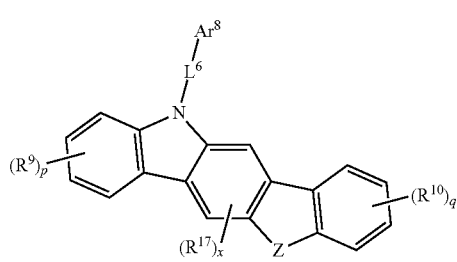

Wherein:

Ar$^6$, Ar$^7$, L$^3$, L$^4$ and L$^5$ are the same as defined in Formula 3,

X$^1$, X$^2$ and X$^3$ are the same as the definition of Z,

R$^{11}$, R$^{12}$, R$^{13}$, R$^{14}$, R$^{15}$ and R$^{16}$ are the same as the definition of R$^9$, or an adjacent plurality of R$^{11}$s, a plurality of R$^{12}$s, a plurality of R$^{13}$s, a plurality of R$^{14}$s, a plurality of R$^{15}$s, a plurality of R$^{16}$s may be bonded to each other to form a ring, R, t and v are each independently an integer of 0 to 4, and s, u and w are each independently an integer of 0 to 3.

Formula 4 may be represented by any one of Formulas 4-1 to 4-6.

<Formulas 4-4>

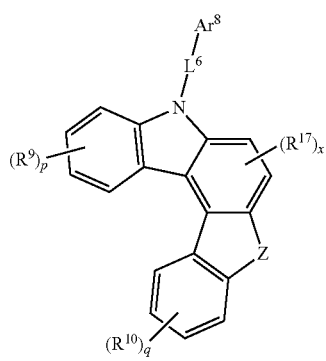

<Formula 4-5>

<Formula 4-1>

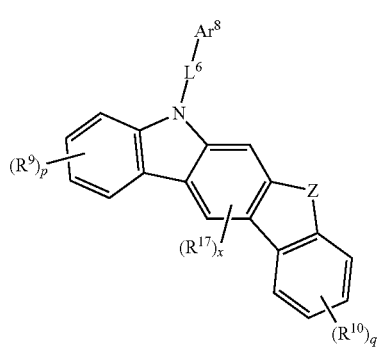

<Formulas 4-6>

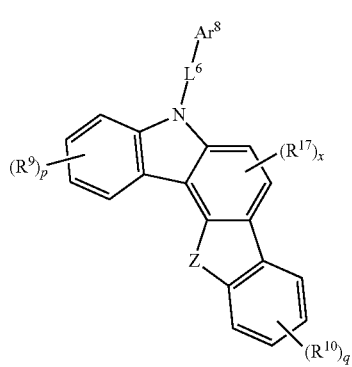

<Formulas 4-2>

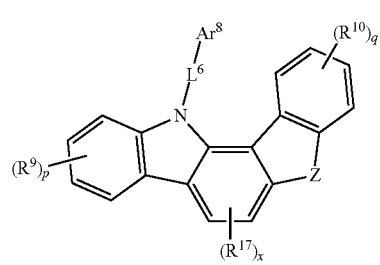

Wherein:

Z, R$^9$, R$^{10}$, Ar$^8$, L$^6$, p and q are the same as the defined in Formula 4, R$^{17}$ is the same as the definition of R$^9$, x is an integer of 0 to 2.

Formula 4 may be represented by any one of Formulas 4-7 to 4-9.

<Formula 4-7>

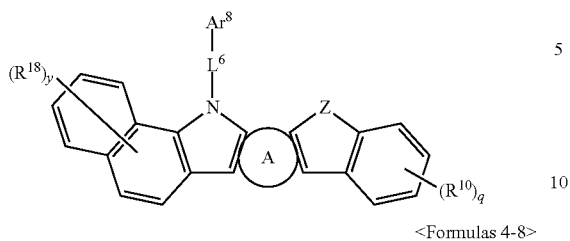

<Formulas 4-8>

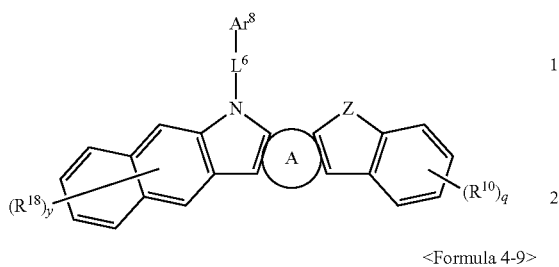

<Formula 4-9>

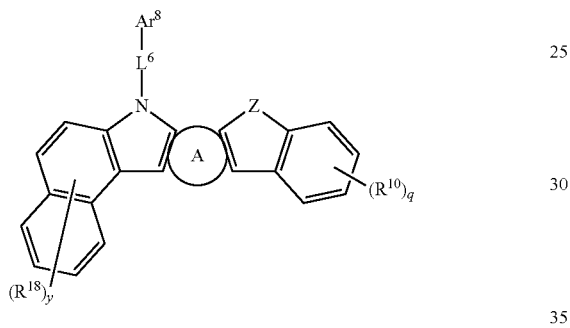

Wherein:
Z, Ring A, $R^{10}$, $Ar^8$, $L^6$ and q are the same as defined in Formula 4,
$R^{18}$ is the same as the definition of $R^9$,
y is an integer of 0 to 6.

Formula 4 may be represented by any one of Formulas 4-10 to 4-12.

<Formula 4-10>

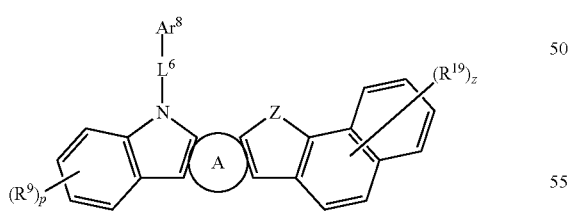

<Formulas 4-11>

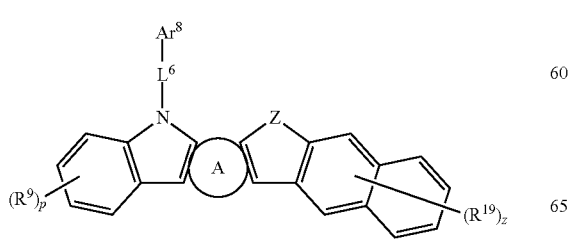

<Formula 4-12>

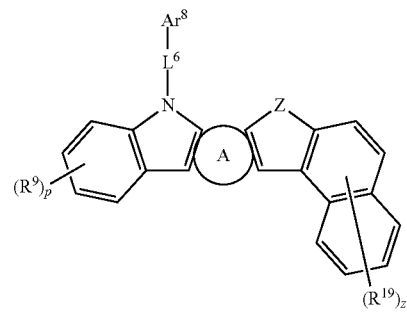

Wherein:
Z, Ring A, $R^9$, $Ar^8$, $L^6$ and q are the same as defined in Formula 4,
$R^{19}$ is the same as the definition of $R^9$,
z is an integer of 0 to 6.

Formula 4 may be represented by any one of Formulas 4-13 to 4-18.

<Formula 4-13>

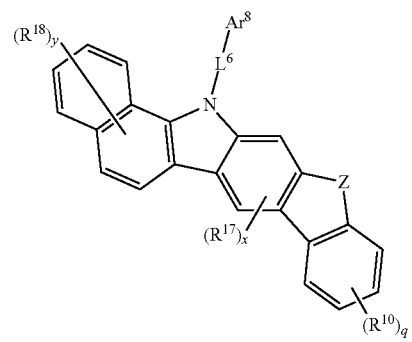

<Formulas 4-14>

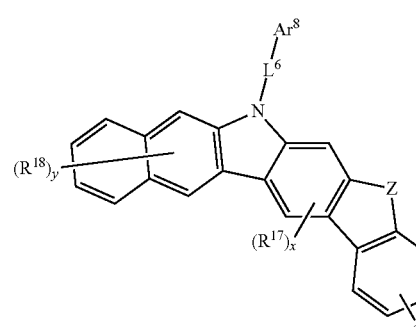

<Formula 4-15>

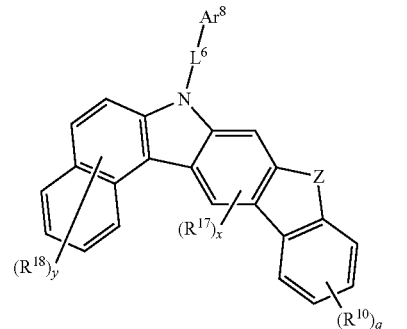

<Formula 4-16>

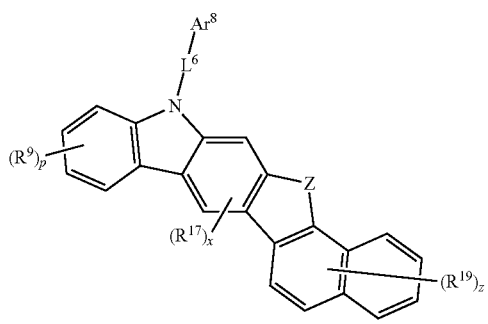

<Formula 4-17>

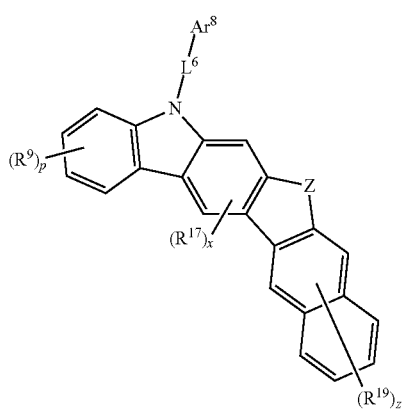

<Formula 4-18>

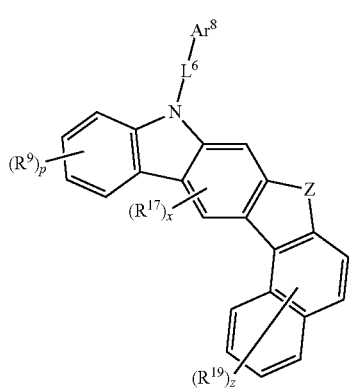

Wherein:
Z, $R^9$, $R^{10}$, $Ar^8$, $L^6$, p and q are the same as defined in Formula 4, $R^{17}$, $R^{18}$ and $R^{19}$ are the same as the definition of $R^9$, X is an integer of 0 to 2, y and z are each independently an integer of 0 to 6.

Formula 4 may be represented by Formula 4-19.

<Formula 4-19>

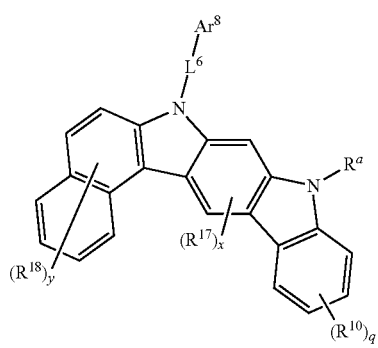

$R^{10}$, $Ar^8$, $L^6$, $R^a$ and q are the same as defined in Formula 4, $R^{17}$ and $R^{18}$ are the same as definition of $R^9$, x is an integer of 0 to 2, y is an integer of 0 to 6.

Specifically, the compound represented by Formula 3 may be any one of the following compounds N-1 to N-96, but is not limited thereto.

N-1

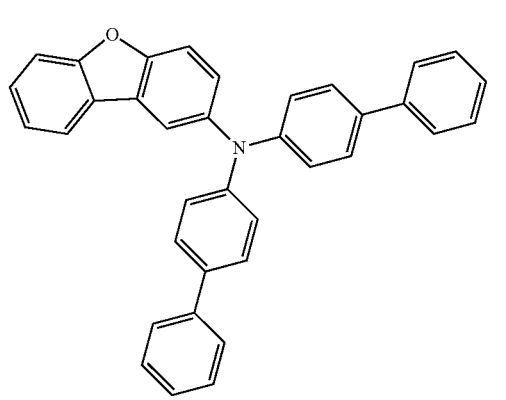

N-2

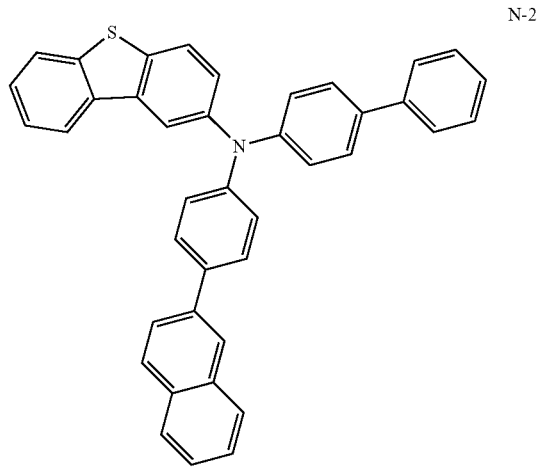

-continued
N-3
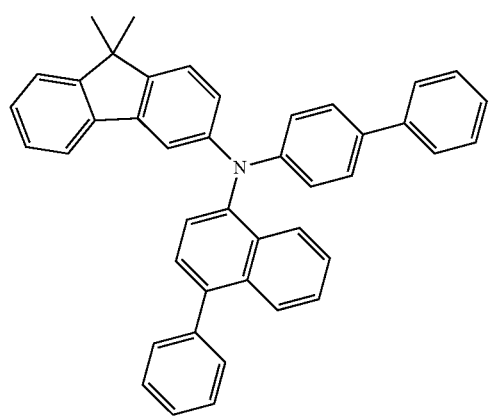
N-4
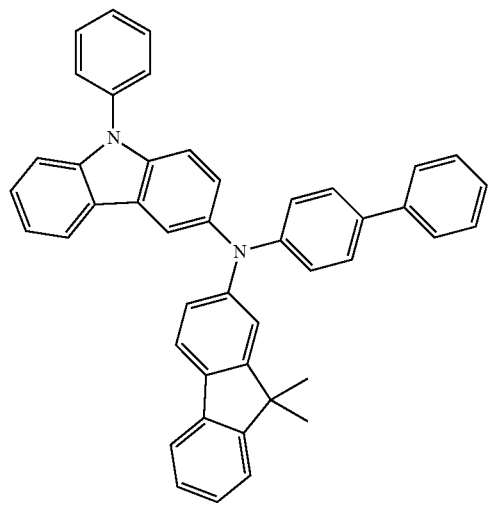
N-5
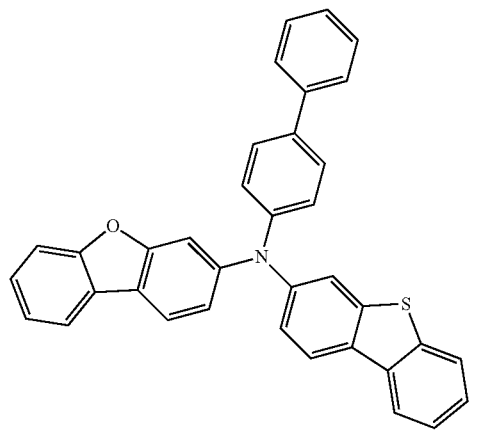
N-6
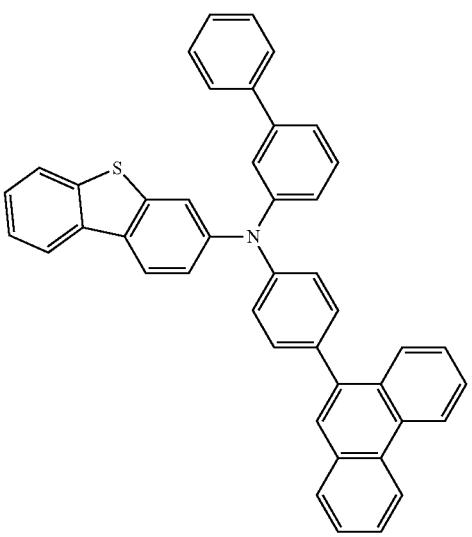
N-7
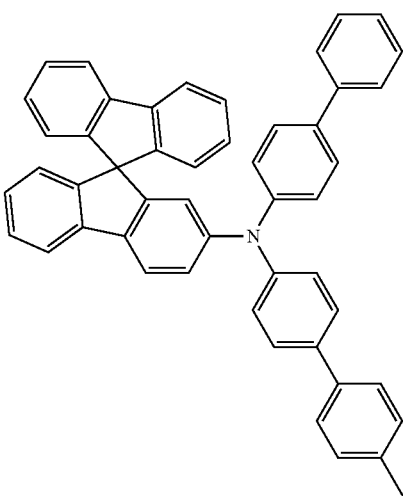
N-8

N-9
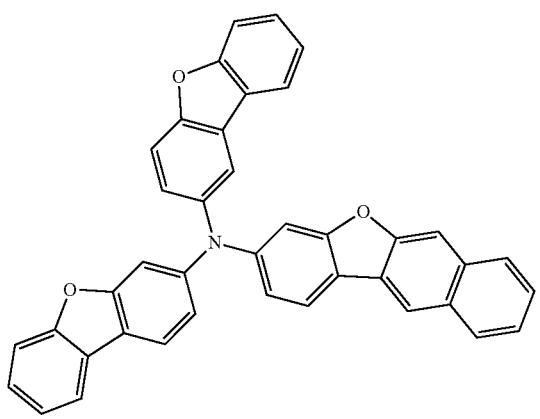
N-10
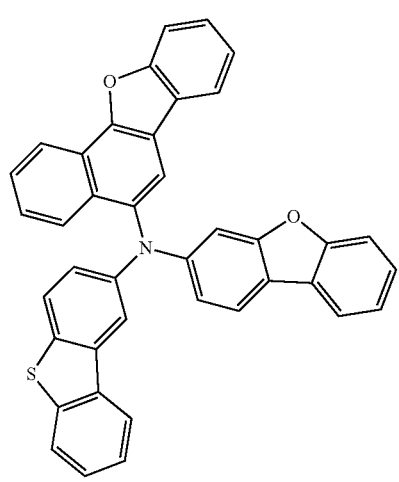
N-11
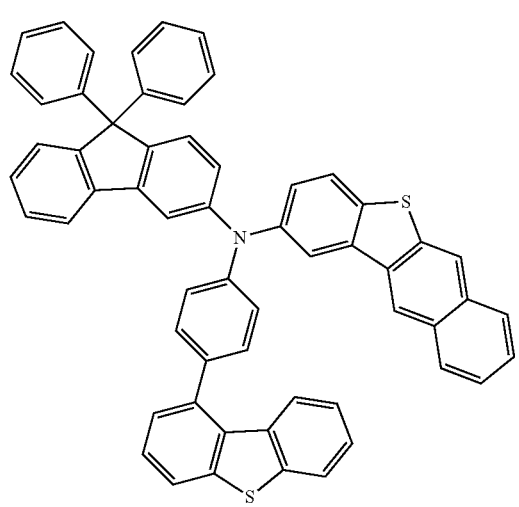
N-12
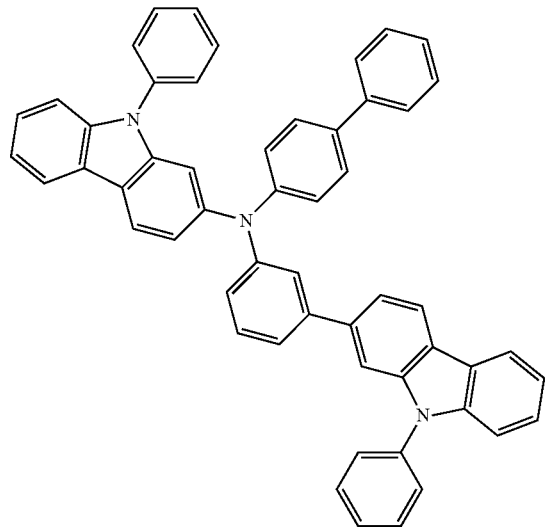
N-13
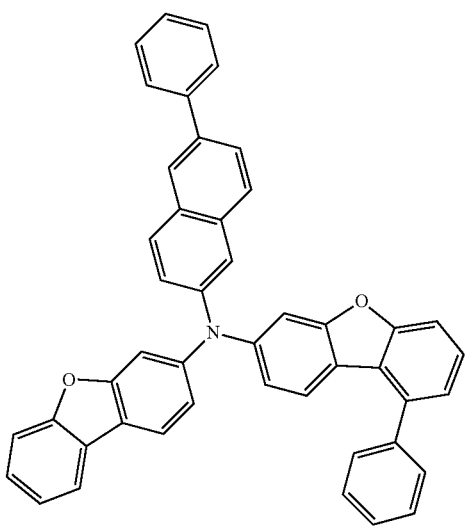
N-14
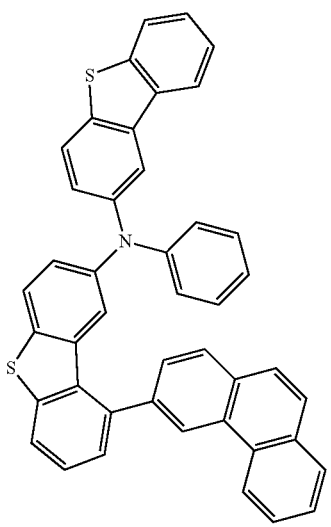

N-15
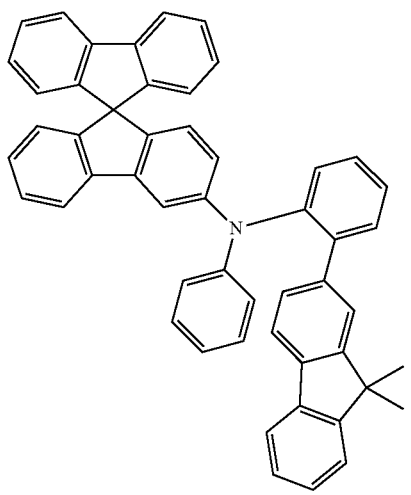
N-18
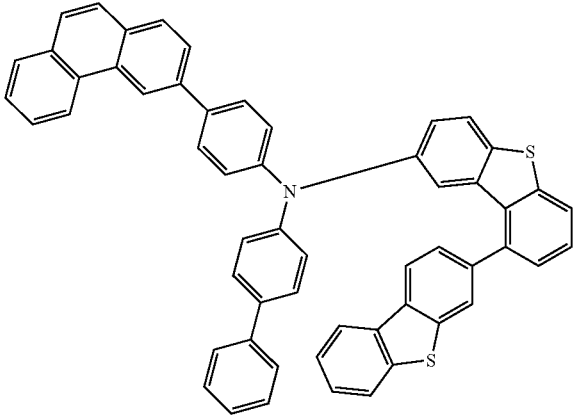
N-16
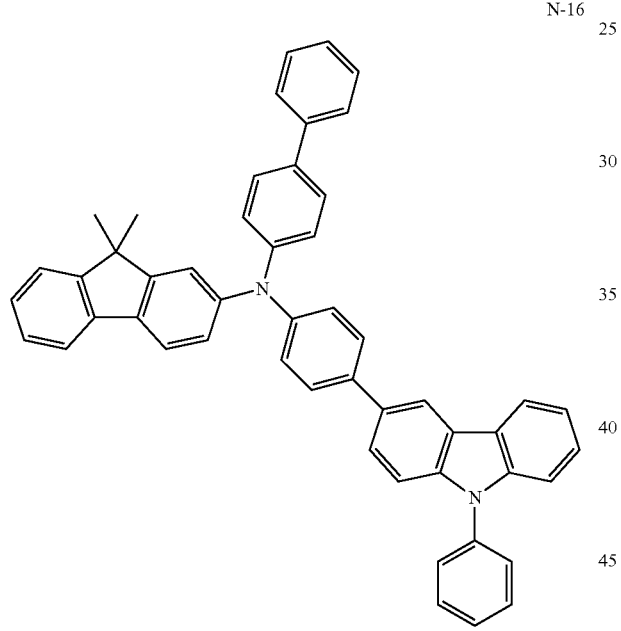
N-19
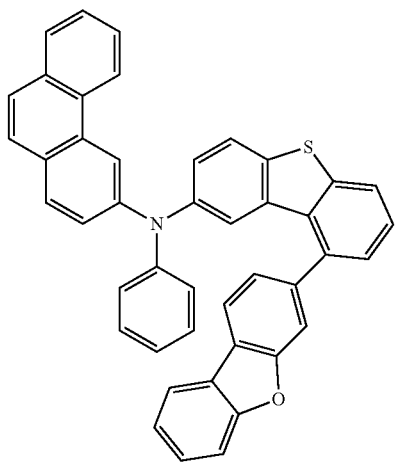
N-17
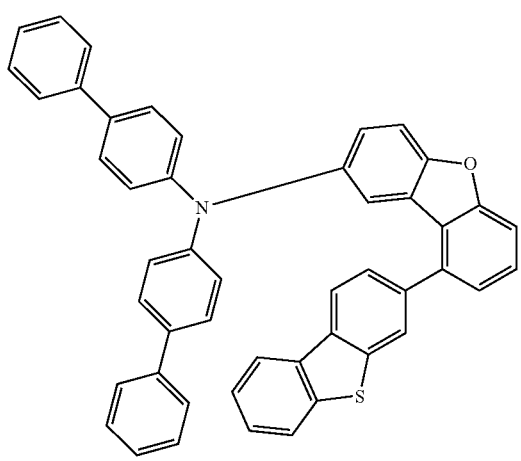
N-20
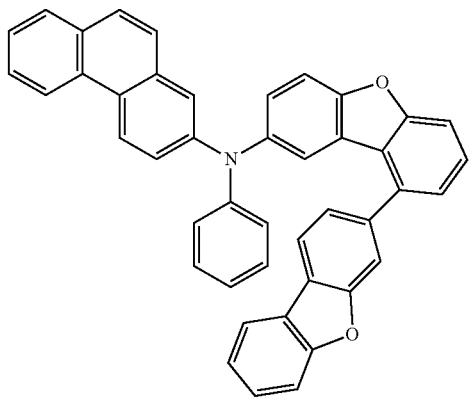

N-21
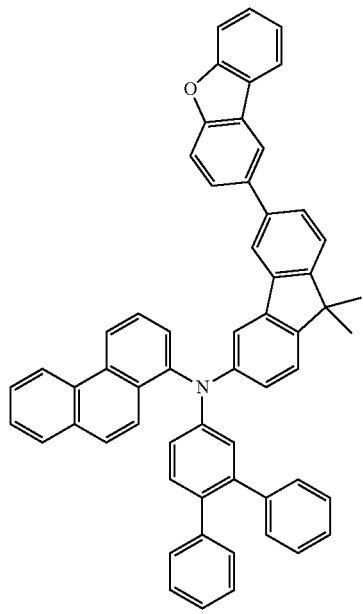
N-22
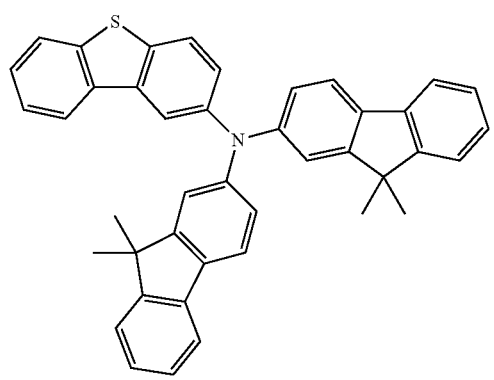
N-23
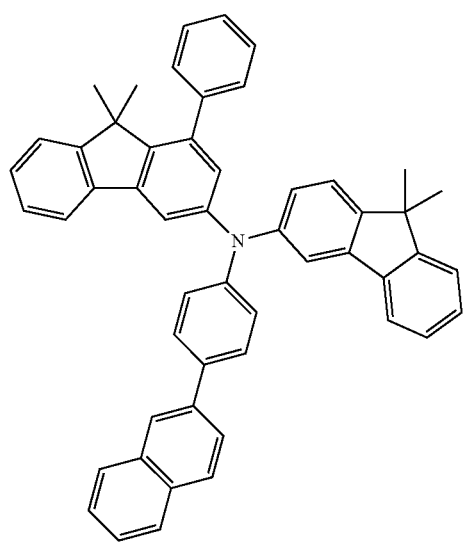
N-24
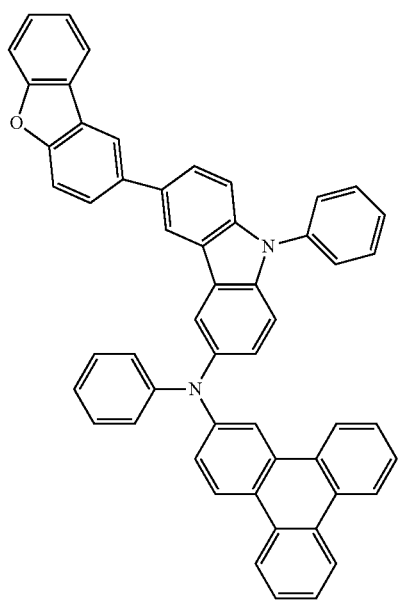
N-25
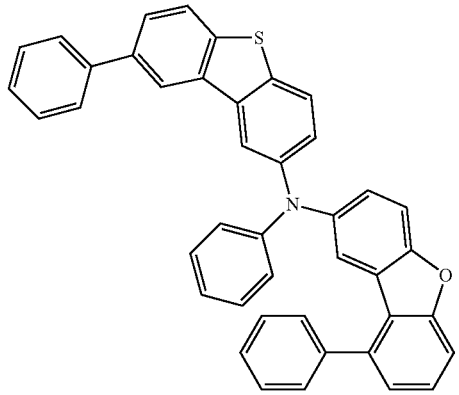
N-26
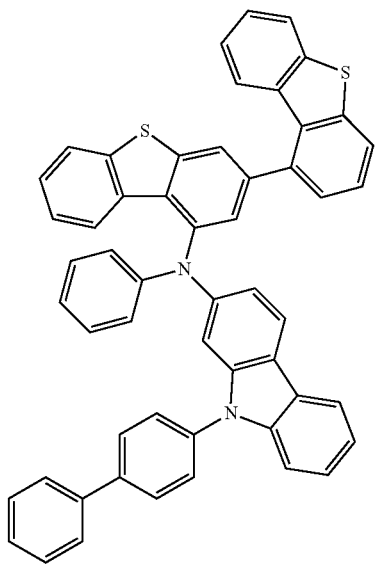

N-27
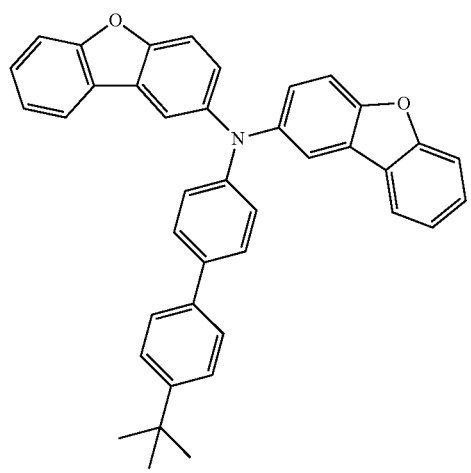
N-30
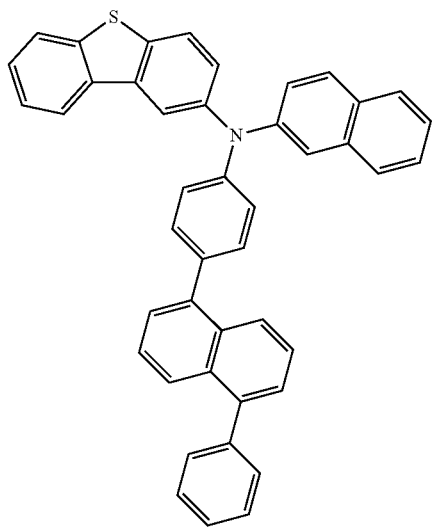
N-28
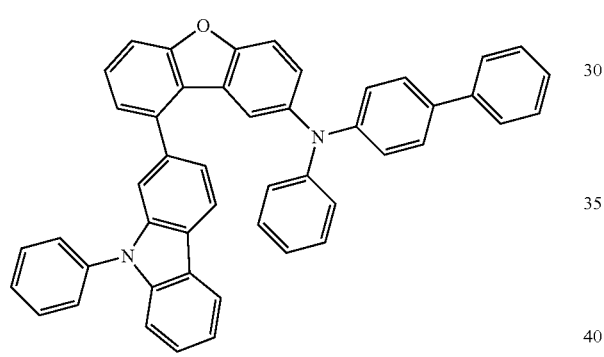
N-29
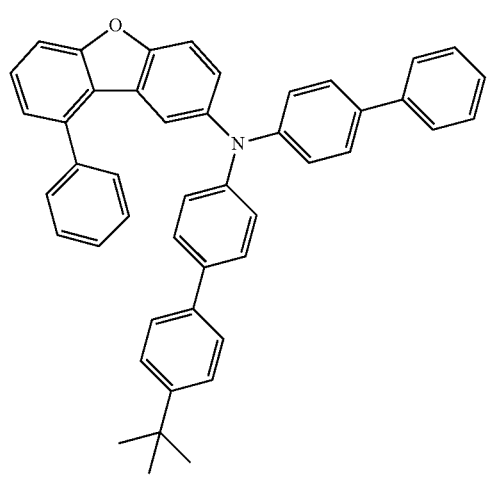
N-31
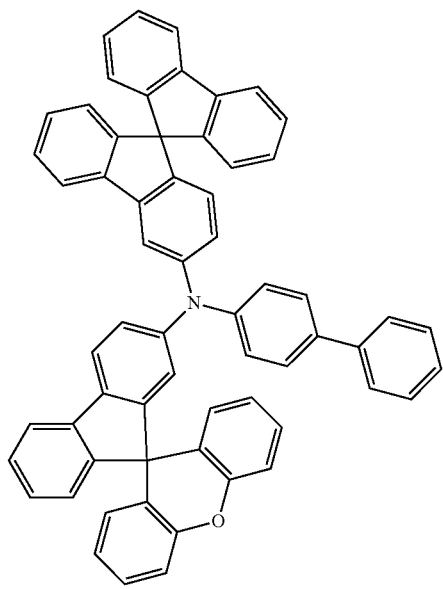

N-32
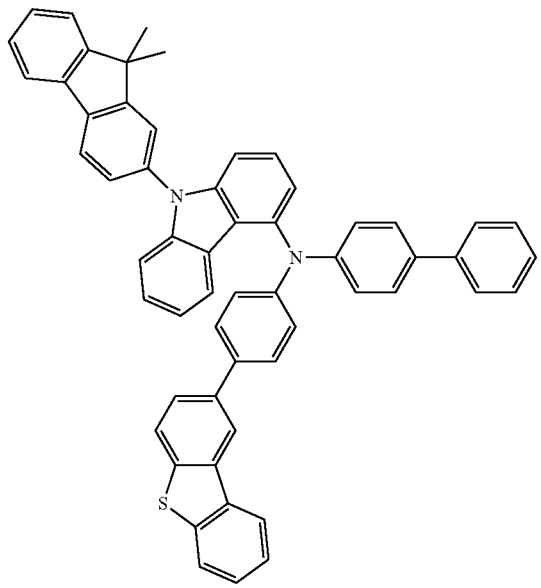
N-33
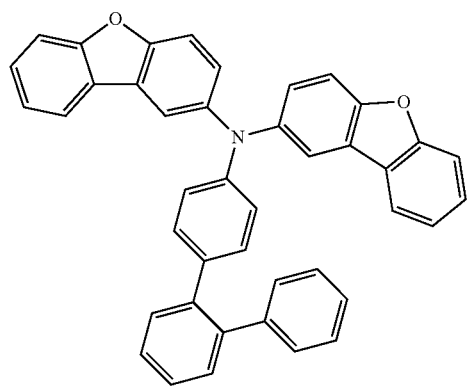
N-34
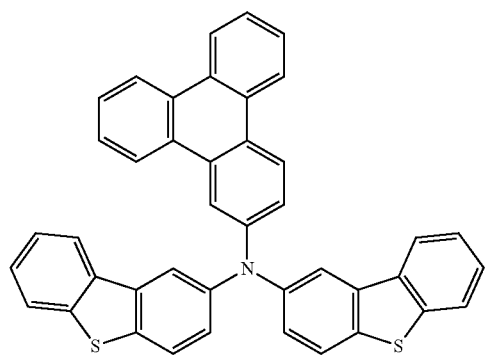
N-35
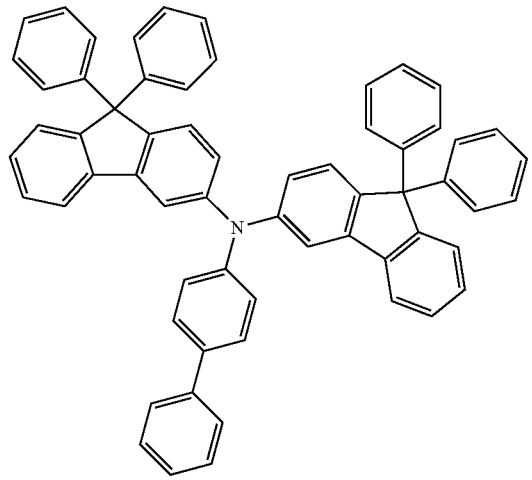
N-36
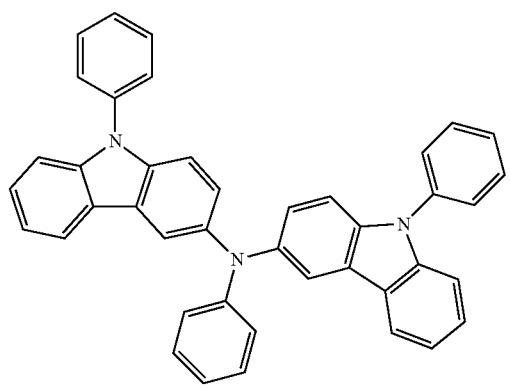
N-37
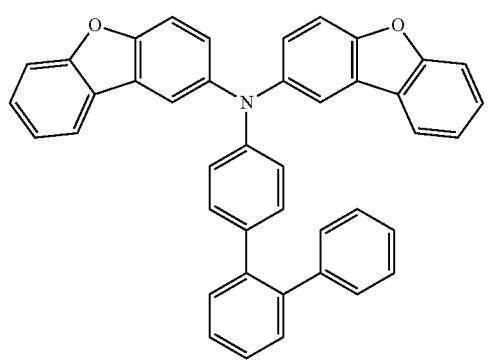
N-38
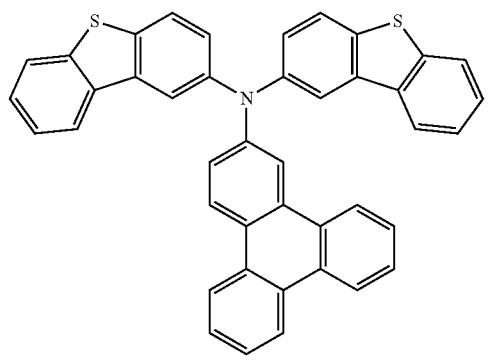

N-39
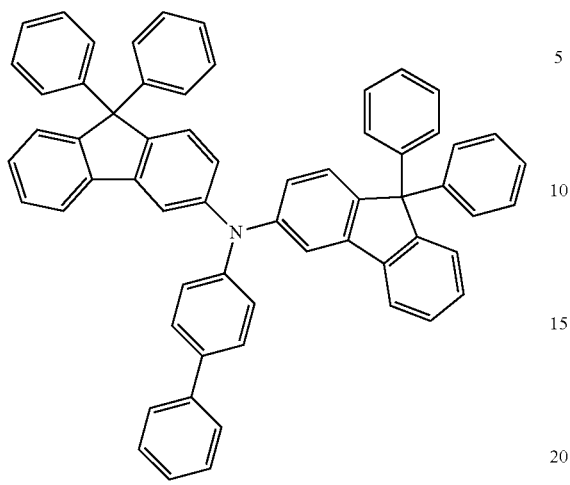
N-42
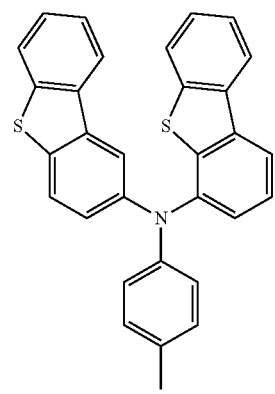
N-40
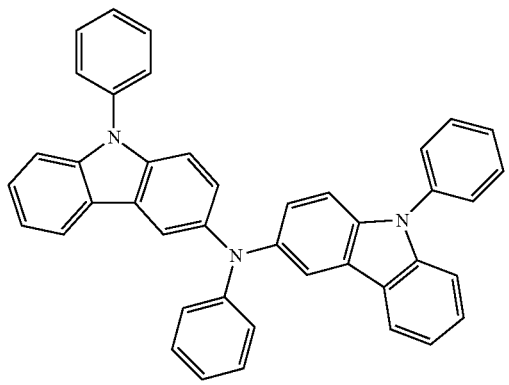
N-43
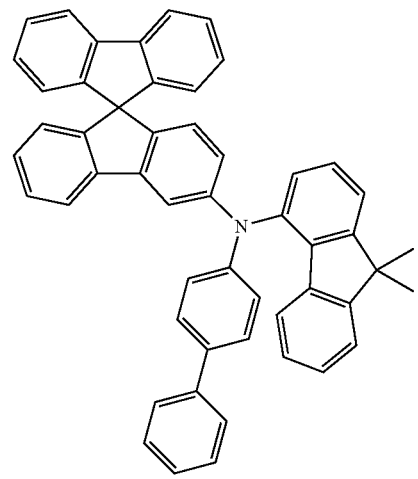
N-41
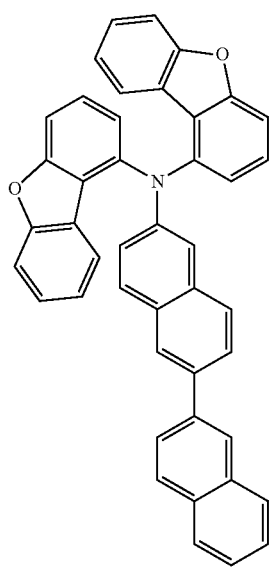
N-44
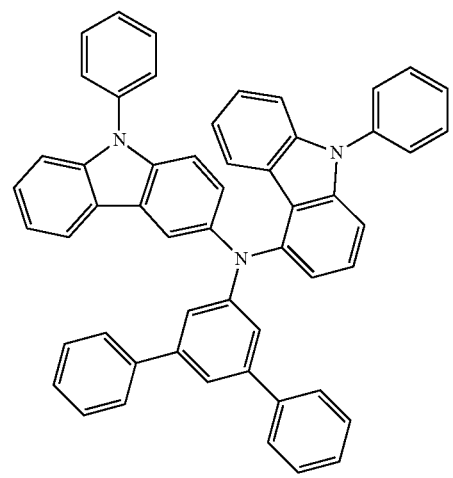

N-45
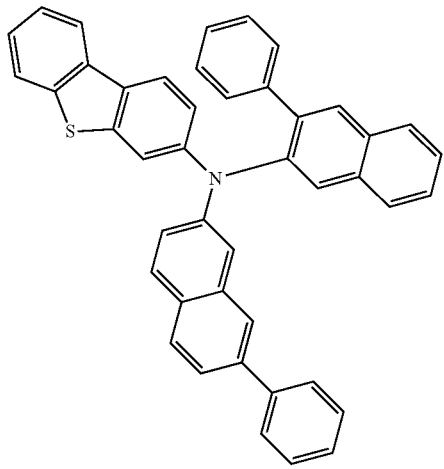
N-46
N-47
N-48
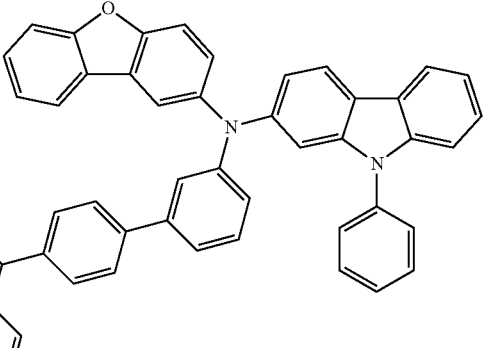
N-49
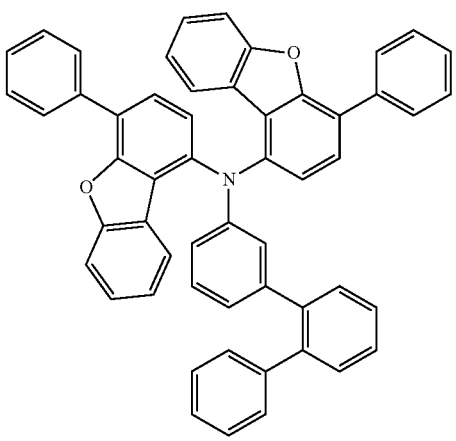
N-50
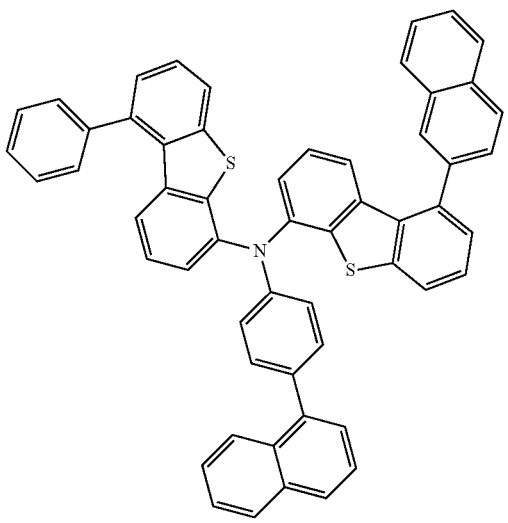

N-51
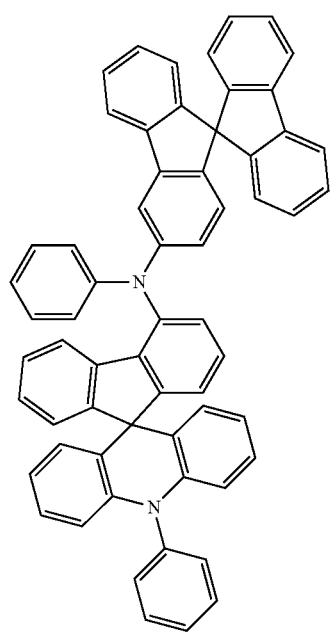
N-52
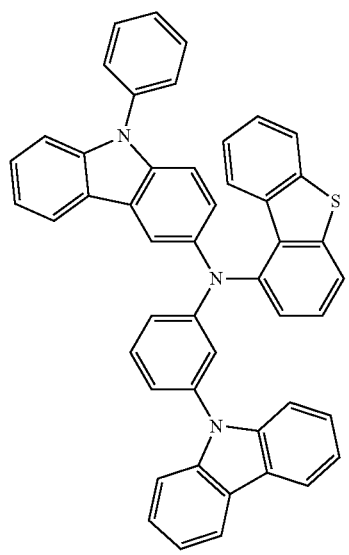
N-53
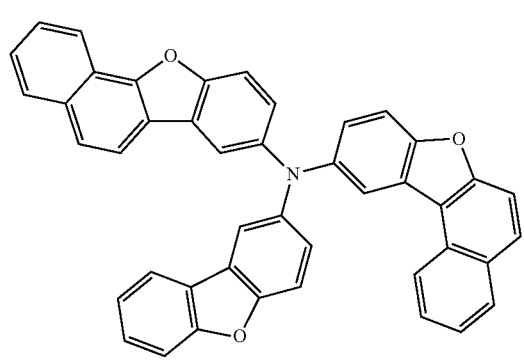
N-54
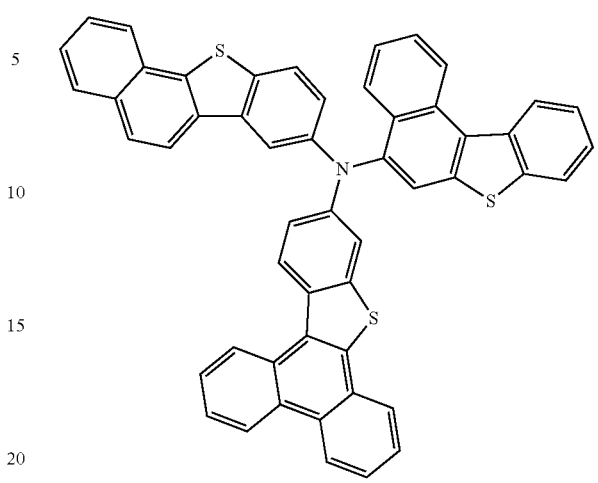
N-55
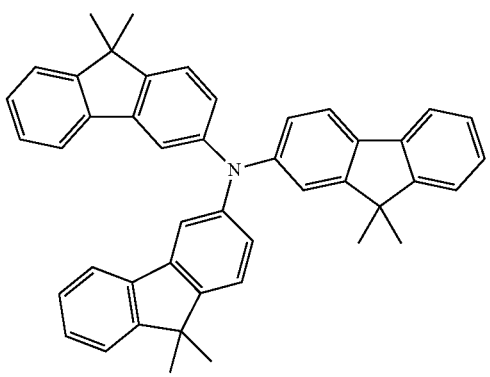
N-56
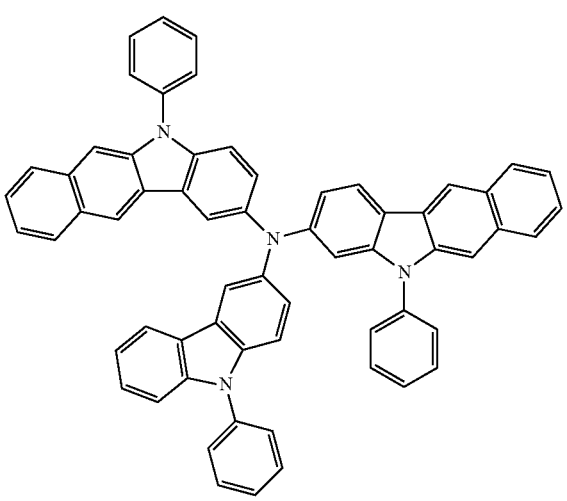

N-57
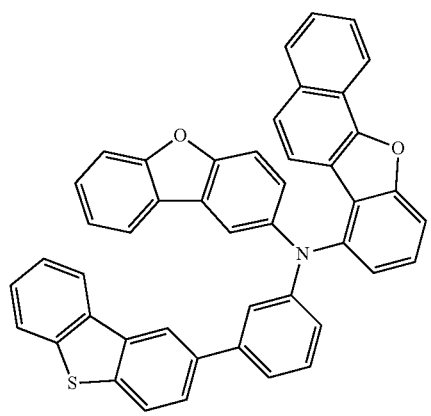
N-58
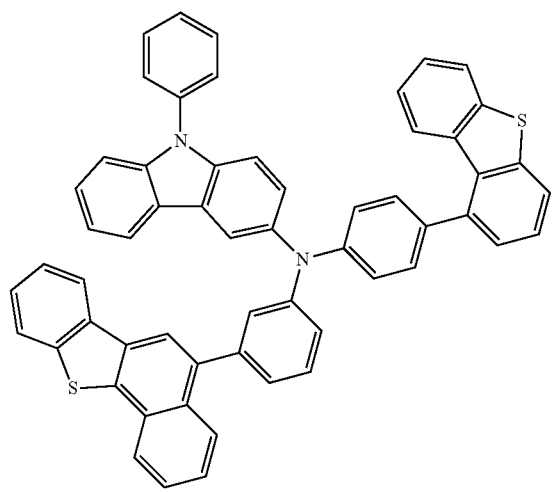
N-59
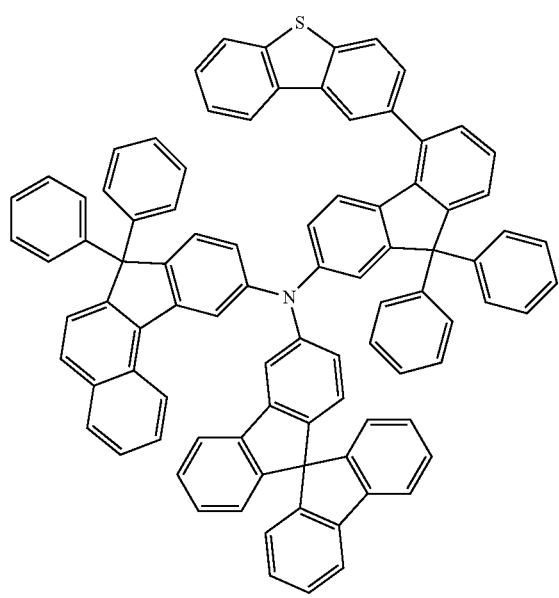
N-60
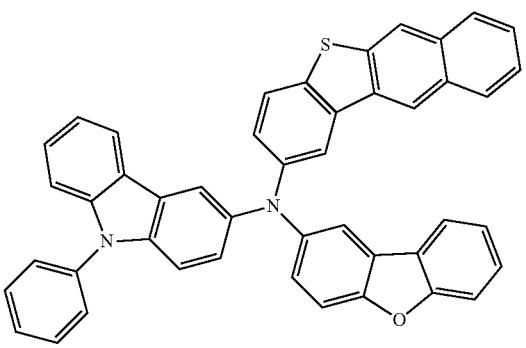
N-61
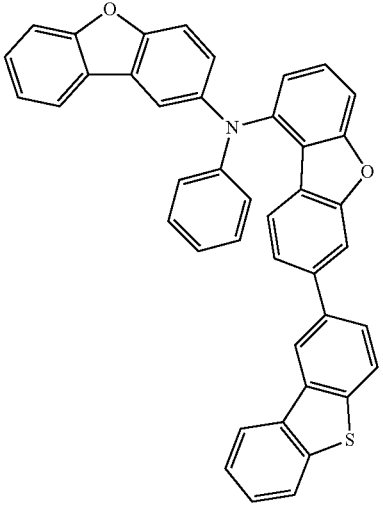
N-62
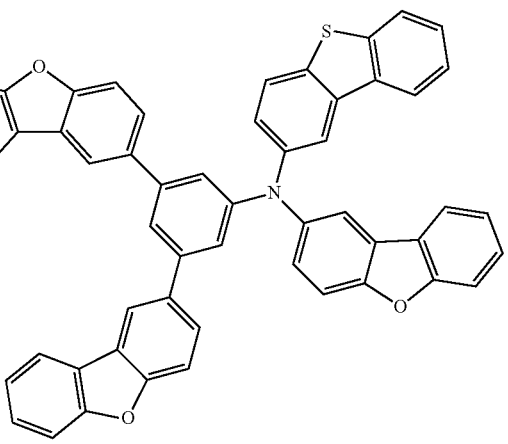

N-63
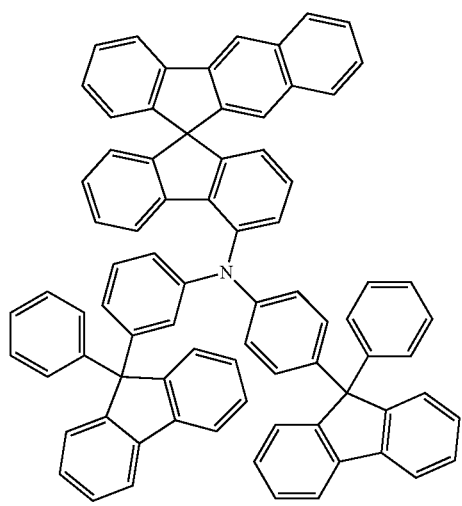
N-66
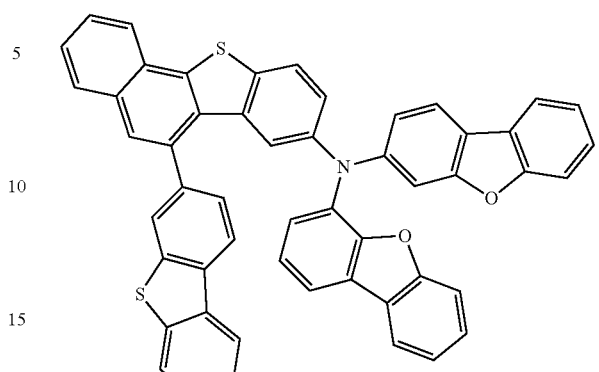
N-64
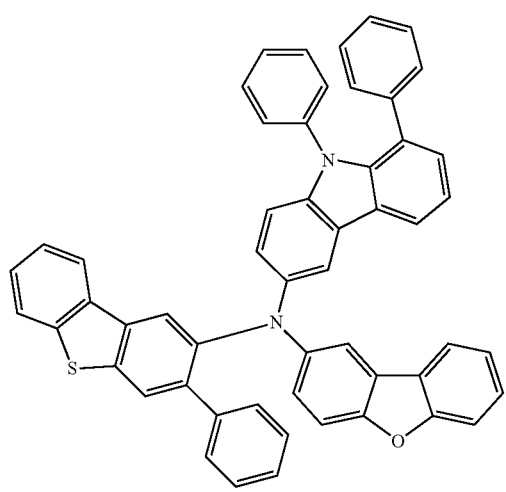
N-67
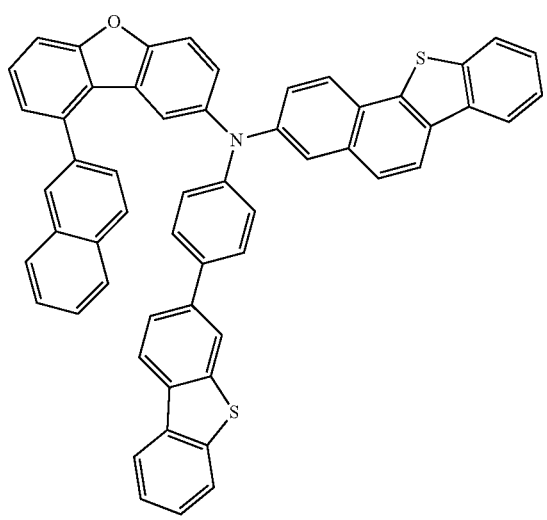
N-65
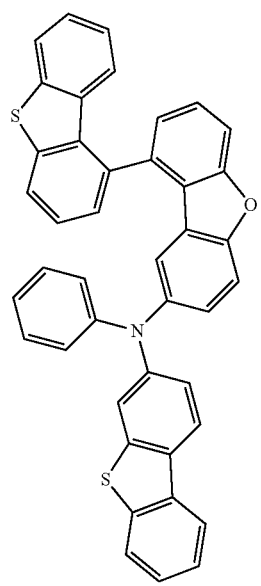
N-68
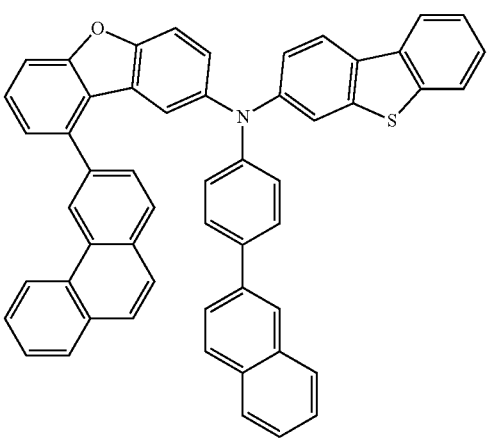

N-69
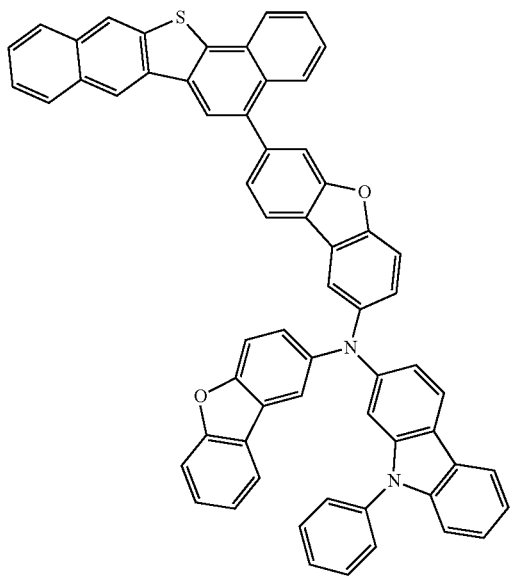
N-70
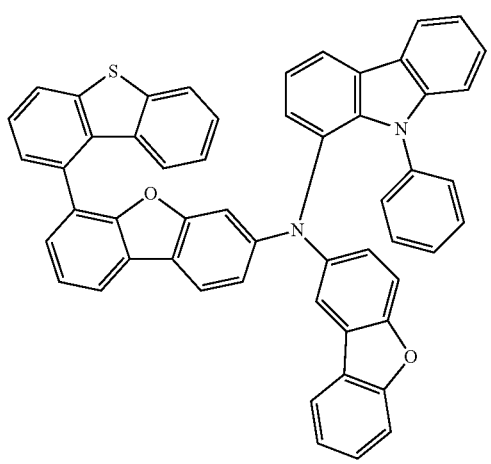
N-71
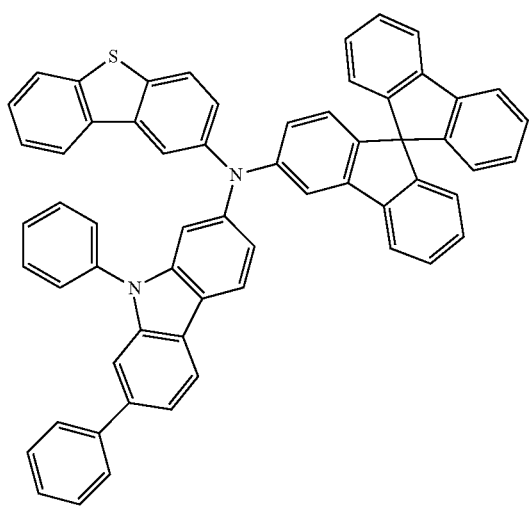
N-72
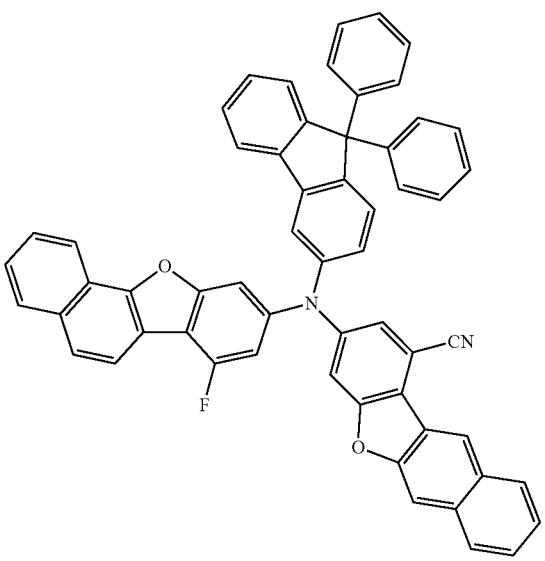
N-73
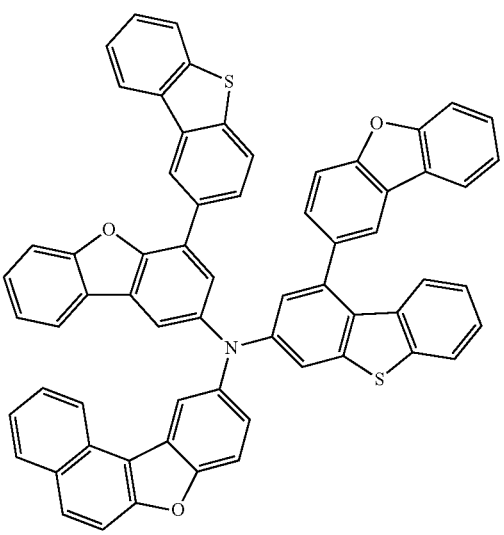
N-74
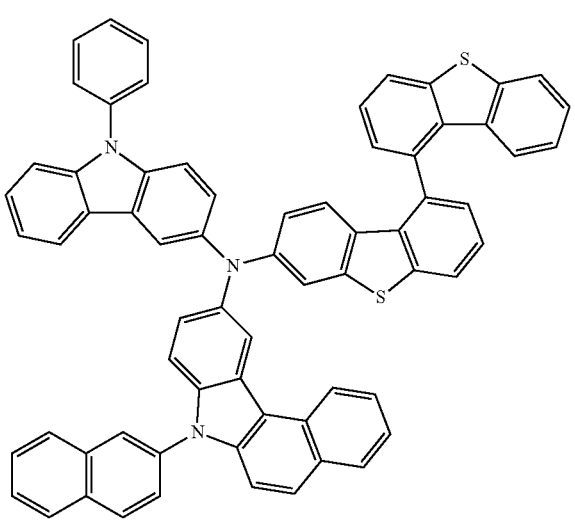

N-75
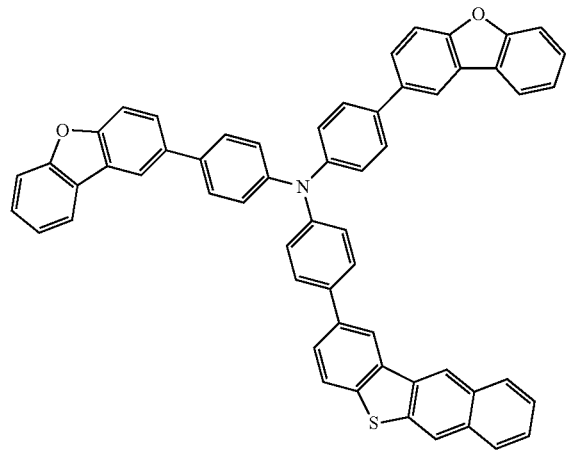
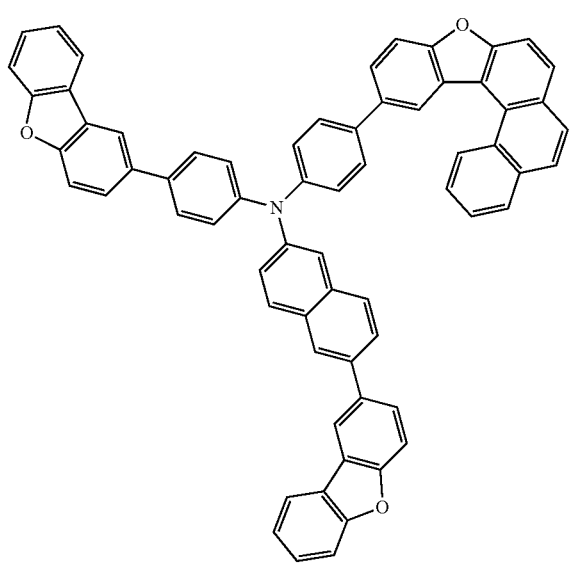
N-77
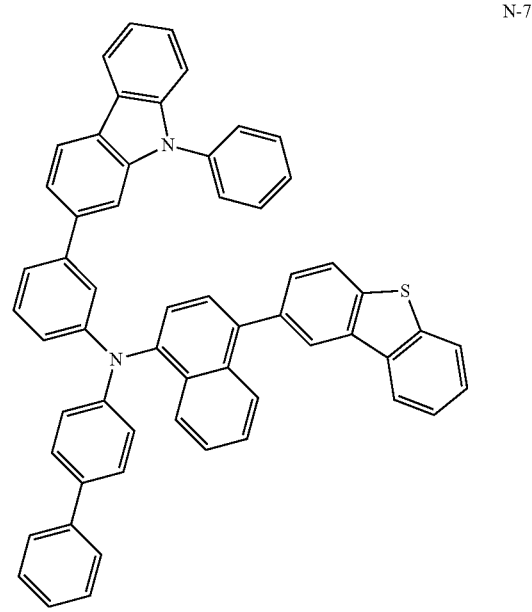
N-78
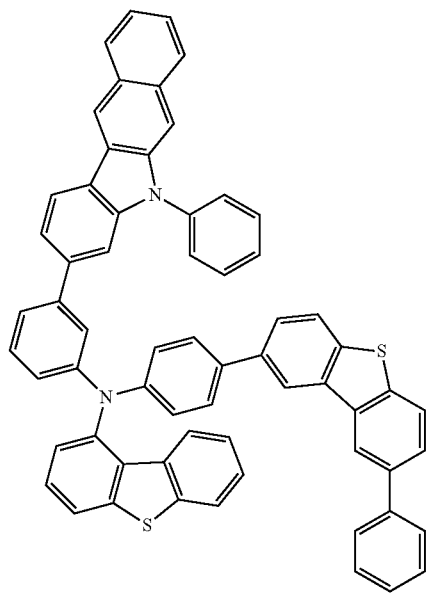
N-79
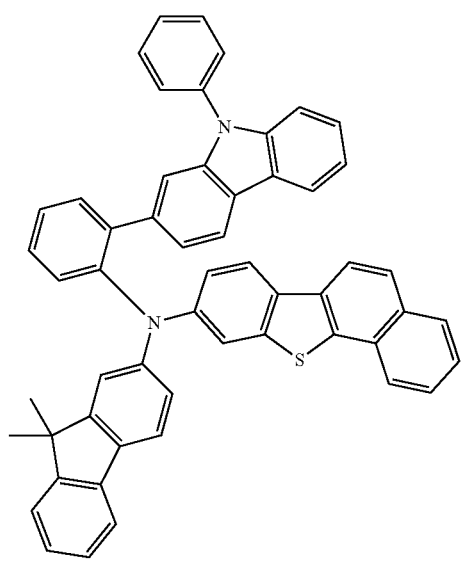

N-80
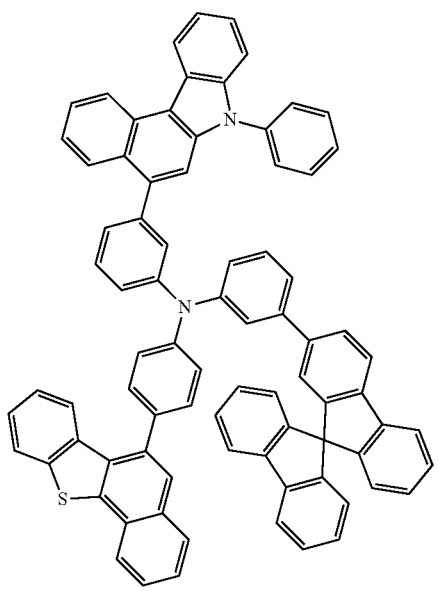
N-83
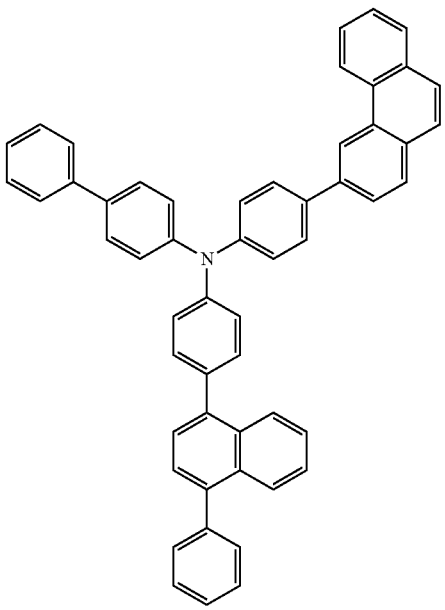
N-81
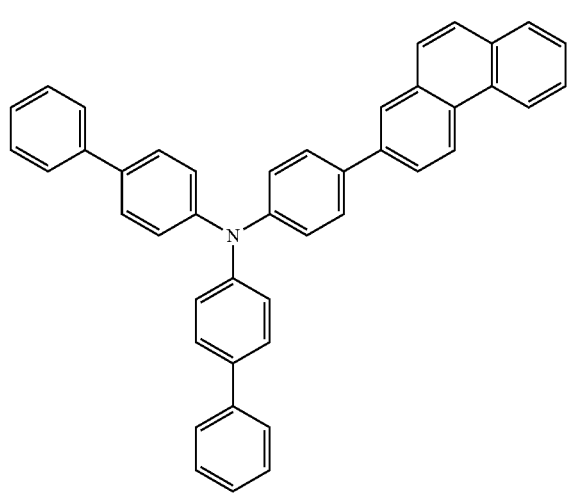
N-82
N-84
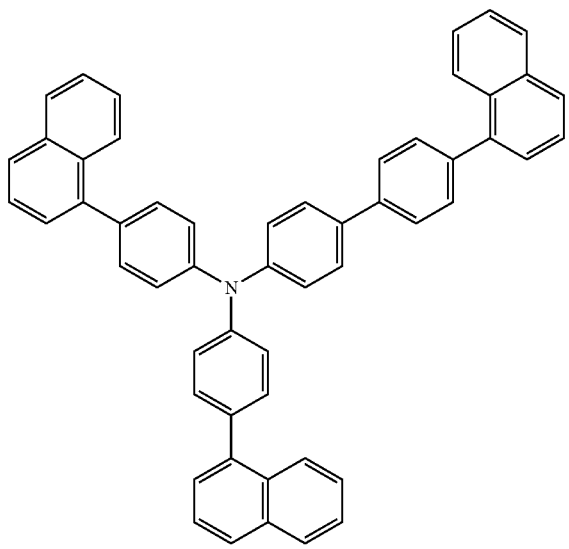

N-85
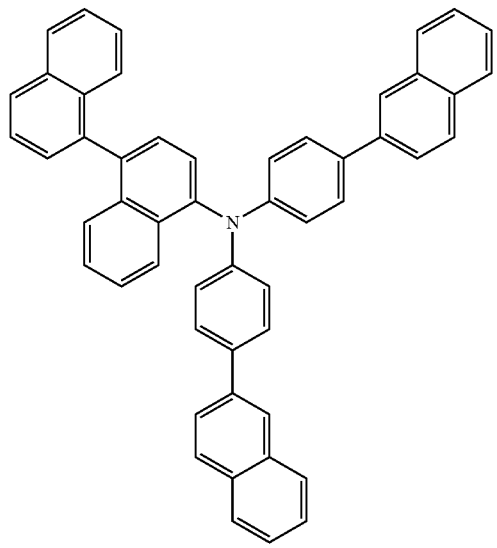
N-88
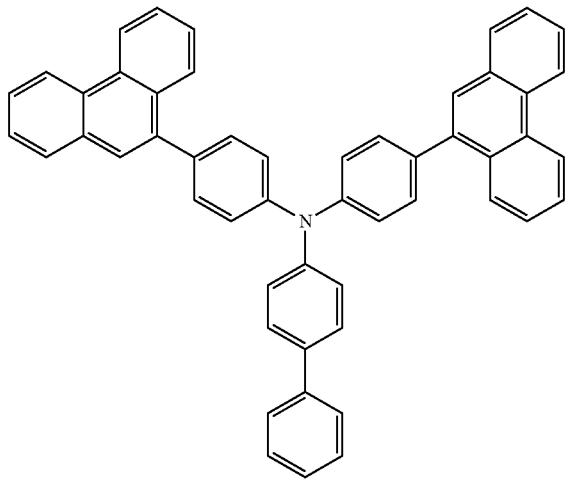
N-86
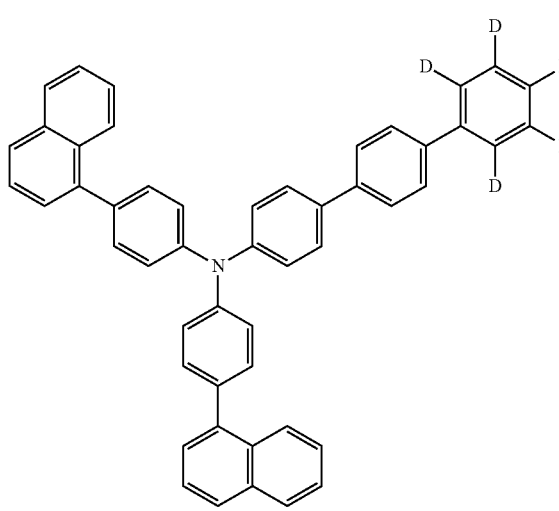
N-89
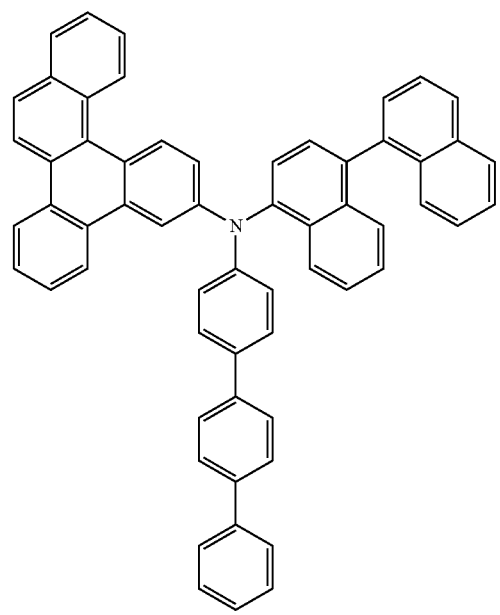
N-87
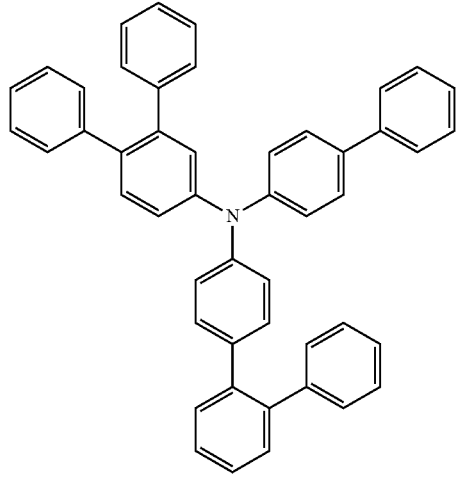
N-90
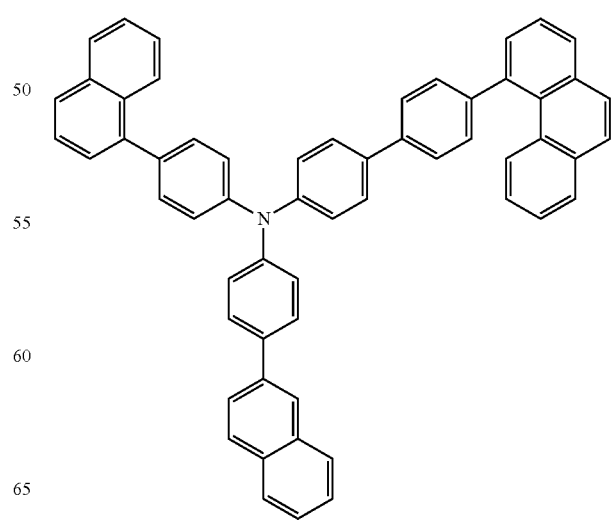

N-91
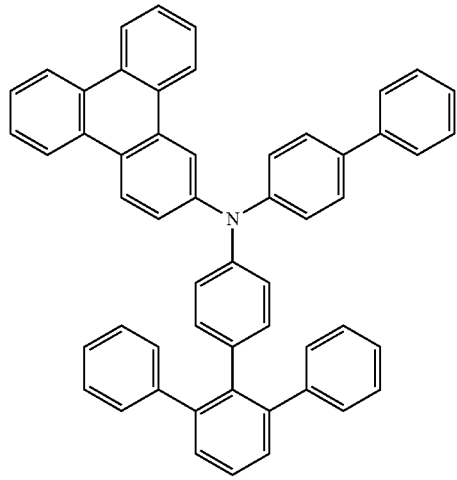
N-92
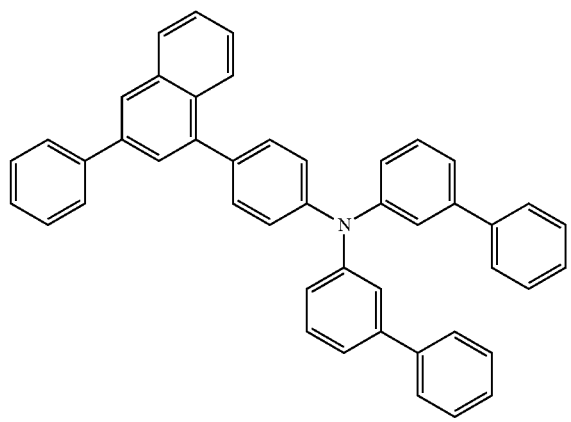
N-93
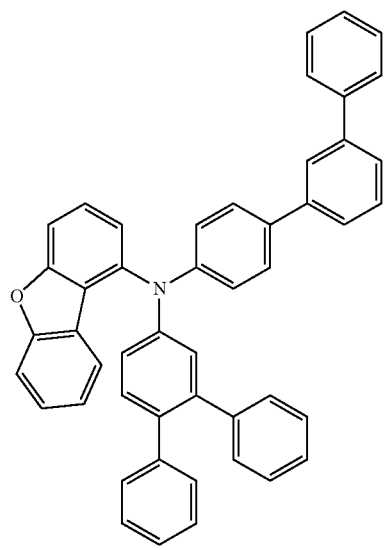
N-94
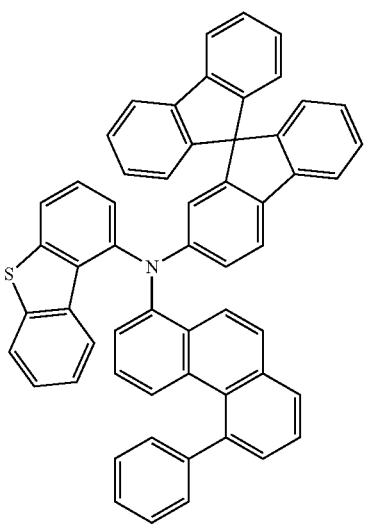
N-95
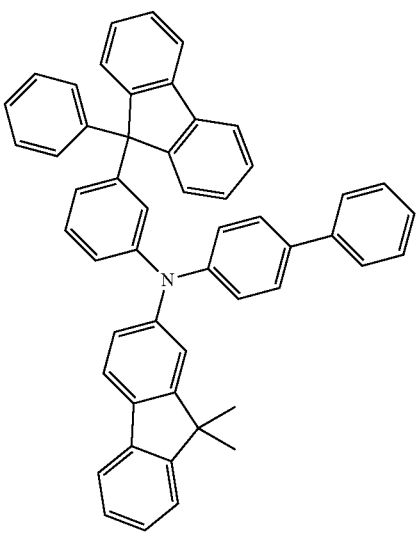
N-96
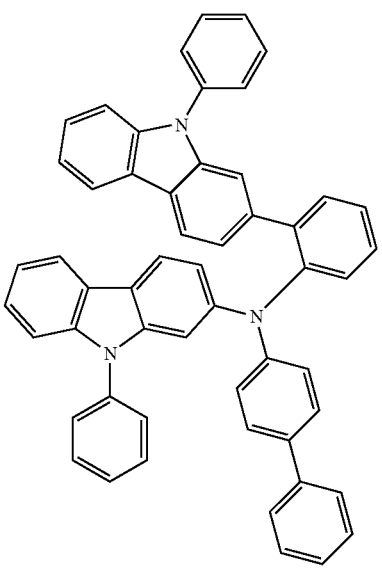

Specifically, the compound represented by Formula 4 may be any one of the following compounds S-1 to S-108, but is not limited thereto.
S-1
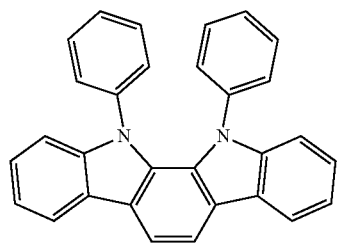
S-2
S-3
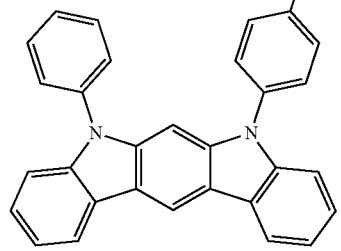
S-4
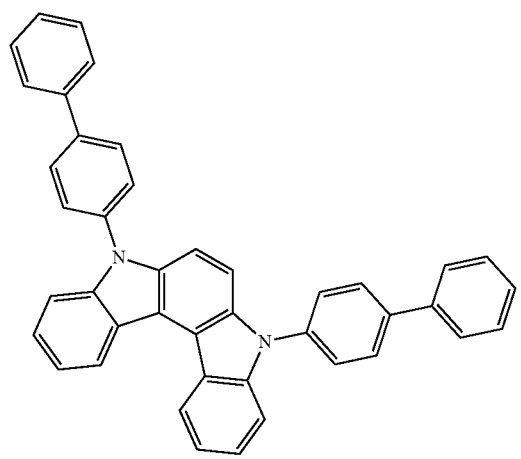
S-5
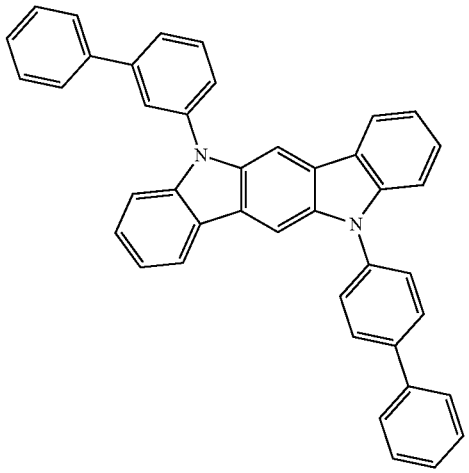
S-6
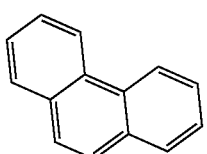
S-7
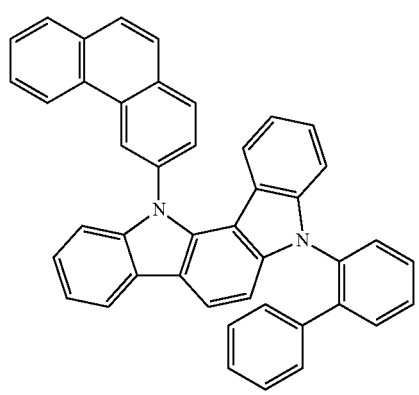

S-8
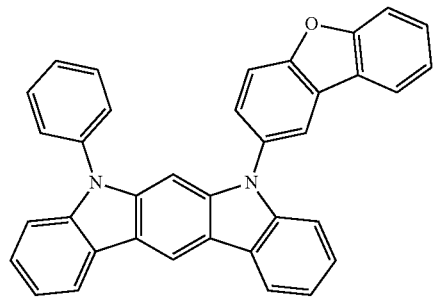
S-9
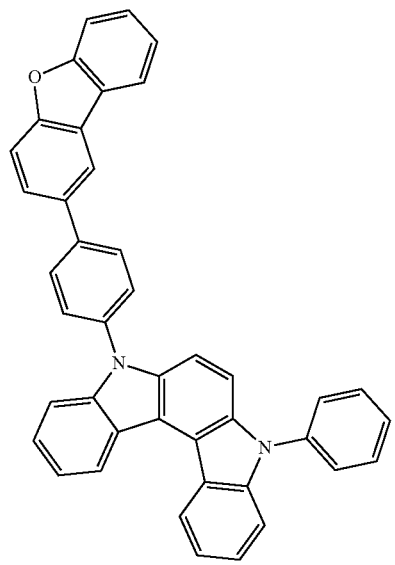
S-10
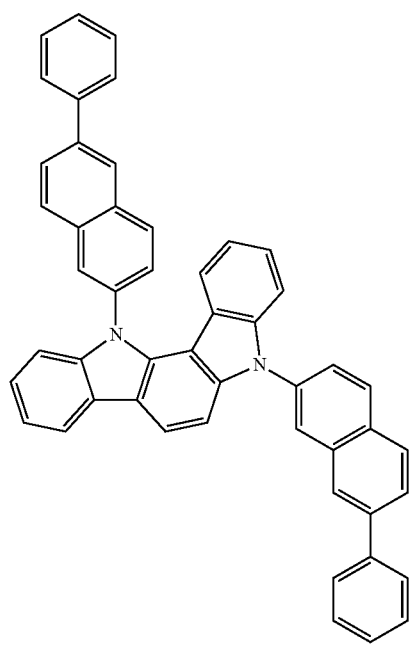
S-11
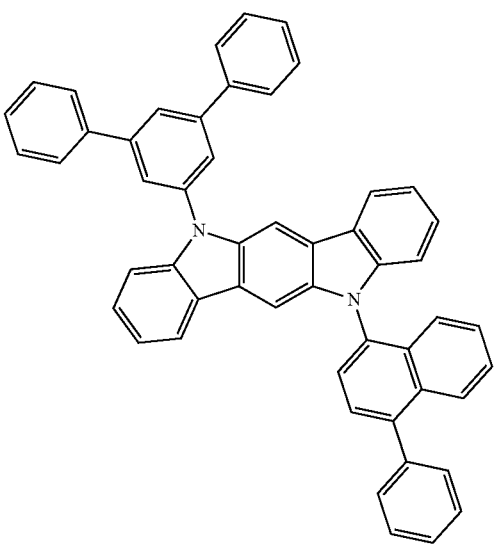
S-12
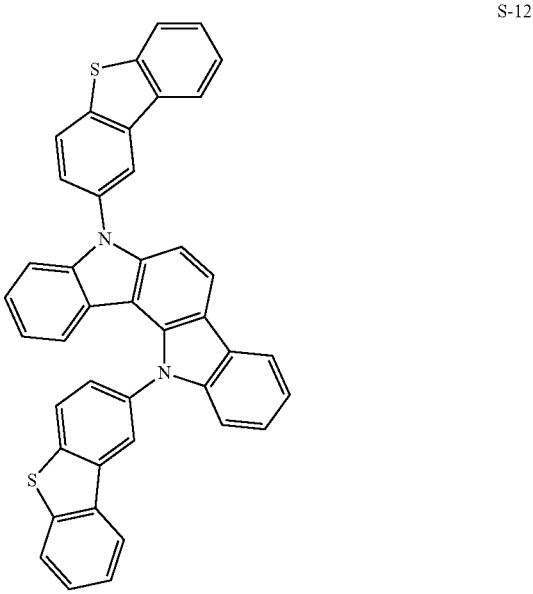
S-13
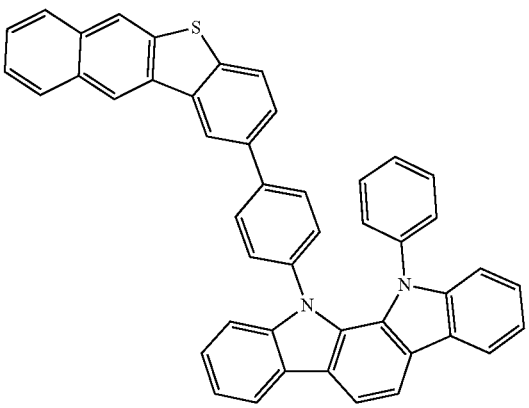

S-14
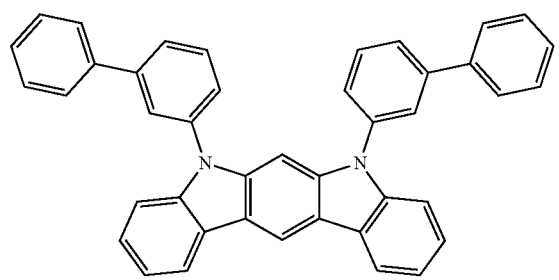
S-15

S-16
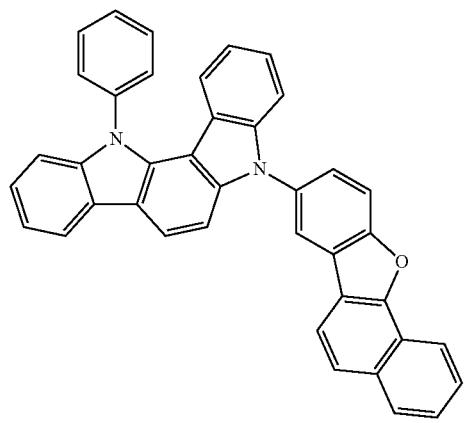
S-17
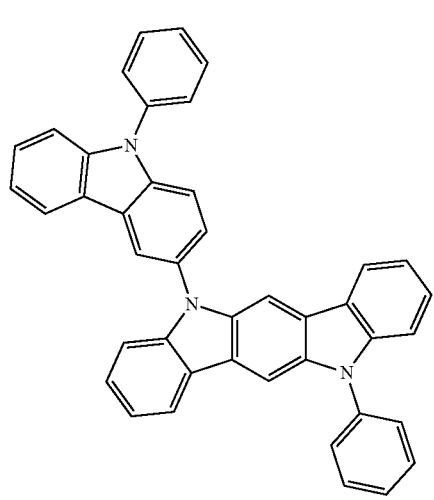
S-18
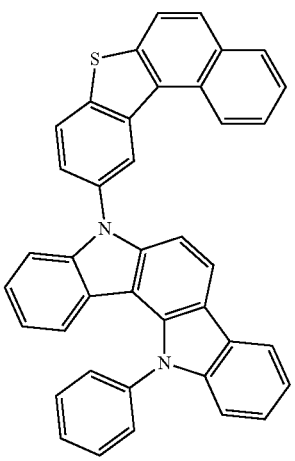
S-19
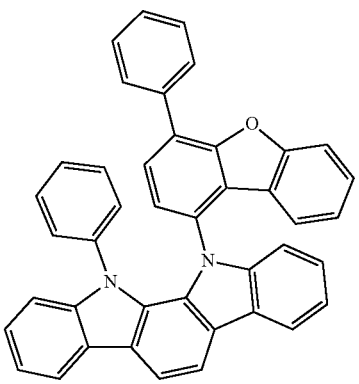
S-20
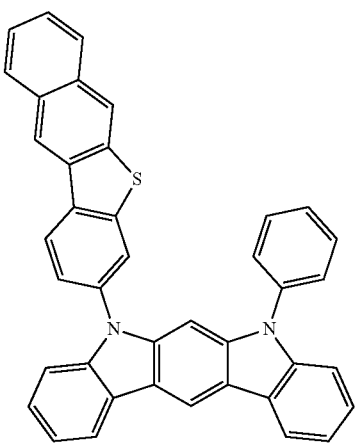

S-21
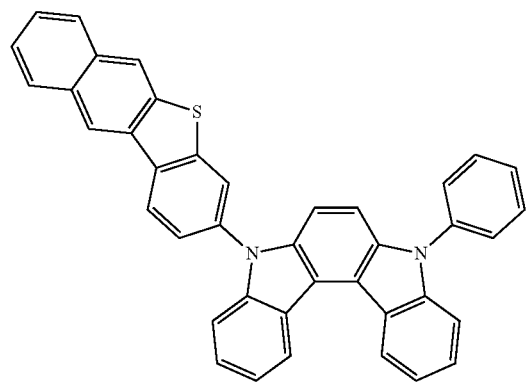
S-22
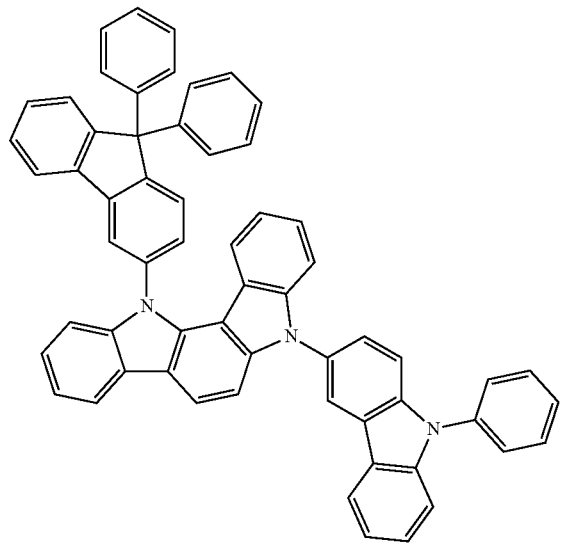
S-23
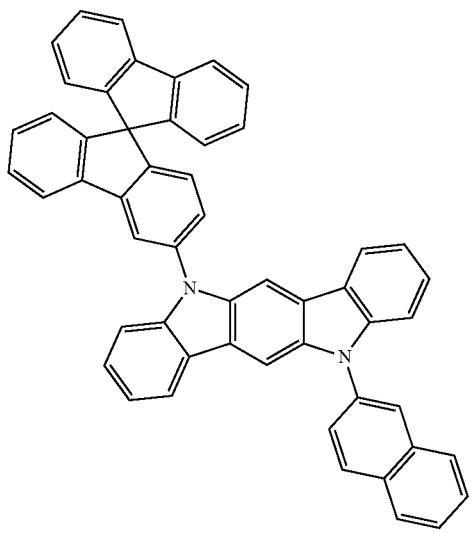
S-24
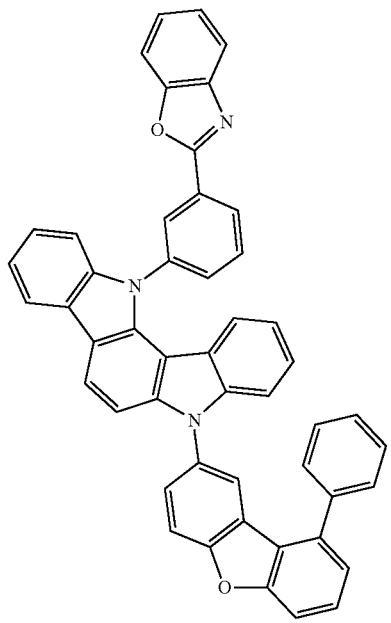
S-25
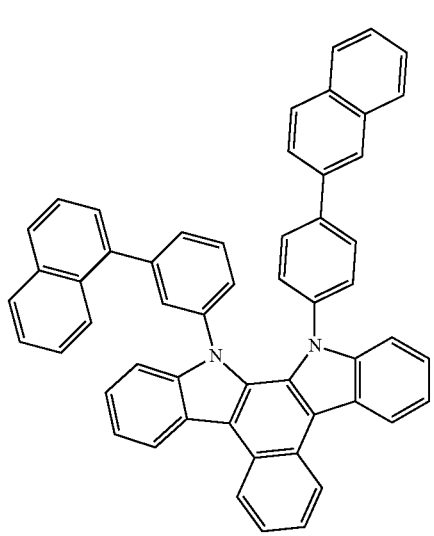
S-26
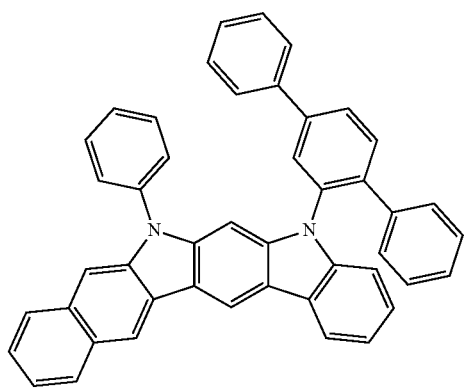

-continued
S-27
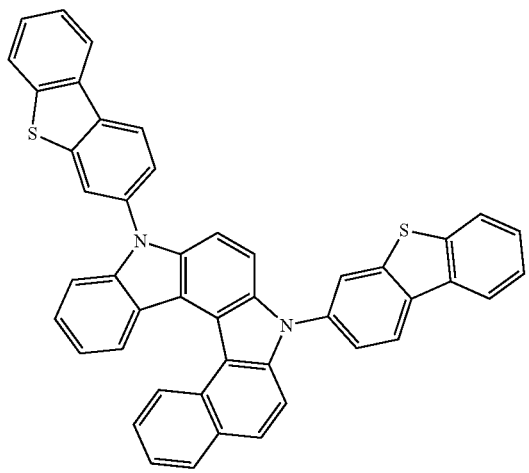
S-28
S-29
S-30
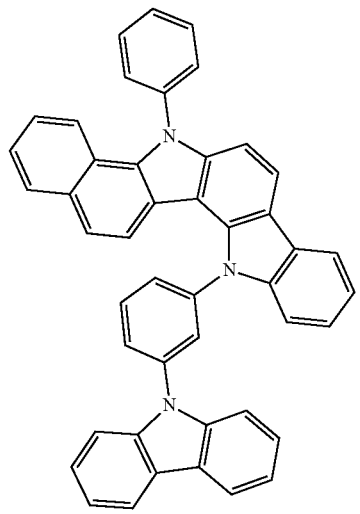
S-31
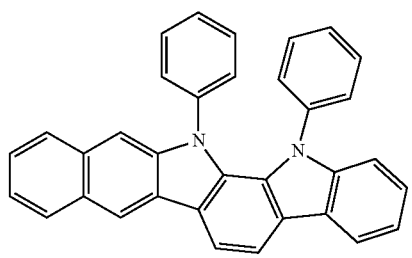
S-32
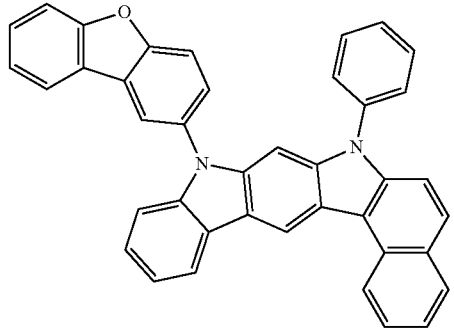
S-33
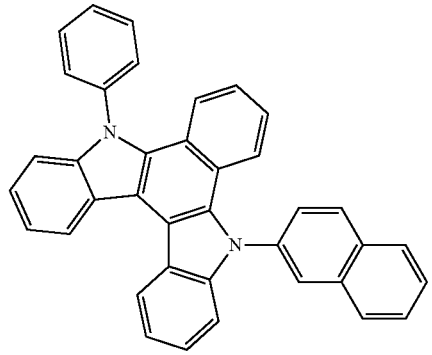

S-34
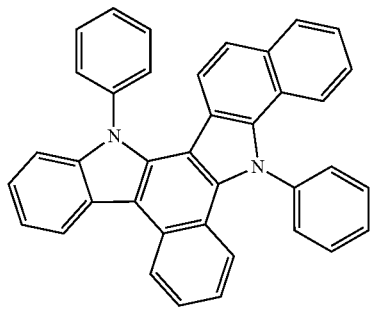
S-35
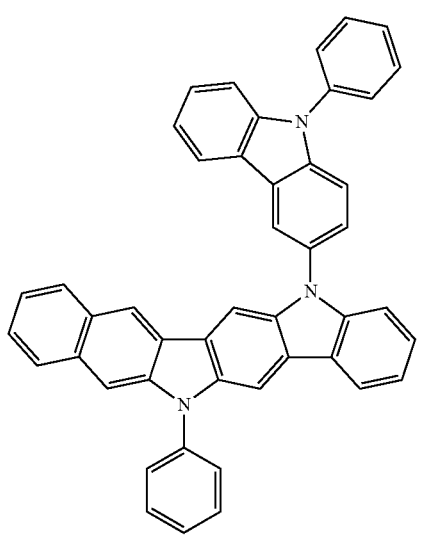
S-36
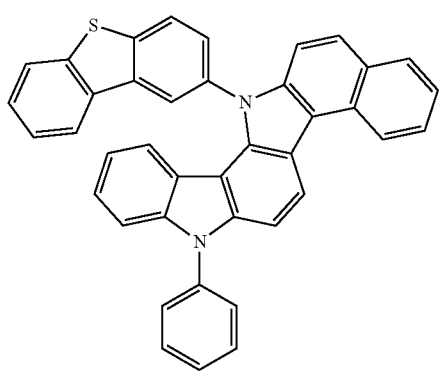
S-37
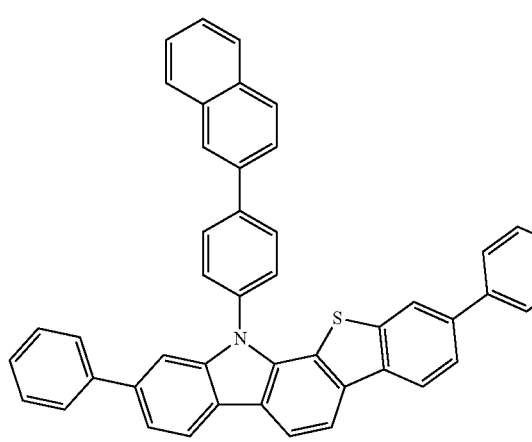
S-38
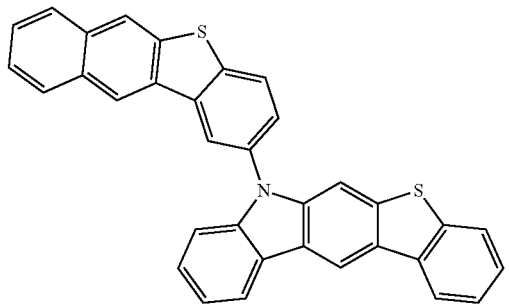
S-39
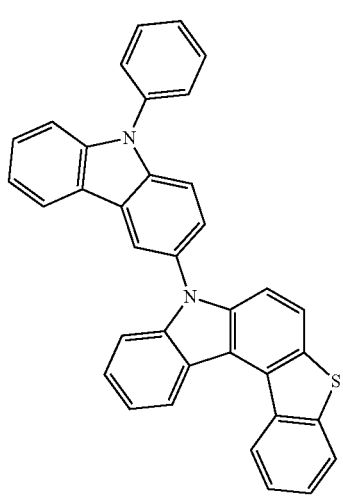
S-40
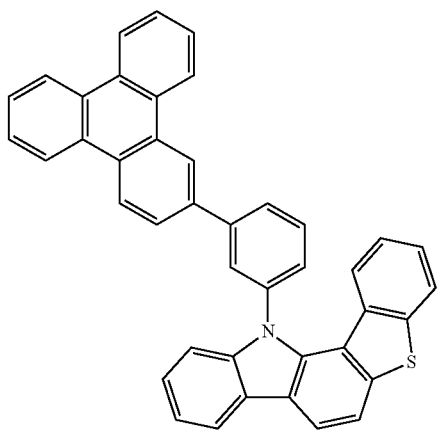

S-41
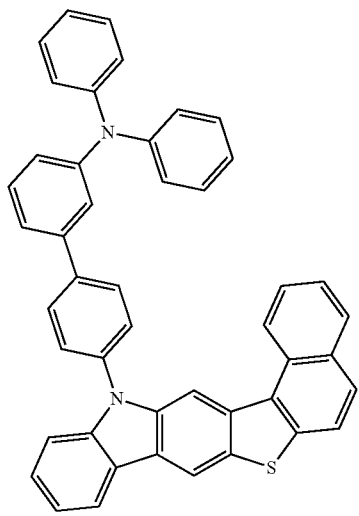
S-44
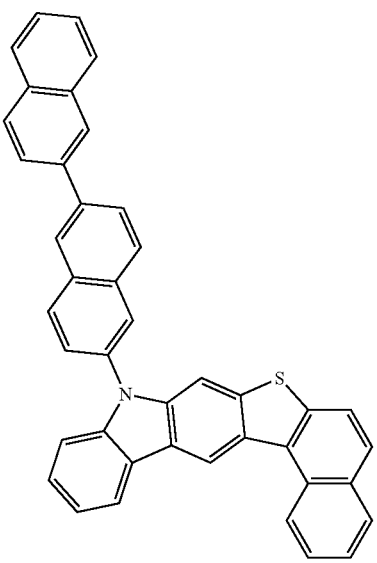
S-42
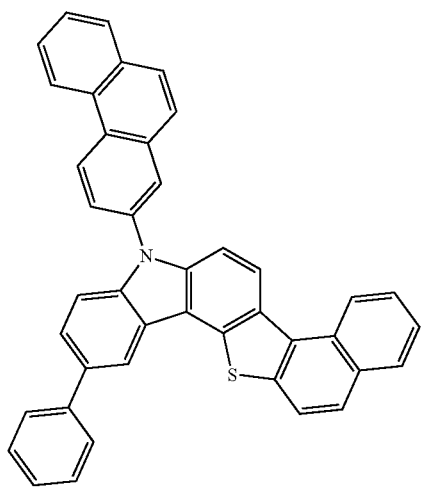
S-45
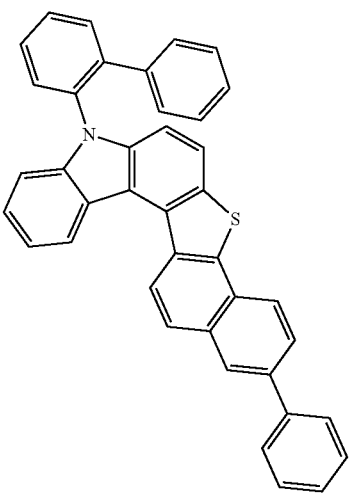
S-43
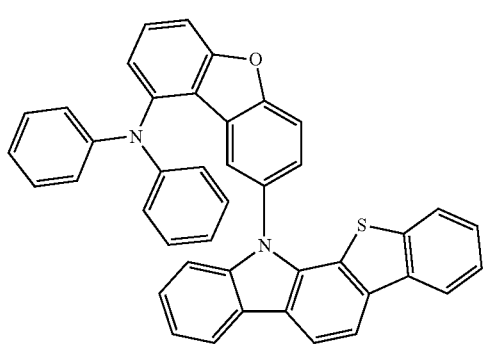
S-46
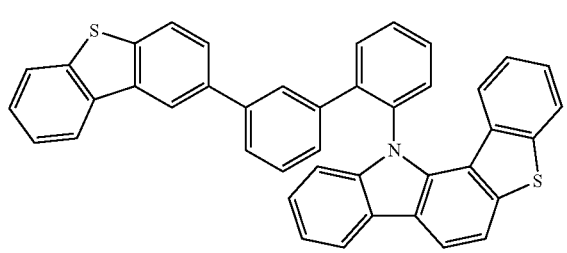

-continued
S-47
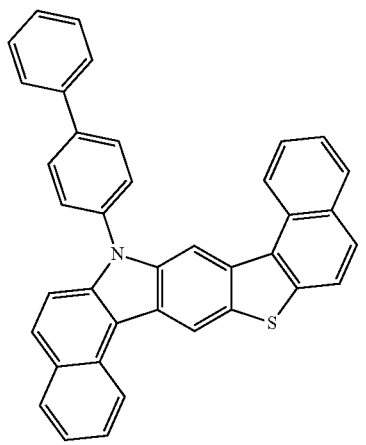
S-48
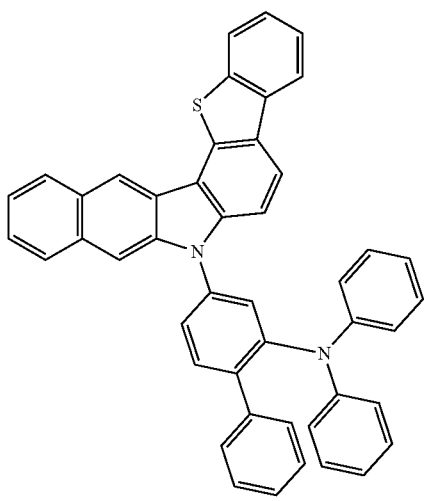
S-49
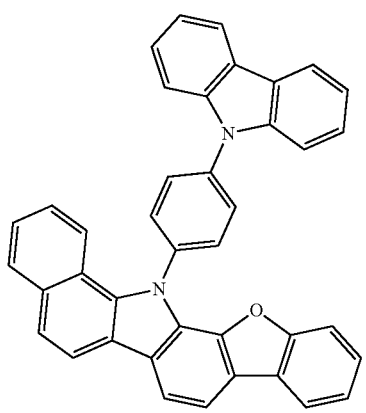
-continued
S-50
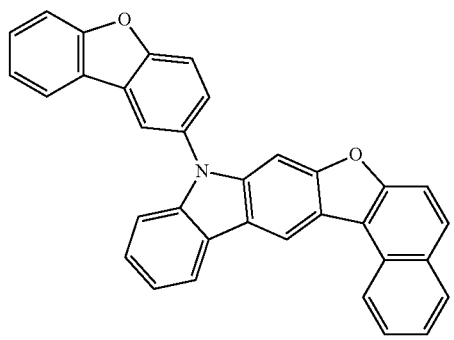
S-51
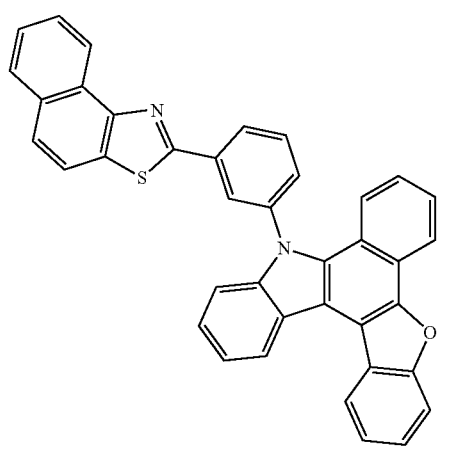
S-52
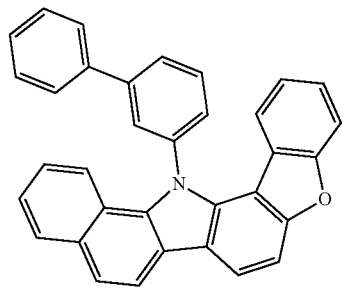
S-53
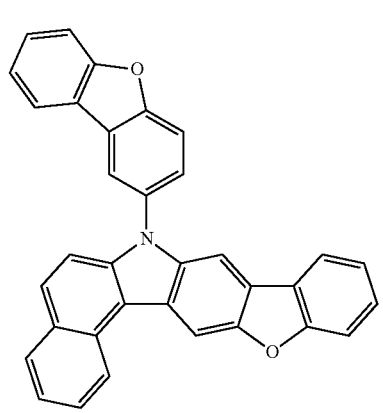

-continued
S-54
S-55
S-56
S-57
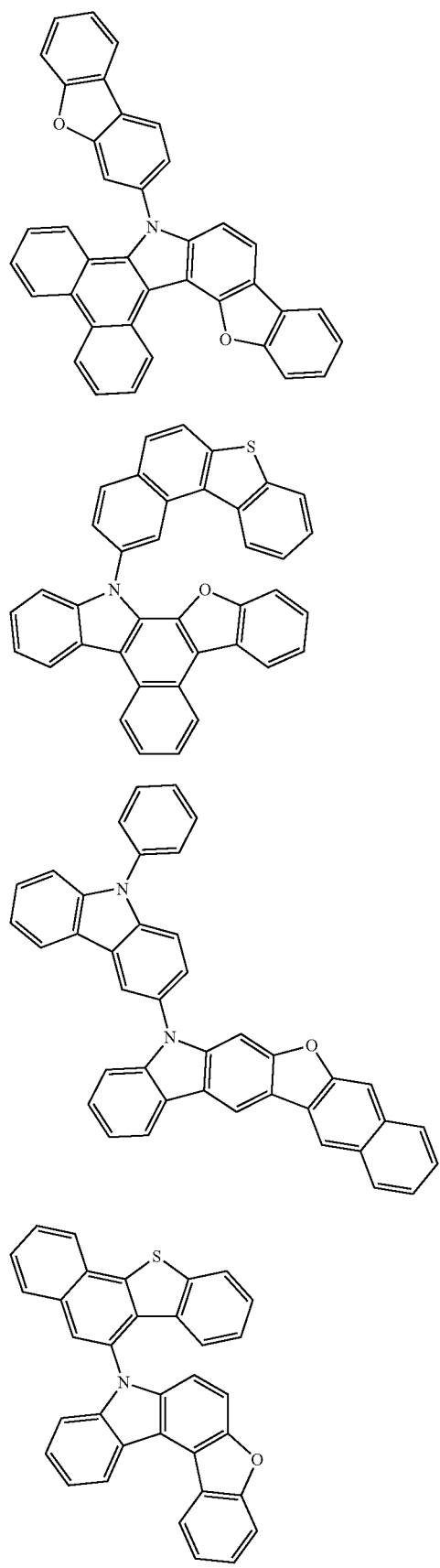
-continued
S-58
S-59
S-60
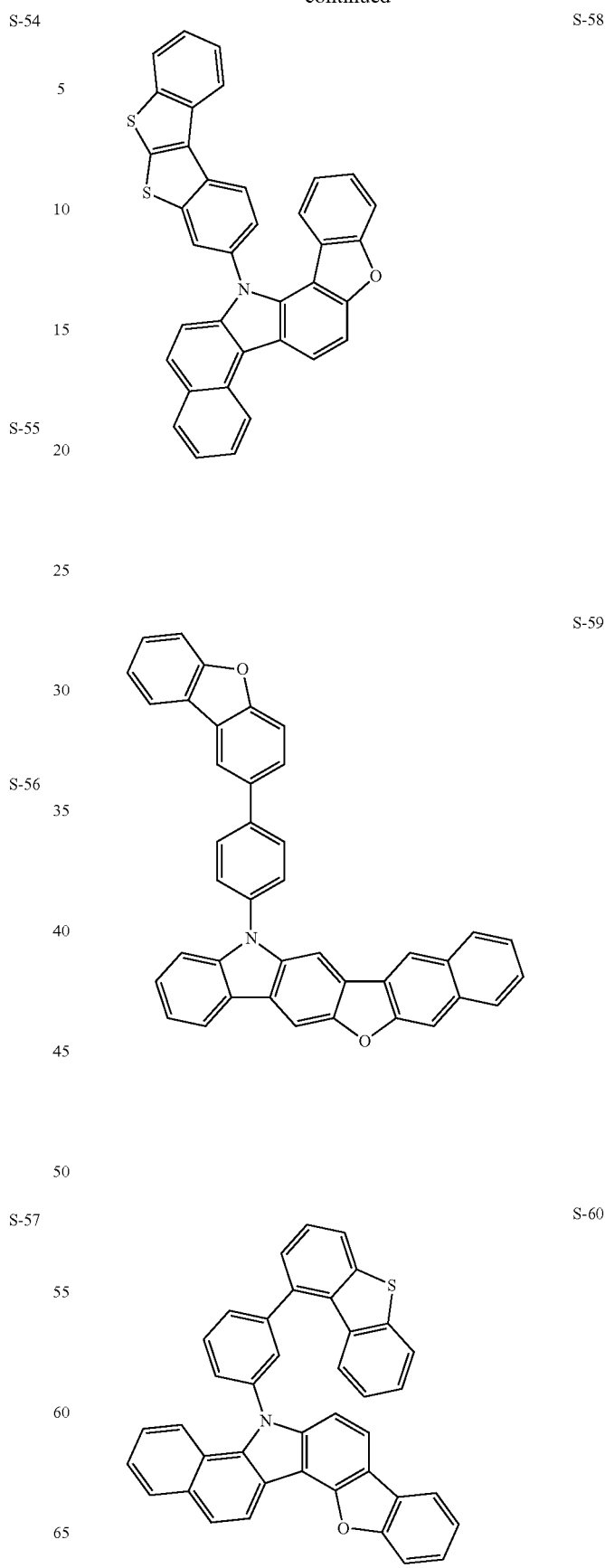

S-61
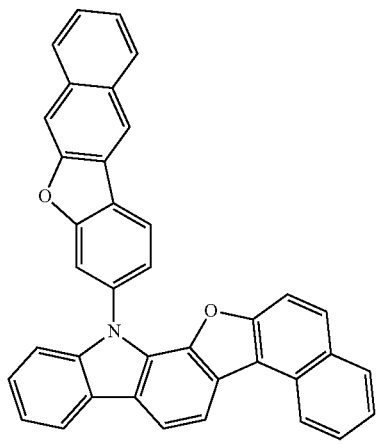
S-64
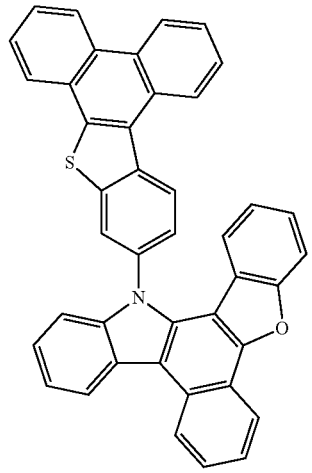
S-62
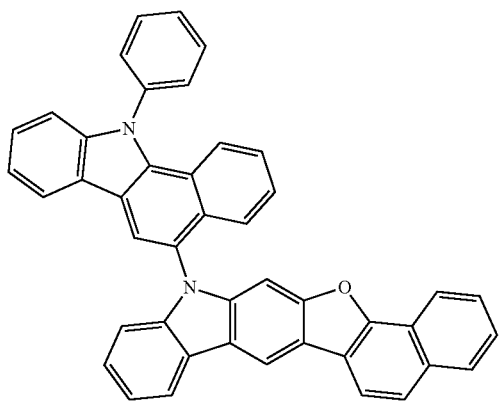
S-65
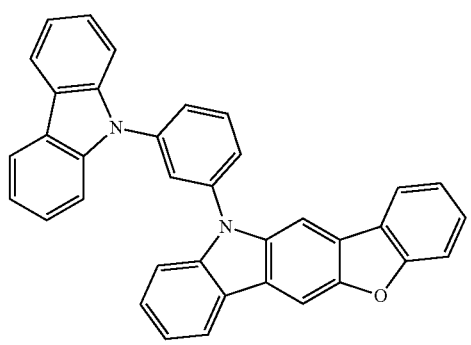
S-66
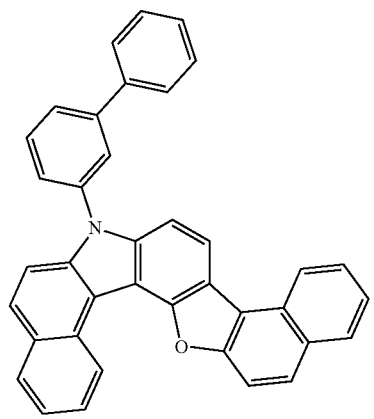
S-63
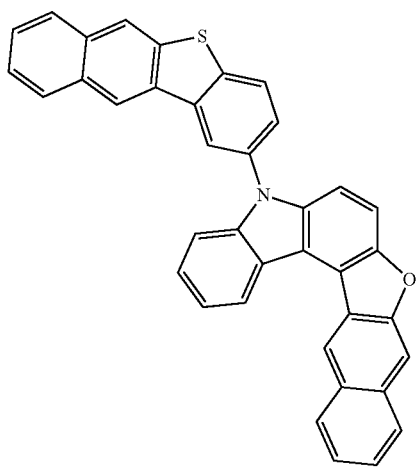
S-67
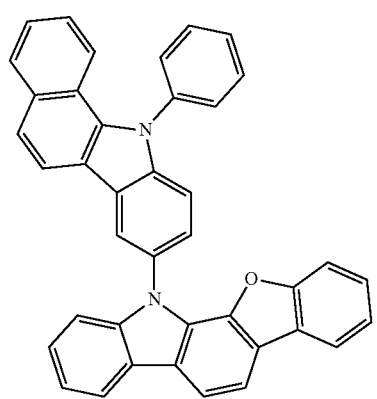

-continued
S-68
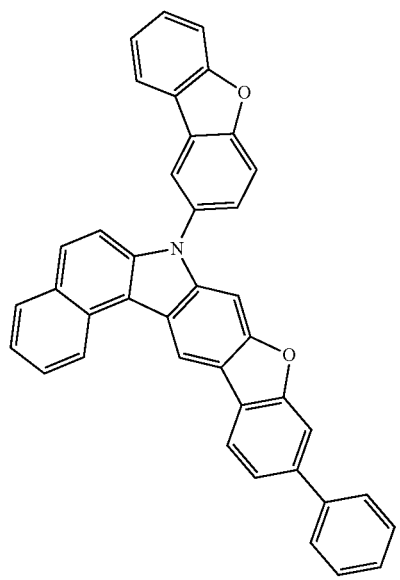
S-69
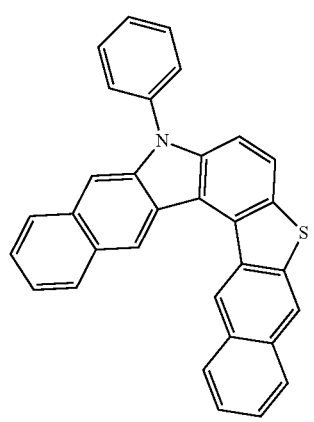
S-70
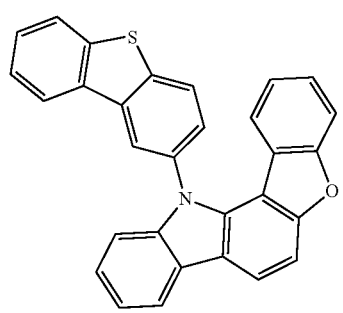
S-71
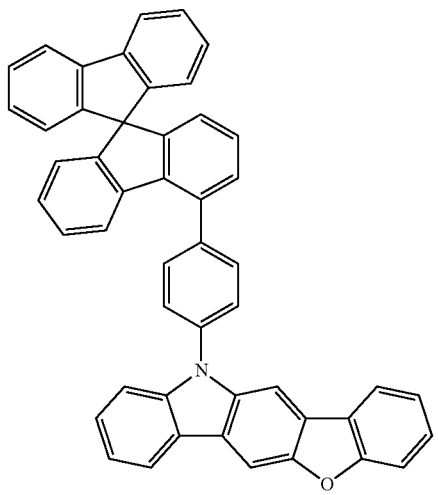
S-72
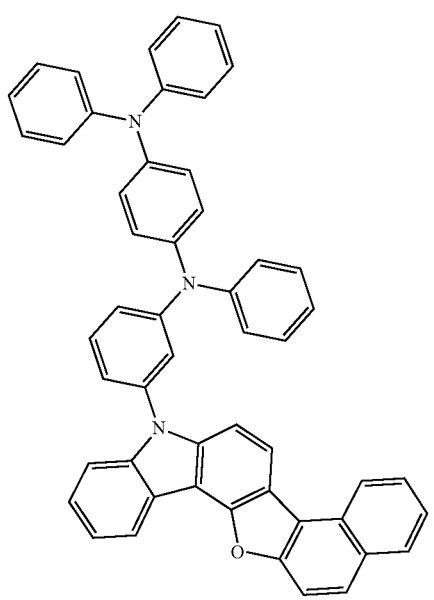
S-73
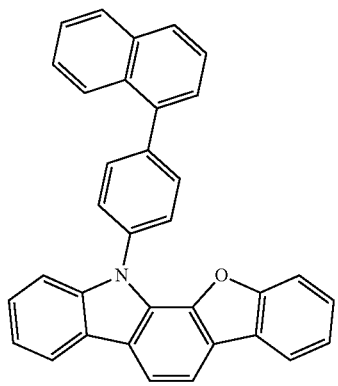

S-74 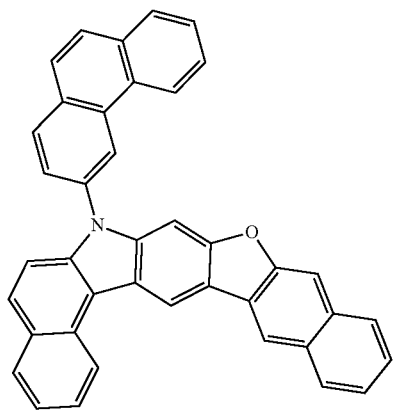
S-75 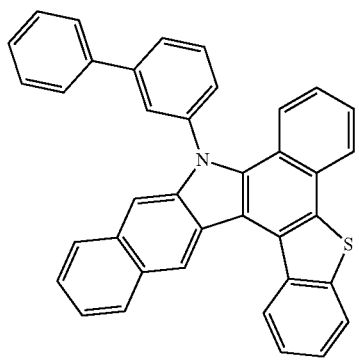
S-76 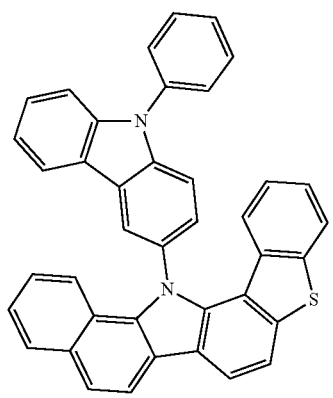
S-77 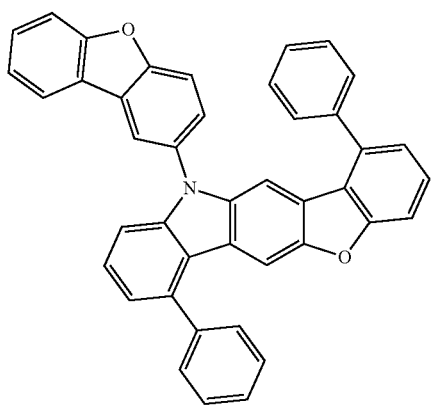
S-78 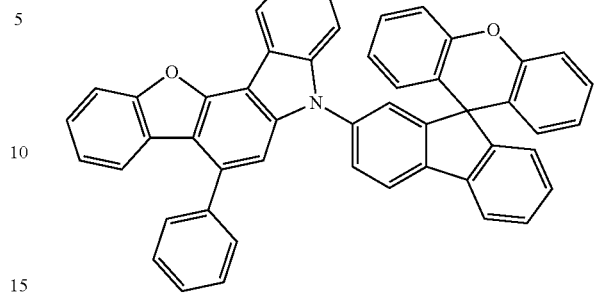
S-79 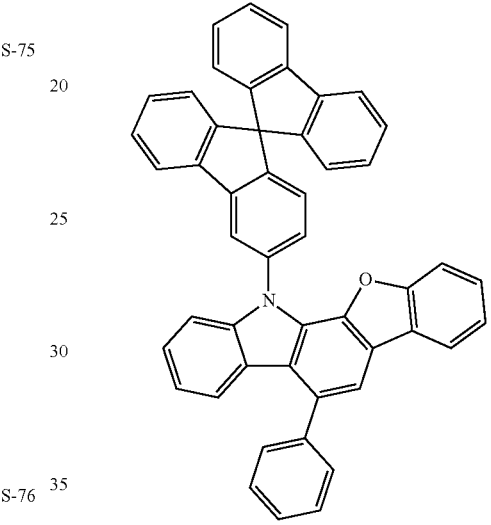
S-80 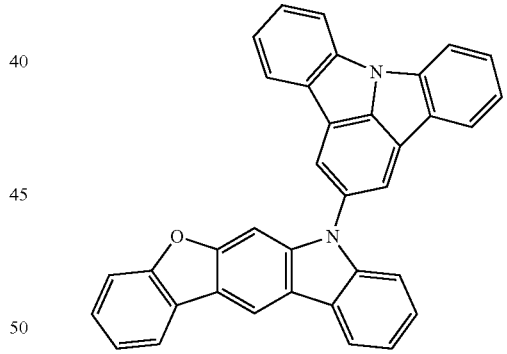
S-81 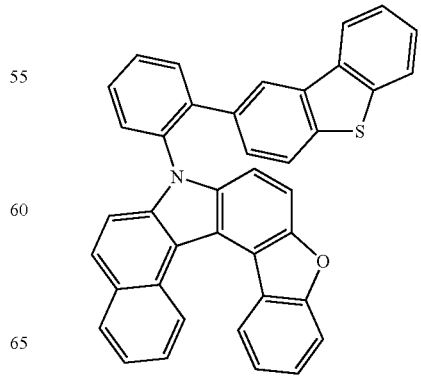

S-82
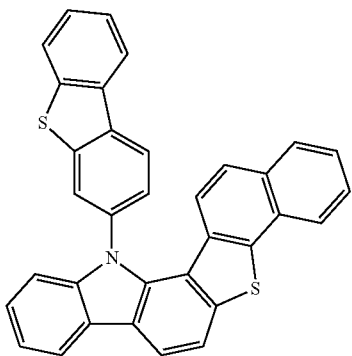
S-85
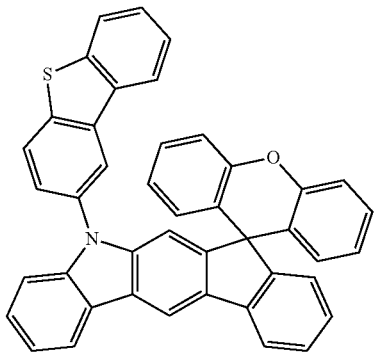
S-83
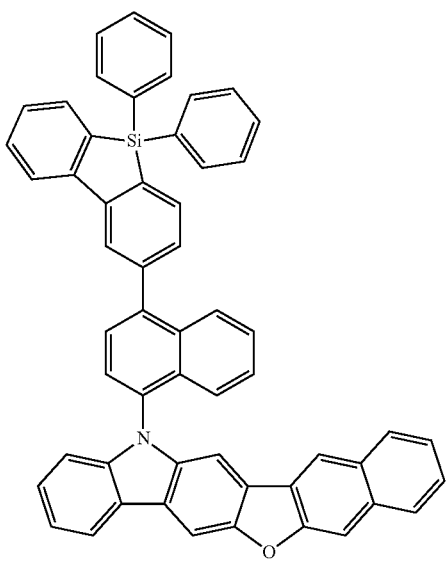
S-86
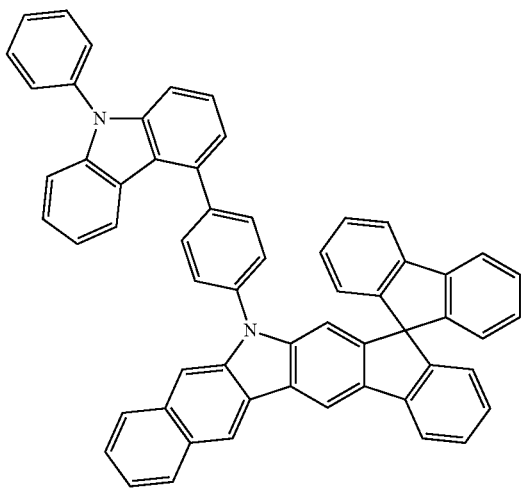
S-84
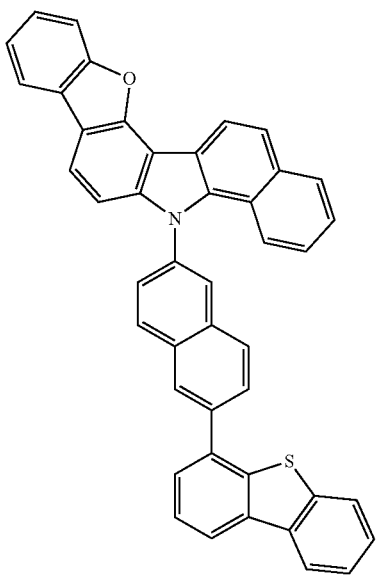
S-87
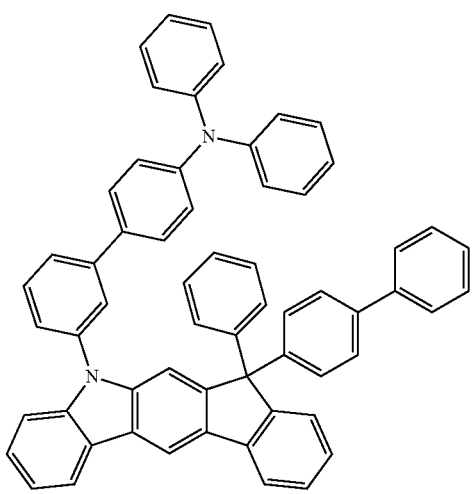

S-88
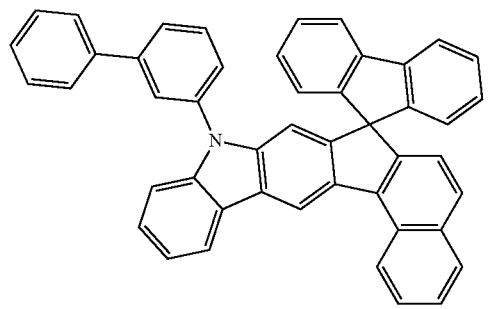
S-89
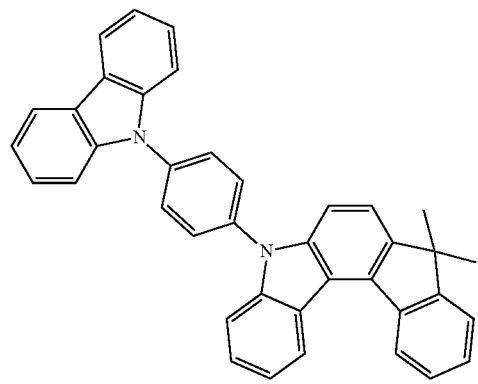
S-90
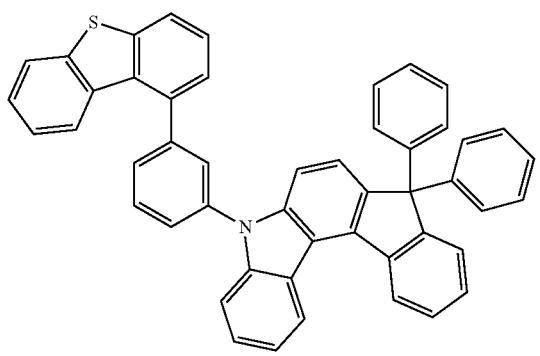
S-91
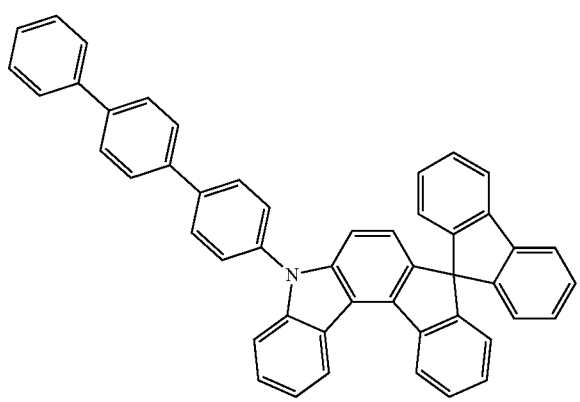
S-92
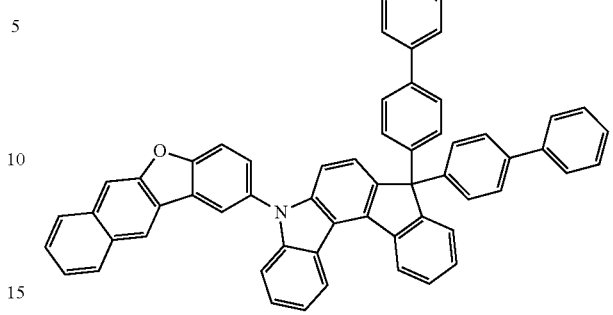
S-93
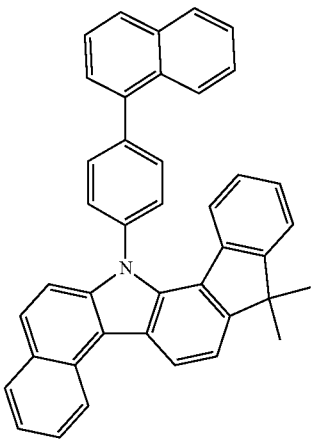
S-94
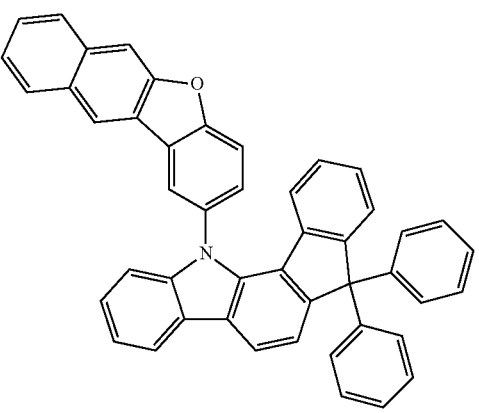
S-95
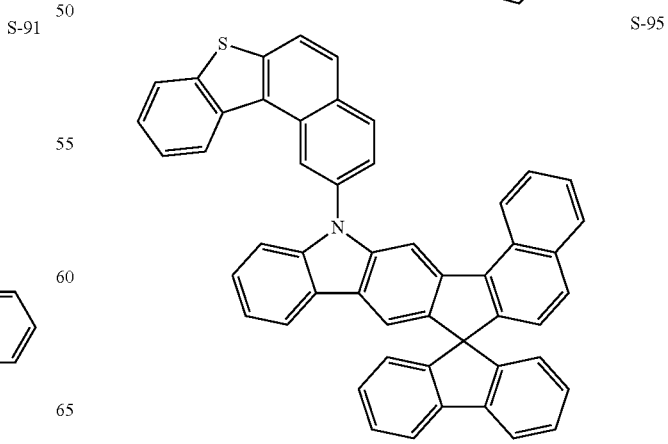

-continued
S-96
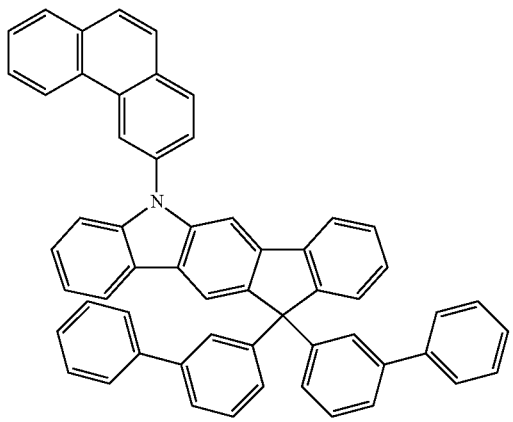
S-97
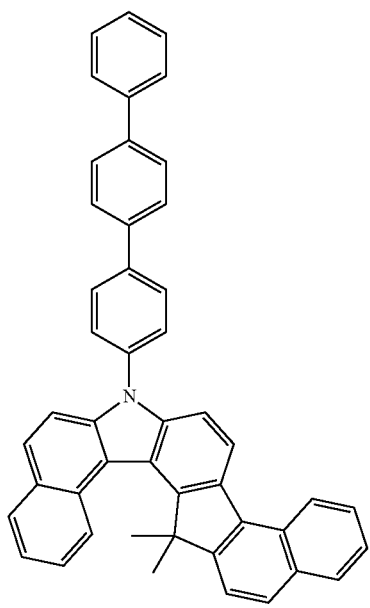
S-98
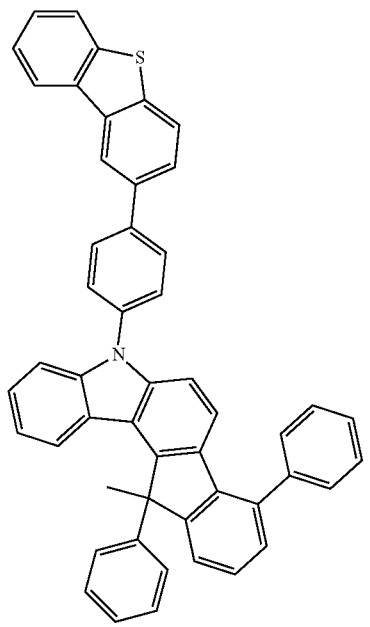
S-99
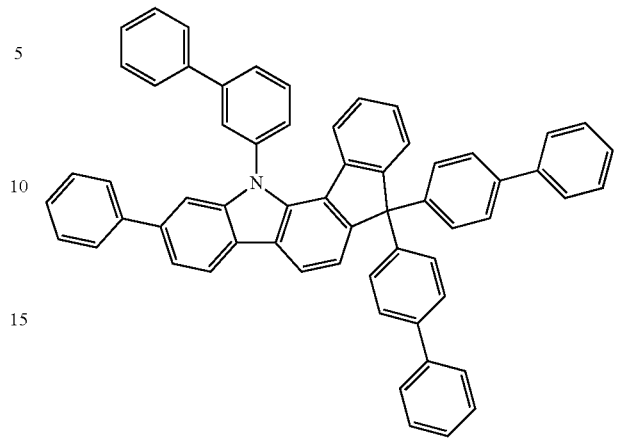
S-100
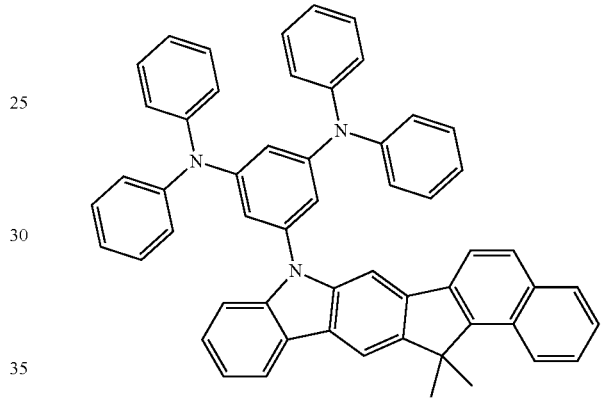
S-101
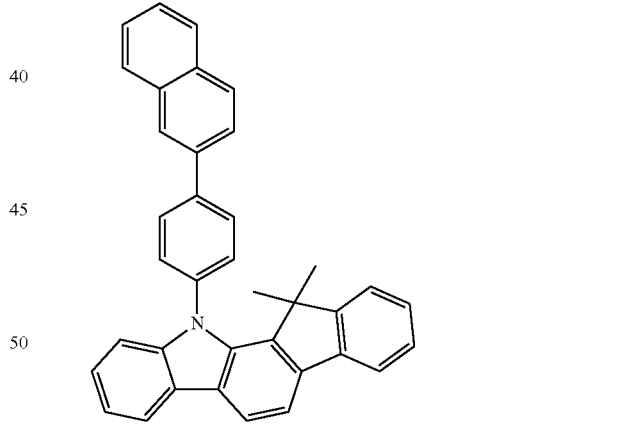
S-102
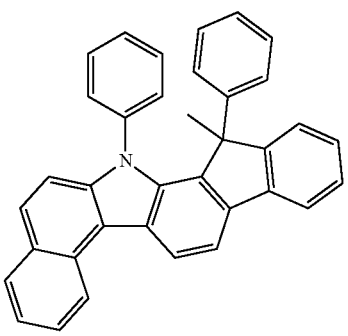

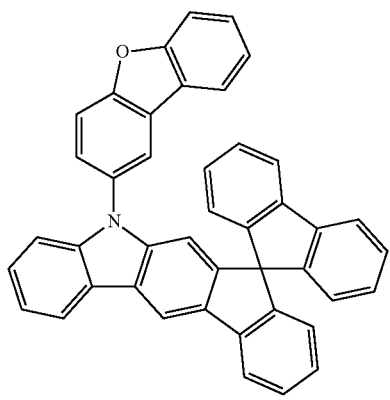

S-103

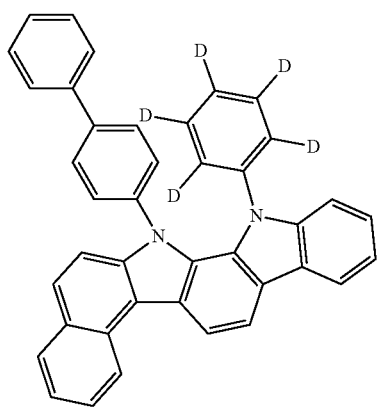

S-104

S-105

S-106

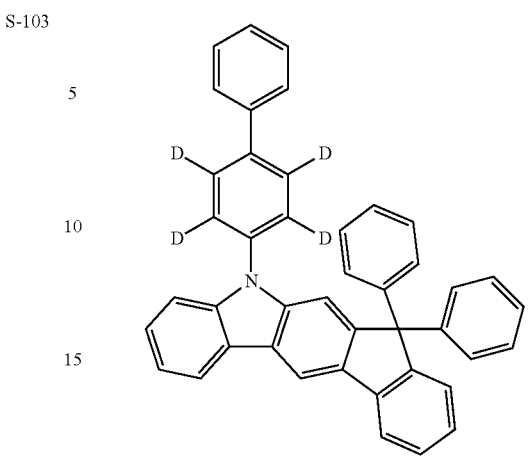

S-107

S-108

In another aspect, the present invention provides a method for reusing the compound represented by Formula 1 comprising:
- a step of depositing an organic light emitting material comprising the compound represented by Formula 1 in a manufacturing process of an organic light emitting device;
- a step of removing impurities from the crude organic light emitting material recovered from the deposition apparatus;
- a step of recovering the removed impurities; and
- a step of purifying the recovered impurities to a purity of 99.9% or higher.

The step of removing impurities from the crude organic light emitting material recovered from the deposition apparatus may preferably comprise performing a pre-purification process to obtain a purity of 98% or more by recrystallization in a recrystallization solvent.

The recrystallization solvent may be preferably a polar solvent having a polarity index (PI) of 5.5 to 7.2.

The recrystallization solvent may be preferably used by mixing a polar solvent having a polarity value of 5.5 to 7.2 and a non-polar solvent having a polarity value of 2.0 to 4.7.

When a mixture of a polar solvent and a non-polar solvent is used, the recrystallization solvent may be used in an amount of 15% (v/v) or less of the non-polar solvent compared to the polar solvent.

The recrystallization solvent may preferably be used by mixing N-Methylpyrrolidone (NMP) single solvent; or a polar solvent mixed any one selected from the group consisting of 1,3-Dimethyl-2-imidazolidinone, 2-pyrrolidone, N, N-Dimethyl formamide, Dimethyl acetamide, and Dimethyl sulfoxide to the N-Methylpyrrolidone; or alone; or mixed non-polar solvents; selected from the group consisting of Toluene, Dichloromethane (DCM), Dichloroethane (DCE), Tetrahydrofuran (THF), Chloroform, Ethyl acetate and Butanone; or a polar solvent and a non-polar solvent.

The pre-purification process may comprise a step of precipitating crystals of by cooling to 0° C. to 5° C. after dissolving the crude organic light emitting material recovered from the deposition apparatus in a polar solvent at 90° C. to 120° C.

The pre-purification process may comprise a step of precipitating crystals by cooling to 35° C. to 40° C., adding a non-polar solvent, and then cooling to 0° C. to 5° C. after dissolving the crude organic light emitting material recovered from the deposition apparatus in a polar solvent at 90° C. to 120° C.

The pre-purification process may comprise a step of precipitating crystals while concentrating the solvent and removing the non-polar solvent, after dissolving the crude organic light emitting material recovered from the deposition apparatus in a non-polar solvent.

The pre-purification process may comprise a step of recrystallizing again with a non-polar solvent after recrystallizing first with a polar solvent.

The step of purifying the recovered impurities to a purity of 99.9% or higher may comprise performing an adsorption separation process to adsorb and remove impurities by adsorbing on the adsorbent.

The adsorbent may be activated carbon, silica gel, alumina, or a material for known adsorption purposes.

The step of purifying the recovered impurities to a purity of 99.9% or higher may comprise performing sublimation purification Referring to FIG. 1, the organic electronic element (100) according to the present invention comprises a first electrode (110), a second electrode (170), an organic material layer comprising single compound represented by Formula 1 or 2 or more compounds between the first electrode (110) and the second electrode (170). Wherein, the first electrode (110) may be an anode or a positive electrode, and the second electrode (170) may be a cathode or a negative electrode. In the case of an inverted organic electronic element, the first electrode may be a cathode, and the second electrode may be an anode.

Figure 2:
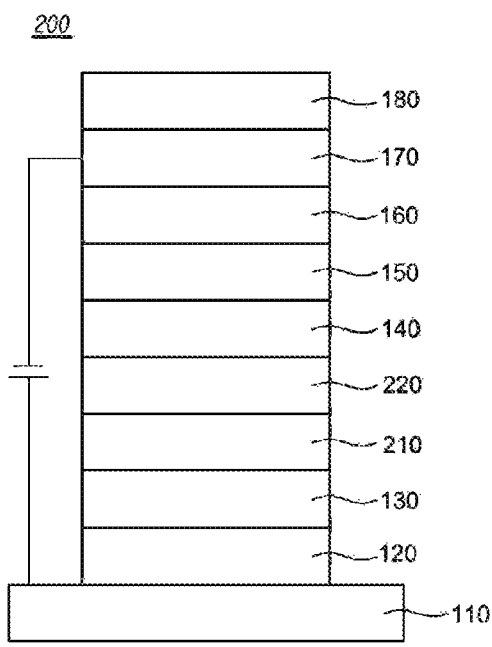

The organic material layer may sequentially comprise a hole injection layer (120), a hole transport layer (130), an emitting layer (140), an electron transport layer (150), and an electron injection layer (160) formed on the first electrode (110). Here, the remaining layers except the emitting layer (140) may not be formed. The organic material layer may further comprise a hole blocking layer, an electron blocking layer, an emitting-auxiliary layer (220), a buffer layer (210), etc., and the electron transport layer (150) and the like may serve as a hole blocking layer (see FIG. 2).

Also, the organic electronic element according to an embodiment of the present invention may further include a protective layer or a light efficiency enhancing layer (180). The light efficiency enhancing layer may be formed on a surface not in contact with the organic material layer among both surfaces of the first electrode or on a surface not in contact with the organic material layer among both surfaces of the second electrode. The compound according to an embodiment of the present invention applied to the organic material layer may be used as a material for a hole injection layer (120), a hole transport layer (130), an emitting-auxiliary layer (220), an electron transport auxiliary layer, an electron transport layer (150), an electron injection layer (160), a host or dopant of an emitting layer (140), a hole blocking layer or the light efficiency enhancing layer. Preferably, for example, the compound according to Formula 1 of the present invention may be used as a material for the emitting layer.

Figure 3:
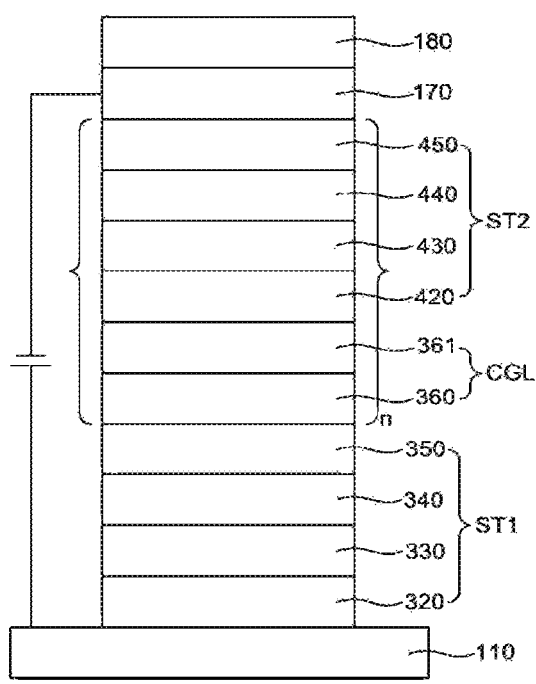

The organic material layer may comprise 2 or more stacks comprising a hole transport layer, an emitting layer, and an electron transport layer sequentially formed on the anode, and may further comprise a charge generation layer formed between the 2 or more stacks (see FIG. 3).

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer comprising the hole injection layer (120), the hole transport layer (130), the emitting layer (140), the electron transport layer (150), and the electron injection layer (160) is formed thereon, and then depositing a material usable as a cathode thereon can manufacture an organic electroluminescent device according to an embodiment of the present invention.

Also, the present invention provides the organic electronic element wherein the organic material layer is formed by one of a spin coating process, a nozzle printing process, an inkjet printing process, a slot coating process, a dip coating process or a roll-to-roll process, and the organic material layer provides an organic electronic element comprising the compound as an electron transport material.

As another specific example, the present invention provides an organic electronic element used by mixing the same or different compounds of the compound represented by Formula 1 to the organic material layer.

Also, the present invention provides an emitting layer composition comprising a compound represented by Formula 1, and provides an organic electronic element comprising the emitting layer.

Also, the present invention also provides an electronic device comprising a display device including the organic electronic element; and a control unit for driving the display device.

According to another aspect, the present invention provides an display device wherein the organic electronic element is at least one of an OLED, an organic solar cell, an organic photo conductor, an organic transistor (organic TFT) and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, Synthesis examples of the compound represented by Formula 1 and preparation examples of the organic electronic element of the present invention will be described in detail by way of example, but are not limited to the following examples.

SYNTHESIS EXAMPLE

The compound (final products) represented by Formula 1 according to the present invention is synthesized by reacting Sub 1 and Sub 2 as in Reaction Scheme 1, but is not limited thereto.

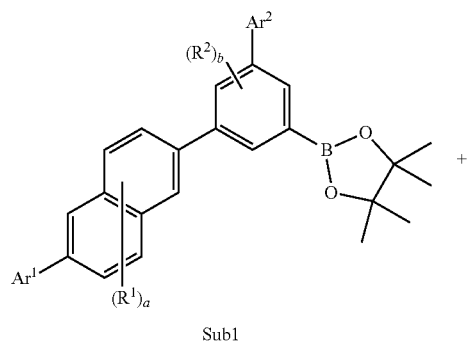

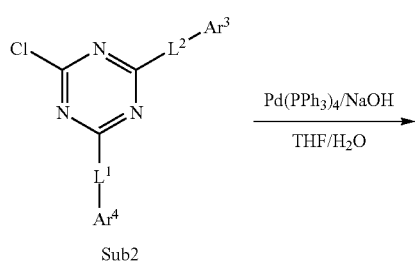

Final Products

I. Synthesis of Sub1

Sub1 of Reaction Scheme 1 is synthesized by the reaction pathway of Reaction Scheme 2, but is not limited thereto.

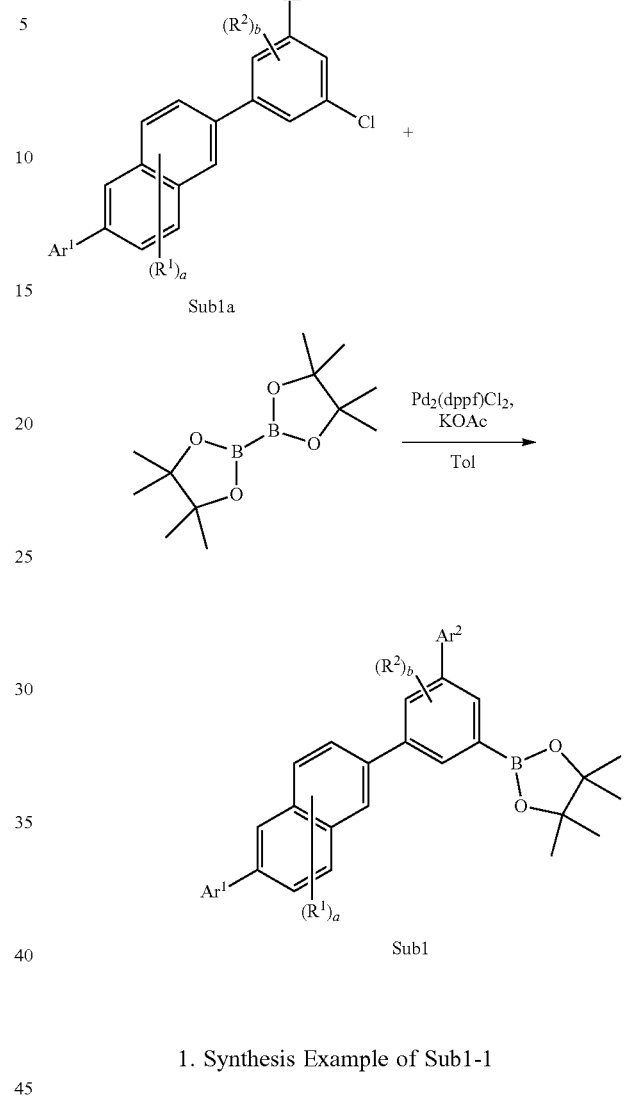

1. Synthesis Example of Sub1-1

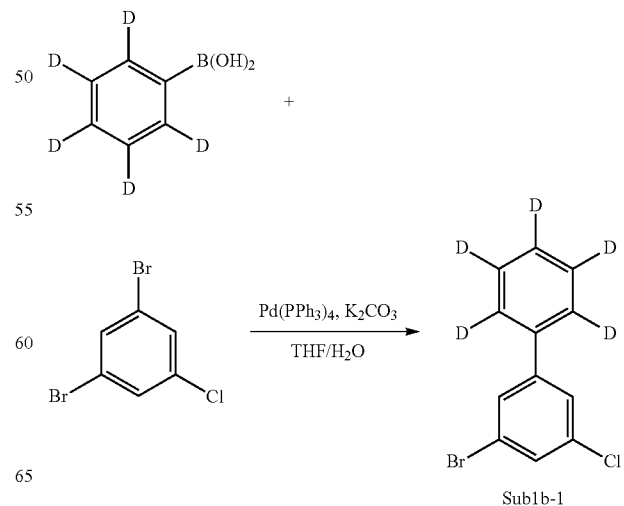

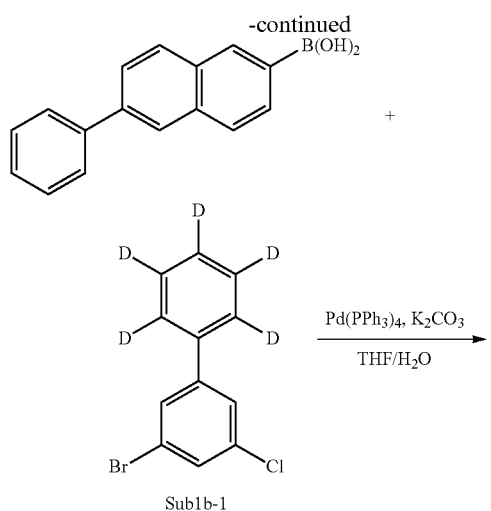

Sub1b-1

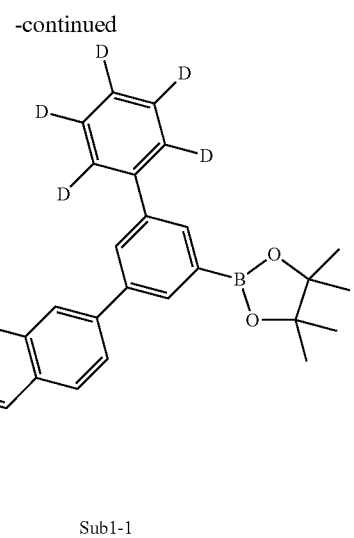

Sub1-1

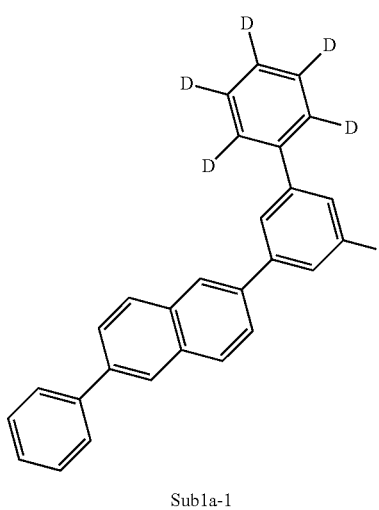

Sub1a-1

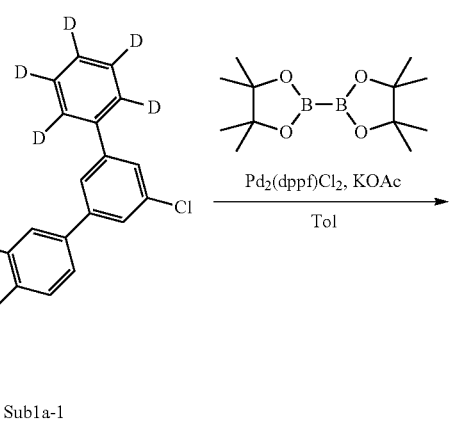

Sub1a-1

(1) Synthesis Example of Sub1 b-1

1,3-dibromo-5-chlorobenzene (100.0 g, 369.89 mmol), (phenyl-d5)boronic acid (42.27 g, 332.90 mmol) were dissolved in THE (Tetrahydrofuran) (1200 mL) in a round bottom flask, and $K_2CO_3$ (102.25 g, 739.78 mmol), $Pd(PPh_3)_4$ (12.82 g, 11.10 mmol), water (400 mL) were added and stirred at 80° C. When the reaction was completed, the mixture was extracted with toluene and water, and the organic layer was dried over $MgSO_4$ and concentrated. Thereafter, the resulting compound was recrystallized after applying a silica gel column to obtain 76.63 g of product (yield: 76.0%).

(2) Synthesis Example of Sub1a-1

Sub1 b-1 (50.0 g, 183.43 mmol), (6-phenylnaphthalen-2-yl)boronic acid (45.51 g, 183.43 mmol) were dissolved in THE (Tetrahydrofuran) (600 mL) in a round bottom flask, and $K_2CO_3$ (50.70 g, 366.86 mmol), $Pd(PPh_3)_4$ (6.36 g, 5.50 mmol), water (200 mL) were added and stirred at 80° C. When the reaction was completed, the mixture was extracted with toluene and water, and the organic layer was dried over $MgSO_4$ and concentrated. Thereafter, the resulting compound was recrystallized after applying a silica gel column to obtain 58.1 g of product (yield: 80.0%).

(3) Synthesis Example of Sub1-1

Sub1a-1 (58.1 g, 146.49 mmol), (Bis(pinacolato)diboron) (55.8 g, 219.73 mmol) were dissolved in Toluene (500 mL) in a round bottom flask and KOAc (28.75 g, 292.97 mmol), Xphos (3.49 g, 7.32 mmol), $Pd_2(dba)_3$ (4.03 g, 4.39 mmol) were added and stirred at 120° C. When the reaction was completed, the mixture was extracted with toluene and water, and the organic layer was dried over $MgSO_4$ and concentrated. Thereafter, the resulting compound was recrystallized after applying a silica gel column to obtain 46.41 g of product (yield: 65.0%).

2. Synthesis Example of Sub1-2

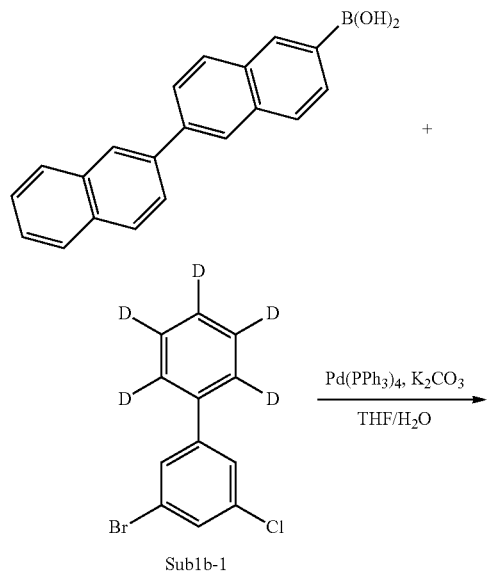

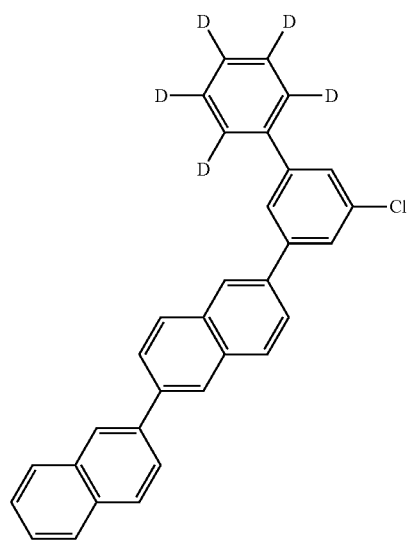

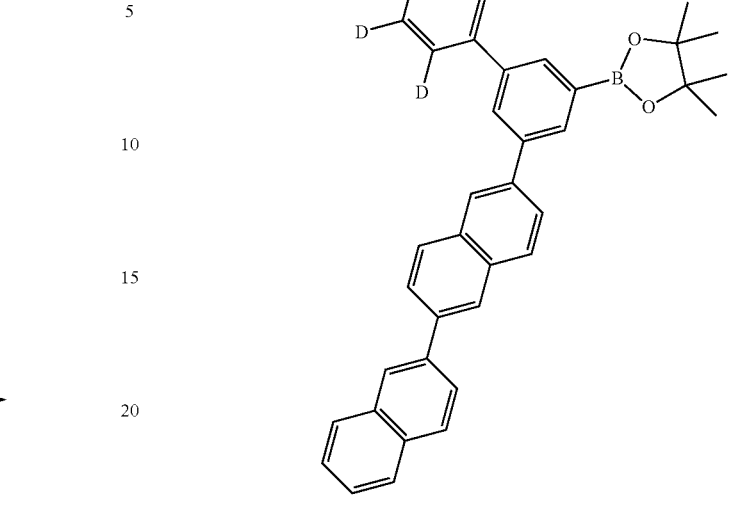

(1) Synthesis Example Sub1a-2

Sub1b-1 (20.1 g, 73.37 mmol), [2,2'-binaphthalen]-6-ylboronic acid (21.88 g, 73.37 mmol) were dissolved in THF (250 mL) in a round bottom flask, and K₂CO₃ (20.28 g, 146.75 mmol), Pd(PPh₃)₄ (2.54 g, 2.20 mmol), water (80 ml) were added, and 26.83 g (yield: 82%) of a product was obtained using the method for synthesizing Sub1a-1.

(2) Synthesis Example Sub1-2

Sub1a-2 (25.0 g, 56.05 Mmol) was Dissolved in Toluene (180 mL) in a round bottom flask, and (Bis(pinacolato) diboron) (21.35 g, 84.08 mmol), KOAc (11.0 g, 112.11 mmol), Xphos (1.34 g, 476.72 mmol), Pd₂(dba)₃ (1.54 g, 1.67 mmol) were added, and 20.19 g (yield: 67%) of a product was obtained using the method for synthesizing Sub1a-1.

3. Synthesis Example of Sub1-4

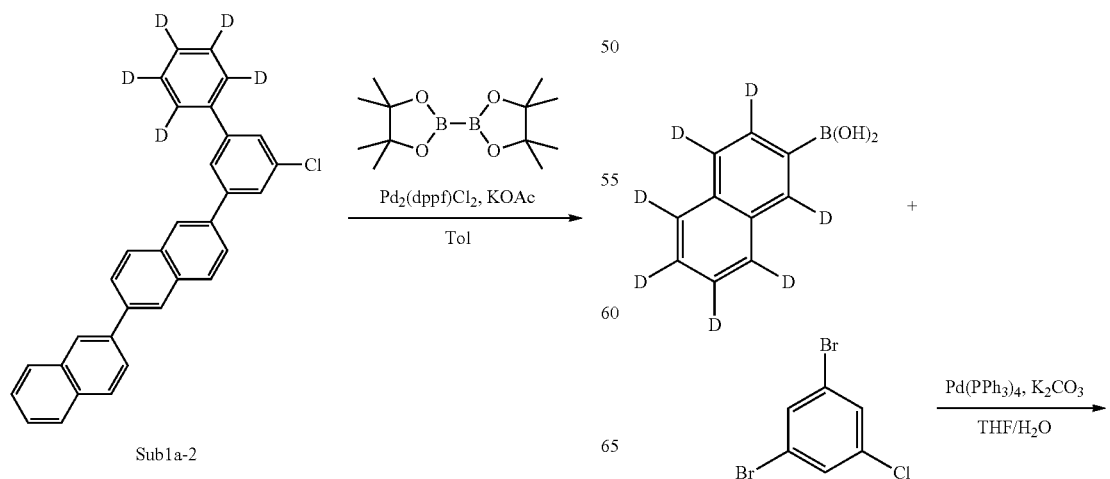

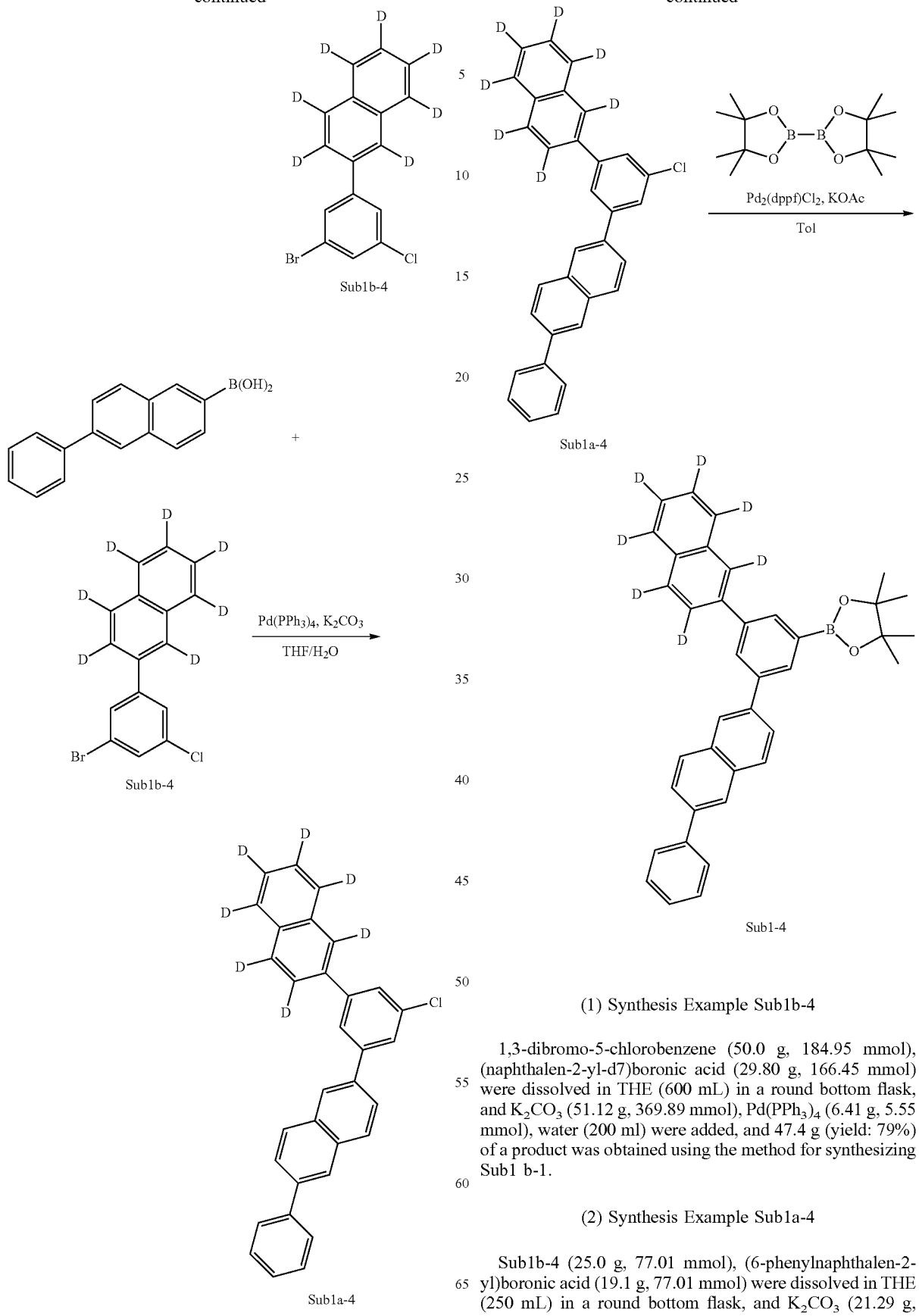

(1) Synthesis Example Sub1b-4

1,3-dibromo-5-chlorobenzene (50.0 g, 184.95 mmol), (naphthalen-2-yl-d7)boronic acid (29.80 g, 166.45 mmol) were dissolved in THF (600 mL) in a round bottom flask, and $K_2CO_3$ (51.12 g, 369.89 mmol), $Pd(PPh_3)_4$ (6.41 g, 5.55 mmol), water (200 ml) were added, and 47.4 g (yield: 79%) of a product was obtained using the method for synthesizing Sub1 b-1.

(2) Synthesis Example Sub1a-4

Sub1b-4 (25.0 g, 77.01 mmol), (6-phenylnaphthalen-2-yl)boronic acid (19.1 g, 77.01 mmol) were dissolved in THF (250 mL) in a round bottom flask, and $K_2CO_3$ (21.29 g, 154.01 mmol), $Pd(PPh_3)_4$ (2.67 g, 2.31 mmol), water (80 ml)

were added, and 29.3 g (yield: 85%) of a product was obtained using the method for synthesizing Sub1a-1.

(3) Synthesis Example Sub1-4

Sub1a-4 (29.0 g, 64.73 mmol) was dissolved in Toluene (220 mL) in a round bottom flask, and (Bis(pinacolato) diboron) (24.6 g, 97.10 mmol), KOAc (12.71 g, 129.46 mmol), Xphos (1.54 g, 3.24 mmol), Pd$_2$(dba)$_3$ (1.78 g, 1.94 mmol) were added, and 22.0 g (yield: 63%) of a product was obtained using the method for synthesizing Sub1a-1.

4. Synthesis Example of Sub1-6

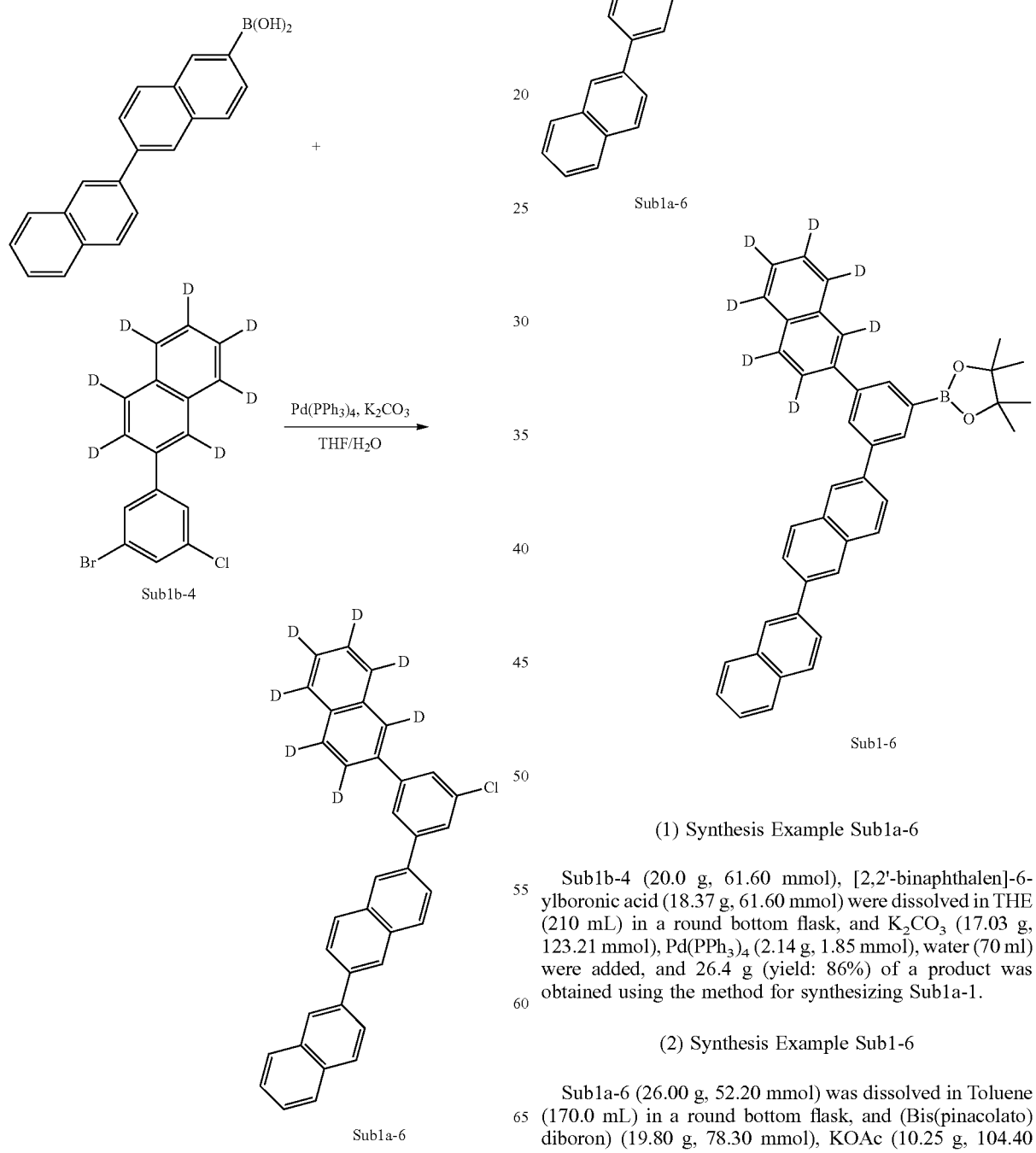

(1) Synthesis Example Sub1a-6

Sub1b-4 (20.0 g, 61.60 mmol), [2,2'-binaphthalen]-6-ylboronic acid (18.37 g, 61.60 mmol) were dissolved in THF (210 mL) in a round bottom flask, and K$_2$CO$_3$ (17.03 g, 123.21 mmol), Pd(PPh$_3$)$_4$ (2.14 g, 1.85 mmol), water (70 ml) were added, and 26.4 g (yield: 86%) of a product was obtained using the method for synthesizing Sub1a-1.

(2) Synthesis Example Sub1-6

Sub1a-6 (26.00 g, 52.20 mmol) was dissolved in Toluene (170.0 mL) in a round bottom flask, and (Bis(pinacolato) diboron) (19.80 g, 78.30 mmol), KOAc (10.25 g, 104.40 mmol), Xphos (1.24 g, 2.61 mmol), Pd$_2$(dba)$_3$ (1.43 g, 1.57 mmol) were added, and 21.54 g (yield: 70%) of a product was obtained using the method for synthesizing Sub1-1.
5. Synthesis Example of Sub1-9
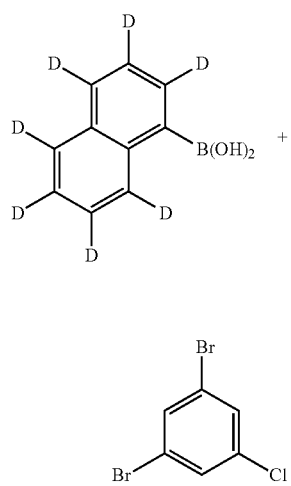
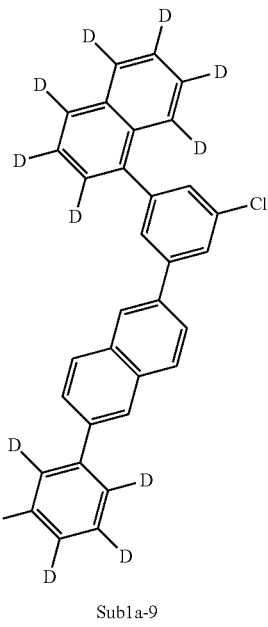
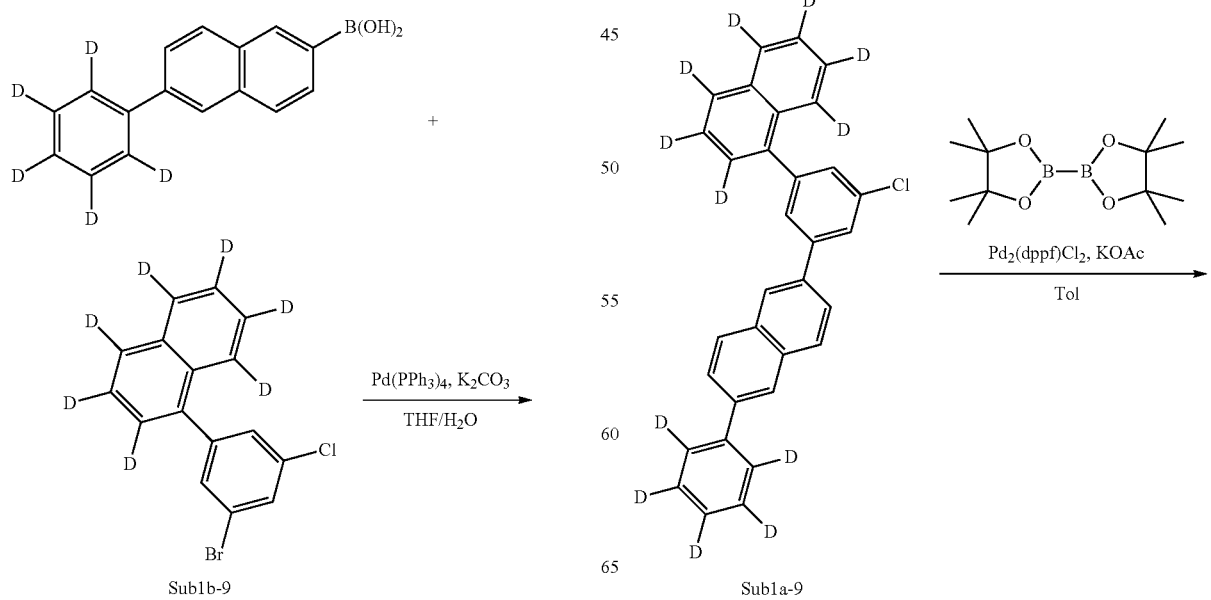

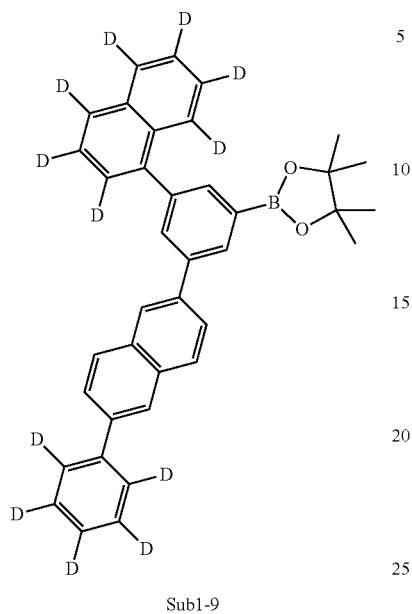

Sub1-9

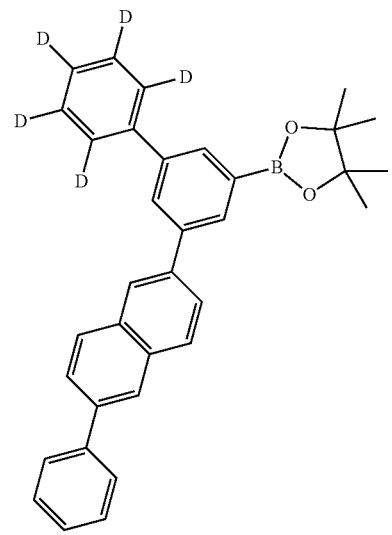

Sub1-1

(1) Synthesis Example Sub1b-9

1,3-dibromo-5-chlorobenzene (50.0 g, 184.95 mmol), (naphthalen-2-yl-d7)boronic acid (29.80 g, 166.45 mmol) were dissolved in THE (600 mL) in a round bottom flask, and $K_2CO_3$ (51.12 g, 369.89 mmol), $Pd(PPh_3)_4$ (6.41 g, 5.55 mmol), water (200 ml) were added, and 39.7 g (yield: 85%) of a product was obtained using the method for synthesizing Sub1 b-1.

(2) Synthesis Example Sub1a-9

Sub1b-9 (30.0 g, 92.41 mmol), (6-(phenyl-d5)naphthalen-2-yl)boronic acid (23.39 g, 92.41 mmol) were dissolved in THE (300 mL) in a round bottom flask, and $K_2CO_3$ (25.54 g, 184.81 mmol), $Pd(PPh_3)_4$ (3.20 g, 2.77 mmol), water (100 ml) were added, and 31.82 g (yield: 76%) of a product was obtained using the method for synthesizing Sub1a-1.

(3) Synthesis Example Sub1-9

Sub1a-9 (30.00 g, 66.22 mmol) was dissolved in Toluene (220 mL) in a round bottom flask, and (Bis(pinacolato) diboron) (21.35 g, 99.33 mmol), KOAc (13.0 g, 132.44 mmol), Xphos (1.58 g, 3.31 mmol), $Pd_2(dba)_3$ (1.82 g, 1.99 mmol) were added, and 23.08 g (yield: 64%) of a product was obtained using the method for synthesizing Sub1-1.

The compound belonging to Sub 1 may be the following compounds, but is not limited thereto, and Table 1 shows the FD-MS (Field Desorption-Mass Spectrometry) values of the compounds belonging to Sub 1.

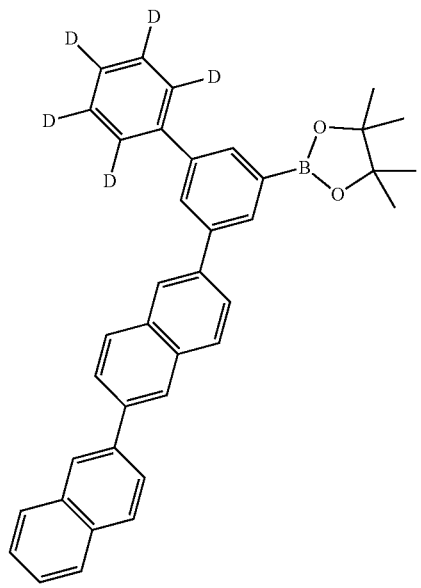

Sub1-2

Sub1-3
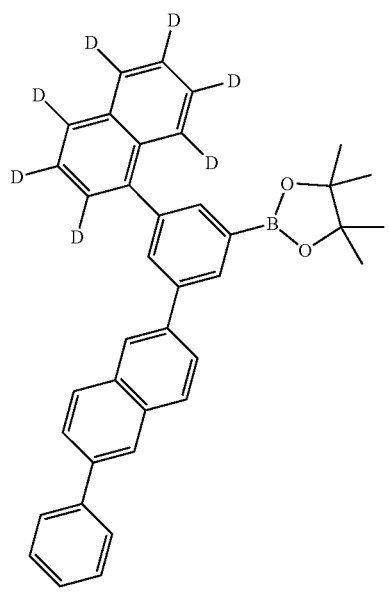
Sub1-5
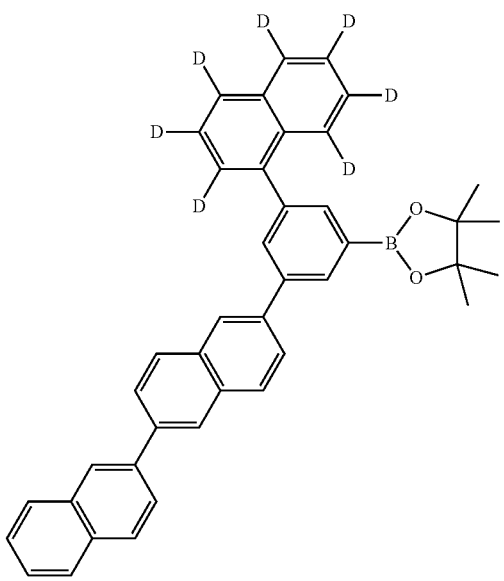
Sub1-4
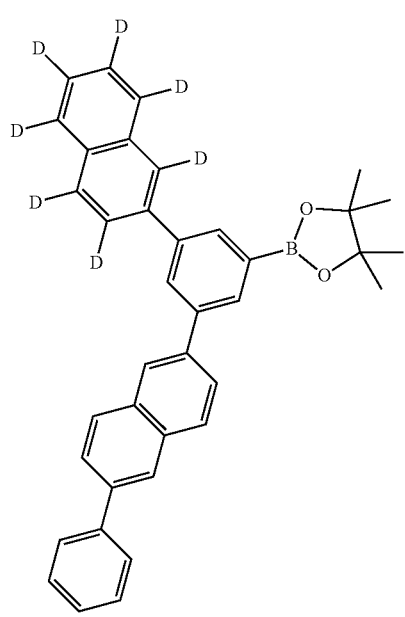
Sub1-6
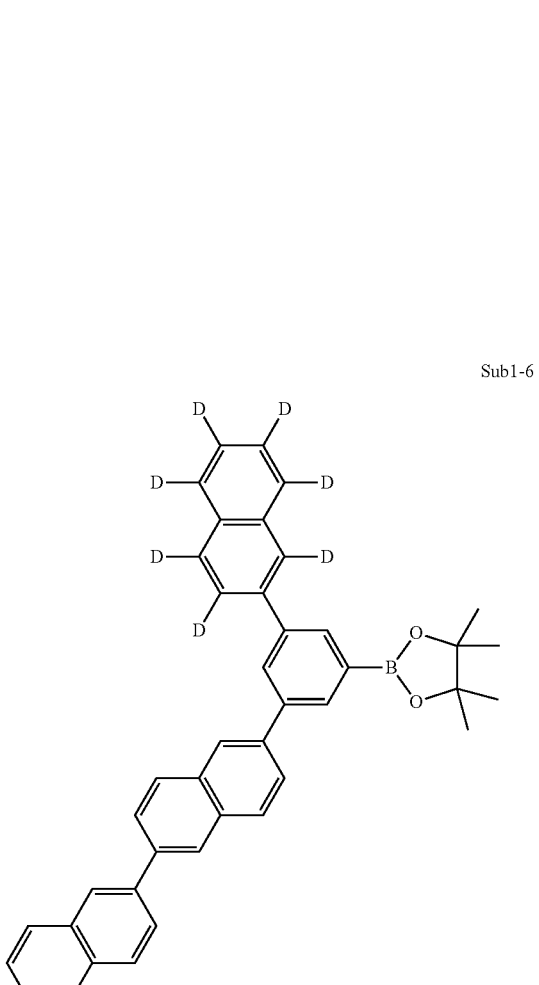

Sub1-7
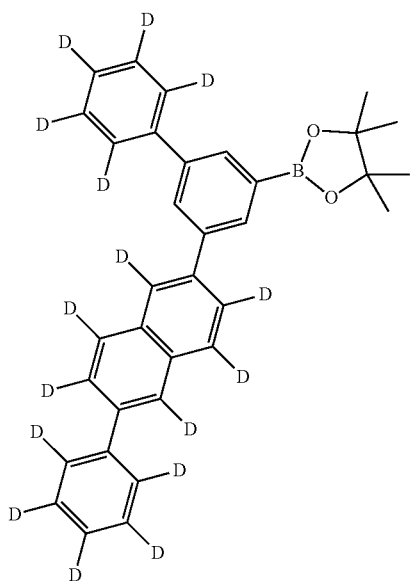
Sub1-8
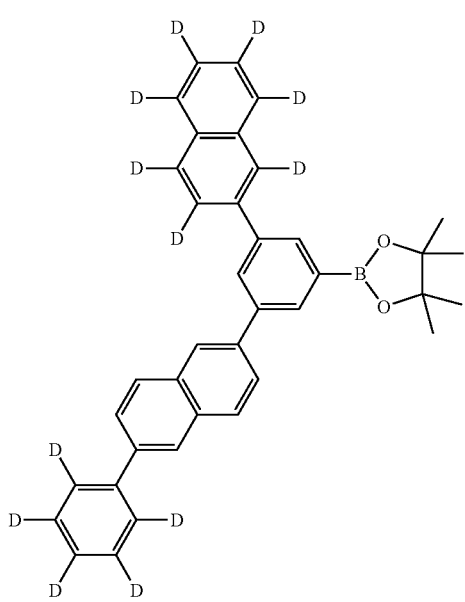
Sub1-9
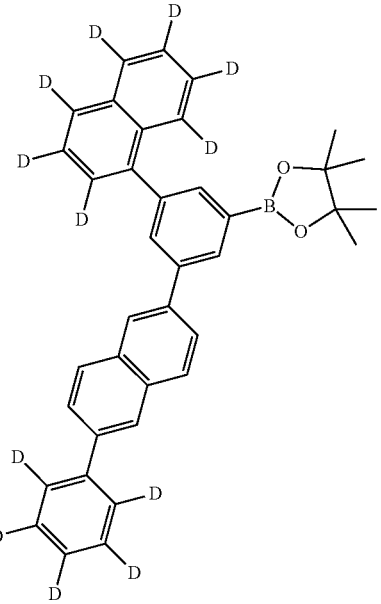
Sub1-10
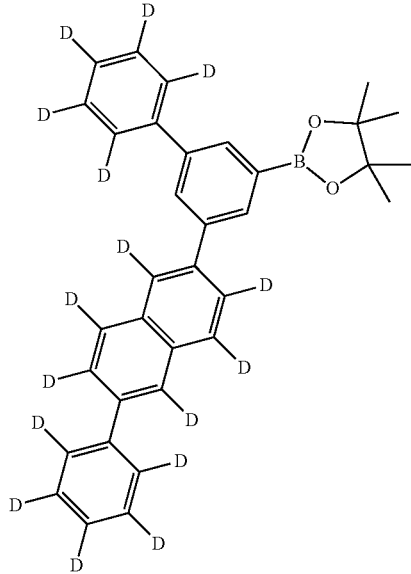

Sub1-11

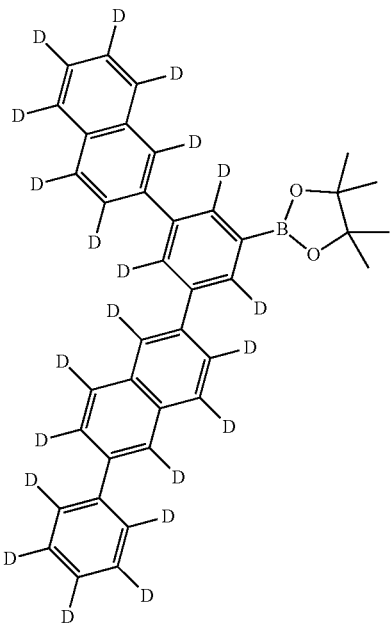

Sub1-12

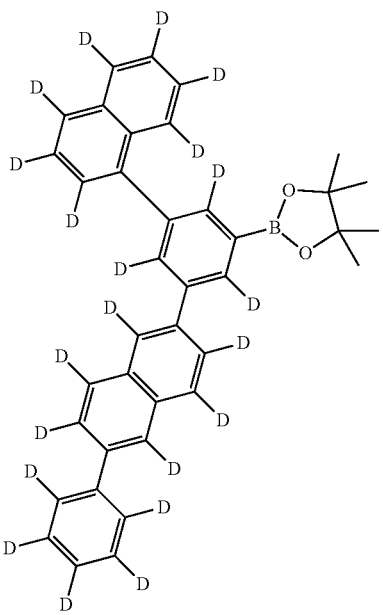

Sub1-13

TABLE 1

| Compound | FD-MS |
| --- | --- |
| Sub1-1 | m/z = 487.27($C_{34}H_{26}D_5BO_2$ = 487.46) |
| Sub1-2 | m/z = 537.29($C_{38}H_{28}D_5BO_2$ = 537.52) |
| Sub1-3 | m/z = 539.30($C_{38}H_{26}D_7BO_2$ = 539.53) |
| Sub1-4 | m/z = 539.30($C_{38}H_{26}D_7BO_2$ = 539.53) |
| Sub1-5 | m/z = 589.32($C_{42}H_{28}D_7BO_2$ = 589.59) |
| Sub1-6 | m/z = 589.32($C_{42}H_{28}D_7BO_2$ = 589.59) |
| Sub1-7 | m/z = 498.34($C_{34}H_{15}D_{16}BO_2$ = 498.53) |
| Sub1-8 | m/z = 544.33($C_{38}H_{21}D_{12}BO_2$ = 544.56) |
| Sub1-9 | m/z = 544.33($C_{38}H_{21}D_{12}BO_2$ = 544.56) |
| Sub1-10 | m/z = 498.34($C_{34}H_{15}D_{16}BO_2$ = 498.53) |
| Sub1-11 | m/z = 553.39($C_{38}H_{12}D_{21}BO_2$ = 553.62) |
| Sub1-12 | m/z = 501.36($C_{34}H_{12}D_{19}BO_2$ = 501.55) |
| Sub1-13 | m/z = 553.39($C_{38}H_{12}D_{21}BO_2$ = 553.62) |

II. Synthesis of Sub2

Sub2 of Reaction Scheme 1 is synthesized by the reaction pathway of Reaction Scheme 3, but is not limited thereto.

<Reaction Scheme 3>

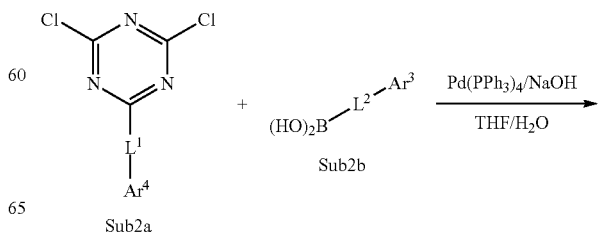

143
-continued

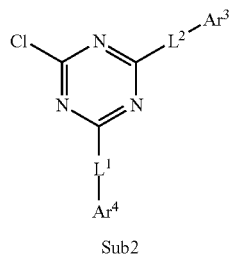

Sub2

1. Synthesis Example of Sub2-2

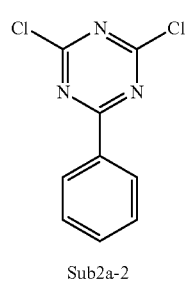

Sub2a-2

+

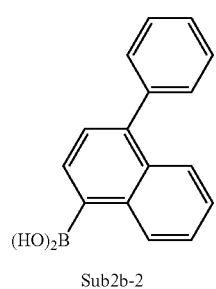

Sub2b-2

Pd(PPh₃)₄/NaOH
⟶
THF/H₂O

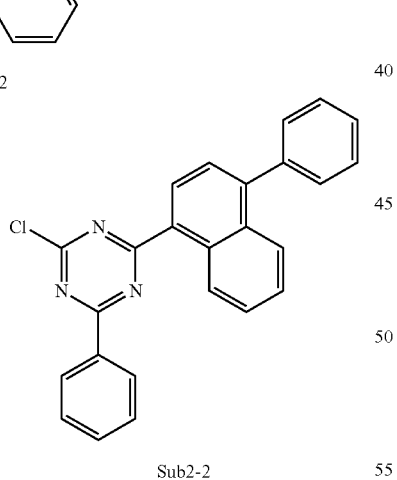

Sub2-2

Sub2a-2 (30.00 g, 132.71 mmol), Sub2b-2 (32.92 g, 132.71 mmol) were dissolved in THF (Tetrahydrofuran) (450 mL) in a round bottom flask, and NaOH (10.61 g, 265.42 mmol), Pd(PPh₃)₄ (4.60 g, 3.98 mmol), water (150 mL) were added and stirred at 80° C. When the reaction was completed, the mixture was extracted with toluene and water, and the organic layer was dried over MgSO₄ and concentrated. Thereafter, the resulting compound was recrystallized after applying a silica gel column to obtain 39.73 g of product (yield: 76.0%).

144

2. Synthesis Example of Sub2-18

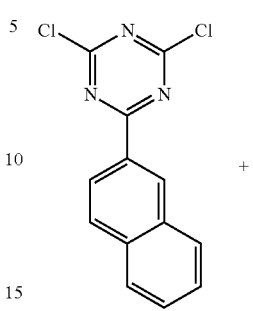

Sub2a-18

+

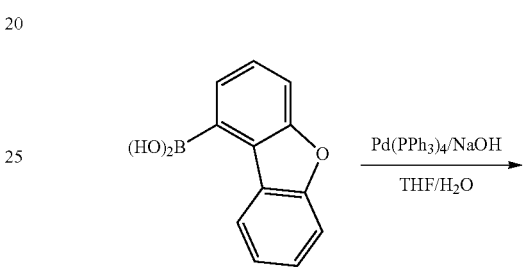

Sub2b-18

Pd(PPh₃)₄/NaOH
⟶
THF/H₂O

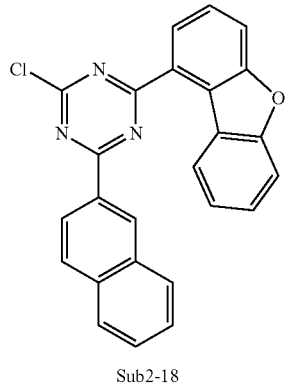

Sub2-18

Sub2a-18 (30.00 g, 108.65 mmol), Sub2b-18 (23.03 g, 108.65 mmol) were dissolved in THF (360 mL) in a round bottom flask, and NaOH (8.69 g, 217.30 mmol), Pd(PPh₃)₄ (3.77 g, 3.26 mmol), water (120 ml) were added, and 32.35 g (yield: 73.1%) of a product was obtained using the method for synthesizing Sub2-1.

3. Synthesis Example of Sub2-40

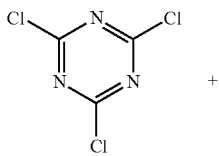

+

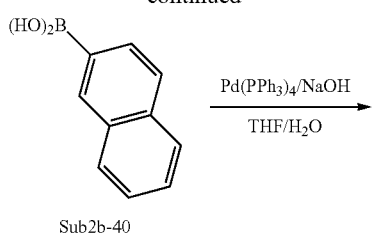
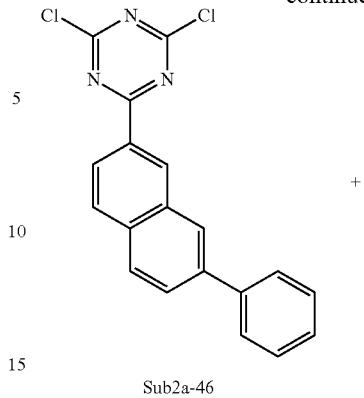

2,4,6-trichloro-1,3,5-triazine (20.00 g, 108.46 mmol), Sub2b-40 (18.65 g, 108.46 mmol) were dissolved in THF (360 mL) in a round bottom flask, and NaOH (13.02 g, 325.38 mmol), Pd(PPh$_3$)$_4$ (3.76 g, 3.25 mmol), water (80 ml) were added, and 25 g (yield: 65.0%) of a product was obtained using the method for synthesizing Sub2-1.

4. Synthesis Example of Sub2-46

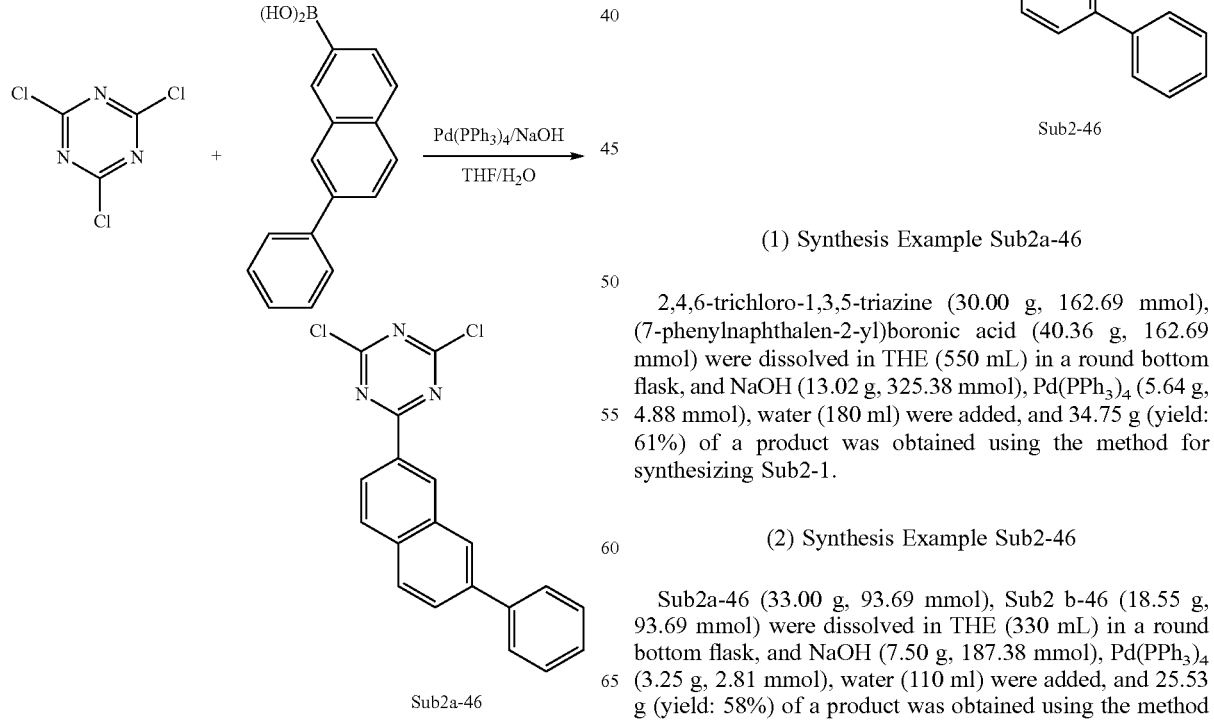

(1) Synthesis Example Sub2a-46

2,4,6-trichloro-1,3,5-triazine (30.00 g, 162.69 mmol), (7-phenylnaphthalen-2-yl)boronic acid (40.36 g, 162.69 mmol) were dissolved in THF (550 mL) in a round bottom flask, and NaOH (13.02 g, 325.38 mmol), Pd(PPh$_3$)$_4$ (5.64 g, 4.88 mmol), water (180 ml) were added, and 34.75 g (yield: 61%) of a product was obtained using the method for synthesizing Sub2-1.

(2) Synthesis Example Sub2-46

Sub2a-46 (33.00 g, 93.69 mmol), Sub2 b-46 (18.55 g, 93.69 mmol) were dissolved in THF (330 mL) in a round bottom flask, and NaOH (7.50 g, 187.38 mmol), Pd(PPh$_3$)$_4$ (3.25 g, 2.81 mmol), water (110 ml) were added, and 25.53 g (yield: 58%) of a product was obtained using the method for synthesizing Sub2-1.

5. Synthesis Example of Sub2-60

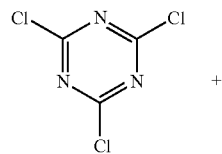

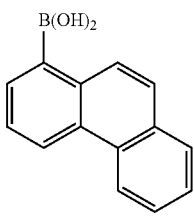

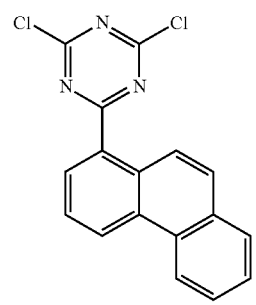

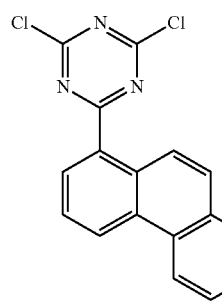

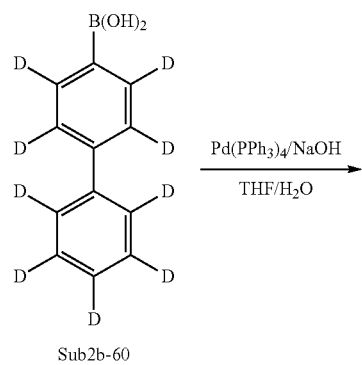

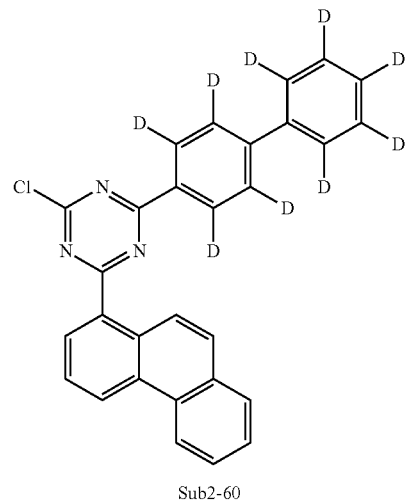

Sub2-60

(1) Synthesis Example Sub2a-60

2,4,6-trichloro-1,3,5-triazine (30.00 g, 162.69 mmol), phenanthren-1-ylboronic acid (36.13 g, 162.69 mmol) were dissolved in THE (550 mL) in a round bottom flask, and NaOH (13.02 g, 325.38 mmol), Pd(PPh$_3$)$_4$ (5.64 g, 4.88 mmol), water (180 ml) were added, and 31.10 g (yield: 58.6%) of a product was obtained using the method for synthesizing Sub2-1.

(2) Synthesis Example Sub2-60

Sub2a-60 (30.00 g, 91.97 mmol), Sub2 b-60 (19.05 g, 91.97 mmol) were dissolved in THE (300 mL) in a round bottom flask, and NaOH (7.36 g, 183.95 mmol), Pd(PPh$_3$)$_4$ (3.19 g, 2.76 mmol), water (100 ml) were added, and 22.88 g (yield: 55.0%) of a product was obtained using the method for synthesizing Sub2-1.

The compound belonging to Sub 2 may be the following compounds, but is not limited thereto, and Table 2 shows the FD-MS (Field Desorption-Mass Spectrometry) values of the compounds belonging to Sub 2.

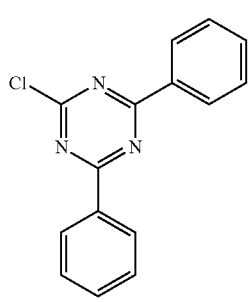

Sub2-1

Sub2-2
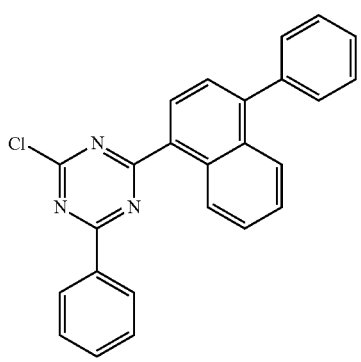
Sub2-3
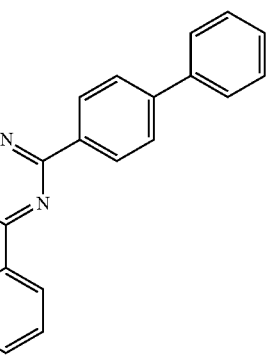
Sub2-4
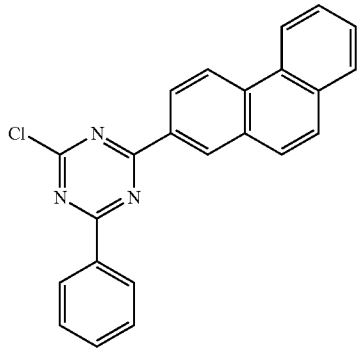
Sub2-5
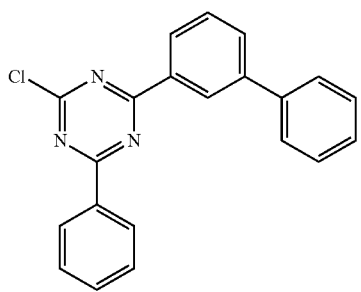
Sub2-6
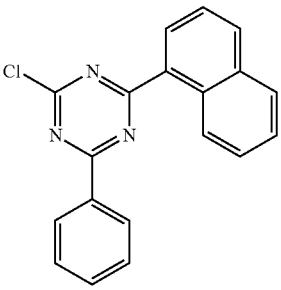
Sub2-7
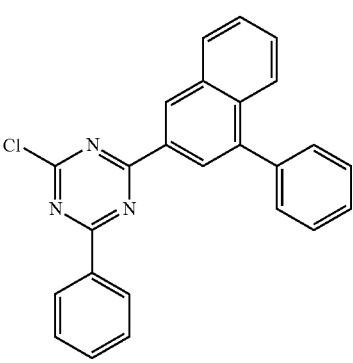
Sub2-8
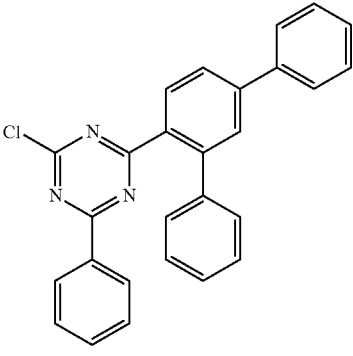
Sub2-9
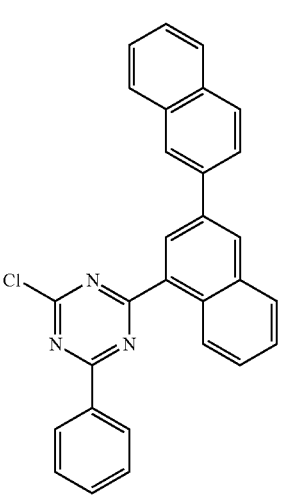

-continued
Sub2-10
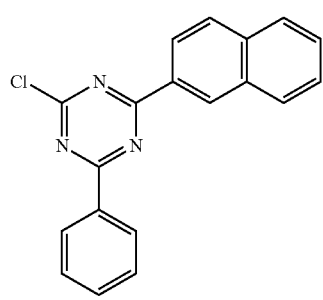
Sub2-14
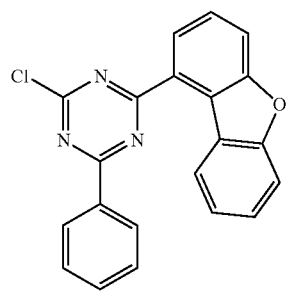
Sub2-11
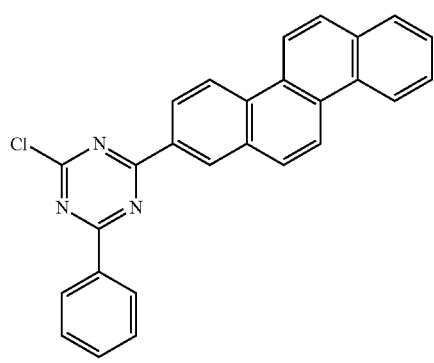
Sub2-15
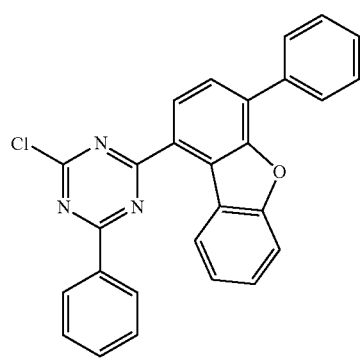
Sub2-12
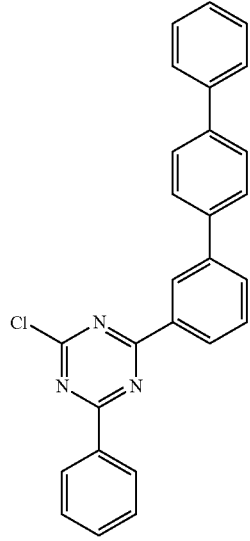
Sub2-16
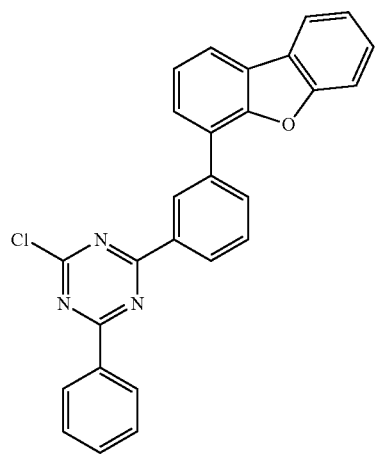
Sub2-13
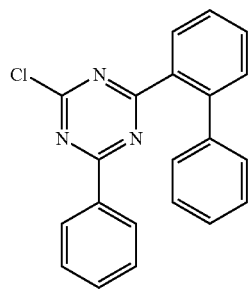
Sub2-17
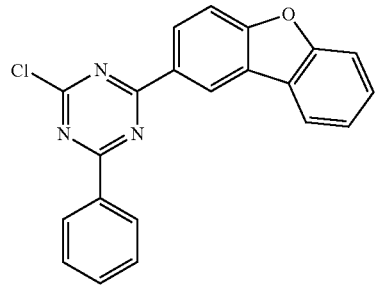

Sub2-18

Sub2-22

Sub2-19

Sub2-23

Sub2-20

Sub2-24

Sub2-21

Sub2-25

Sub2-26 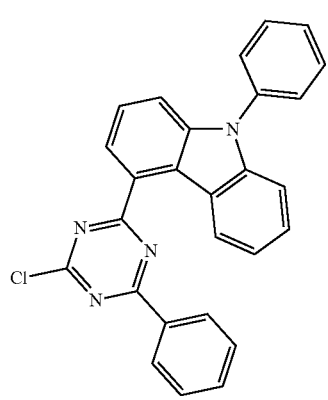
Sub2-27 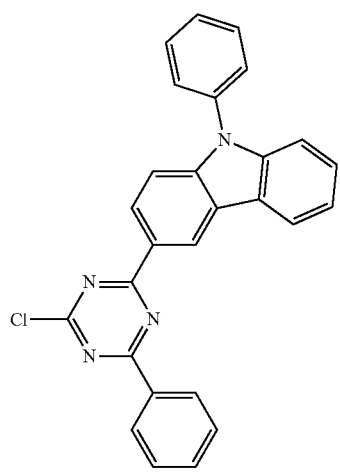
Sub2-28 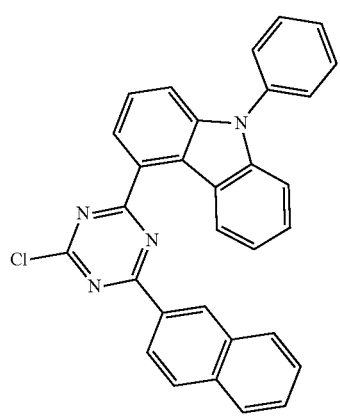
Sub2-29 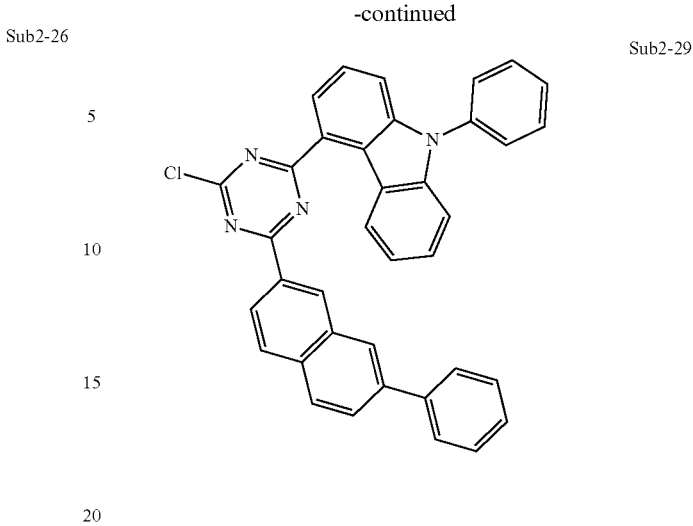
Sub2-30 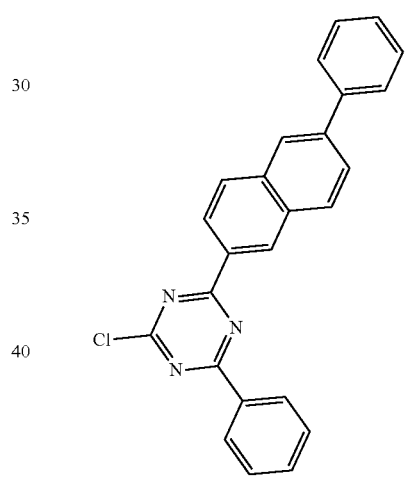
Sub2-31 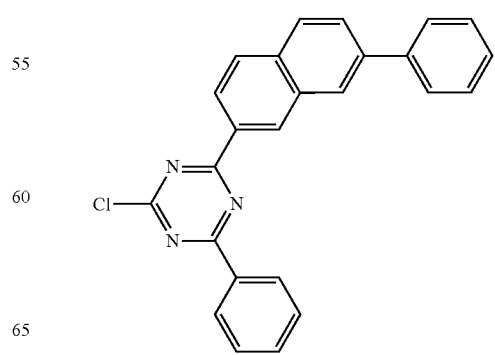

Sub2-32
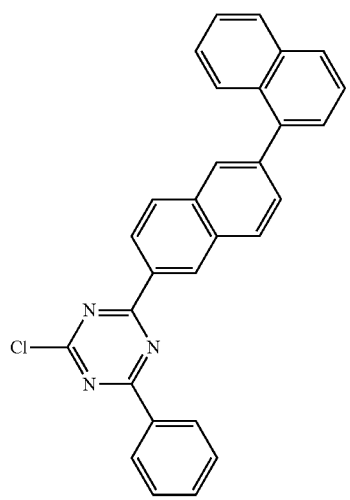
Sub2-33
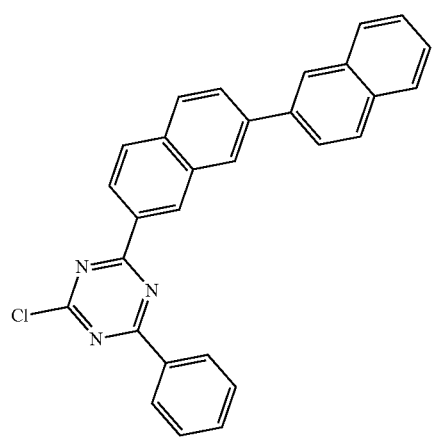
Sub2-34
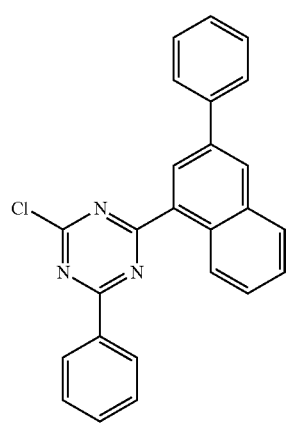
Sub2-35
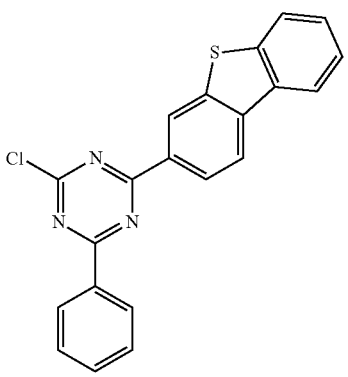
Sub2-36
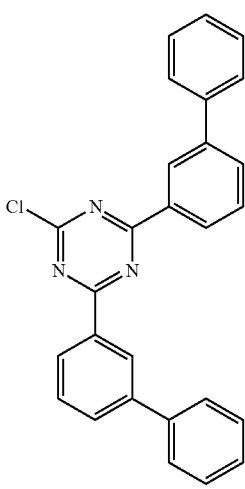
Sub2-37
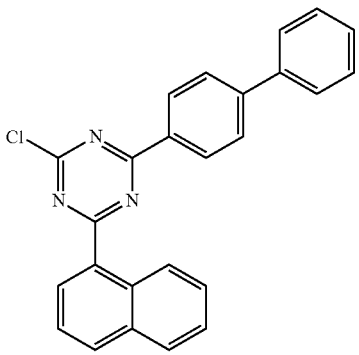
Sub2-38
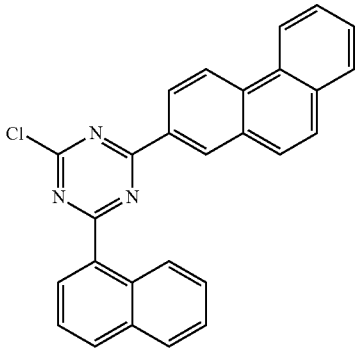

Sub2-39
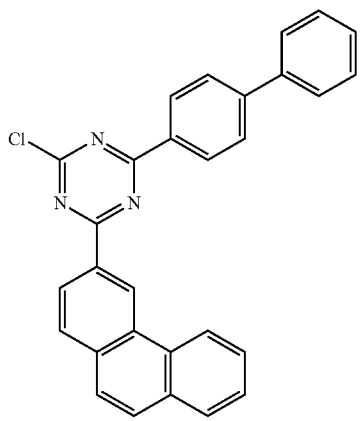
Sub2-43
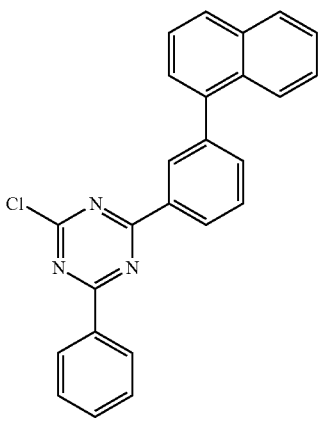
Sub2-40
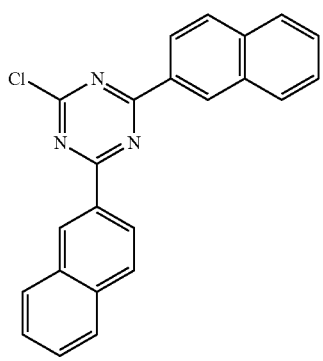
Sub2-44
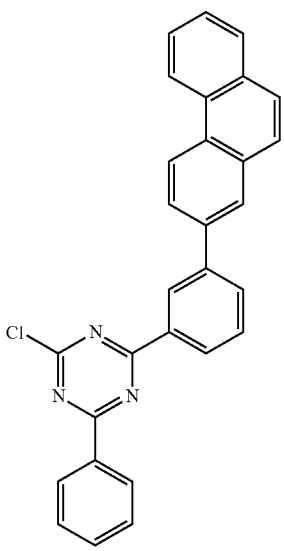
Sub2-41
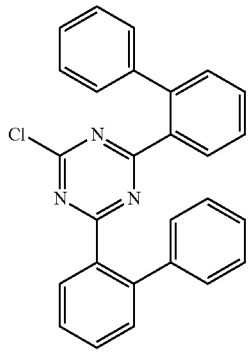
Sub2-42
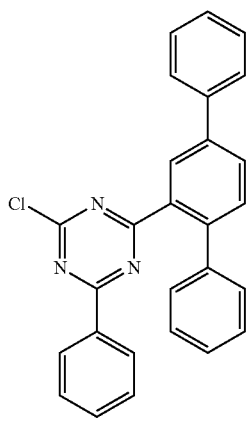
Sub2-45

Sub2-46
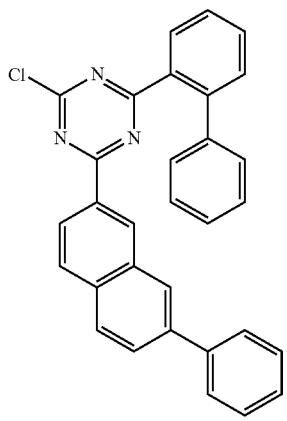
Sub2-47
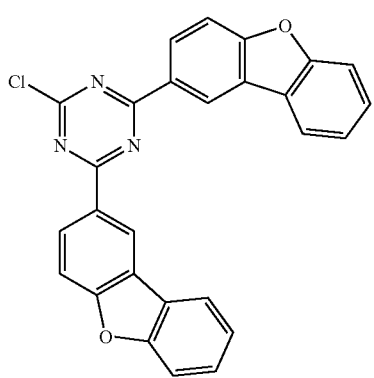
Sub2-48
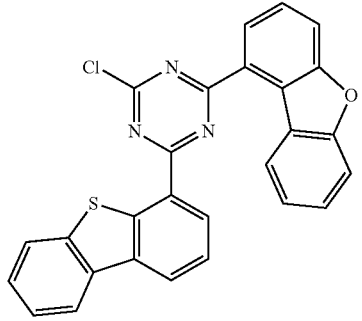
Sub2-49
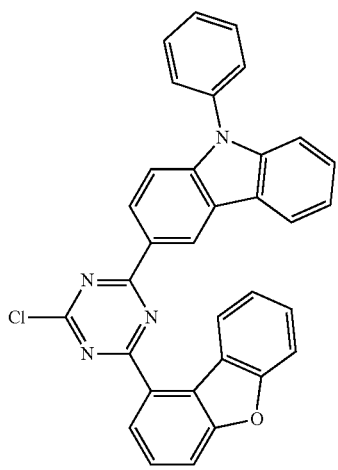
Sub2-50
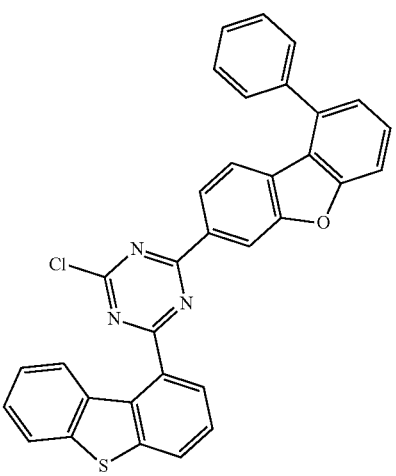
Sub2-51
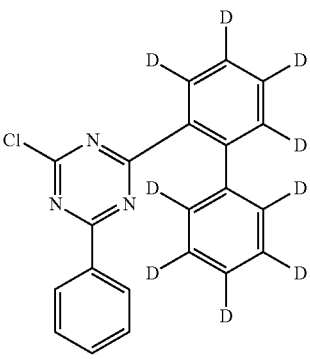
Sub2-52
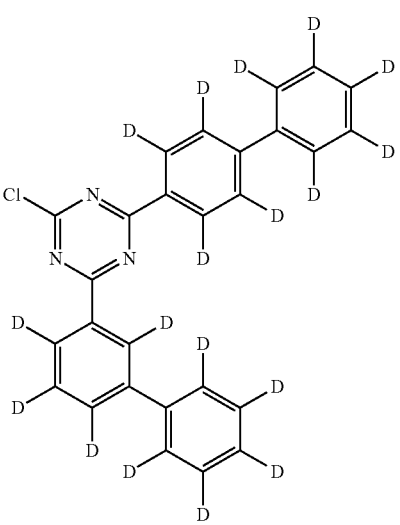

Sub2-53
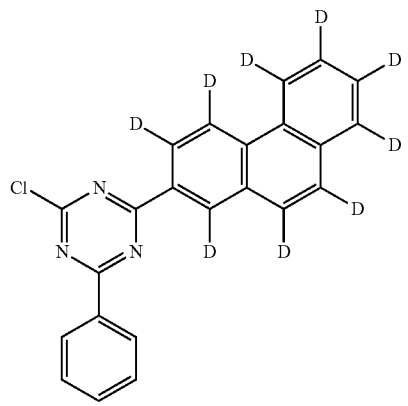
Sub2-54
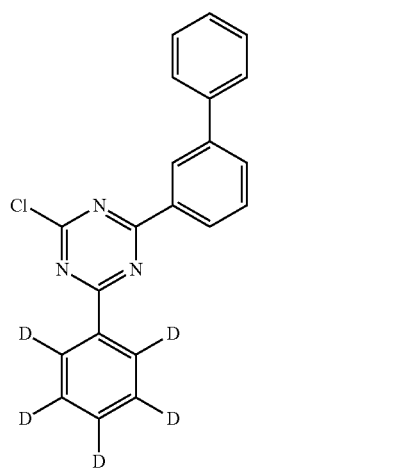
Sub2-55
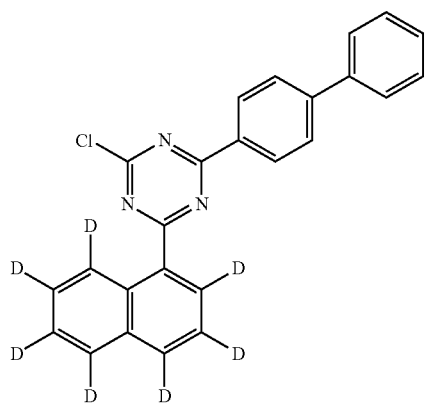
Sub2-56
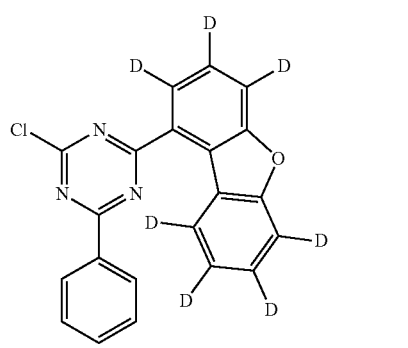
Sub2-57
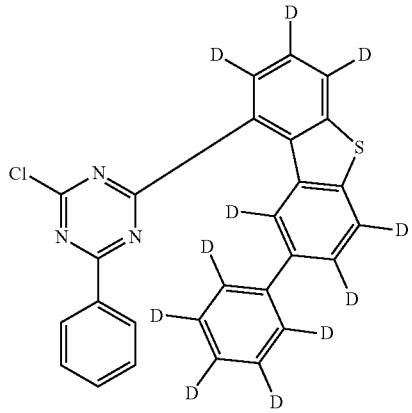
Sub2-58
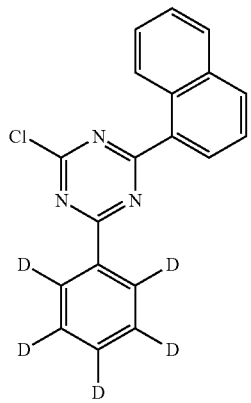
Sub2-59
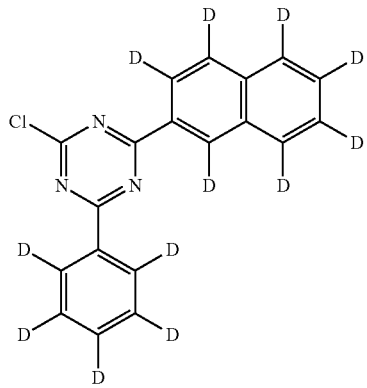

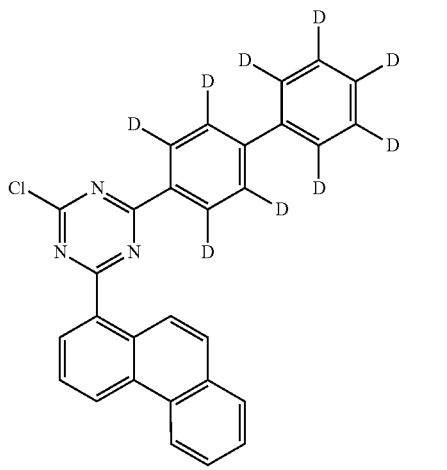

Sub2-60

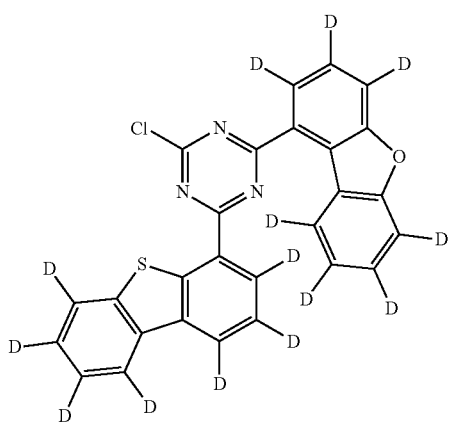

Sub2-61

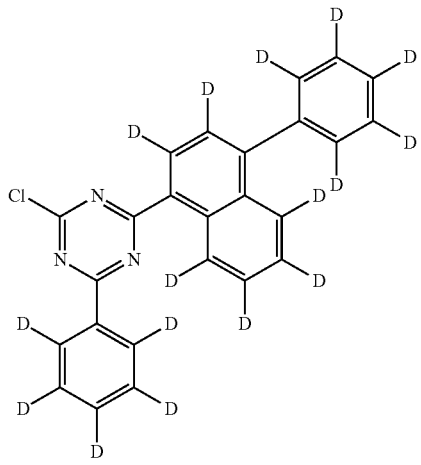

Sub2-62

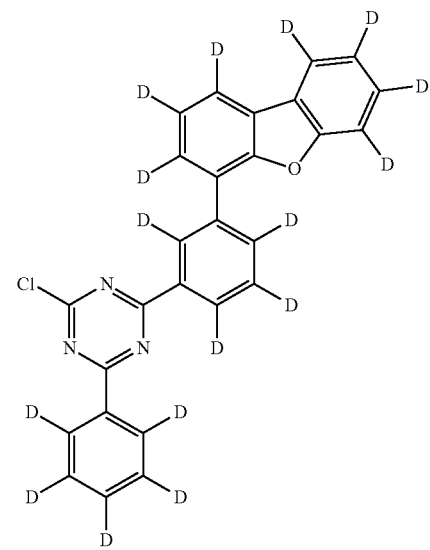

Sub2-63

Sub2-64

TABLE 2

| Compound | FD-MS |
|---|---|
| Sub2-1  | m/z = 267.06($C_{15}H_{10}ClN_3$ = 267.72) |
| Sub2-2  | m/z = 393.10($C_{25}H_{16}ClN_3$ = 393.87) |
| Sub2-3  | m/z = 343.09($C_{21}H_{14}ClN_3$ = 343.81) |
| Sub2-4  | m/z = 367.09($C_{23}H_{14}ClN_3$ = 367.84) |
| Sub2-5  | m/z = 343.09($C_{21}H_{14}ClN_3$ = 343.81) |
| Sub2-6  | m/z = 317.07($C_{19}H_{12}ClN_3$ = 317.78) |
| Sub2-7  | m/z = 393.10($C_{25}H_{16}ClN_3$ = 393.87) |
| Sub2-8  | m/z = 419.12($C_{27}H_{18}ClN_3$ = 419.91) |
| Sub2-9  | m/z = 443.12($C_{29}H_{18}ClN_3$ = 443.93) |
| Sub2-10 | m/z = 317.07($C_{19}H_{12}ClN_3$ = 317.78) |
| Sub2-11 | m/z = 417.10($C_{27}H_{18}ClN_3$ = 417.90) |
| Sub2-12 | m/z = 419.12($C_{27}H_{18}ClN_3$ = 419.91) |
| Sub2-13 | m/z = 343.09($C_{21}H_{14}ClN_3$ = 343.81) |
| Sub2-14 | m/z = 357.07($C_{21}H_{12}ClN_3O$ = 357.80) |
| Sub2-15 | m/z = 443.12($C_{29}H_{18}ClN_3O$ = 443.93) |
| Sub2-16 | m/z = 433.10($C_{27}H_{16}ClN_3O$ = 433.89) |
| Sub2-17 | m/z = 357.07($C_{21}H_{12}ClN_3O$ = 357.80) |
| Sub2-18 | m/z = 407.08($C_{25}H_{14}ClN_3O$ = 407.86) |
| Sub2-19 | m/z = 433.10($C_{27}H_{16}ClN_3O$ = 433.89) |
| Sub2-20 | m/z = 483.11($C_{31}H_{18}ClN_3O$ = 483.95) |
| Sub2-21 | m/z = 407.08($C_{25}H_{14}ClN_3O$ = 407.86) |
| Sub2-22 | m/z = 449.08($C_{27}H_{16}ClN_3S$ = 449.96) |
| Sub2-23 | m/z = 473.08($C_{29}H_{16}ClN_3S$ = 473.98) |
| Sub2-24 | m/z = 525.11($C_{33}H_{20}ClN_3S$ = 526.05) |
| Sub2-25 | m/z = 457.10($C_{29}H_{16}ClN_3O$ = 457.92) |
| Sub2-26 | m/z = 432.11($C_{27}H_{17}ClN_4$ = 432.91) |
| Sub2-27 | m/z = 432.11($C_{27}H_{17}ClN_4$ = 432.91) |
| Sub2-28 | m/z = 482.13($C_{31}H_{19}ClN_4$ = 482.97) |

TABLE 2-continued

| Compound | FD-MS |
|---|---|
| Sub2-29 | m/z = 558.16($C_{37}H_{23}ClN_4$ = 559.07) |
| Sub2-30 | m/z = 393.10($C_{25}H_{16}ClN_3$ = 393.87) |
| Sub2-31 | m/z = 393.10($C_{25}H_{16}ClN_3$ = 393.87) |
| Sub2-32 | m/z = 443.12($C_{29}H_{18}ClN_3$ = 443.93) |
| Sub2-33 | m/z = 443.12($C_{29}H_{18}ClN_3$ = 443.93) |
| Sub2-34 | m/z = 393.10($C_{25}H_{16}ClN_3$ = 393.87) |
| Sub2-35 | m/z = 373.04($C_{21}H_{12}ClN_3S$ = 373.86) |
| Sub2-36 | m/z = 419.12($C_{27}H_{18}ClN_3$ = 419.91) |
| Sub2-37 | m/z = 393.10($C_{25}H_{16}ClN_3$ = 393.87) |
| Sub2-38 | m/z = 417.10($C_{27}H_{18}ClN_3$ = 417.90) |
| Sub2-39 | m/z = 443.12($C_{29}H_{18}ClN_3O$ = 443.93) |
| Sub2-40 | m/z = 367.09($C_{23}H_{14}ClN_3$ = 367.84) |
| Sub2-41 | m/z = 419.12($C_{27}H_{18}ClN_3$ = 419.91) |
| Sub2-42 | m/z = 419.12($C_{27}H_{18}ClN_3$ = 419.91) |
| Sub2-43 | m/z = 393.10($C_{25}H_{16}ClN_3$ = 393.87) |
| Sub2-44 | m/z = 469.13($C_{31}H_{20}ClN_3$ = 469.97) |
| Sub2-45 | m/z = 443.12($C_{29}H_{18}ClN_3O$ = 443.93) |
| Sub2-46 | m/z = 469.13($C_{31}H_{20}ClN_3$ = 469.97) |
| Sub2-47 | m/z = 447.08($C_{27}H_{14}ClN_3O_2$ = 447.88) |
| Sub2-48 | m/z = 463.05($C_{27}H_{14}ClN_3OS$ = 463.94) |
| Sub2-49 | m/z = 522.12($C_{33}H_{19}ClN_4O$ = 522.99) |
| Sub2-50 | m/z = 539.09($C_{33}H_{18}ClN_3OS$ = 540.04) |
| Sub2-51 | m/z = 352.14($C_{21}H_5D_9ClN_3$ = 352.87) |
| Sub2-52 | m/z = 437.23($C_{27}D_{18}ClN_3$ = 438.02) |
| Sub2-53 | m/z = 376.14($C_{23}H_5D_9ClN_3$ = 376.89) |
| Sub2-54 | m/z = 348.12($C_{21}H_9D_5ClN_3$ = 348.84) |
| Sub2-55 | m/z = 400.15($C_{25}H_9D_7ClN_3$ = 400.92) |
| Sub2-56 | m/z = 364.11($C_{21}H_5D_7ClN_3O$ = 364.84) |
| Sub2-57 | m/z = 460.14($C_{27}H_5D_{11}ClN_3S$ = 461.02) |
| Sub2-58 | m/z = 322.10($C_{19}H_7D_5ClN_3$ = 322.81) |
| Sub2-59 | m/z = 329.15($C_{19}D_{12}ClN_3$ = 329.85) |
| Sub2-60 | m/z = 452.18($C_{29}H_9D_9ClN_3$ = 452.99) |
| Sub2-61 | m/z = 477.14($C_{27}D_{14}ClN_3OS$ = 478.02) |
| Sub2-62 | m/z = 409.20($C_{25}D_{16}ClN_3$ = 409.97) |
| Sub2-63 | m/z = 449.20($C_{27}D_{16}ClN_3O$ = 449.99) |
| Sub2-64 | m/z = 381.18($C_{23}D_{14}ClN_3$ = 381.92) |

III. Synthesis of Final Product

1. Synthesis Example of P-1

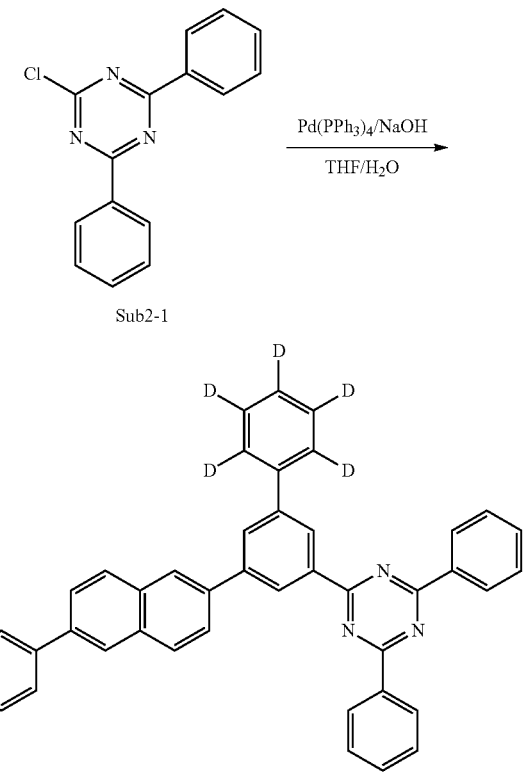

Sub2-1

P-1

Sub1-1 (15.00 g, 30.77 mmol), Sub2-1 (8.23 g, 30.77 mmol) were dissolved in THF (Tetrahydrofuran) (150 mL) in a round bottom flask, and NaOH (2.46 g, 61.54 mmol), Pd(PPh$_3$)$_4$ (0.71 g, 0.62 mmol), water (50 mL) were added and stirred at 80° C. When the reaction was completed, the mixture was extracted with toluene and water, and the organic layer was dried over MgSO$_4$ and concentrated. Thereafter, the resulting compound was recrystallized after applying a silica gel column to obtain 15.56 g of product (yield: 85.3%).

2. Synthesis Example of P-21

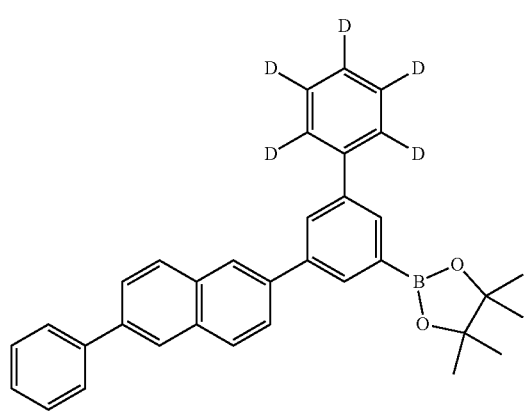

Sub1-1

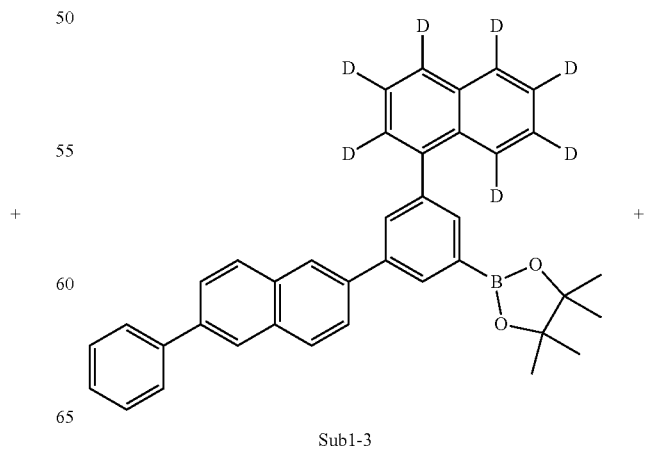

Sub1-3

169

-continued

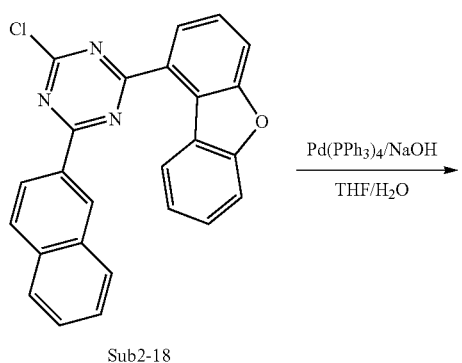

Sub2-18

Pd(PPh₃)₄/NaOH
―――――――→
THF/H₂O

170

-continued

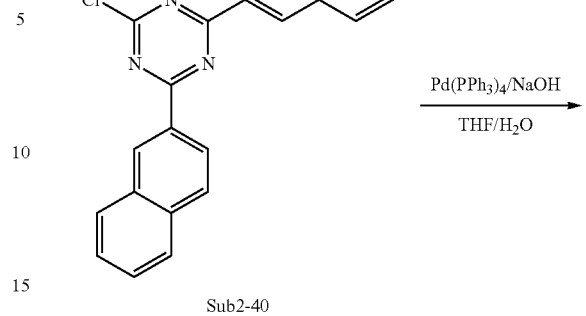

Sub2-40

Pd(PPh₃)₄/NaOH
―――――――→
THF/H₂O

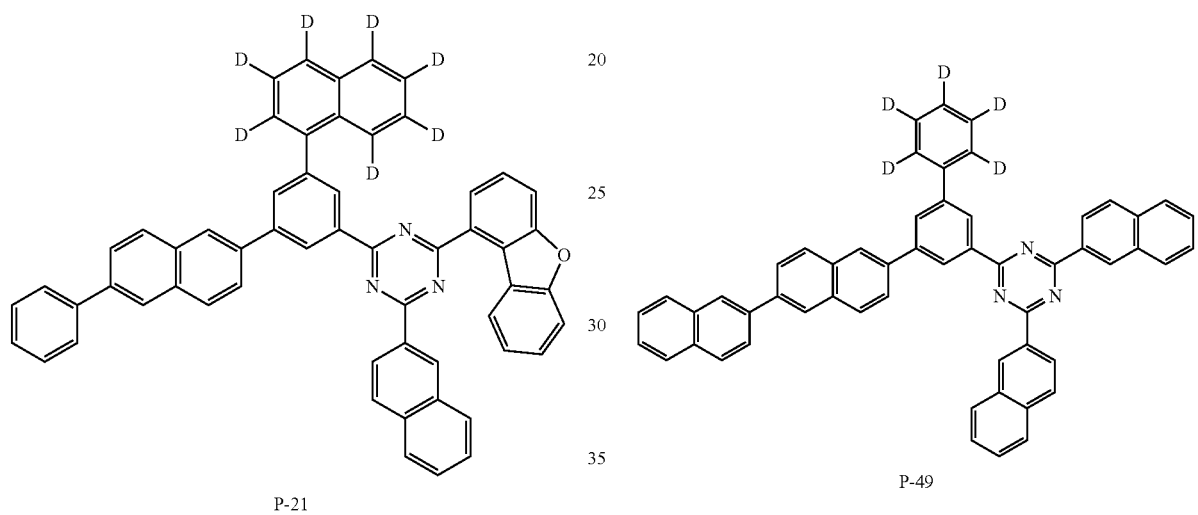

P-21

P-49

Sub1-3 (15.00 g, 27.80 mmol), Sub2-18 (11.34 g, 27.80 mmol) were dissolved in THF (140 mL) in a round bottom flask, and NaOH (2.22 g, 55.60 mmol), Pd(PPh₃)₄ (0.64 g, 0.56 mmol), water (45 ml) were added, and 19.14 g (yield: 87.7%) of a product was obtained using the method for synthesizing P-1.

3. Synthesis Example of P-49

Sub1-2 (15.00 g, 27.91 mmol), Sub2-40 (10.26 g, 27.91 mmol) were dissolved in THF (140 mL) in a round bottom flask, and NaOH (2.23 g, 55.81 mmol), Pd(PPh₃)₄ (0.64 g, 0.56 mmol), water (45 ml) were added, and 16.79 g (yield: 81.0%) of a product was obtained using the method for synthesizing P-1.

4. Synthesis Example of P-56

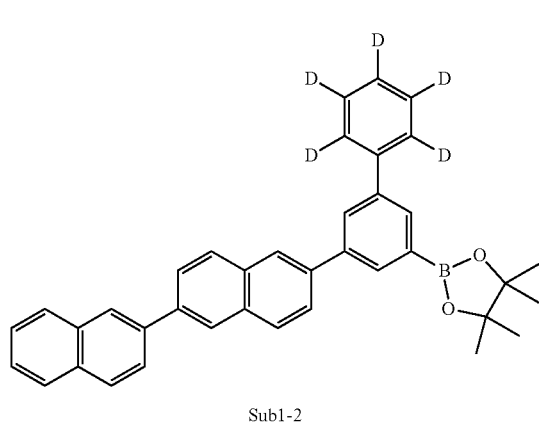

Sub1-2

+

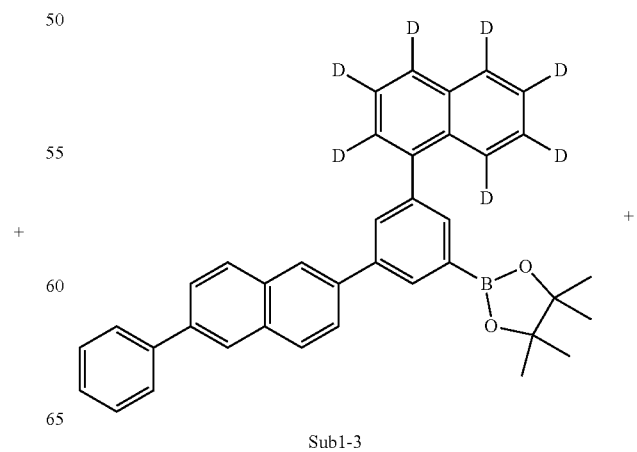

Sub1-3

+

5. Synthesis Example of P-69
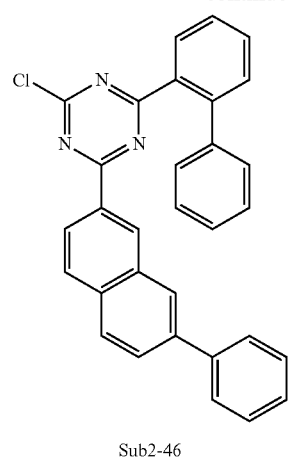
Sub2-46
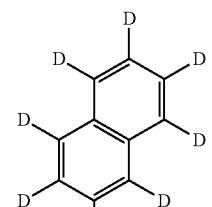
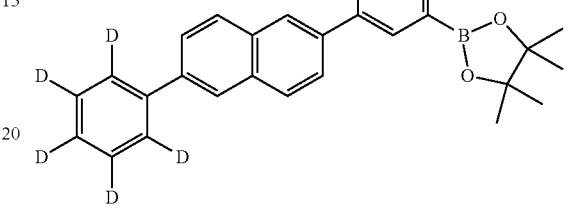
Sub1-8
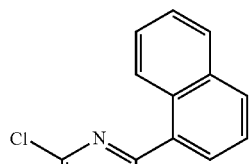
Sub2-58
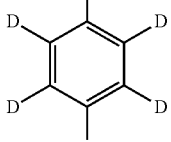
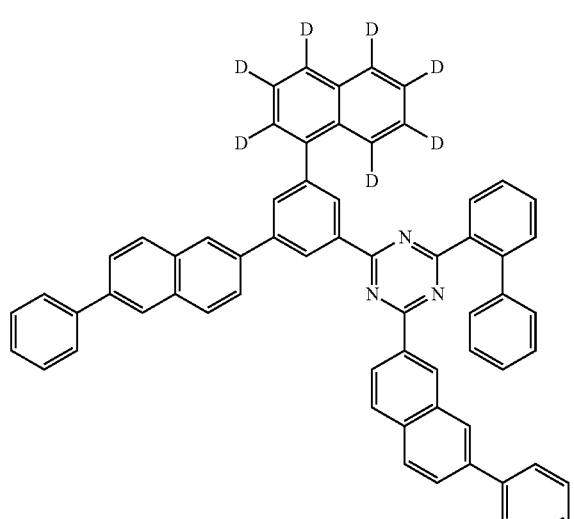
P-56
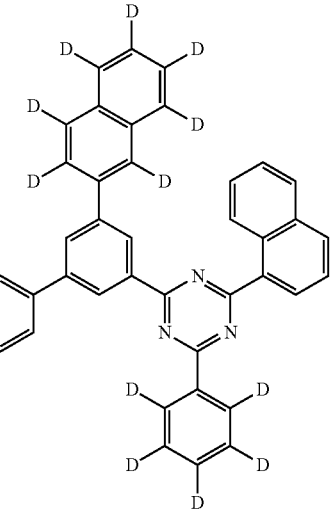
P-69
Sub1-3 (15.00 g, 27.80 mmol), Sub2-46 (13.07 g, 27.80 mmol) were dissolved in THF (140 mL) in a round bottom flask, and NaOH (2.23 g, 55.60 mmol), Pd(PPh$_3$)$_4$ (0.64 g, 0.56 mmol), water (45 ml) were added, and 19.19 g (yield: 81.5%) of a product was obtained using the method for synthesizing P-1.
Sub1-8 (15.00 g, 27.55 mmol), Sub2-58 (8.89 g, 27.55 mmol) were dissolved in THF (135 mL) in a round bottom flask, and, NaOH (2.20 g, 55.09 mmol), Pd(PPh$_3$)$_4$ (0.64 g, 0.55 mmol), water (40 ml) were added, and 15.34 g (yield: 79.0%) of a product was obtained using the method for synthesizing P-1.

Meanwhile, the FD-MS values of the compounds P-1 to P-76 of the present invention prepared according to the Synthesis Example as described above are shown in Table 3.

TABLE 3

| Compound | FD-MS |
|---|---|
| P-1 | m/z = 592.27($C_{43}H_{24}D_5N_3$ = 592.76) |
| P-2 | m/z = 668.30($C_{49}H_{28}D_5N_3$ = 668.85) |
| P-3 | m/z = 718.31($C_{53}H_{30}D_5N_3$ = 718.91) |
| P-4 | m/z = 692.30($C_{51}H_{28}D_5N_3$ = 692.88) |
| P-5 | m/z = 642.28($C_{47}H_{26}D_5N_3$ = 642.82) |
| P-6 | m/z = 718.31($C_{53}H_{30}D_5N_3$ = 718.91) |
| P-7 | m/z = 692.30($C_{51}H_{28}D_5N_3$ = 692.88) |
| P-8 | m/z = 768.33($C_{57}H_{32}D_5N_3$ = 768.97) |
| P-9 | m/z = 644.30($C_{47}H_{24}D_7N_3$ = 644.83) |
| P-10 | m/z = 796.36($C_{59}H_{32}D_7N_3$ = 797.02) |
| P-11 | m/z = 820.36($C_{61}H_{32}D_7N_3$ = 821.05) |
| P-12 | m/z = 694.31($C_{51}H_{26}D_7N_3$ = 694.89) |
| P-13 | m/z = 644.30($C_{47}H_{24}D_7N_3$ = 644.83) |
| P-14 | m/z = 794.34($C_{59}H_{30}D_7N_3$ = 795.01) |
| P-15 | m/z = 796.36($C_{59}H_{32}D_7N_3$ = 797.02) |
| P-16 | m/z = 720.33($C_{53}H_{28}D_7N_3$ = 720.93) |
| P-17 | m/z = 682.28($C_{49}H_{26}D_5N_3O$ = 682.84) |
| P-18 | m/z = 758.31($C_{55}H_{30}D_5N_3O$ = 758.94) |
| P-19 | m/z = 758.31($C_{55}H_{30}D_5N_3O$ = 758.94) |
| P-20 | m/z = 732.29($C_{53}H_{28}D_5N_3O$ = 732.90) |
| P-21 | m/z = 784.32($C_{57}H_{28}D_7N_3O$ = 784.97) |
| P-22 | m/z = 710.34($C_{59}H_{30}D_7N_3O$ = 811.01) |
| P-23 | m/z = 860.35($C_{63}H_{32}D_7N_3O$ = 861.07) |
| P-24 | m/z = 784.32($C_{57}H_{28}D_7N_3O$ = 784.97) |
| P-25 | m/z = 826.31($C_{59}H_{30}D_7N_3S$ = 827.07) |
| P-26 | m/z = 850.31($C_{61}H_{30}D_7N_3S$ = 851.09) |
| P-27 | m/z = 902.35($C_{65}H_{34}D_7N_3S$ = 903.17) |
| P-28 | m/z = 834.34($C_{61}H_{30}D_7N_3O$ = 835.03) |
| P-29 | m/z = 757.33($C_{55}H_{31}D_5N_4$ = 757.95) |
| P-30 | m/z = 757.33($C_{55}H_{31}D_5N_4$ = 757.95) |
| P-31 | m/z = 859.37($C_{63}H_{33}D_7N_4$ = 860.08) |
| P-32 | m/z = 935.40($C_{69}H_{37}D_7N_4$ = 936.18) |
| P-33 | m/z = 770.34($C_{57}H_{30}D_7N_3$ = 770.99) |
| P-34 | m/z = 770.34($C_{57}H_{30}D_7N_3$ = 770.99) |
| P-35 | m/z = 820.36($C_{61}H_{32}D_7N_3$ = 821.05) |
| P-36 | m/z = 820.36($C_{61}H_{32}D_7N_3$ = 821.05) |
| P-37 | m/z = 694.31($C_{51}H_{26}D_7N_3$ = 694.89) |
| P-38 | m/z = 694.31($C_{51}H_{26}D_7N_3$ = 694.89) |
| P-39 | m/z = 744.33($C_{55}H_{28}D_7N_3$ = 744.95) |
| P-40 | m/z = 820.36($C_{61}H_{32}D_7N_3$ = 821.05) |
| P-41 | m/z = 784.32($C_{57}H_{28}D_7N_3O$ = 784.97) |
| P-42 | m/z = 800.30($C_{57}H_{28}D_7N_3S$ = 801.03) |
| P-43 | m/z = 820.36($C_{61}H_{32}D_7N_3$ = 821.05) |
| P-44 | m/z = 800.30($C_{57}H_{28}D_7N_3S$ = 801.03) |
| P-45 | m/z = 744.33($C_{55}H_{28}D_7N_3$ = 744.95) |
| P-46 | m/z = 718.31($C_{53}H_{30}D_5N_3$ = 718.91) |
| P-47 | m/z = 742.31($C_{55}H_{30}D_5N_3$ = 742.94) |
| P-48 | m/z = 768.33($C_{57}H_{32}D_5N_3$ = 768.97) |
| P-49 | m/z = 742.31($C_{55}H_{30}D_5N_3$ = 742.94) |
| P-50 | m/z = 794.34($C_{59}H_{30}D_7N_3$ = 795.01) |
| P-51 | m/z = 794.34($C_{59}H_{30}D_7N_3$ = 795.01) |
| P-52 | m/z = 768.33($C_{57}H_{32}D_5N_3$ = 768.97) |
| P-53 | m/z = 846.37($C_{63}H_{34}D_7N_3$ = 847.08) |
| P-54 | m/z = 820.36($C_{61}H_{32}D_7N_3$ = 821.05) |
| P-55 | m/z = 744.33($C_{55}H_{28}D_7N_3$ = 744.95) |
| P-56 | m/z = 846.37($C_{63}H_{34}D_7N_3$ = 847.08) |
| P-57 | m/z = 824.32($C_{59}H_{28}D_7N_3O_2$ = 824.99) |
| P-58 | m/z = 840.29($C_{59}H_{28}D_7N_3OS$ = 841.05) |
| P-59 | m/z = 899.36($C_{65}H_{33}DN_4O$ = 900.10) |
| P-60 | m/z = 916.33($C_{65}H_{32}DN_3OS$ = 917.15) |
| P-61 | m/z = 603.34($C_{43}H_{13}D_{16}N_3$ = 603.82) |
| P-62 | m/z = 677.36($C_{49}H_{19}D_{14}N_3$ = 677.91) |
| P-63 | m/z = 762.44($C_{55}H_{14}D_{23}N_3$ = 763.06) |
| P-64 | m/z = 701.36($C_{51}H_{19}D_{14}N_3$ = 701.93) |
| P-65 | m/z = 725.36($C_{53}H_{23}D_{12}N_3$ = 725.96) |
| P-66 | m/z = 777.39($C_{57}H_{23}D_{14}N_3$ = 778.03) |

TABLE 3-continued

| Compound | FD-MS |
|---|---|
| P-67 | m/z = 689.32($C_{49}H_{19}D_{12}N_3O$ = 689.88) |
| P-68 | m/z = 785.36($C_{55}H_{19}D_{16}N_3S$ = 786.06) |
| P-69 | m/z = 704.37($C_{51}H_{16}D_{17}N_3$ = 704.95) |
| P-70 | m/z = 711.42($C_{51}H_9D_{24}N_3$ = 711.99) |
| P-71 | m/z = 762.44($C_{55}H_{14}D_{23}N_3$ = 763.06) |
| P-72 | m/z = 788.46($C_{57}H_{12}D_{25}N_3$ = 789.10) |
| P-73 | m/z = 868.47($C_{59}D_{35}N_3OS$ = 869.22) |
| P-74 | m/z = 748.50($C_{53}D_{35}N_3$ = 749.10) |
| P-75 | m/z = 788.50($C_{55}D_{35}N_3O$ = 789.12) |
| P-76 | m/z = 772.50($C_{55}D_{35}N_3$ = 773.12) |

Synthesis Example 2

1. Synthesis Example of N-12

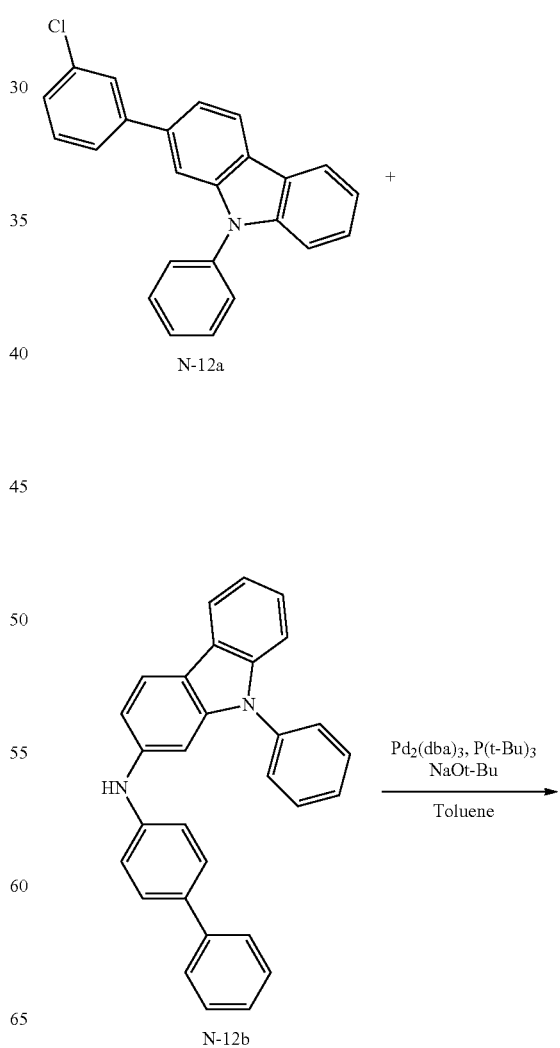

-continued

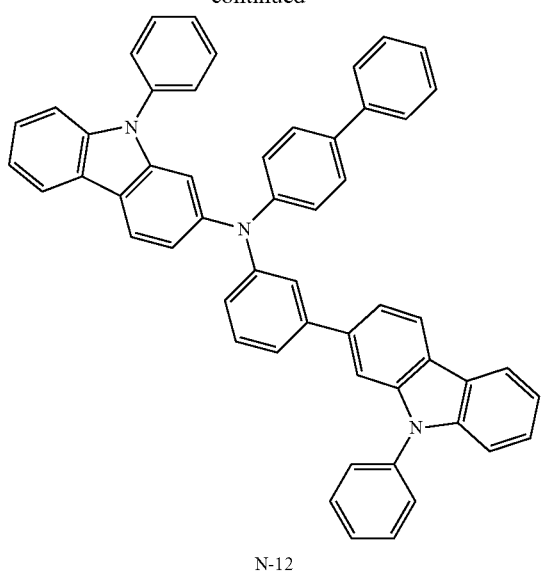

N-12

N-12a (30 g, 0.08 mol), N-12b (34.8 g, 0.08 mol), Pd$_2$(dba)$_3$ (2.3 g, 0.003 mol), NaOt-Bu (24.5 g, 0.25 mol), P(t-Bu)$_3$ (2.1 g, 0.005 mol), Toluene (170 mL) were added and reacted at 135° C. for 6 hours. When the reaction was completed, 53 g (85.8%) of product N-12 was obtained using the separation method of P-1.

2. Synthesis Example of N-19

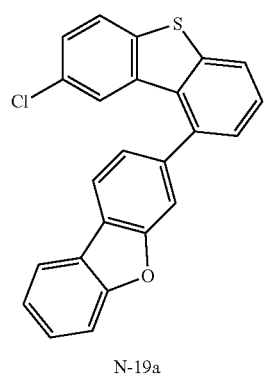

N-19a

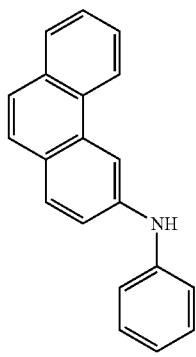

N-19b

-continued

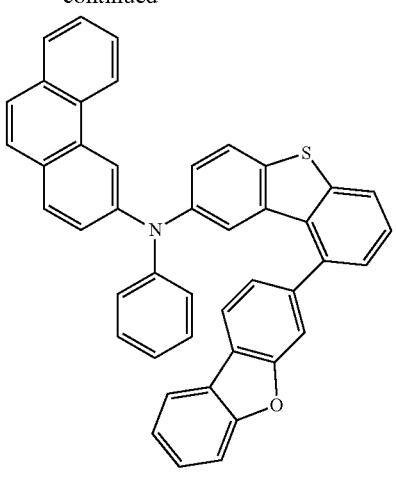

N-19

N-19a (50 g, 0.13 mol), N-19b (35 g, 0.13 mol), Pd$_2$(dba)$_3$ (3.6 g, 0.004 mol), NaOt-Bu (37.6 g, 0.40 mol), P(t-Bu)$_3$ (3.2 g, 0.008 mol), Toluene (260 mL) were added and reacted at 135° C. for 6 hours. When the reaction was completed, 67 ag (83.4%) of product N-19 was obtained using the separation method of P-1.

3. Synthesis Example of S-32

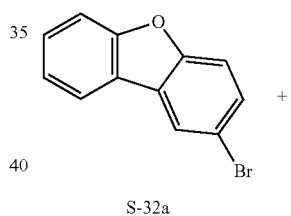

S-32a

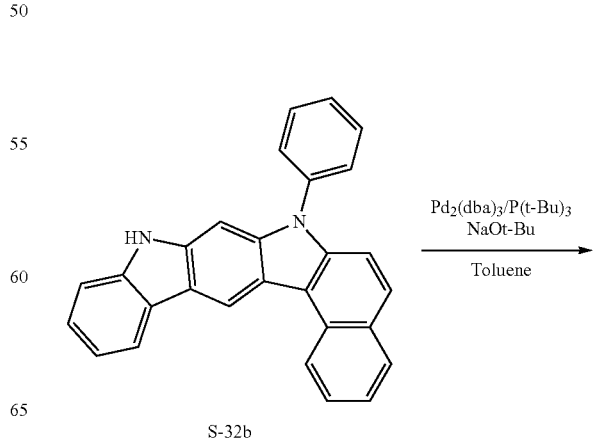

S-32b

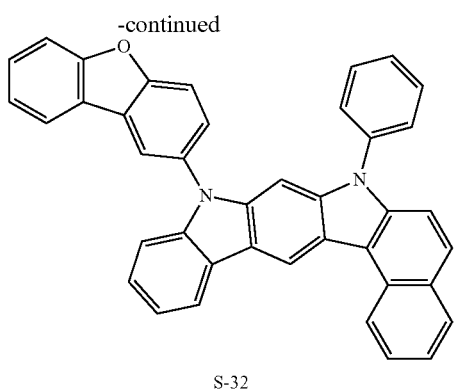

S-32

S-32a (10 g, 0.04 mol), S-32b (15.6 g, 0.04 mol), Pd$_2$(dba)$_3$ (1.1 g, 0.001 mol), NaOt-Bu (11.7 g, 0.12 mol), P(t-Bu)$_3$ (1.0 g, 0.002 mol), Toluene (80 mL) were added and reacted at 135° C. for 6 hours. When the reaction was completed, 18 g (80.8%) of product S-32 was obtained using the separation method of P-1.

4. Synthesis Example of S-74

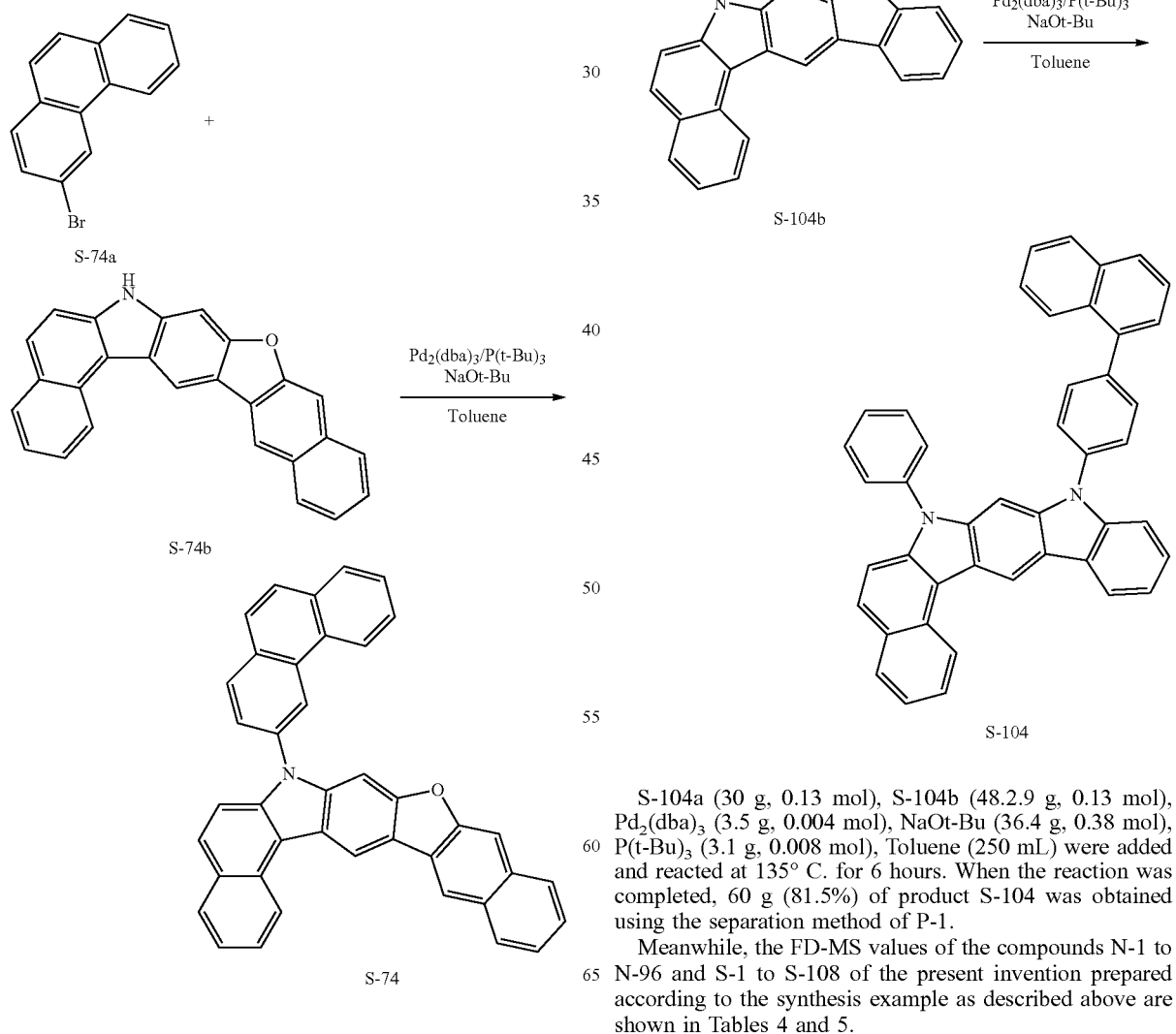

S-74a (15 g, 0.06 mol), S-74b (20.9 g, 0.06 mol), Pd$_2$(dba)$_3$ (1.6 g, 0.002 mol), NaOt-Bu (16.9 g, 0.18 mol), P(t-Bu)$_3$ (1.4 g, 0.004 mol), Toluene (120 mL) were added and reacted at 135° C. for 6 hours. When the reaction was completed, 27 g (86.4%) of product S-74 was obtained using the separation method of P-1.

5. Synthesis of S-104

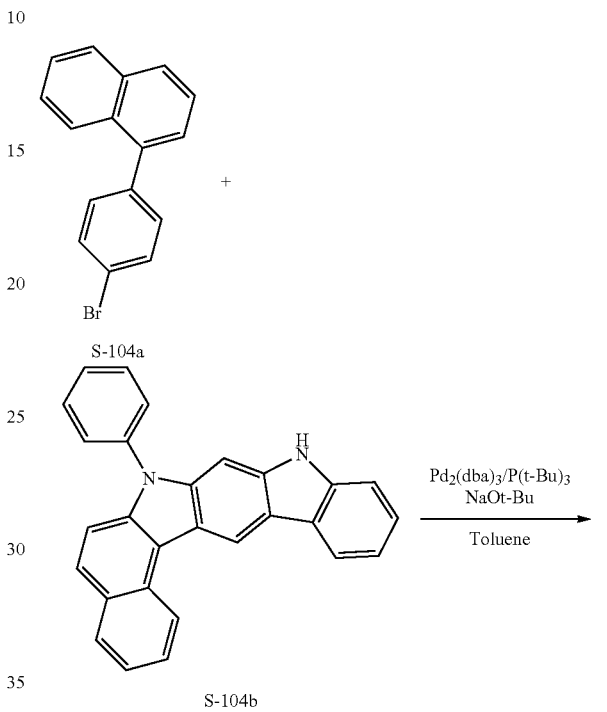

S-104a (30 g, 0.13 mol), S-104b (48.2.9 g, 0.13 mol), Pd$_2$(dba)$_3$ (3.5 g, 0.004 mol), NaOt-Bu (36.4 g, 0.38 mol), P(t-Bu)$_3$ (3.1 g, 0.008 mol), Toluene (250 mL) were added and reacted at 135° C. for 6 hours. When the reaction was completed, 60 g (81.5%) of product S-104 was obtained using the separation method of P-1.

Meanwhile, the FD-MS values of the compounds N-1 to N-96 and S-1 to S-108 of the present invention prepared according to the synthesis example as described above are shown in Tables 4 and 5.

TABLE 4

| Compound | FD-MS |
| --- | --- |
| N-1 | m/z = 487.19($C_{36}H_{25}NO$ = 487.6) |
| N-2 | m/z = 553.19($C_{40}H_{27}NS$ = 553.72) |
| N-3 | m/z = 563.26($C_{43}H_{33}N$ = 563.74) |
| N-4 | m/z = 602.27($C_{45}H_{34}N_2$ = 602.78) |
| N-5 | m/z = 517.15($C_{36}H_{23}NOS$ = 517.65) |
| N-6 | m/z = 603.2($C_{44}H_{29}NS$ = 603.78) |
| N-7 | m/z = 735.29($C_{57}H_{37}N$ = 735.93) |
| N-8 | m/z = 562.24($C_{42}H_{30}N_2$ = 562.72) |
| N-9 | m/z = 565.17($C_{40}H_{23}NO_3$ = 565.63) |
| N-10 | m/z = 581.14($C_{40}H_{23}NO_2S$ = 581.69) |
| N-11 | m/z = 823.24($C_{59}H_{37}NS_2$ = 824.07) |
| N-12 | m/z = 727.3($C_{54}H_{37}N_3$ = 727.91) |
| N-13 | m/z = 627.22($C_{46}H_{29}NO_2$ = 627.74) |
| N-14 | m/z = 633.16($C_{44}H_{27}NS_2$ = 633.83) |
| N-15 | m/z = 675.29($C_{52}H_{37}N$ = 675.88) |
| N-16 | m/z = 678.3($C_{51}H_{38}N_2$ = 678.88) |
| N-17 | m/z = 669.21($C_{48}H_{31}NOS$ = 669.84) |
| N-18 | m/z = 785.22($C_{56}H_{35}NS_2$ = 786.02) |
| N-19 | m/z = 617.18($C_{44}H_{27}NOS$ = 617.77) |
| N-20 | m/z = 601.2($C_{44}H_{27}NO_2$ = 601.71) |
| N-21 | m/z = 779.32($C_{59}H_{41}NO$ = 779.98) |
| N-22 | m/z = 583.23($C_{42}H_{33}NS$ = 583.79) |
| N-23 | m/z = 679.32($C_{52}H_{41}N$ = 679.91) |
| N-24 | m/z = 726.27($C_{54}H_{34}N_2O$ = 726.88) |
| N-25 | m/z = 593.18($C_{42}H_{27}NOS$ = 593.74) |
| N-26 | m/z = 774.22($C_{54}H_{34}N_2S_2$ = 775) |
| N-27 | m/z = 557.24($C_{40}H_{31}NO_2$ = 557.69) |
| N-28 | m/z = 652.25($C_{48}H_{32}N_2O$ = 652.8) |
| N-29 | m/z = 619.29($C_{46}H_{37}NO$ = 619.81) |
| N-30 | m/z = 603.2($C_{44}H_{29}NS$ = 603.78) |
| N-31 | m/z = 813.3($C_{62}H_{39}NO$ = 814) |
| N-32 | m/z = 784.29($C_{57}H_{40}N_2S$ = 785.02) |
| N-33 | m/z = 577.2($C_{42}H_{27}NO_2$ = 577.68) |
| N-34 | m/z = 607.14($C_{42}H_{25}NS_2$ = 607.79) |
| N-35 | m/z = 801.34($C_{62}H_{43}N$ = 802.03) |
| N-36 | m/z = 575.24($C_{42}H_{29}N_3$ = 575.72) |
| N-37 | m/z = 577.2($C_{42}H_{27}NO_2$ = 577.68) |
| N-38 | m/z = 607.14($C_{42}H_{25}NS_2$ = 607.79) |
| N-39 | m/z = 801.34($C_{62}H_{43}N$ = 802.03) |
| N-40 | m/z = 575.24($C_{42}H_{29}N_3$ = 575.72) |
| N-41 | m/z = 601.2($C_{44}H_{27}NO_2$ = 601.71) |
| N-42 | m/z = 471.11($C_{31}H_{21}NS_2$ = 471.64) |
| N-43 | m/z = 675.29($C_{52}H_{37}N$ = 675.88) |
| N-44 | m/z = 727.3($C_{54}H_{37}N_3$ = 727.91) |
| N-45 | m/z = 603.2($C_{44}H_{29}NS$ = 603.78) |
| N-46 | m/z = 561.16($C_{38}H_{27}NS_2$ = 561.76) |
| N-47 | m/z = 799.32($C_{62}H_{41}N$ = 800.02) |
| N-48 | m/z = 702.27($C_{52}H_{34}N_2O$ = 702.86) |
| N-49 | m/z = 729.27($C_{54}H_{35}NO_2$ = 729.88) |
| N-50 | m/z = 785.22($C_{56}H_{35}NS_2$ = 786.02) |
| N-51 | m/z = 812.32($C_{62}H_{40}N_2$ = 813.02) |
| N-52 | m/z = 681.22($C_{48}H_{31}N_3S$ = 681.86) |
| N-53 | m/z = 615.18($C_{44}H_{25}NO_3$ = 615.69) |
| N-54 | m/z = 763.15($C_{52}H_{29}NS_3$ = 763.99) |
| N-55 | m/z = 593.31($C_{45}H_{39}N$ = 593.81) |
| N-56 | m/z = 840.33($C_{62}H_{40}N_4$ = 841.03) |
| N-57 | m/z = 657.18($C_{46}H_{27}NO_2S$ = 657.79) |
| N-58 | m/z = 824.23($C_{58}H_{36}N_2S_2$ = 825.06) |
| N-59 | m/z = 1195.42($C_{91}H_{57}NS$ = 1196.52) |
| N-60 | m/z = 656.19($C_{46}H_{28}N_2OS$ = 656.8) |
| N-61 | m/z = 607.16($C_{42}H_{25}NO_2S$ = 607.73) |
| N-62 | m/z = 773.2($C_{54}H_{31}NO_3S$ = 773.91) |
| N-63 | m/z = 1013.4($C_{79}H_{51}N$ = 1014.28) |
| N-64 | m/z = 758.24($C_{54}H_{34}N_2OS$ = 758.94) |
| N-65 | m/z = 623.14($C_{42}H_{25}NOS_2$ = 623.79) |
| N-66 | m/z = 763.16($C_{52}H_{29}NO_2S$ = 763.93) |
| N-67 | m/z = 799.2($C_{56}H_{33}NOS_2$ = 800.01) |
| N-68 | m/z = 743.23($C_{54}H_{33}NOS$ = 743.92) |
| N-69 | m/z = 872.25($C_{62}H_{36}N_2O_2S$ = 873.04) |
| N-70 | m/z = 772.22($C_{54}H_{32}N_2O_2S$ = 772.92) |
| N-71 | m/z = 830.28($C_{61}H_{38}N_2S$ = 831.05) |
| N-72 | m/z = 808.25($C_{58}H_{33}FN_2O_2$ = 808.91) |
| N-73 | m/z = 929.21($C_{64}H_{35}NO_3S_2$ = 930.11) |
| N-74 | m/z = 963.27($C_{68}H_{41}N_3S$ = 964.22) |
| N-75 | m/z = 809.24($C_{58}H_{35}NO_2S$ = 809.98) |
| N-76 | m/z = 893.29($C_{66}H_{39}NO_3$ = 894.04) |
| N-77 | m/z = 794.28($C_{58}H_{38}N_2S$ = 795.02) |
| N-78 | m/z = 900.26($C_{64}H_{40}N_2S_2$ = 901.16) |
| N-79 | m/z = 758.28($C_{55}H_{38}N_2S$ = 758.98) |
| N-80 | m/z = 1082.37($C_{81}H_{50}N_2S$ = 1083.37) |
| N-81 | m/z = 573.25($C_{44}H_{31}N$ = 573.74) |
| N-82 | m/z = 649.28($C_{50}H_{35}N$ = 649.84) |
| N-83 | m/z = 699.29($C_{54}H_{37}N$ = 699.9) |
| N-84 | m/z = 699.29($C_{54}H_{37}N$ = 699.9) |
| N-85 | m/z = 673.28($C_{52}H_{35}N$ = 673.86) |
| N-86 | m/z = 649.28($C_{50}H_{35}N$ = 649.84) |
| N-87 | m/z = 625.28($C_{48}H_{35}N$ = 625.82) |
| N-88 | m/z = 673.28($C_{52}H_{35}N$ = 673.86) |
| N-89 | m/z = 773.31($C_{60}H_{39}N$ = 773.98) |
| N-90 | m/z = 749.31($C_{58}H_{39}N$ = 749.96) |
| N-91 | m/z = 699.29($C_{54}H_{37}N$ = 699.9) |
| N-92 | m/z = 599.26($C_{46}H_{33}N$ = 599.78) |
| N-93 | m/z = 639.26($C_{48}H_{33}NO$ = 639.8) |
| N-94 | m/z = 765.25($C_{57}H_{35}NS$ = 765.97) |
| N-95 | m/z = 677.31($C_{52}H_{39}N$ = 677.89) |
| N-96 | m/z = 727.3($C_{54}H_{37}N_3$ = 727.91) |

TABLE 5

| Compound | FD-MS |
| --- | --- |
| S-1 | m/z = 408.16($C_{30}H_{20}N_2$ = 408.5) |
| S-2 | m/z = 534.21($C_{40}H_{26}N_2$ = 534.66) |
| S-3 | m/z = 560.23($C_{42}H_{28}N_2$ = 560.7) |
| S-4 | m/z = 584.23($C_{44}H_{28}N_2$ = 584.72) |
| S-5 | m/z = 560.23($C_{42}H_{28}N_2$ = 560.7) |
| S-6 | m/z = 634.24($C_{48}H_{30}N_2$ = 634.78) |
| S-7 | m/z = 610.24($C_{46}H_{30}N_2$ = 610.76) |
| S-8 | m/z = 498.17($C_{36}H_{22}N_2O$ = 498.59) |
| S-9 | m/z = 574.2($C_{42}H_{26}N_2O$ = 574.68) |
| S-10 | m/z = 660.26($C_{50}H_{32}N_2$ = 660.82) |
| S-11 | m/z = 686.27($C_{52}H_{34}N_2$ = 686.86) |
| S-12 | m/z = 620.14($C_{42}H_{24}N_2S_2$ = 620.79) |
| S-13 | m/z = 640.2($C_{46}H_{28}N_2S$ = 640.8) |
| S-14 | m/z = 560.23($C_{42}H_{28}N_2$ = 560.7) |
| S-15 | m/z = 558.21($C_{42}H_{26}N_2$ = 558.68) |
| S-16 | m/z = 548.19($C_{40}H_{24}N_2O$ = 548.65) |
| S-17 | m/z = 573.22($C_{42}H_{27}N_3$ = 573.7) |
| S-18 | m/z = 564.17($C_{40}H_{24}N_2S$ = 564.71) |
| S-19 | m/z = 574.2($C_{42}H_{26}N_2O$ = 574.68) |
| S-20 | m/z = 564.17($C_{40}H_{24}N_2S$ = 564.71) |
| S-21 | m/z = 564.17($C_{40}H_{24}N_2S$ = 564.71) |
| S-22 | m/z = 813.31($C_{61}H_{39}N_3$ = 814) |
| S-23 | m/z = 696.26($C_{53}H_{32}N_2$ = 696.85) |
| S-24 | m/z = 691.23($C_{49}H_{29}N_3O_2$ = 691.79) |
| S-25 | m/z = 710.27($C_{54}H_{34}N_2$ = 710.88) |
| S-26 | m/z = 610.24($C_{46}H_{30}N_2$ = 610.76) |
| S-27 | m/z = 670.15($C_{46}H_{26}N_2S_2$ = 670.85) |
| S-28 | m/z = 640.29($C_{48}H_{36}N_2$ = 640.83) |
| S-29 | m/z = 598.2($C_{44}H_{26}N_2O$ = 598.71) |
| S-30 | m/z = 623.24($C_{46}H_{29}N_3$ = 623.76) |
| S-31 | m/z = 458.18($C_{34}H_{22}N_2$ = 458.56) |
| S-32 | m/z = 548.19($C_{40}H_{24}N_2O$ = 548.65) |
| S-33 | m/z = 508.19($C_{38}H_{24}N_2$ = 508.62) |
| S-34 | m/z = 508.19($C_{38}H_{24}N_2$ = 508.62) |
| S-35 | m/z = 623.24($C_{46}H_{29}N_3$ = 623.76) |
| S-36 | m/z = 564.17($C_{40}H_{24}N_2S$ = 564.71) |
| S-37 | m/z = 627.2($C_{46}H_{29}NS$ = 627.81) |
| S-38 | m/z = 505.1($C_{34}H_{19}NS_2$ = 505.65) |
| S-39 | m/z = 514.15($C_{36}H_{22}N_2S$ = 514.65) |
| S-40 | m/z = 575.17($C_{42}H_{25}NS$ = 575.73) |
| S-41 | m/z = 642.21($C_{46}H_{30}N_2S$ = 642.82) |
| S-42 | m/z = 575.17($C_{42}H_{25}NS$ = 575.73) |
| S-43 | m/z = 606.18($C_{42}H_{26}N_2OS$ = 606.74) |
| S-44 | m/z = 575.17($C_{42}H_{25}NS$ = 575.73) |
| S-45 | m/z = 551.17($C_{40}H_{25}NS$ = 551.71) |
| S-46 | m/z = 607.14($C_{42}H_{25}NS_2$ = 607.79) |
| S-47 | m/z = 525.16($C_{38}H_{23}NS$ = 525.67) |
| S-48 | m/z = 642.21($C_{46}H_{30}N_2S$ = 642.82) |
| S-49 | m/z = 548.19($C_{40}H_{24}N_2O$ = 548.65) |
| S-50 | m/z = 473.14($C_{34}H_{19}NO_2$ = 473.53) |
| S-51 | m/z = 566.15($C_{39}H_{22}N_2OS$ = 566.68) |
| S-52 | m/z = 459.16($C_{34}H_{21}NO$ = 459.55) |

TABLE 5-continued

| Compound | FD-MS |
|---|---|
| S-53 | m/z = 473.14($C_{34}H_{19}NO_2$ = 473.53) |
| S-54 | m/z = 523.16($C_{38}H_{21}NO_2$ = 523.59) |
| S-55 | m/z = 539.13($C_{38}H_{21}NOS$ = 539.65) |
| S-56 | m/z = 548.19($C_{40}H_{24}N_2O$ = 548.65) |
| S-57 | m/z = 489.12($C_{34}H_{19}NOS$ = 489.59) |
| S-58 | m/z = 545.09($C_{36}H_{19}NOS_2$ = 545.67) |
| S-59 | m/z = 549.17($C_{40}H_{23}NO_2$ = 549.63) |
| S-60 | m/z = 565.15($C_{40}H_{23}NOS$ = 565.69) |
| S-61 | m/z = 523.16($C_{38}H_{21}NO_2$ = 523.59) |
| S-62 | m/z = 598.2($C_{44}H_{26}N_2O$ = 598.71) |
| S-63 | m/z = 539.13($C_{38}H_{21}NOS$ = 539.65) |
| S-64 | m/z = 589.15($C_{42}H_{23}NOS$ = 589.71) |
| S-65 | m/z = 498.17($C_{36}H_{22}N_2O$ = 498.59) |
| S-66 | m/z = 509.18($C_{38}H_{23}NO$ = 509.61) |
| S-67 | m/z = 548.19($C_{40}H_{24}N_2O$ = 548.65) |
| S-68 | m/z = 549.17($C_{40}H_{23}NO_2$ = 549.63) |
| S-69 | m/z = 449.12($C_{32}H_{19}NS$ = 449.57) |
| S-70 | m/z = 439.1($C_{30}H_{17}NOS$ = 439.53) |
| S-71 | m/z = 647.22($C_{49}H_{29}NO$ = 647.78) |
| S-72 | m/z = 717.28($C_{52}H_{35}N_3O$ = 717.87) |
| S-73 | m/z = 459.16($C_{34}H_{21}NO$ = 459.55) |
| S-74 | m/z = 533.18($C_{40}H_{23}NO$ = 533.63) |
| S-75 | m/z = 525.16($C_{38}H_{23}NS$ = 525.67) |
| S-76 | m/z = 564.17($C_{40}H_{24}N_2S$ = 564.71) |
| S-77 | m/z = 575.19($C_{42}H_{25}NO_2$ = 575.67) |
| S-78 | m/z = 663.22($C_{49}H_{29}NO_2$ = 663.78) |
| S-79 | m/z = 647.22($C_{49}H_{29}NO$ = 647.78) |
| S-80 | m/z = 496.16($C_{36}H_{20}N_2O$ = 496.57) |
| S-81 | m/z = 565.15($C_{40}H_{23}NOS$ = 565.69) |
| S-82 | m/z = 505.1($C_{34}H_{19}NS_2$ = 505.65) |
| S-83 | m/z = 765.25($C_{56}H_{35}NOSi$ = 765.99) |
| S-84 | m/z = 615.17($C_{44}H_{25}NOS$ = 615.75) |
| S-85 | m/z = 603.17($C_{43}H_{25}NOS$ = 603.74) |
| S-86 | m/z = 772.29($C_{59}H_{36}N_2$ = 772.95) |
| S-87 | m/z = 802.33($C_{61}H_{42}N_2$ = 803.02) |
| S-88 | m/z = 607.23($C_{47}H_{29}N$ = 607.76) |
| S-89 | m/z = 524.23($C_{39}H_{28}N_2$ = 524.67) |
| S-90 | m/z = 665.22($C_{49}H_{31}NS$ = 665.85) |
| S-91 | m/z = 633.25($C_{49}H_{31}N$ = 633.79) |
| S-92 | m/z = 775.29($C_{59}H_{37}NO$ = 775.95) |
| S-93 | m/z = 535.23($C_{41}H_{29}N$ = 535.69) |
| S-94 | m/z = 623.22($C_{47}H_{29}NO$ = 623.76) |
| S-95 | m/z = 687.2($C_{51}H_{29}NS$ = 687.86) |
| S-96 | m/z = 735.29($C_{57}H_{37}N$ = 735.93) |
| S-97 | m/z = 611.26($C_{47}H_{33}N$ = 611.79) |
| S-98 | m/z = 679.23($C_{50}H_{33}NS$ = 679.88) |
| S-99 | m/z = 787.32($C_{61}H_{41}N$ = 788.01) |
| S-100 | m/z = 743.33($C_{55}H_{41}N_3$ = 743.95) |
| S-101 | m/z = 485.21($C_{37}H_{27}N$ = 485.63) |
| S-102 | m/z = 471.2($C_{36}H_{25}N$ = 471.6) |
| S-103 | m/z = 571.19($C_{43}H_{25}NO$ = 571.68) |
| S-104 | m/z = 584.23($C_{44}H_{28}N_2$ = 584.72) |
| S-105 | m/z = 539.24($C_{40}H_{21}D_5N_2$ = 539.69) |
| S-106 | m/z = 453.15($C_{32}H_{15}NS$ = 471.6) |
| S-107 | m/z = 563.26($C_{43}H_{26}D_4NO$ = 563.74) |
| S-108 | m/z = 589.26($C_{44}H_{23}D_5N_2$ = 584.72) |

Otherwise, the synthesis examples of the present invention represented by the Formulas 1 to 4 have been described, but these are all based on the Buchwald-Hartwig cross coupling reaction, Miyaura boration reaction, Suzuki cross-coupling reaction, Intramolecular acid-induced cyclization reaction (*J. mater. Chem.* 1999, 9, 2095.), Pd(II)-catalyzed oxidative cyclization reaction (*Org. Lett.* 2011, 13, 5504), and PPh$_3$-mediated reductive cyclization reaction (*J. Org. Chem.* 2005, 70, 5014.), and It will be easily understood by those skilled in the art that the reaction proceeds even when other substituents defined in Formulas 2 to 5 are bonded in addition to the substituents specified in the specific synthesis examples.

[Device Data]

[Example 1] Red Organic Light Emitting Device (Phosphorescent Host)

An organic light emitting device was fabricated according to a conventional method using the compound obtained through synthesis as a light emitting host material for the emitting layer. First, after vacuum depositing N$^1$-(naphthalen-2-yl)-N$^4$, N$^4$-bis(4-(naphthalen-2-yl(phenyl)amino)phenyl)-N$^1$-phenylbenzene-1,4-diamine (hereinafter abbreviated as 2-TNATA) on the ITO layer (anode) formed on the glass substrate to form a hole injection layer with a thickness of 60 nm, as a hole transport compound on the hole injection layer, 4,4-bis[N-(1-naphthyl)-N-phenylamino]biphenyl (hereinafter abbreviated as —NPD) was vacuum deposited to a thickness of 60 nm to form a hole transport layer. An emitting auxiliary layer was formed by vacuum depositing tris(4-(9H-carbazol-9-yl)phenyl)amine (hereinafter abbreviated as TCTA) to a thickness of 10 nm as an emitting auxiliary layer material on top of the hole transport layer. After forming the emitting auxiliary layer, as a host on the emitting auxiliary layer, the present compound P-1 represented by Formula 1 and the present compound N-12 represented by Formula 3 were used in a weight ratio (5:5), and an emitting layer having a thickness of 30 nm was deposited by doping (piq)$_2$Ir(acac) as a dopant material in a weight ratio of 95:5. Next, (1,1'-biphenyl-4-olato)bis(2-methyl-8-quinolinolato)aluminum (hereinafter abbreviated as BAlq) was vacuum deposited to a thickness of 10 nm as a hole blocking layer, and as an electron transport layer, bis(10-hydroxybenzo[h]quinolinato)beryllium (hereinafter, Alq3) was formed to a thickness of 25 nm. Thereafter, LiF, an alkali metal halide, was deposited to a thickness of 0.2 nm as an electron injection layer, and then Al was deposited to a thickness of 150 nm and used as a cathode, thereby manufacturing an organic light emitting device.

[Example 2] to [Example 26]

An organic light emitting device was manufactured in the same manner as in Example 1, except for the fact that the compound of the present invention described in Table 6 was used instead of the compound P-1 of the present invention as the host material of the emitting layer, and except for the fact that the compound of the present invention described in Table 6 was used instead of the compound N-12 of the present invention.

[Comparative Example 1] to [Comparative Example 3]

An organic light emitting device was manufactured in the same manner as in Example 1, except that Comparative Compound A or Comparative Compound C was used instead of the compound P-1 of the present invention as the host material of the emitting layer.

[Comparative Compound A>

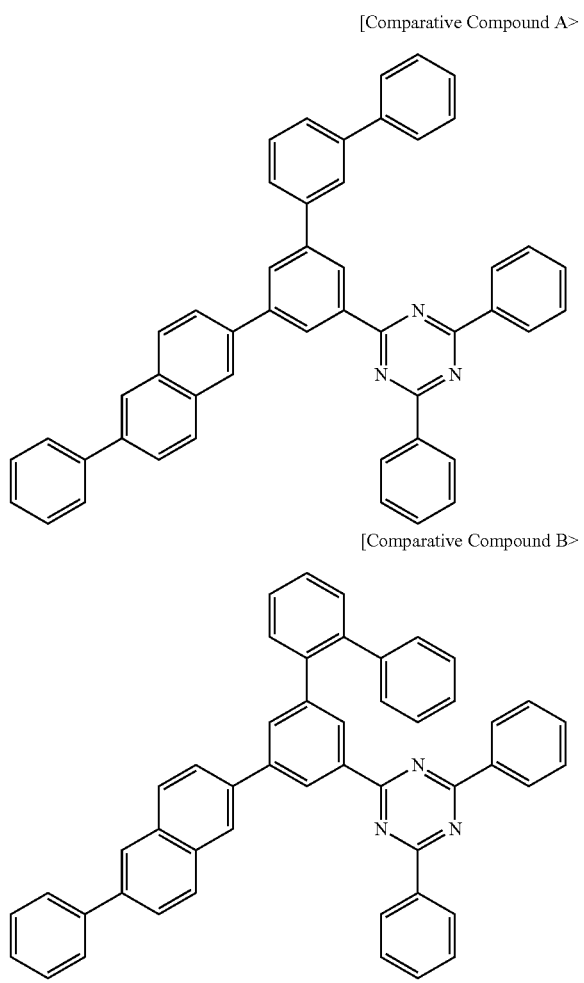

[Comparative Compound B>

[Comparative Compound c>

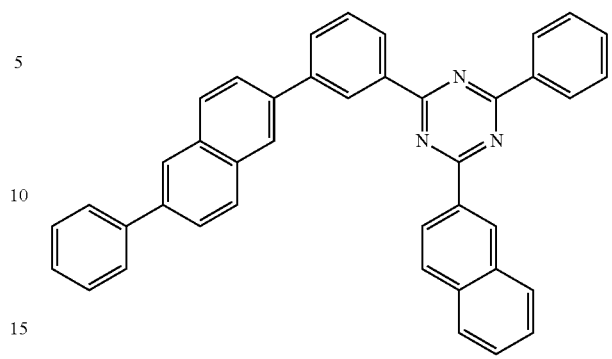

To the organic electroluminescent device manufactured by Examples 1 to 26, Comparative Examples 1 and 3 prepared as describe above, Electroluminescence (EL) characteristics were measured with a PR-650 of Photoresearch Co., by applying a forward bias DC voltage. As a result of the measurement, T95 life was measured at a standard luminance of 2,500 cd/m² through life measuring apparatus manufactured by McScience. Table 6 shows the results of device fabrication and evaluation.

This measuring device is independent form possible day-to-day variations of deposition rates, vacuum quality or other tool performance parameters, and allows assessing performance of new material in comparison with comparative compound under the same conditions.

At the time of assessment, each field contained 4 identically prepared OLEDs including a comparative compound, and since the performance of each of a total of 12 OLEDs in 3 fields is evaluated, the statistical evaluation of the obtained experimental results unequivocally showed the statistical significance.

TABLE 6

| | First compound | Second compound | Voltage | Current Density (mA/cm²) | Efficiency (cd/A) | T(95) |
|---|---|---|---|---|---|---|
| Comparative example 1 | comparative compound A | compound (N-12) | 5.4 | 13.4 | 18.6 | 101.6 |
| Comparative example 2 | comparative compound B | compound (N-12) | 5.6 | 12.7 | 19.7 | 100.3 |
| Comparative example 3 | comparative compound C | compound (N-12) | 5.5 | 13.8 | 18.1 | 103.4 |
| Example 1 | compound (P-1) | compound (N-12) | 5.0 | 9.4 | 26.5 | 108.8 |
| Example 2 | compound (P-4) | compound (N-12) | 5.0 | 9.4 | 26.7 | 109.5 |
| Example 3 | compound (P-5) | compound (N-12) | 4.9 | 9.7 | 25.7 | 107.5 |
| Example 4 | compound (P-9) | compound (N-12) | 5.0 | 9.6 | 26.0 | 107.9 |
| Example 5 | compound (P-13) | compound (N-12) | 4.9 | 9.9 | 25.2 | 106.5 |
| Example 6 | compound (P-17) | compound (N-12) | 5.1 | 9.7 | 25.9 | 112.0 |
| Example 7 | compound (P-29) | compound (N-12) | 5.2 | 10.0 | 25.0 | 106.4 |
| Example 8 | compound (P-37) | compound (N-12) | 4.9 | 9.9 | 25.2 | 106.6 |
| Example 9 | compound (P-38) | compound (N-12) | 4.9 | 10.2 | 24.4 | 105.3 |
| Example 10 | compound (P-61) | compound (N-12) | 5.0 | 9.4 | 26.5 | 109.2 |
| Example 11 | compound (P-70) | compound (N-12) | 5.0 | 9.6 | 26.1 | 108.3 |
| Example 12 | compound (P-1) | compound (N-17) | 4.8 | 9.0 | 27.9 | 115.3 |
| Example 13 | compound (P-5) | compound (N-17) | 4.7 | 9.2 | 27.0 | 113.9 |
| Example 14 | compound (P-9) | compound (N-17) | 4.8 | 9.2 | 27.3 | 114.4 |
| Example 15 | compound (P-13) | compound (N-17) | 4.7 | 9.4 | 26.5 | 112.9 |
| Example 16 | compound (P-17) | compound (N-17) | 4.9 | 9.1 | 27.4 | 118.7 |
| Example 17 | compound (P-1) | compound (S-32) | 4.9 | 9.1 | 27.6 | 119.6 |
| Example 18 | compound (P-5) | compound (S-32) | 4.9 | 9.3 | 26.8 | 118.2 |
| Example 19 | compound (P-9) | compound (S-32) | 4.9 | 9.2 | 27.1 | 118.8 |
| Example 20 | compound (P-13) | compound (S-32) | 4.9 | 9.5 | 26.2 | 117.2 |
| Example 21 | compound (P-17) | compound (S-32) | 5.0 | 9.2 | 27.2 | 123.2 |

TABLE 6-continued

|  | First compound | Second compound | Voltage | Current Density (mA/cm²) | Efficiency (cd/A) | T(95) |
|---|---|---|---|---|---|---|
| Example 22 | compound (P-1) | compound (S-108) | 4.9 | 8.7 | 28.7 | 122.9 |
| Example 23 | compound (P-5) | compound (S-108) | 4.8 | 9.0 | 27.8 | 121.4 |
| Example 24 | compound (P-9) | compound (S-108) | 4.8 | 8.9 | 28.1 | 121.9 |
| Example 25 | compound (P-13) | compound (S-108) | 4.8 | 9.2 | 27.2 | 120.4 |
| Example 26 | compound (P-17) | compound (S-108) | 4.9 | 8.9 | 28.2 | 126.5 |

As can be seen from the results of Table 6, when a red organic light emitting device is manufactured using the material for an organic light emitting device of the present invention as a phosphorescent host material, the compound of the present invention is very excellent in terms of efficiency and exhibits remarkable characteristics compared to the case of using comparative compounds A to C.

As can be seen from the above, it can be seen that a significant difference in characteristics appears depending on the type of the first compound and the second compound, when a host of the emitting layer is formed by mixing a plurality of compounds. Similarly, it shows a difference in driving voltage, efficiency, and lifespan depending on the type of the second compound.

Comparing Comparative Compound C with the compound of the present invention, the compound of the present invention differs from Comparative Compound C in that a deuterium-substituted phenyl group or a deuterium-substituted naphthyl group is further substituted. On the contrary, in the case of Comparative Compound A and Comparative Compound B, it can be seen that there is a structural difference in that a biphenyl group is substituted instead of a deuterium-substituted phenyl group or a deuterium-substituted naphthyl group, unlike the compounds of the present invention. That is, it can be seen that a difference occurs in the overall efficiency of the device due to the structural difference.

As a result, it can be confirmed that the device results of Examples 1 to 26 prepared with the compounds of the present invention represented by Formula 1, Formula 3 or Formula 4 show remarkably excellent results, and that the device performance is superior to other comparative compounds not described herein.

Table 7 describes the calculated Reorganization Energy values of Comparative Compounds A to Comparative Compounds C and P-1. The RE values listed in Table 7 refer to values obtained by calculating $RE_{hole}$.

TABLE 7

|  | Comparative compound A | Comparative compound B | Comparative compound C | P-1 |
|---|---|---|---|---|
| Reorganization Energy | 0.182 | 0.219 | 0.155 | 0.235 |

Referring to Table 7 in detail, the compound P-1 of the present invention has a higher RE value than Comparative Compounds A to C. These RE values are different depending on the substituent of the triazine, and in the case of the present invention, a higher RE value is obtained, which means low mobility and slow HOD.

That is, the light emitting zone can be narrowed by lowering the mobility of holes injected into the emitting layer due to a low RE value, and light generation can be concentrated through the narrowed light emitting zone to increase efficiency. However, there is a disadvantage that the lifespan is lowered opposite to the efficiency (trade-off), and the lifespan can be increased by using deuterium. That is, due to the substitution of deuterium, diffusion and reaction rates such as lowering of the movement rate of molecules can be delayed, and thus lifespan can be improved.

Therefore, due to the synergistic effect caused by substituting deuterium in a specific substituent as in the present invention, it seems that the efficiency is dramatically increased while the lifespan is maintained.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed

What is claimed is:

1. A compound represented by Formula 1:

<Formula 1>

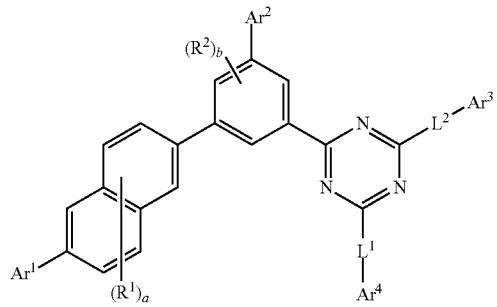

wherein:
Ar¹ is a substituent represented by Formula 1-A or Formula 1-B:

<Formula 1-A>

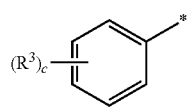

<Formula 1-B>

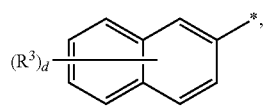

Ar² is a substituent represented by Formula 1-C or Formula 1-D:

<Formula 1-C>

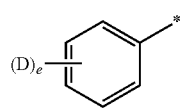

<Formula 1-D>

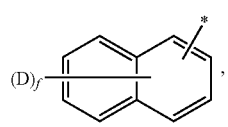

Ar³ and Ar⁴ are each independently an $C_6$-$C_{60}$ aryl group; or a $C_2$-$C_{60}$ heterocyclic group including at least one heteroatom of O, N, S, Si or P, $R^1$ and $R^2$ are each the same or different, and each independently a hydrogen; or deuterium, $L^1$ and $L^2$ are each independently a single bond; a $C_6$-$C_{60}$ arylene group; a $C_2$-$C_{60}$ heterocyclic group including at least one heteroatom of O, N, S, Si or P, a is an integer of 0 to 6, b is an integer of 0 to 3,
wherein in Formula 1-A to 1-D,
$R^3$ is each the same or different, and each independently a hydrogen; or deuterium;
D means deuterium,
c is an integer of 0 to 5, d is an integer of 0 to 7, e is an integer of 1 to 5, f is an integer of 1 to 7,
* means a position to be bonded,
wherein the aryl group, arylene group and heterocyclic group may be substituted with one or more substituents selected from the group consisting of deuterium; $C_6$-$C_{20}$ aryl group; and $C_6$-$C_{20}$ aryl group substituted with deuterium.

2. The compound of claim 1, wherein Formula 1 is represented by any one of Formulas 1-1 to 1-4:

<Formula 1-1>

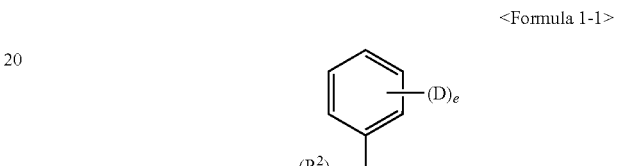

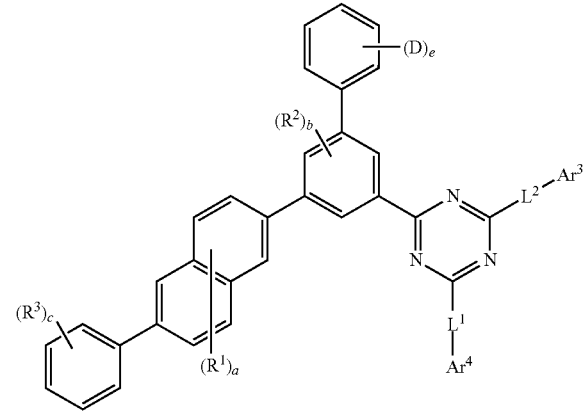

<Formula 1-2>

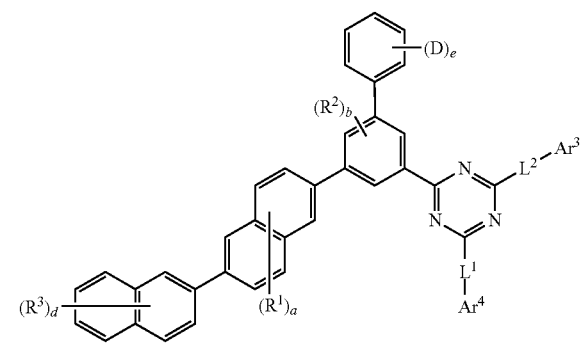

<Formula 1-3>

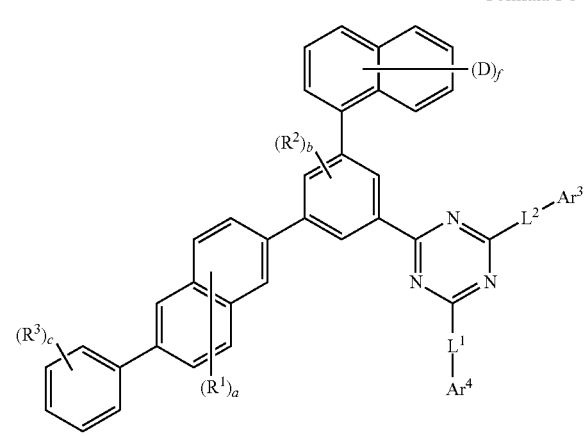

<Formula 1-4>
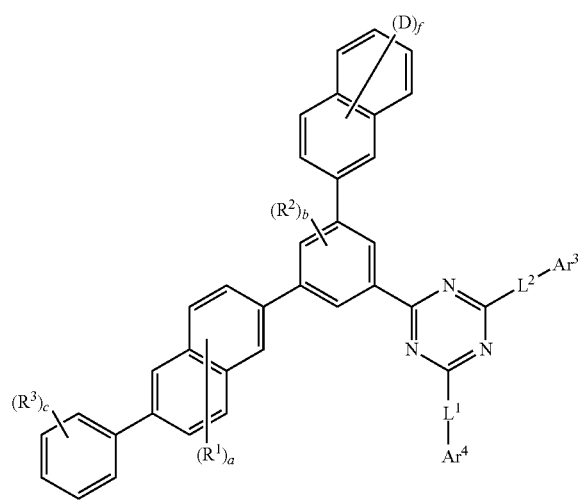
wherein, R¹, R², R³, L¹, L², Ar³, Ar⁴, a, b, c, d, e, f and D are the same as defined in claim 1.
3. The compound of claim 1, wherein at least one of L¹ and L² is represented by any one of Formula a-1 to Formula a-20:
<Formula a-1>
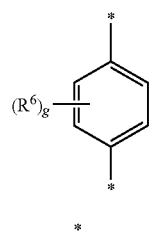
<Formula a-2>
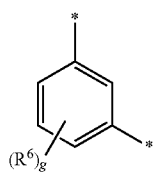
<Formula a-3>
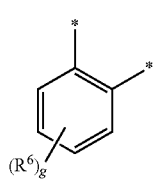
<Formula a-4>
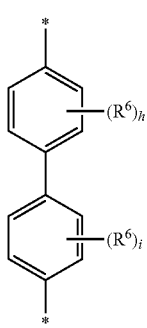
<Formula a-5>
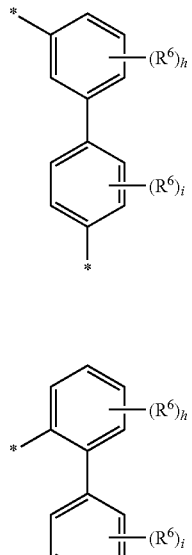
<Formula a-6>
<Formula a-7>
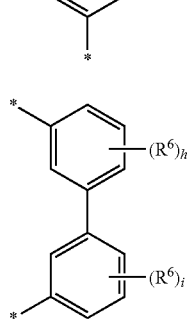
<Formula a-8>
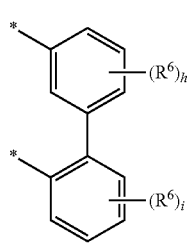
<Formula a-9>
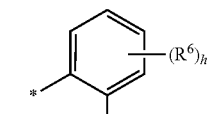
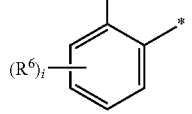
<Formula a-10>
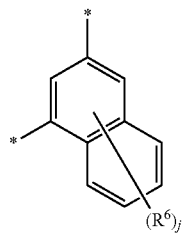

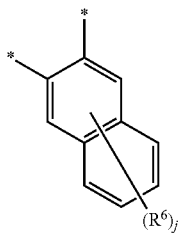
<Formula a-11>

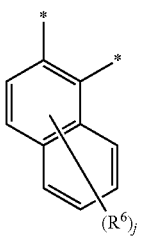
<Formula a-12>

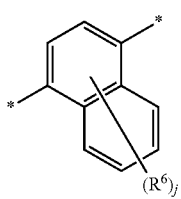
<Formula a-13>

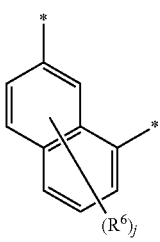
<Formula a-14>

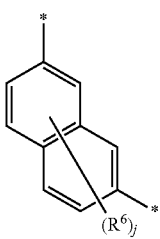
<Formula a-15>

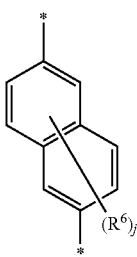
<Formula a-16>

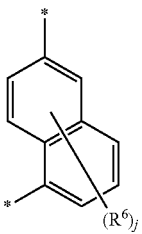
<Formula a-17>

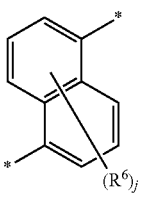
<Formula a-18>

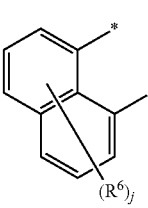
<Formula a-19>

<Formula a-20> wherein:
$R^6$ is each the same or different, and each independently deuterium; $C_6$-$C_{20}$ aryl group; and $C_6$-$C_{20}$ aryl group substituted with deuterium;

g, h and i are each independently an integer of 0 to 4, j is an integer of 0 to 6, k is an integer of 0 to 8,

* means a moiety bonded to triazine or $Ar^3$ or $Ar^4$.

4. The compound of claim 1, wherein at least one of $Ar^3$ and $Ar^4$ is represented by any one of the following Formula b-1 to Formula b-12:

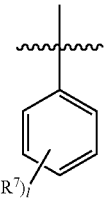
<Formula b-1>

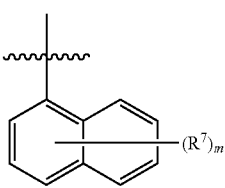
<Formula b-2>

-continued

<Formula b-3>

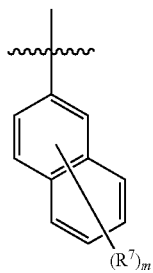

<Formula b-4>

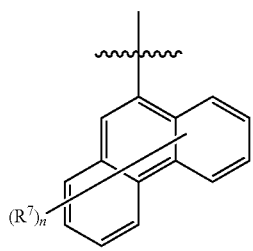

<Formula b-5>

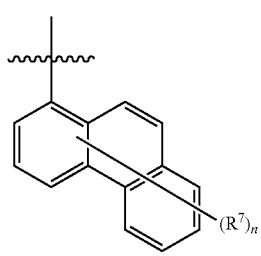

<Formula b-6>

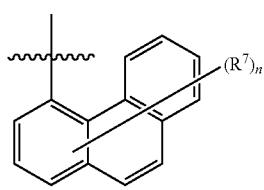

<Formula b-7>

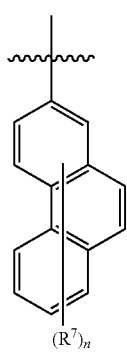

<Formula b-8>

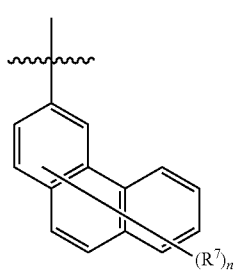

-continued

<Formula b-9>

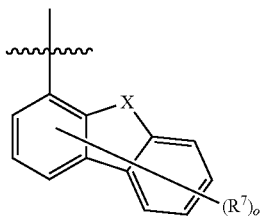

<Formula b-10>

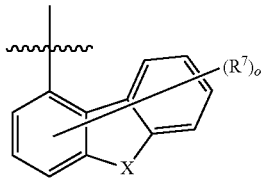

<Formula b-11>

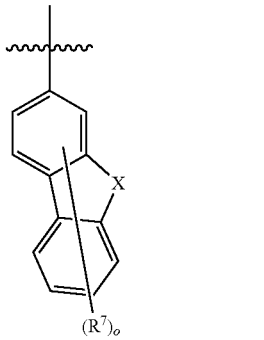

<Formula b-12> wherein:

X is $NR^8$, O or S, $R^7$ is each the same or different, and each independently deuterium; $C_6$-$C_{20}$ aryl group; and $C_6$-$C_{20}$ aryl group substituted with deuterium;

$R^8$ is an $C_6$-$C_{60}$ aryl group; or a $C_2$-$C_{60}$ heterocyclic group including at least one heteroatom of O, N, S, Si or P;

l is an integer of 0 to 5, m and o are each independently an integer of 0 to 7, n is an integer of 0 to 9, ⌇ means a part that binds to $L^1$ or $L^2$.

5. The compound of claim 1, wherein the compound represented by Formula 1 is any one of Compounds P-1 to P-76:

195 196
P-1
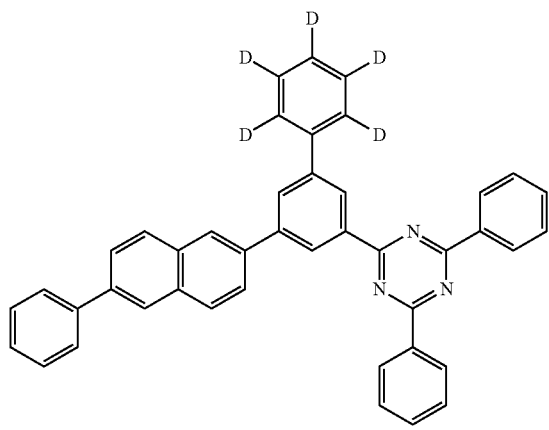
P-2
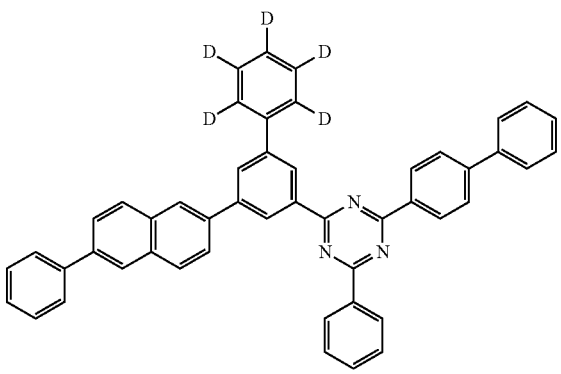
P-3
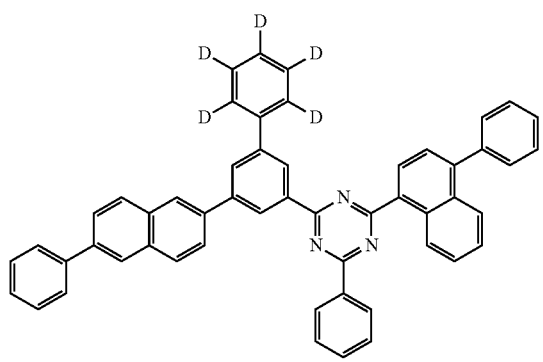
P-4
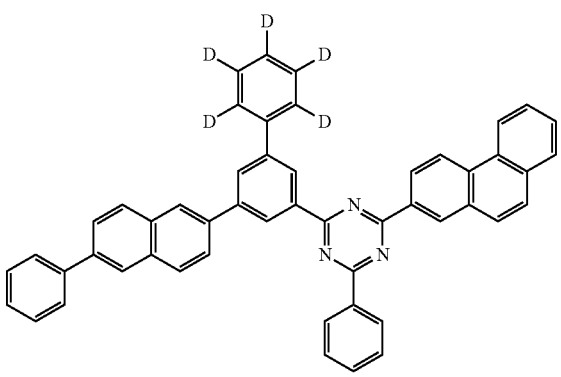
P-5
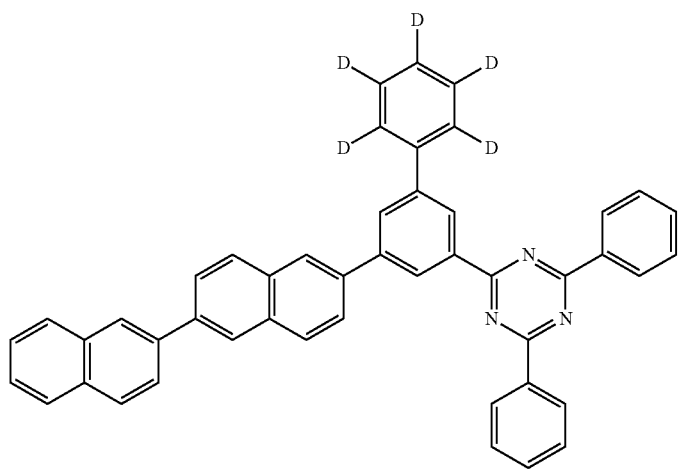

P-6
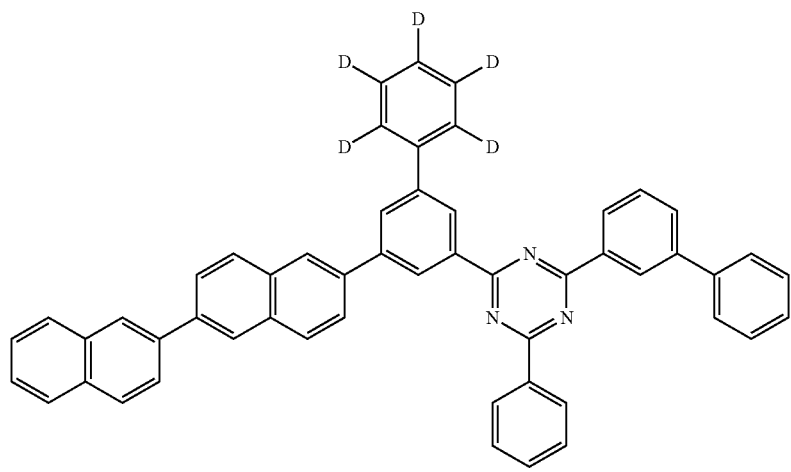
P-7
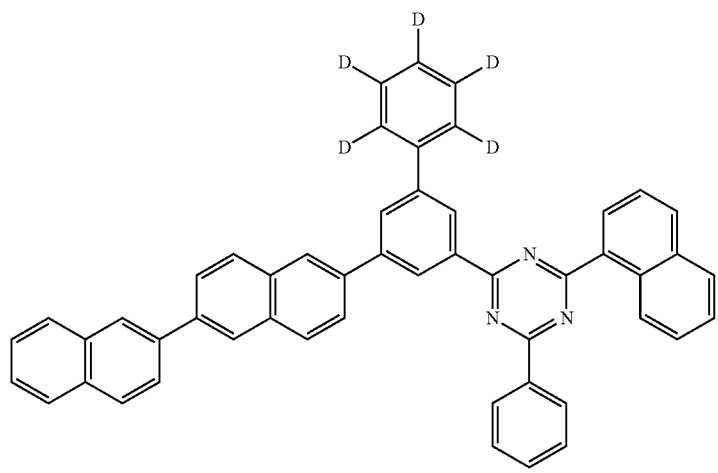
P-8
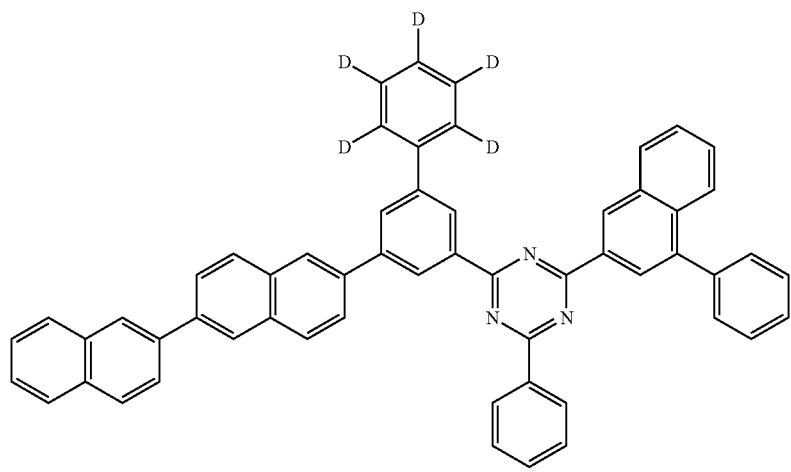

-continued
P-9
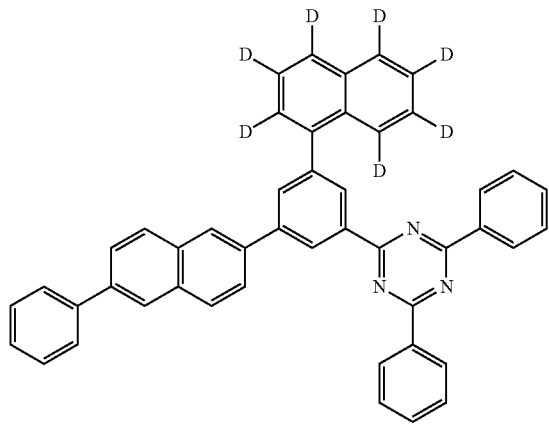
P-10
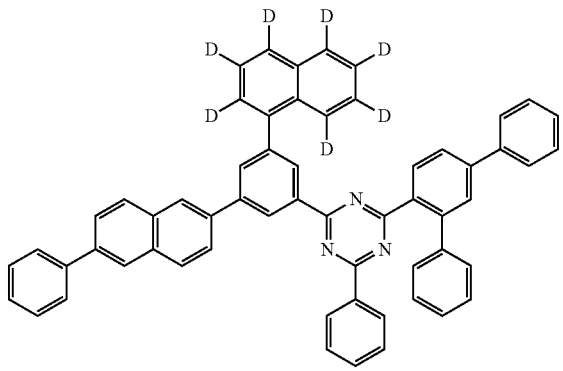
P-11
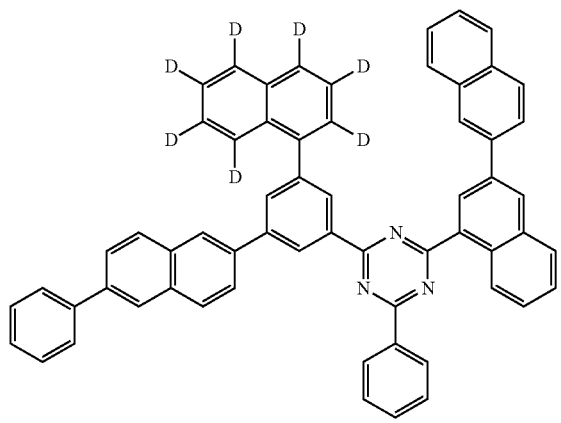
P-12
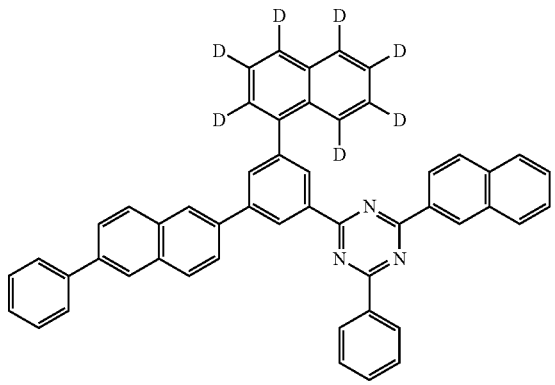
P-13
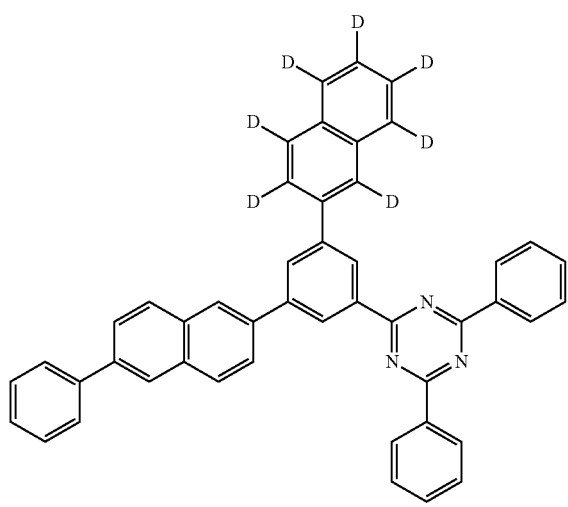

-continued
P-14
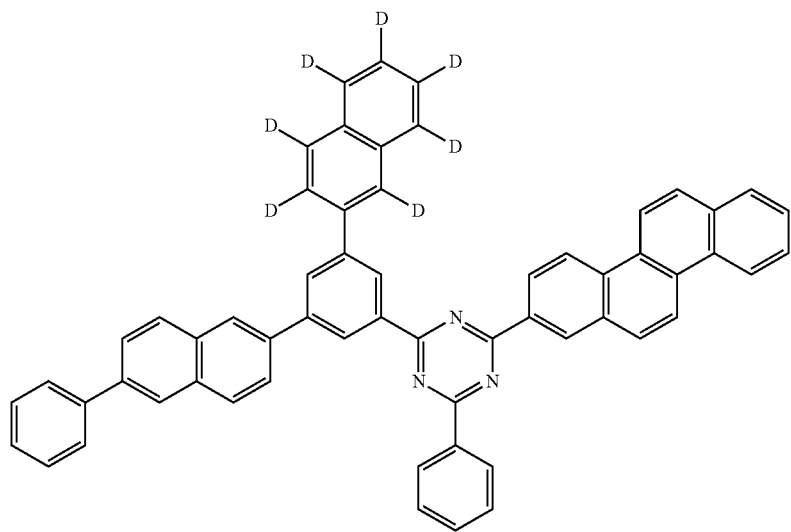
P-15 P-16
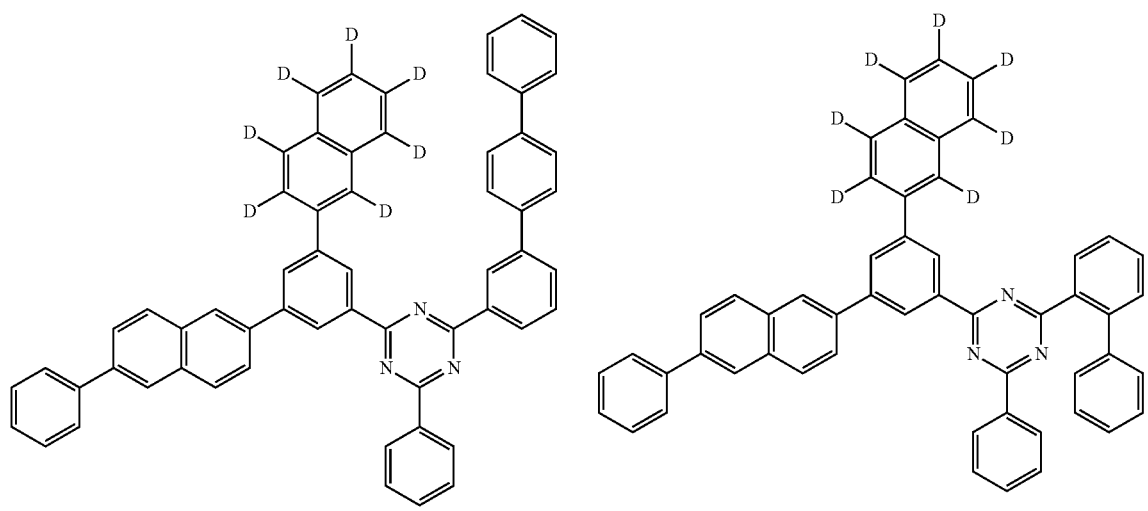
P-17 P-18
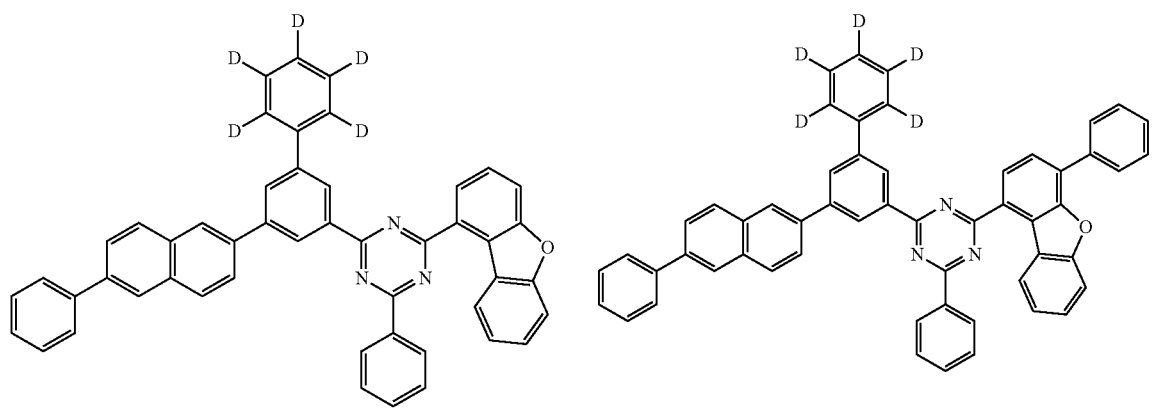

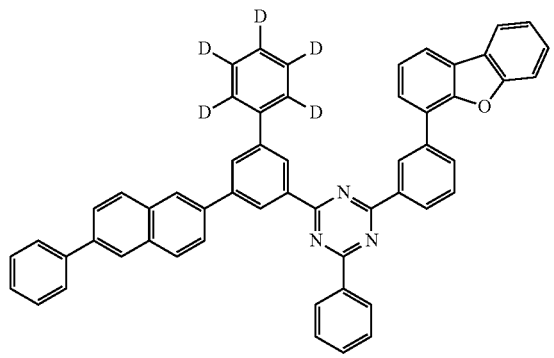
P-19
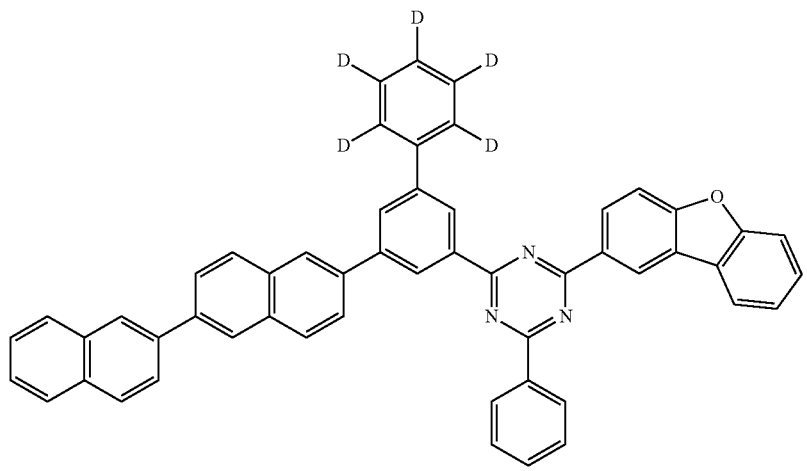
P-20
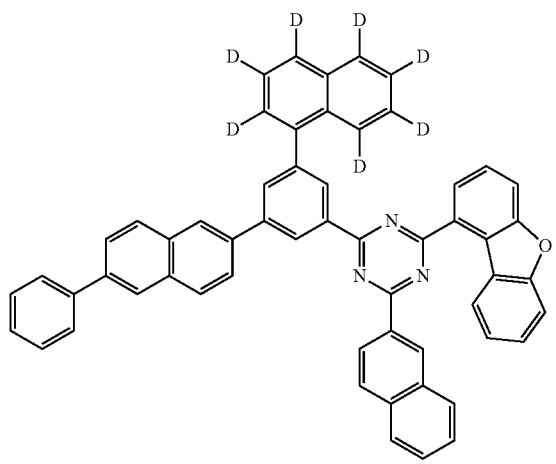
P-21
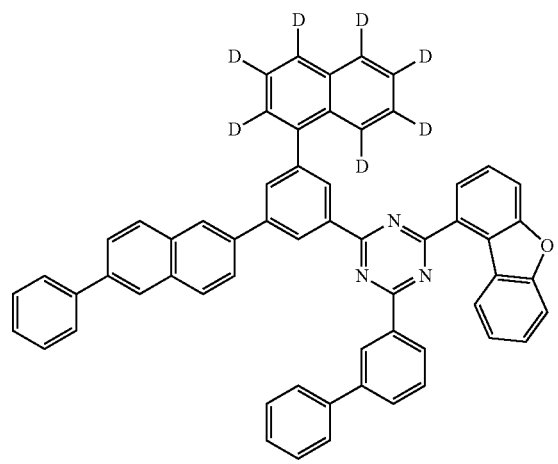
P-22

-continued
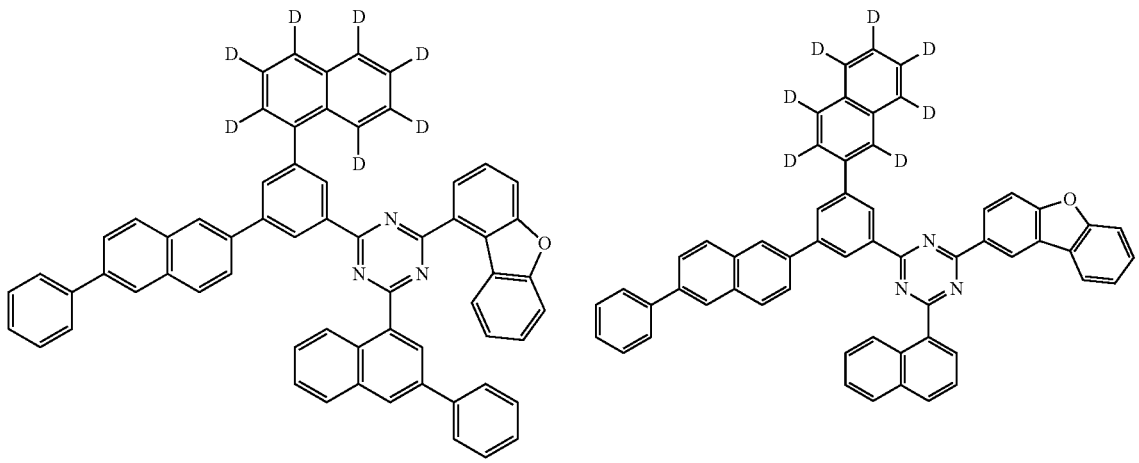
P-23
P-24
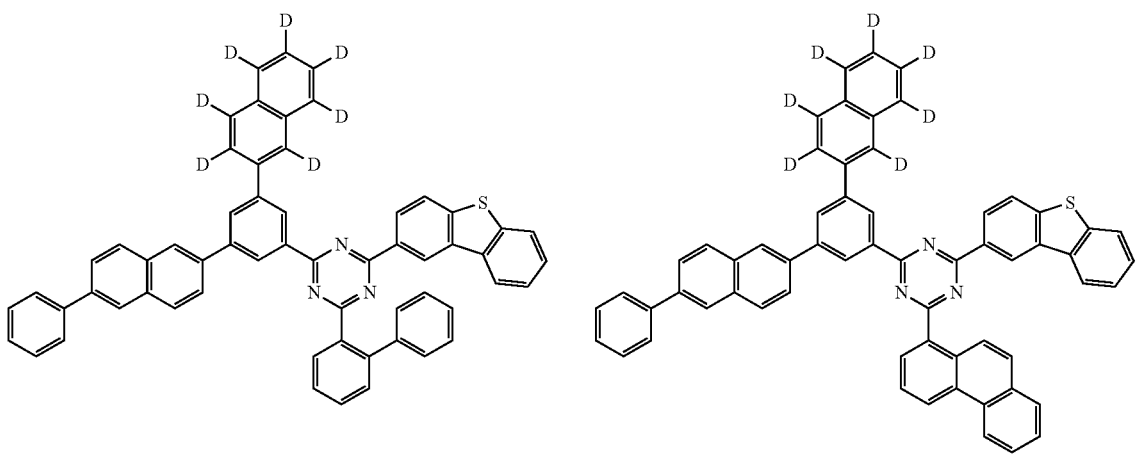
P-25
P-26
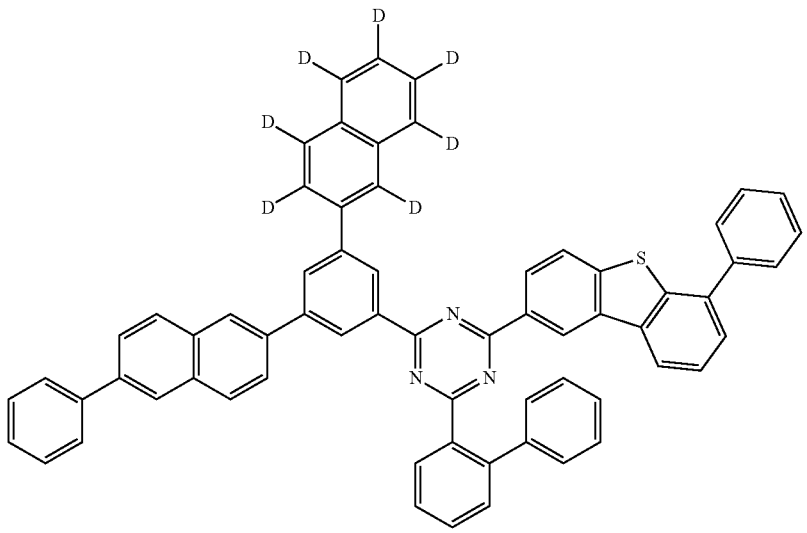
P-27

-continued
P-28
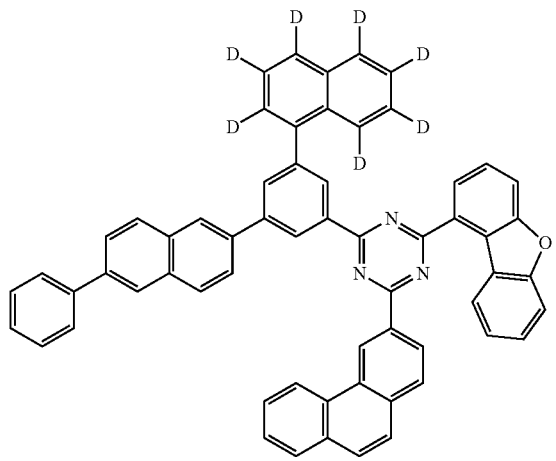
P-29
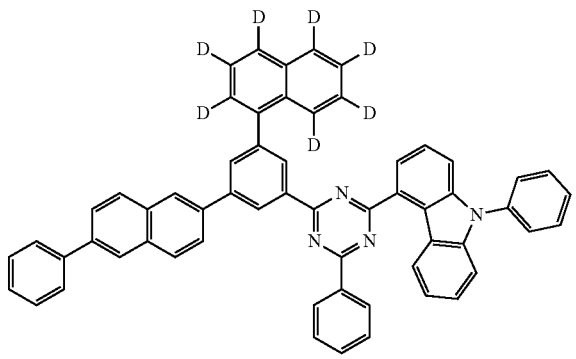
P-30
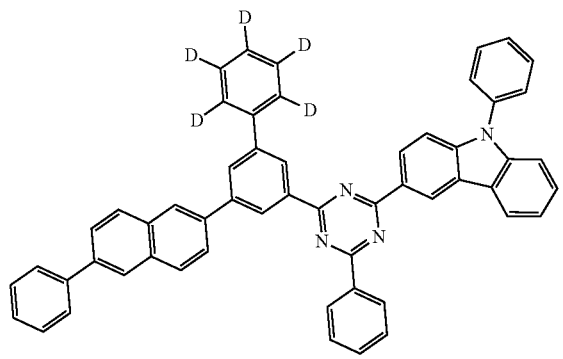
P-31
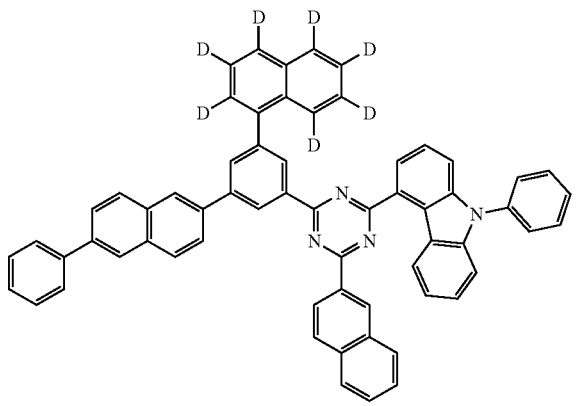
P-32
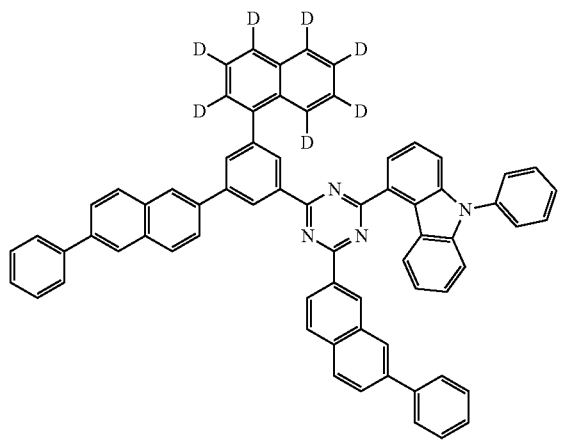

P-33
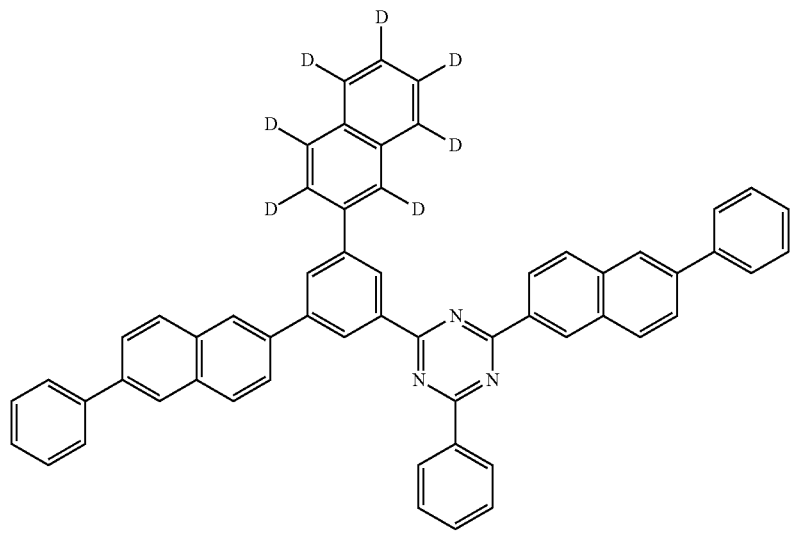
P-34
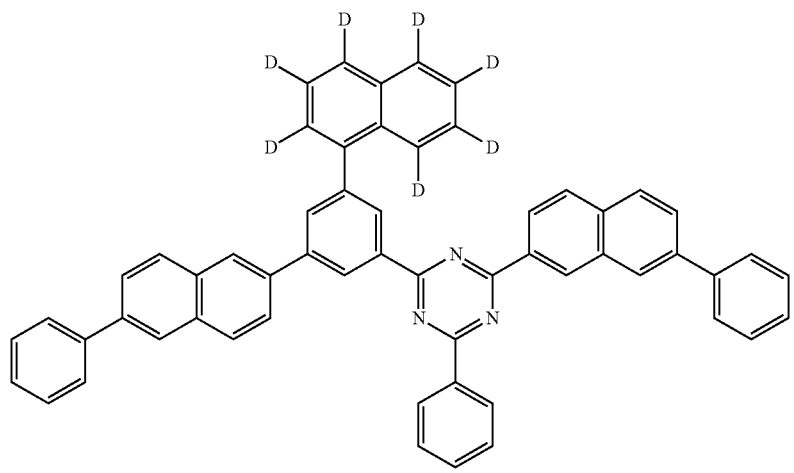
P-35
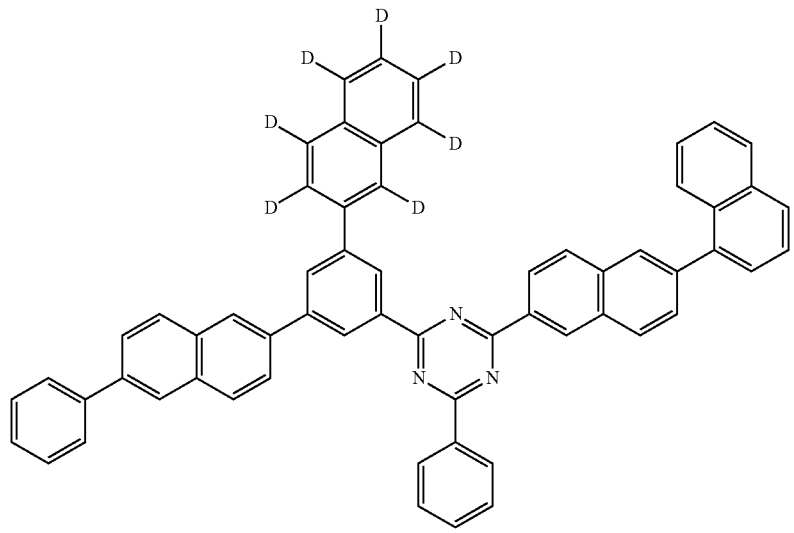

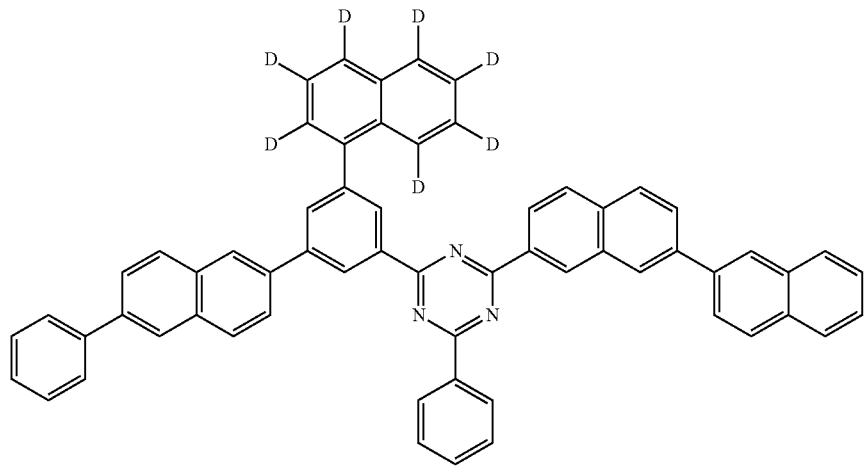
P-36
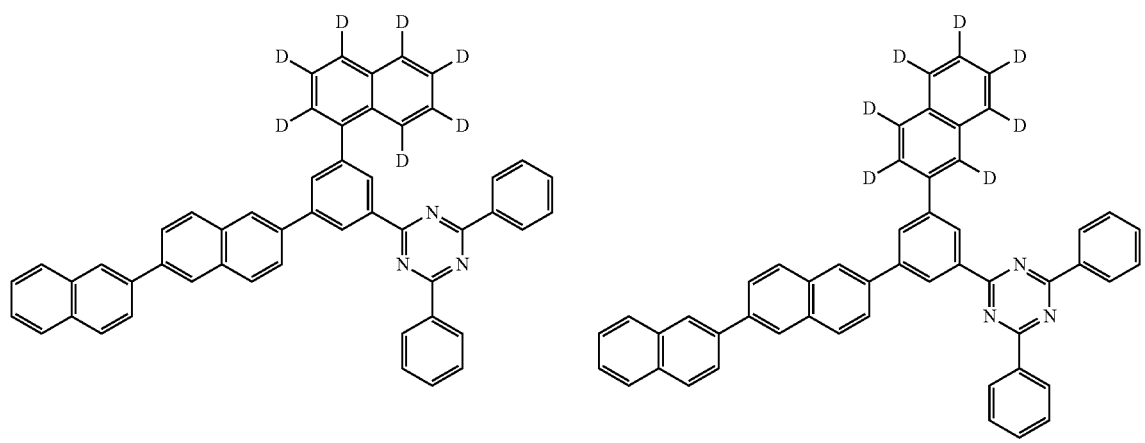
P-37     P-38
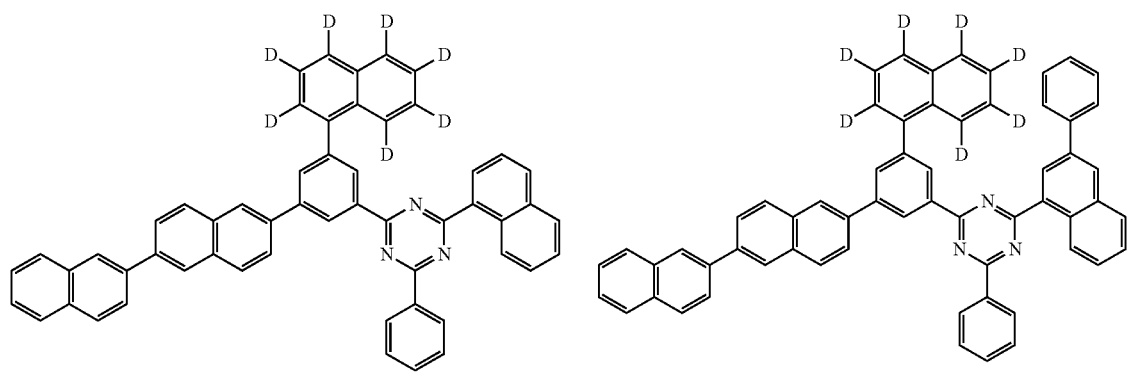
P-39     P-40

P-41
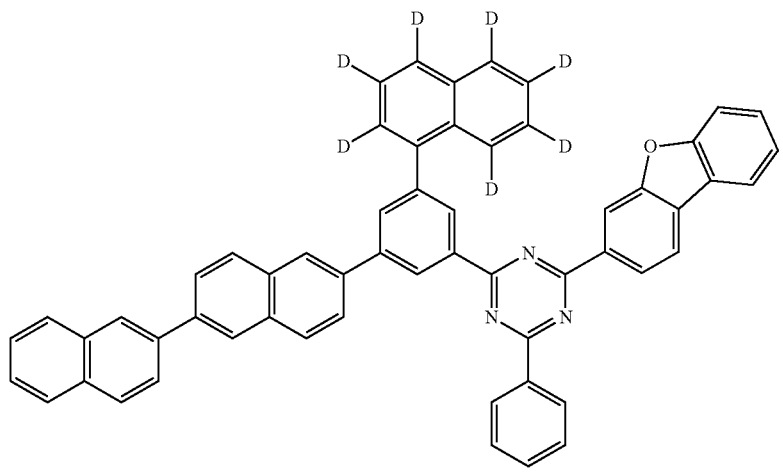
P-42
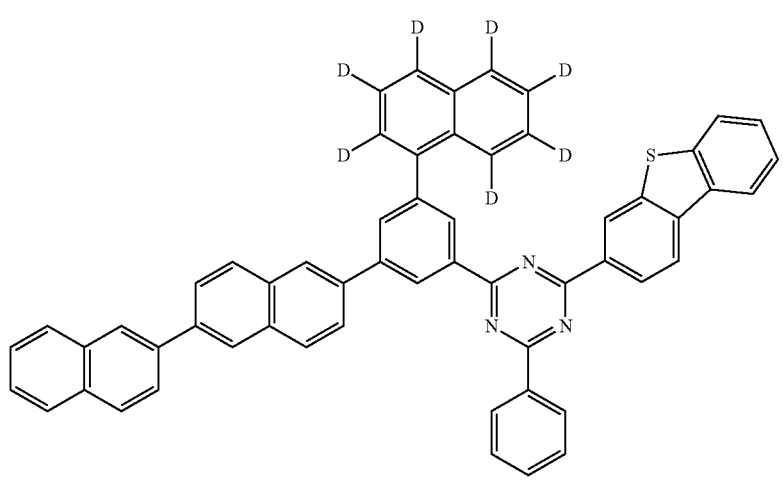
P-43
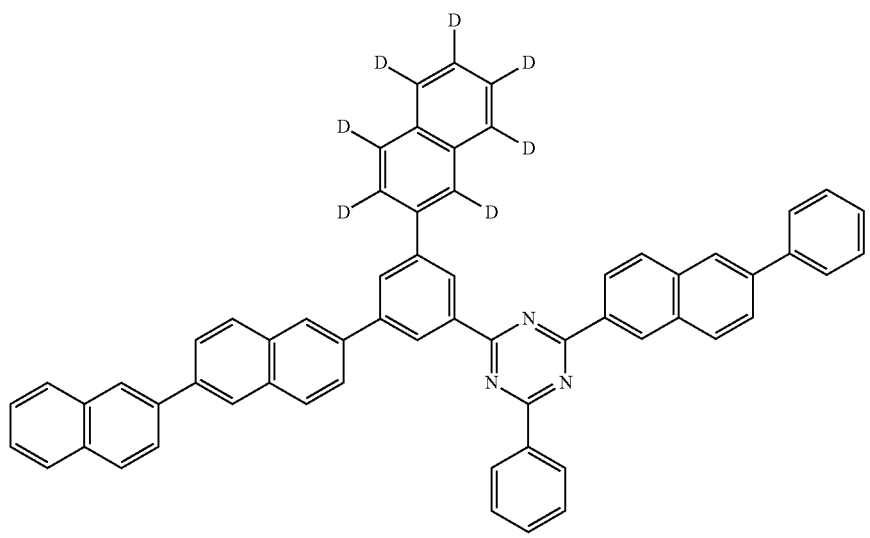

-continued
P-44
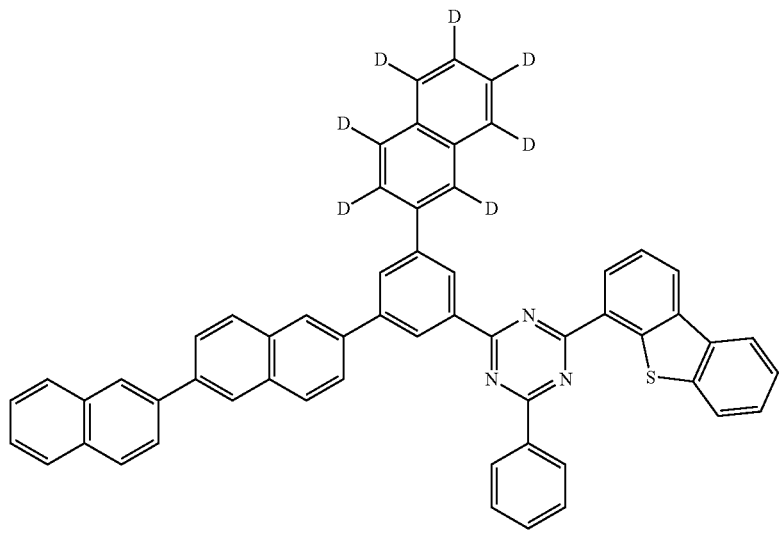
P-45
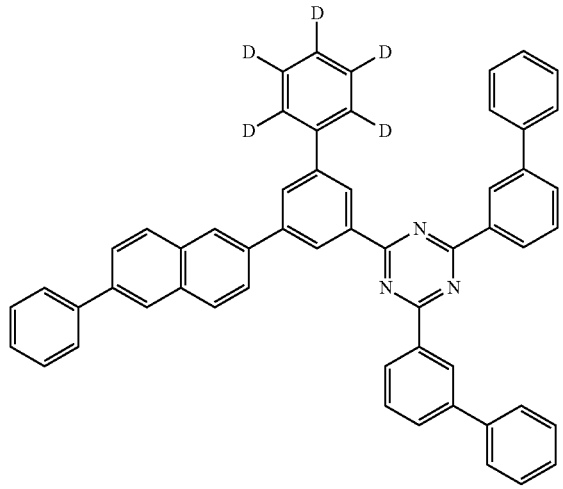
P-46
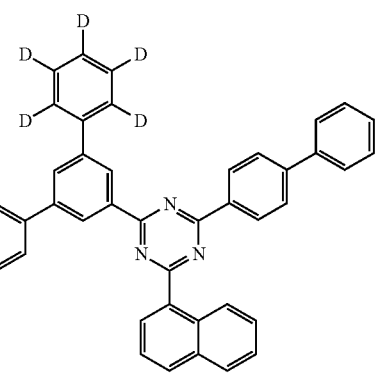
P-47
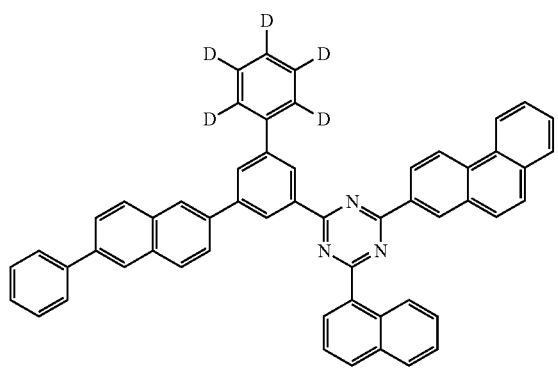
P-48
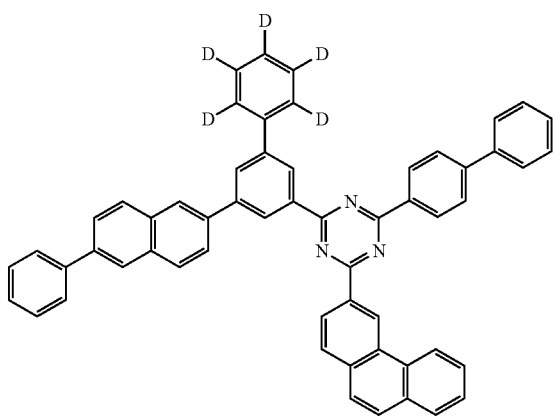

-continued
P-49
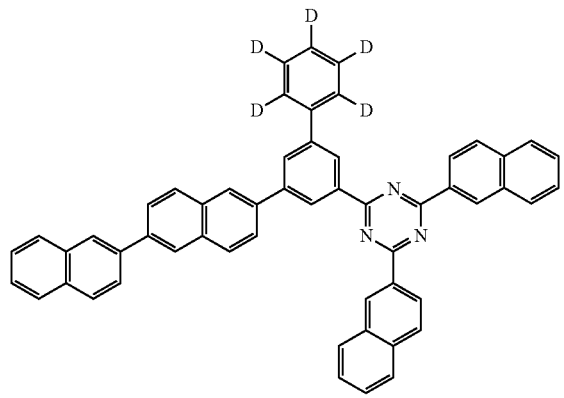
P-50
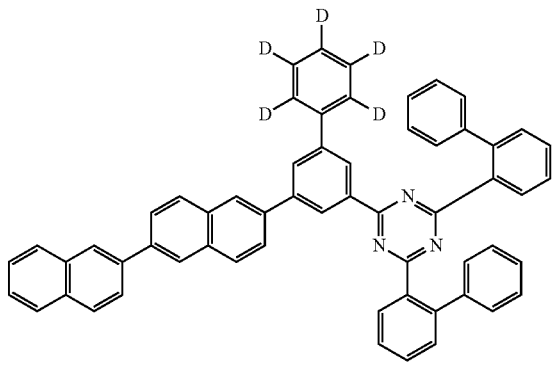
P-51
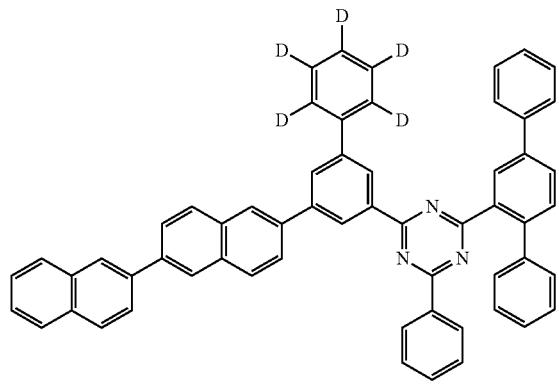
P-52
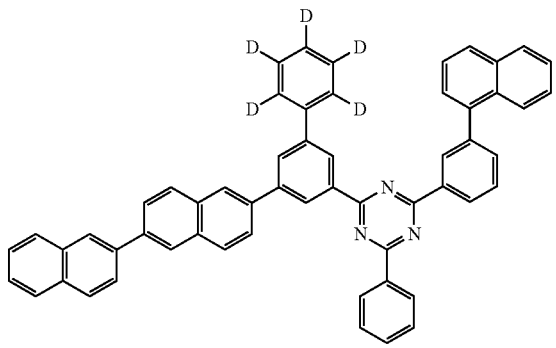
P-53
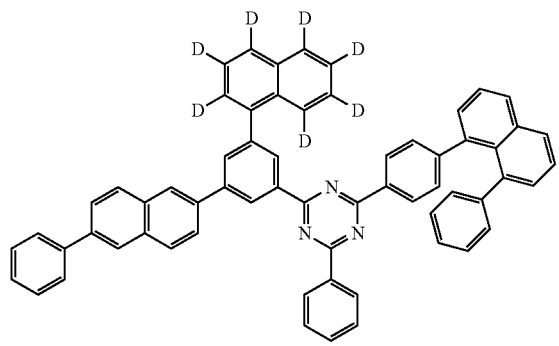
P-54
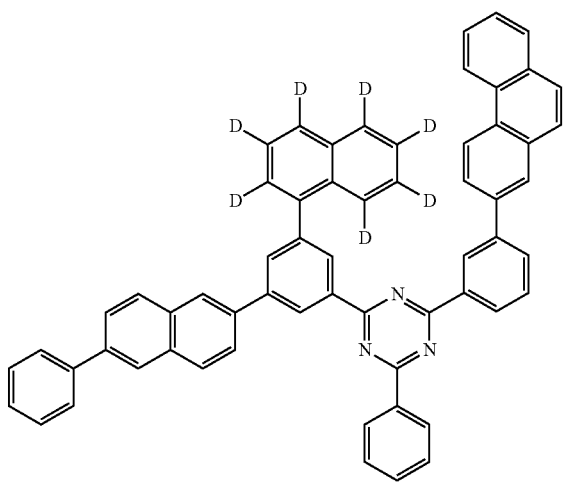

-continued
P-55
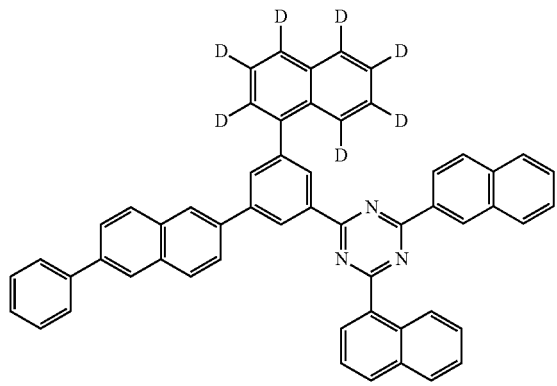
P-56
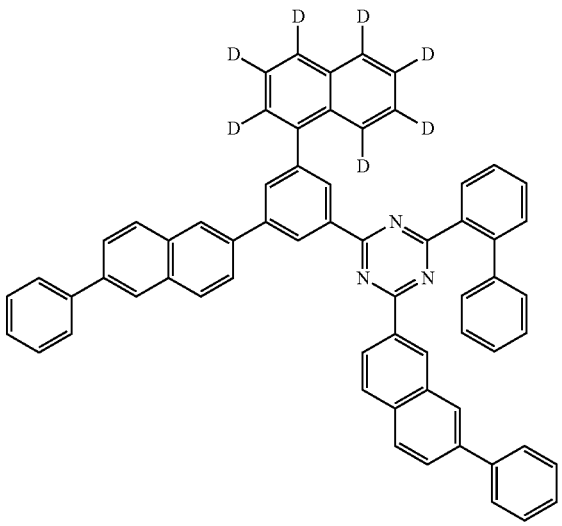
P-57
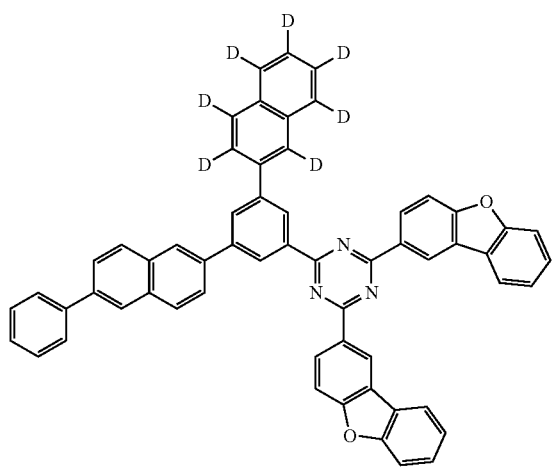
P-58
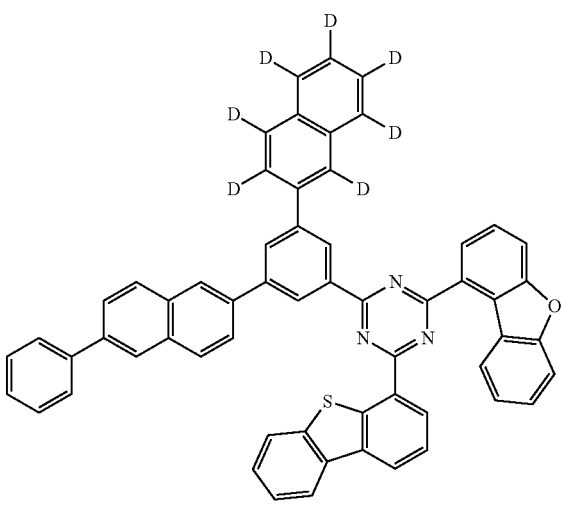
P-59
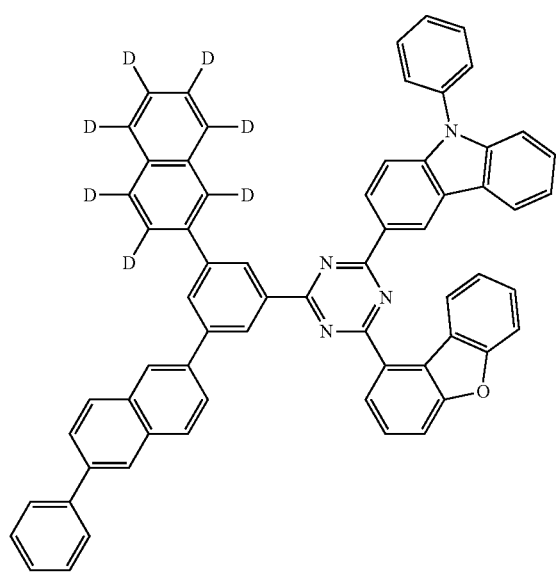
P-60
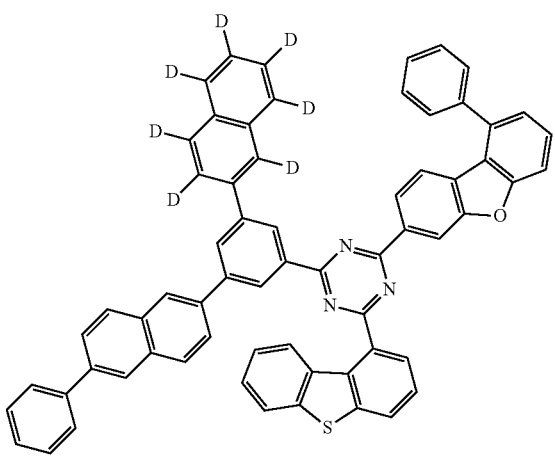

-continued
P-61
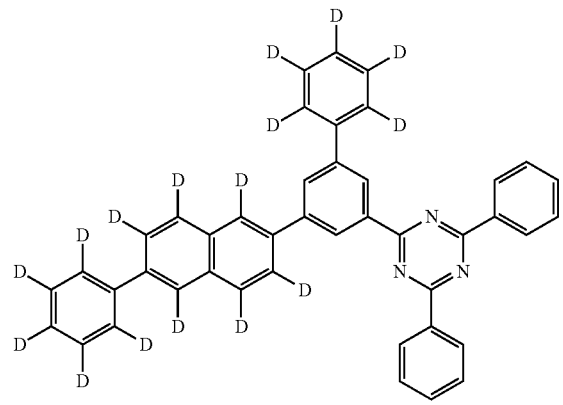
P-62
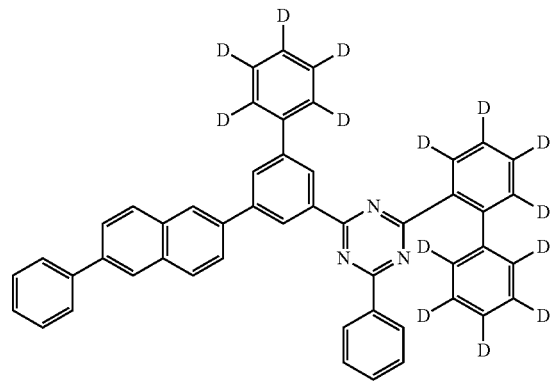
P-63
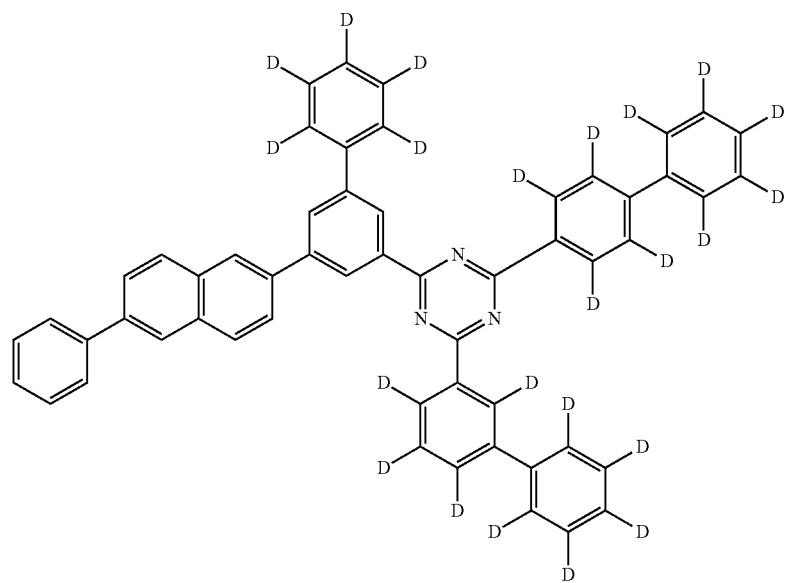
P-64
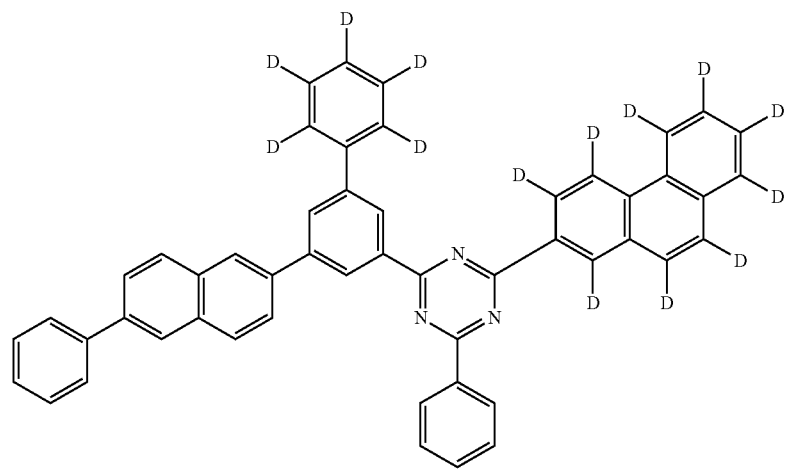

-continued
P-65
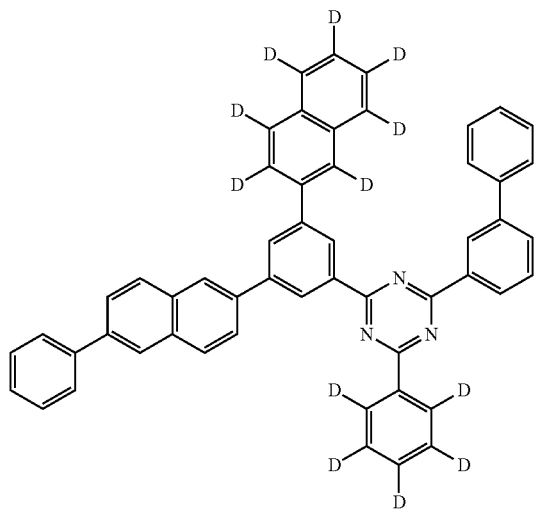
P-66
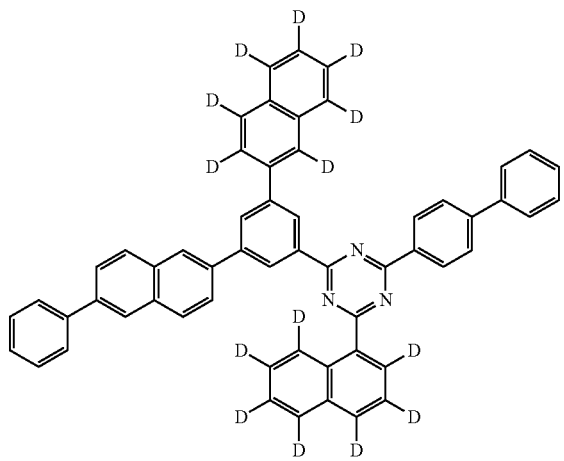
P-67
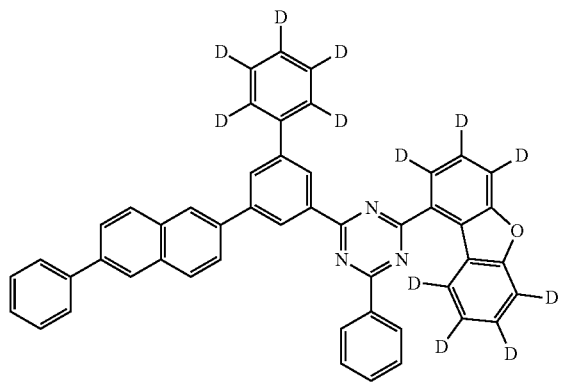
P-68
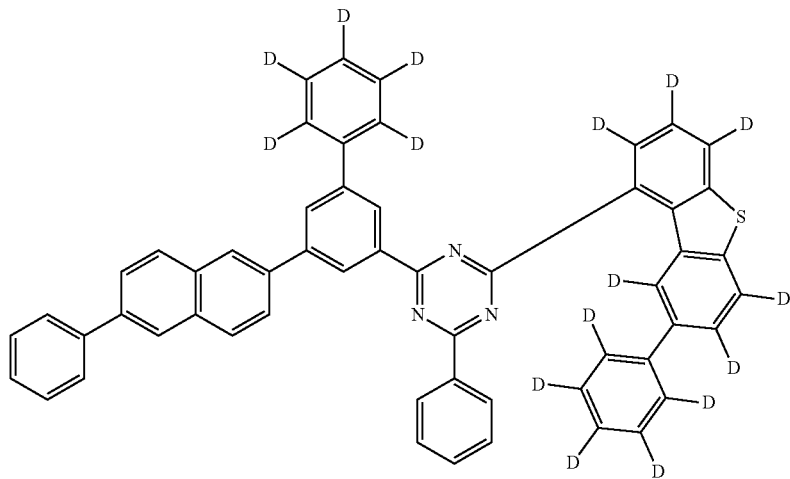

P-69
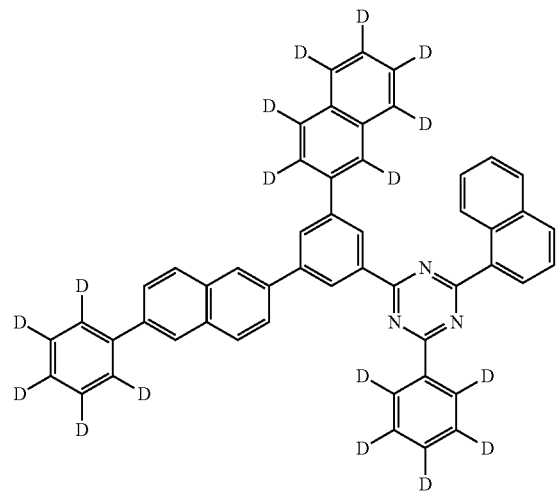
P-70
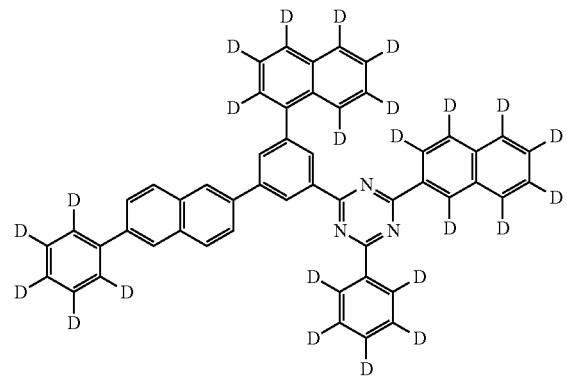
P-71
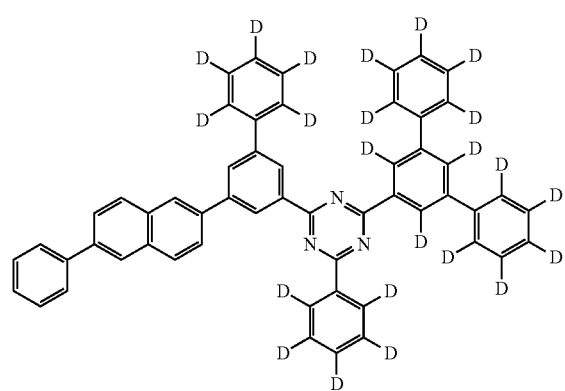
P-72
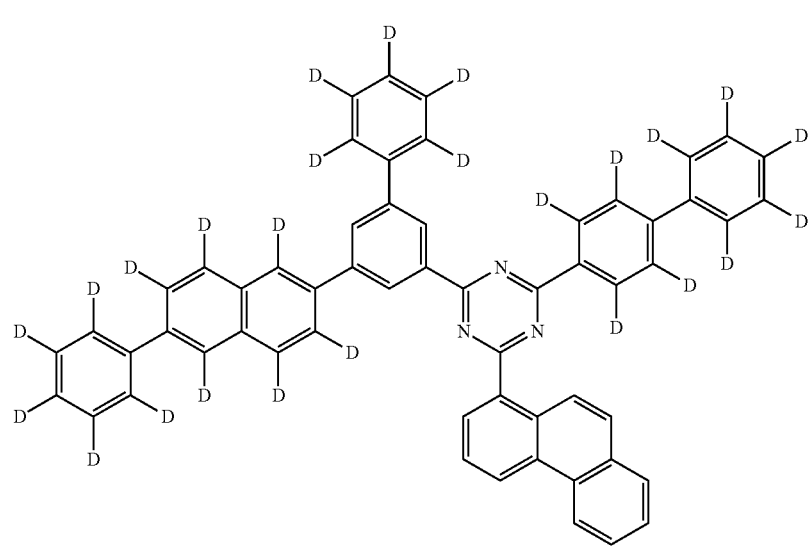

P-73
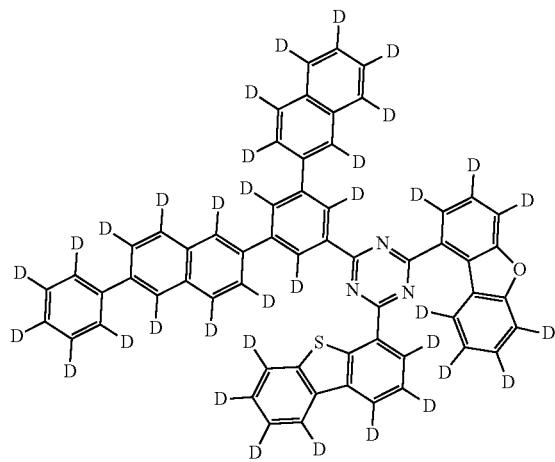
P-74
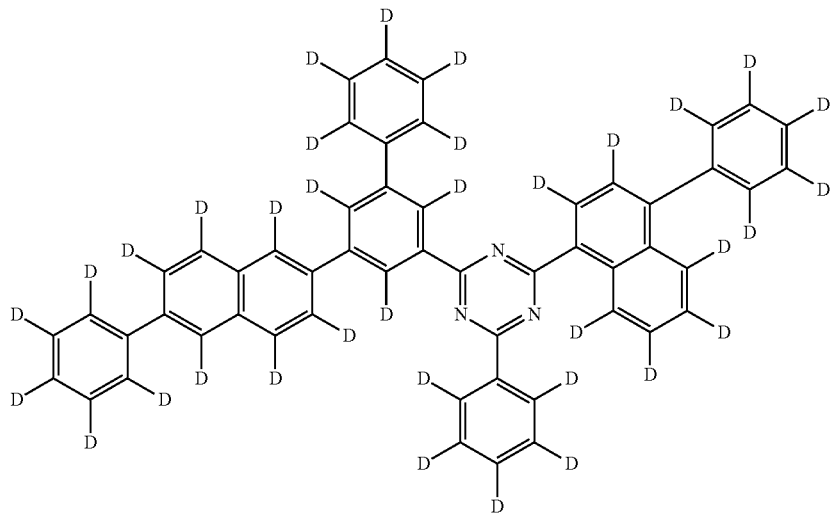
P-75
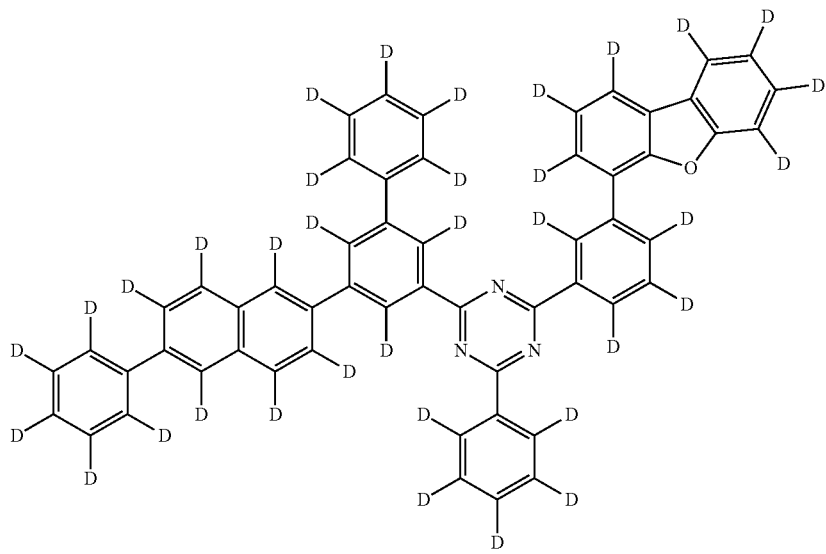

P-76

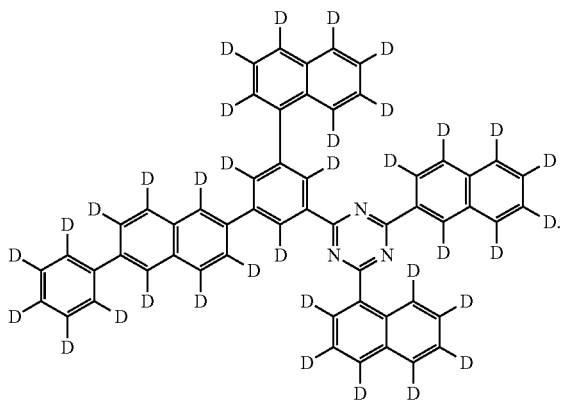

6. An organic electronic element comprising a first electrode; a second electrode; and an organic material layer formed between the first electrode and the second electrode, wherein the organic material layer comprises an emitting layer, and wherein the emitting layer is a phosphorescent emitting layer and comprises a first host compound represented by Formula 1 of claim 1, and a second host compound represented by Formula 3 or Formula 4:

<Formula 3>

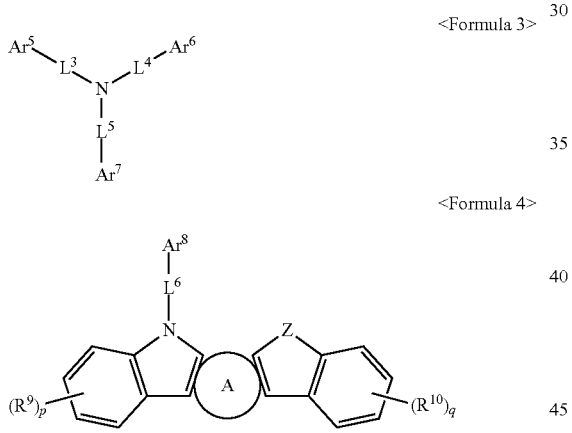

<Formula 4> wherein:

$L^3$, $L^4$, $L^5$ and $L^6$ are each independently selected from the group consisting of a single bond; a $C_6$-$C_{60}$ arylene group; fluorenylene group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

$Ar^5$, $Ar^6$ and $Ar^7$ are each independently selected from the group consisting of an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring;

$Ar^8$ is each independently selected from the group consisting of an $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-$NR^bR^c$;

Z is O, S, CR'R" or $NR^a$,

Ring A is an $C_6$-$C_{20}$ aryl group, $R^9$ and $R^{10}$ are each independently the same or different, and each independently selected from the group consisting of hydrogen; deuterium; halogen; a cyano group; a nitro group; an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or a plurality of adjacent $R^9$s or a plurality of $R^{10}$s may be bonded to each other to form a ring, p and q are each independently an integer 0 to 4, L' is each independently selected from the group consisting of a single bond; a $C_6$-$C_{60}$ arylene group; fluorenylene group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

$R^b$ and $R^c$ are each independently selected from the group consisting of an $C_6$-$C_{60}$ aryl group; a fluorenyl group; a $C_2$-$C_{60}$ heterocyclic group including at least one heteroatom of O, N, S, Si or P; a $C_3$-$C_{60}$ aliphatic ring;

R' and R" are each independently selected from the group consisting of hydrogen; deuterium; an $C_6$-$C_{60}$ aryl group; a fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or R' and R" may be bonded to each other to form a ring, $R^a$ is an $C_6$-$C_{60}$ aryl group; or a $C_2$-$C_{60}$ heterocyclic group including at least one heteroatom of O, N, S, Si or P, wherein the aryl group, arylene group, heterocyclic group, fluorenyl group, fluorenylene group, aliphatic ring group, fused ring group, alkyl group, alkenyl group, alkynyl group, alkoxyl group, and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

7. The organic electronic element of claim 6, wherein the compound represented by Formula 3 is any one of Compounds N-1 to N-96:

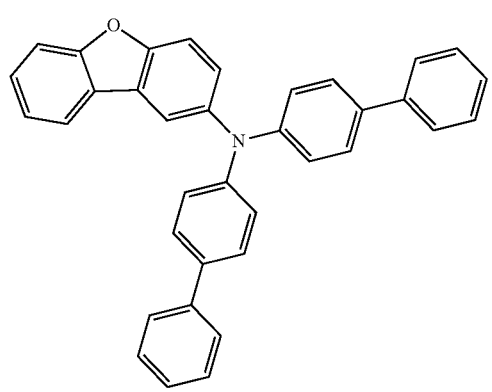

N-1

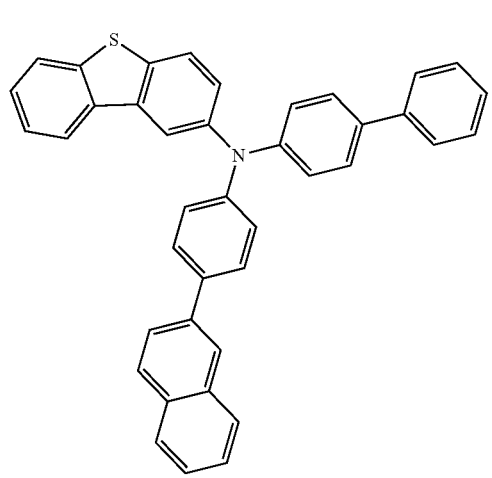

N-2

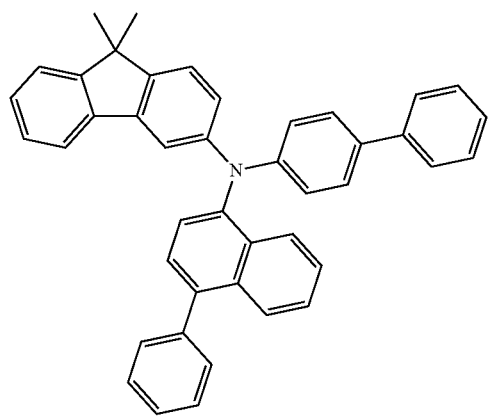

N-3

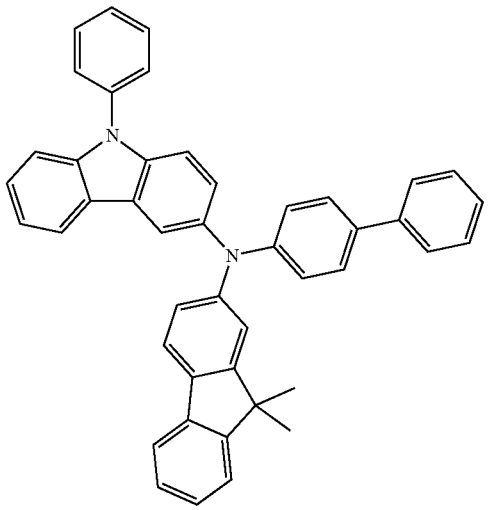

N-4

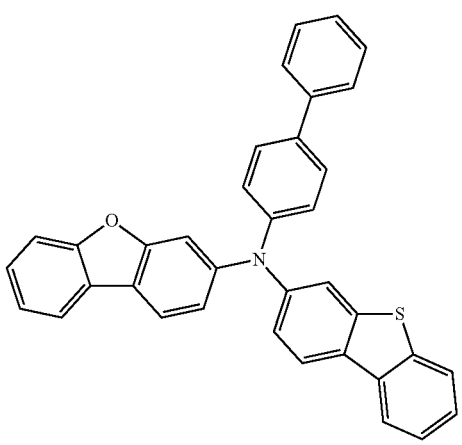

N-5

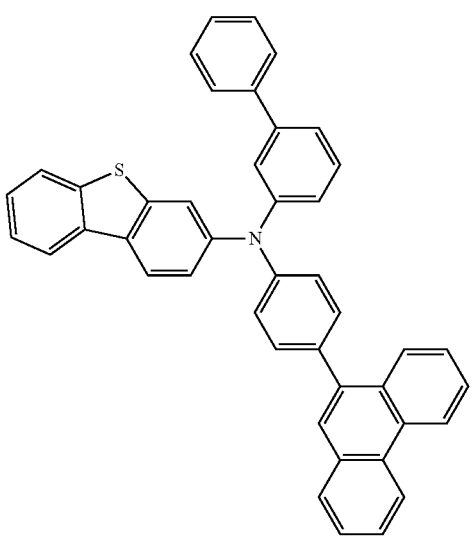

N-6

N-7
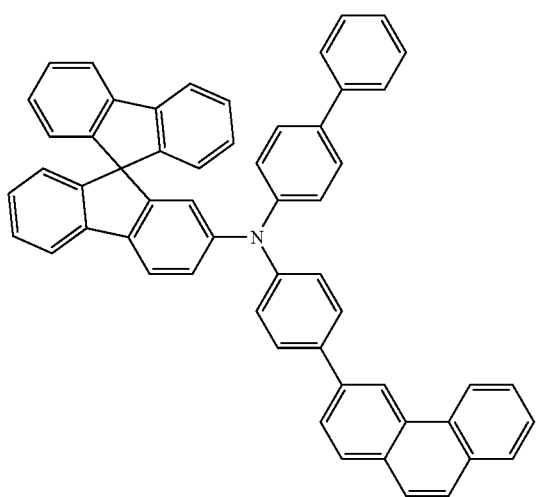
N-10
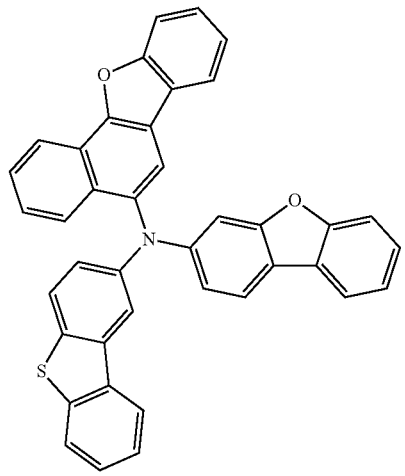
N-8
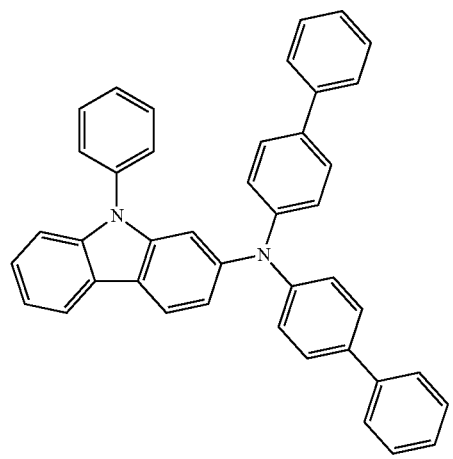
N-11
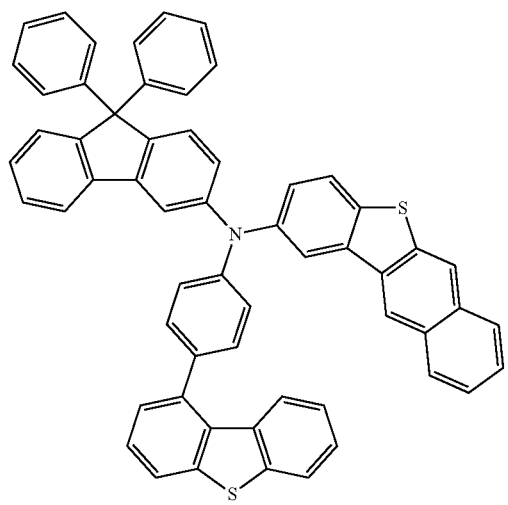
N-9
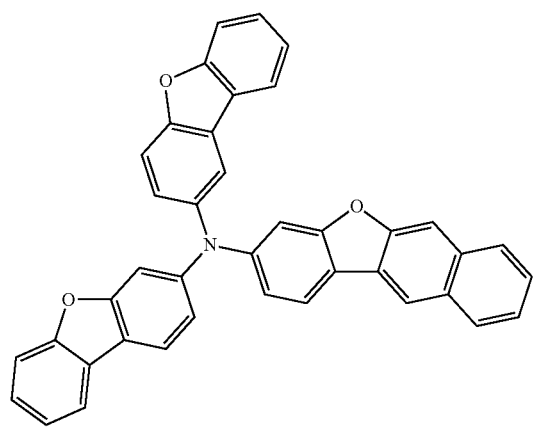
N-12
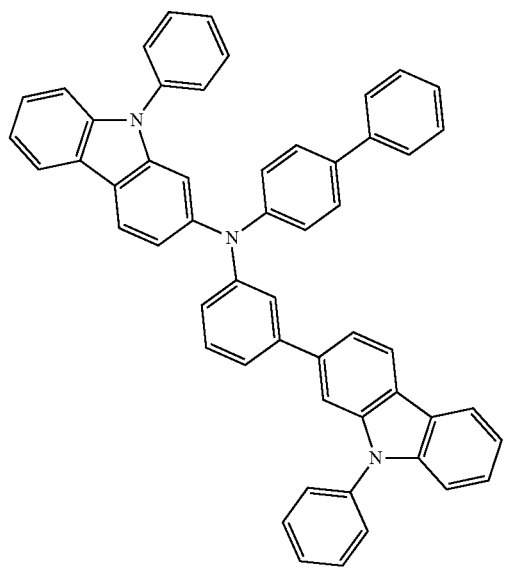

-continued

N-13

N-14

N-15

N-16

N-17

N-18

N-19
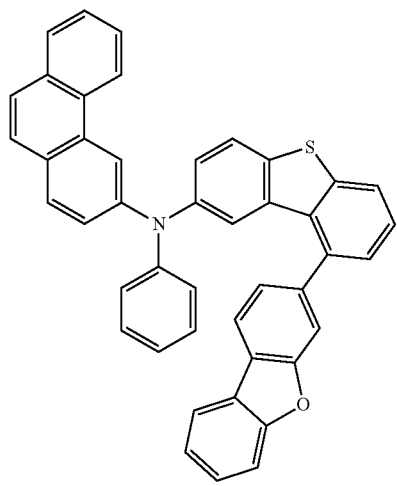
N-20
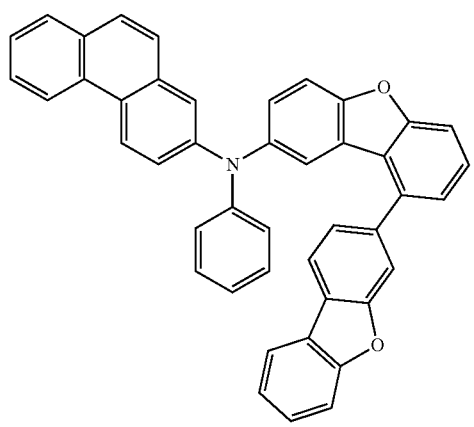
N-21
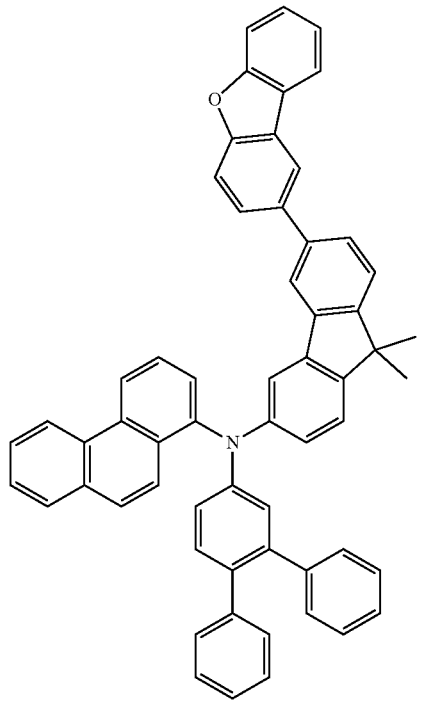
N-22
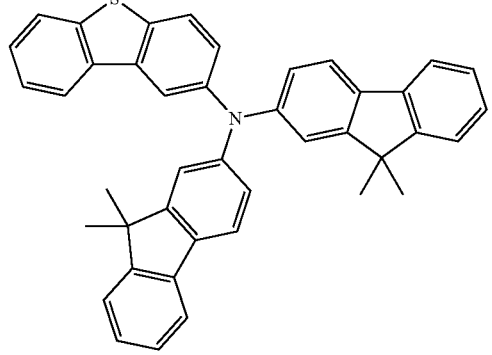
N-23
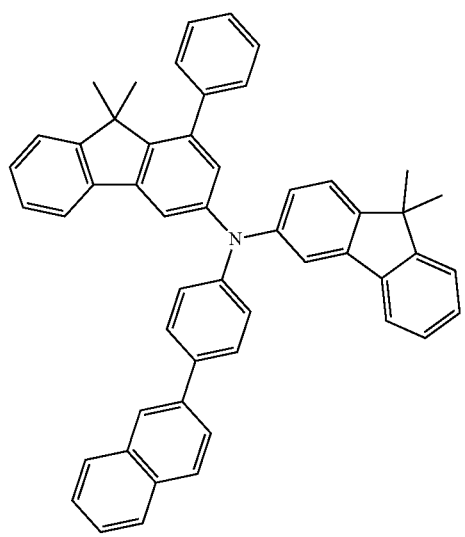
N-24
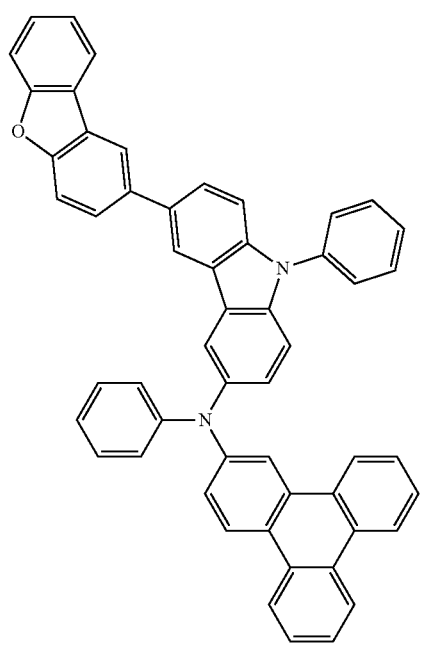

N-25
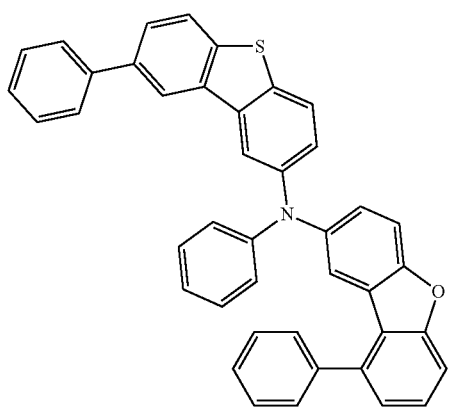
N-26
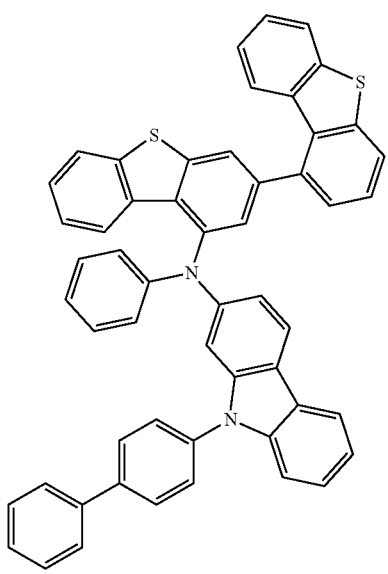
N-27
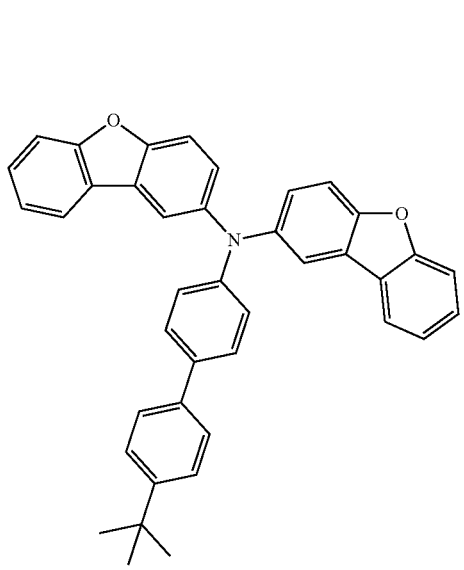
N-28
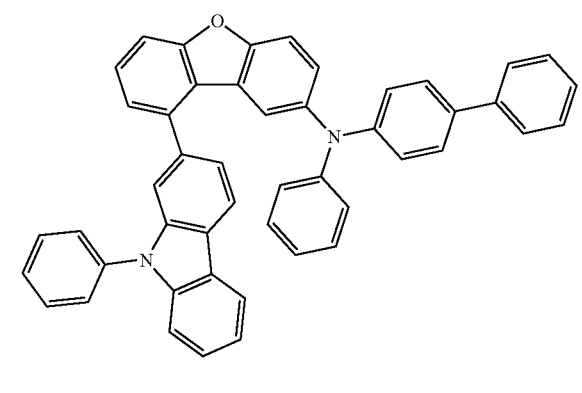
N-29
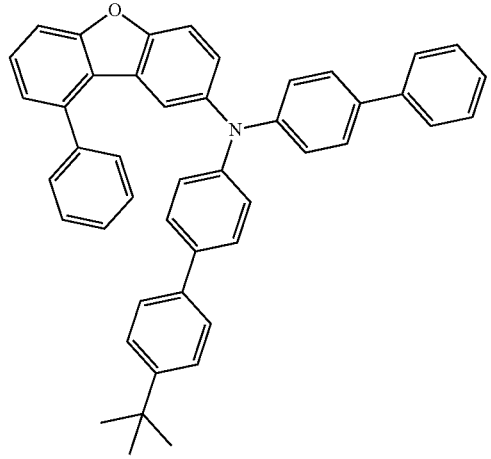
N-30
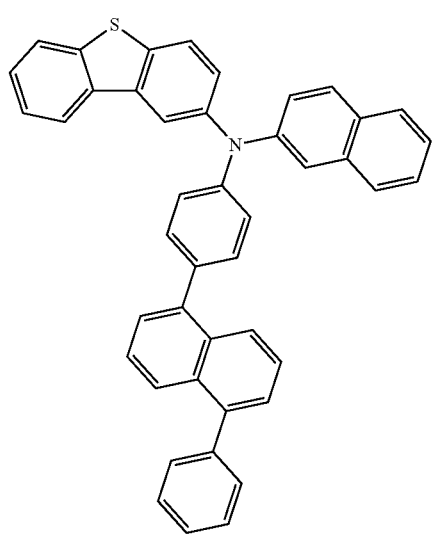

N-31
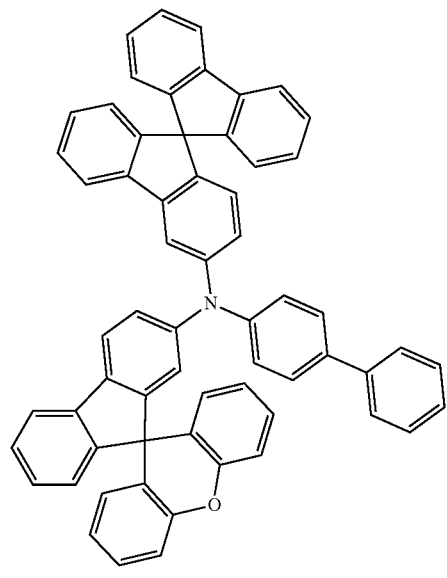
N-32
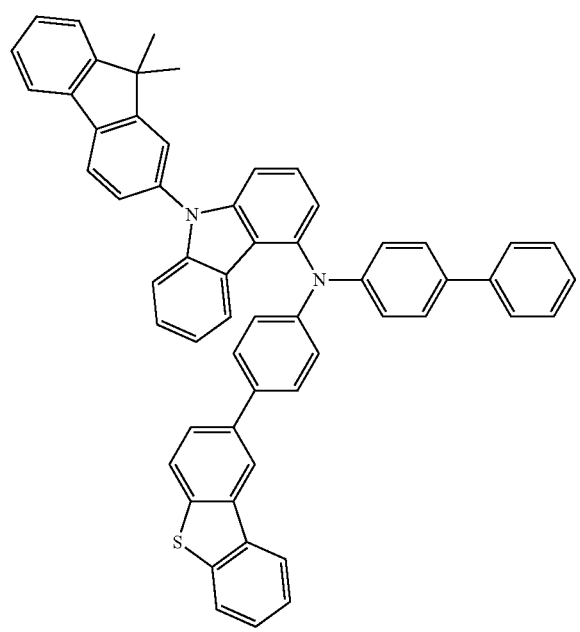
N-33
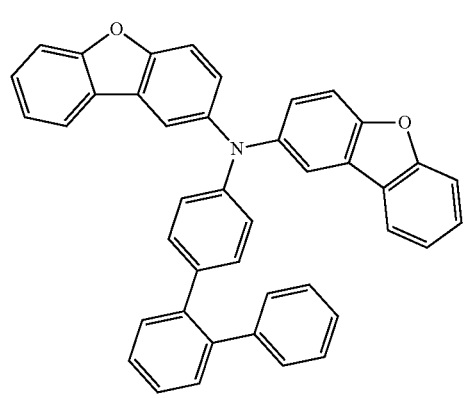
N-34
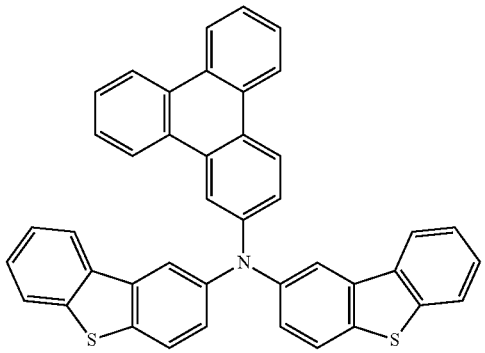
N-35
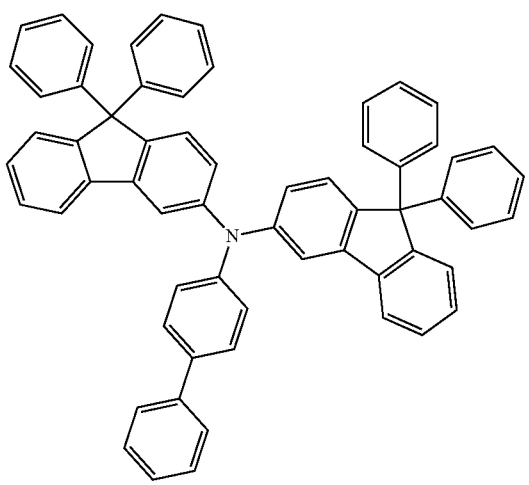
N-36
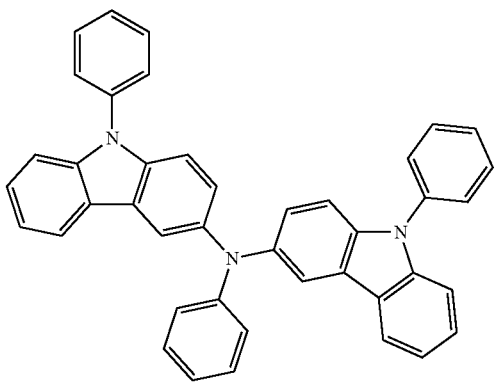
N-37
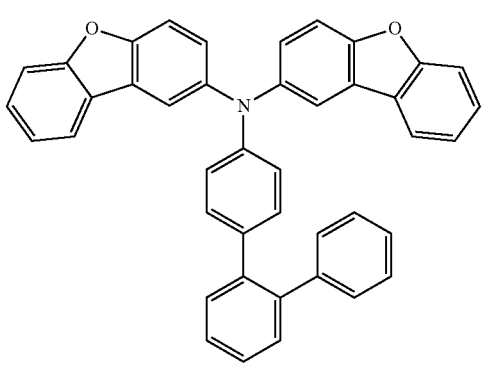

243
-continued
N-38
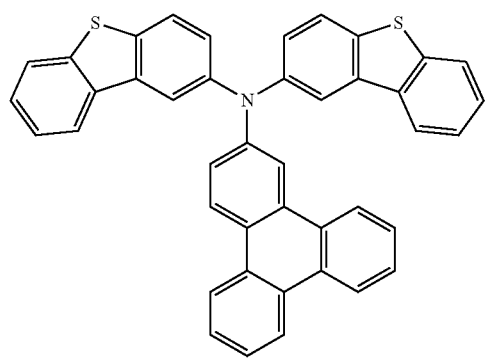
N-39
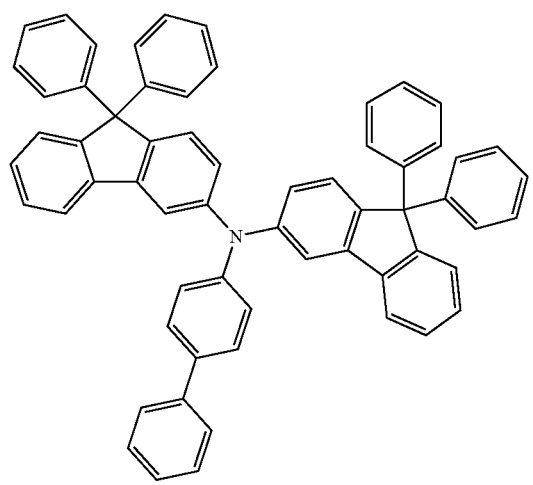
N-40
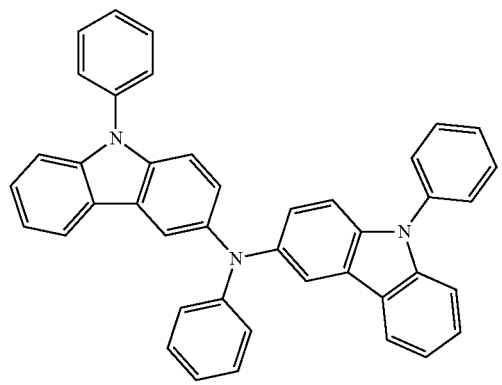
244
-continued
N-41
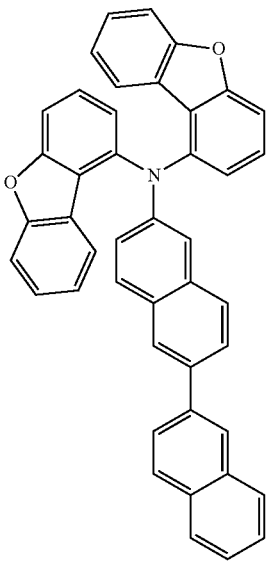
N-42
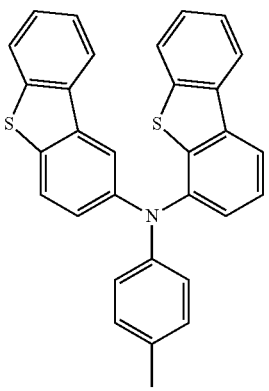
N-43
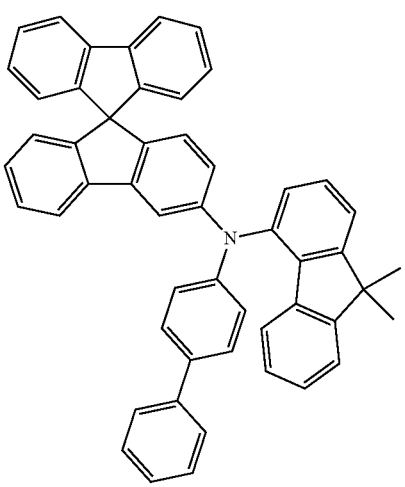

N-44
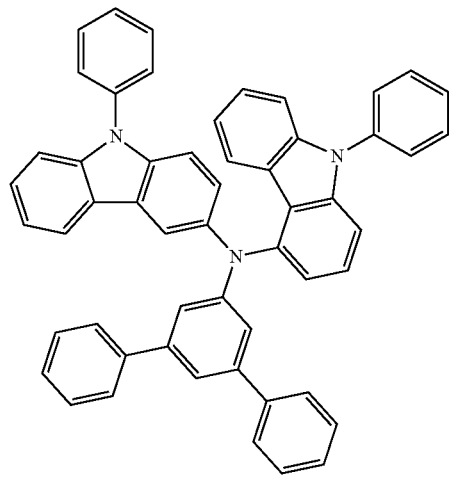
N-45
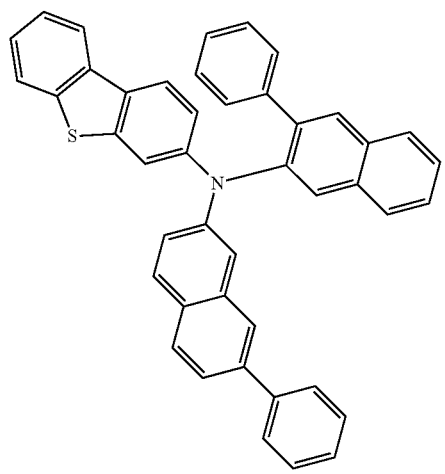
N-46
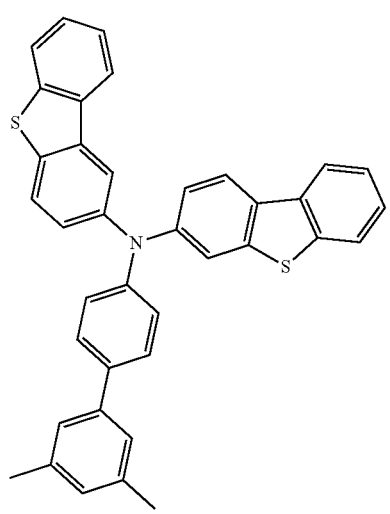
N-47
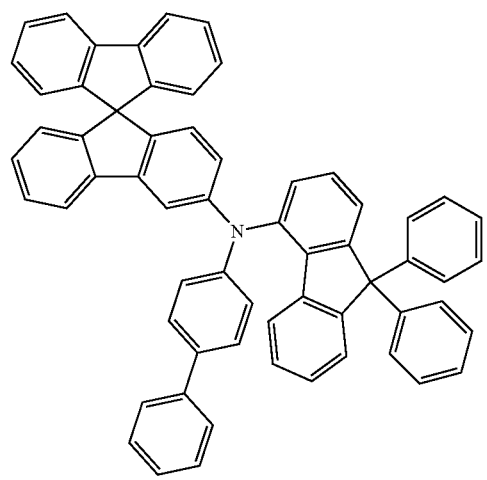
N-48
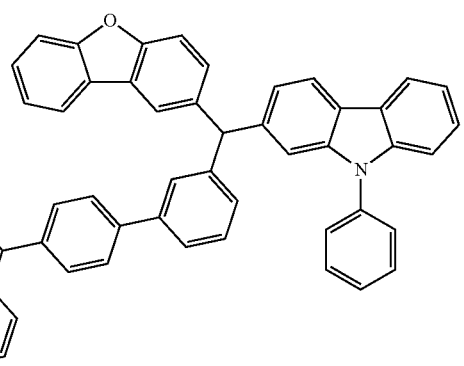
N-49
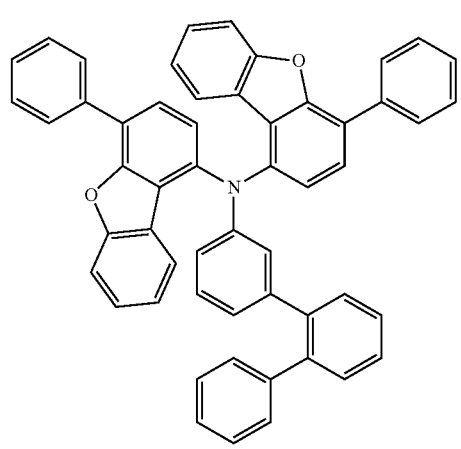

N-50
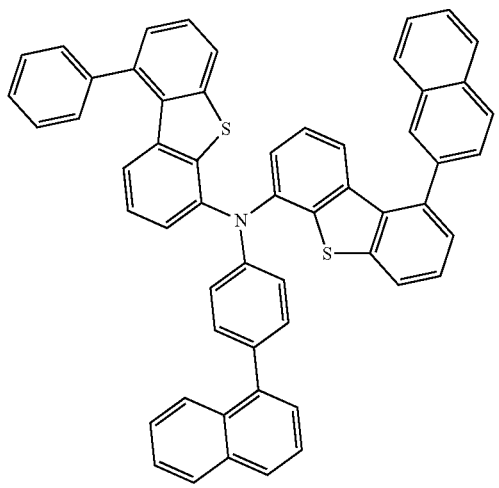
N-52
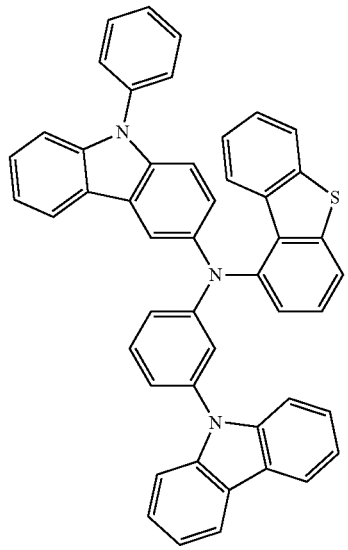
N-53
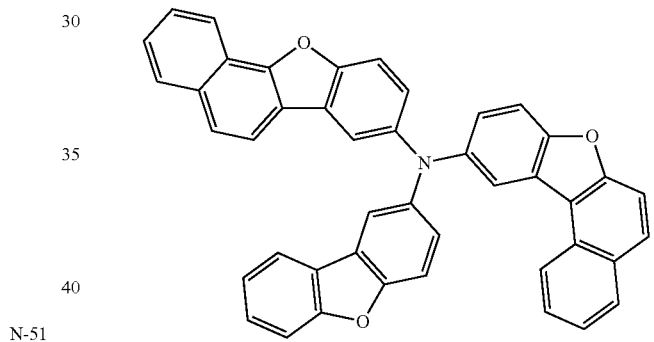
N-51
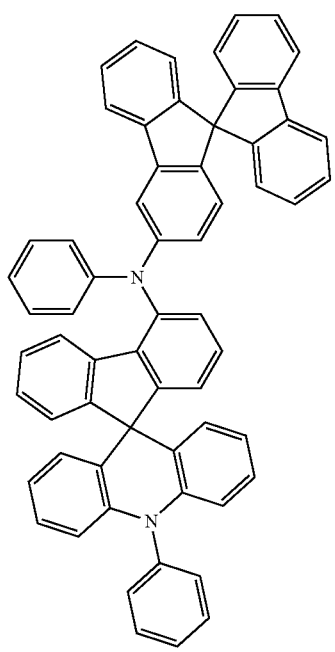
N-54
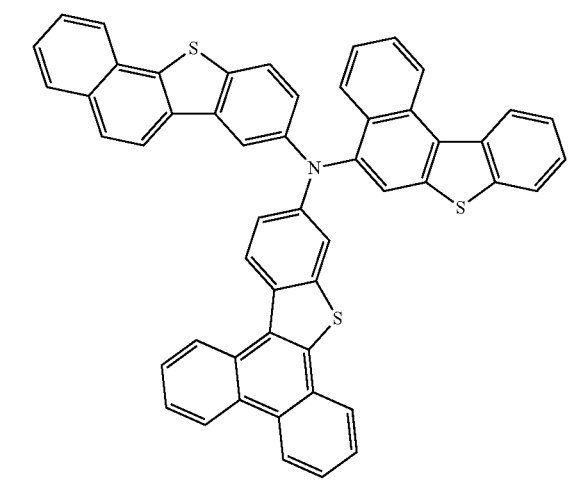

N-55
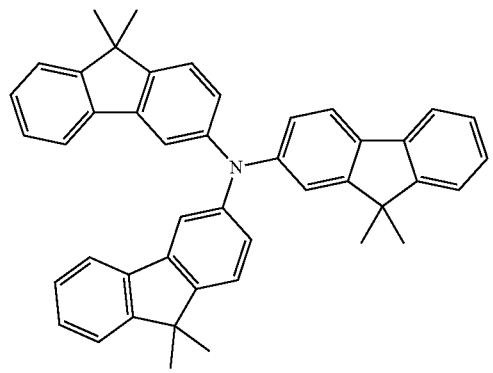
N-58
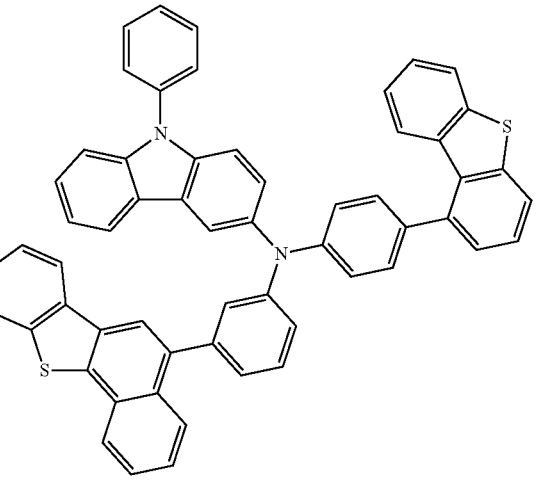
N-56
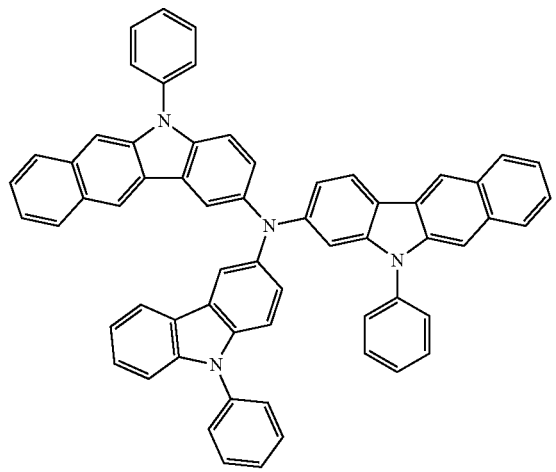
N-59
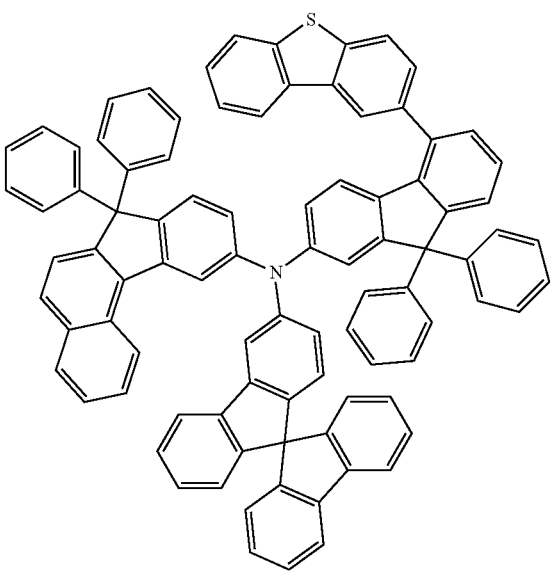
N-57
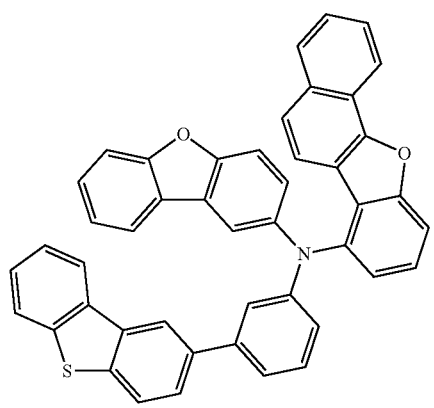
N-60
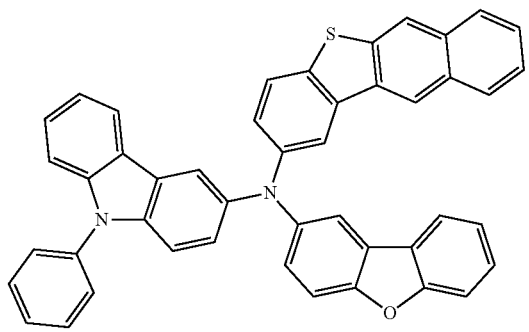

N-61
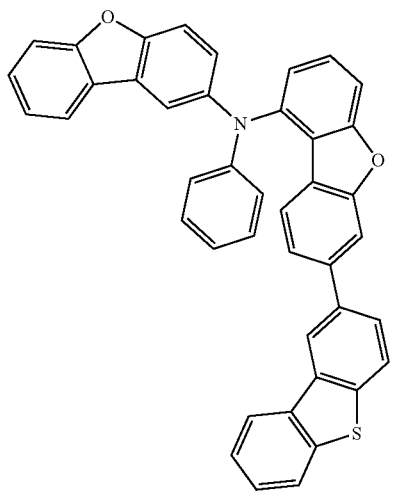
N-62
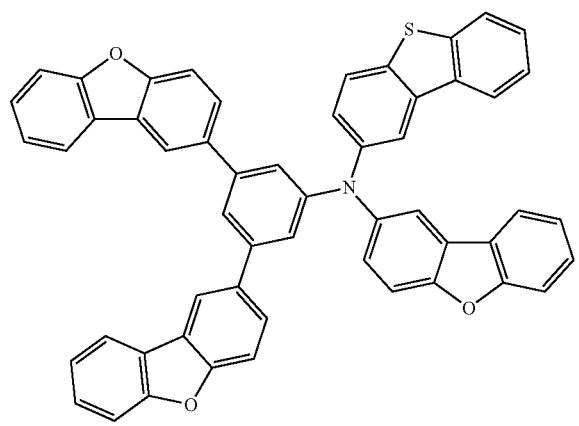
N-63
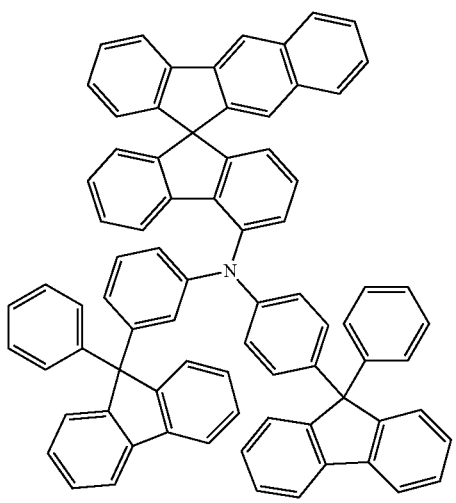
N-64
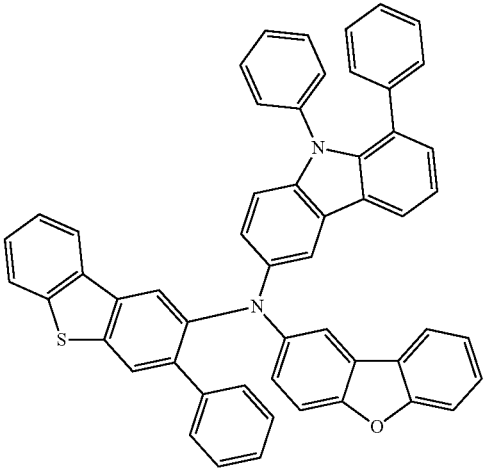
N-65
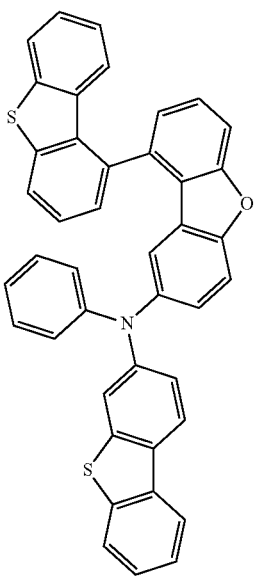
N-66
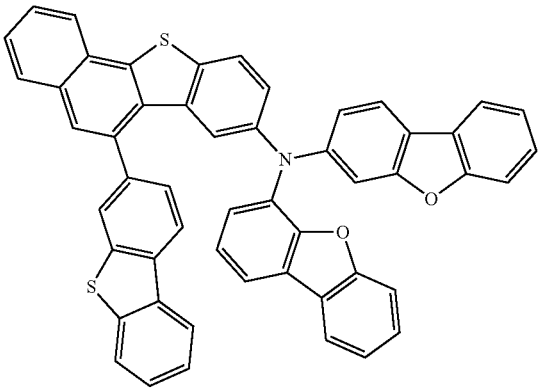

-continued
N-67
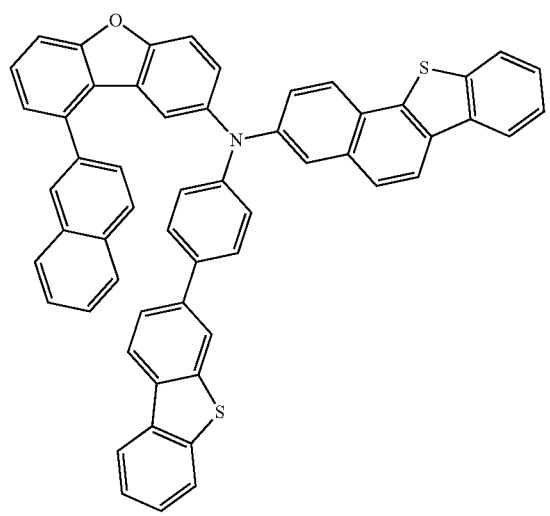
N-68
N-69
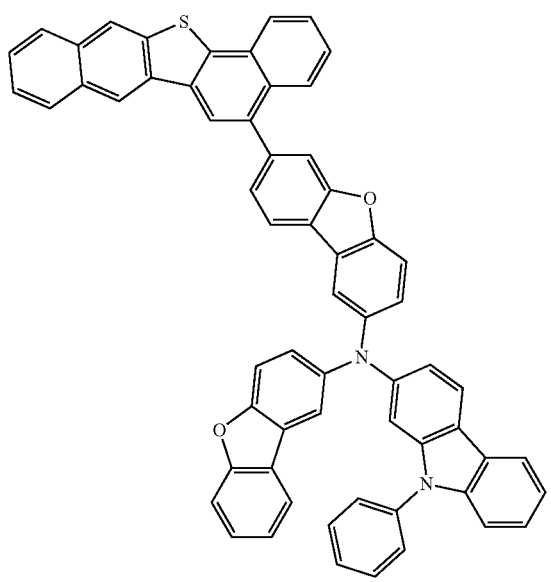
-continued
N-70
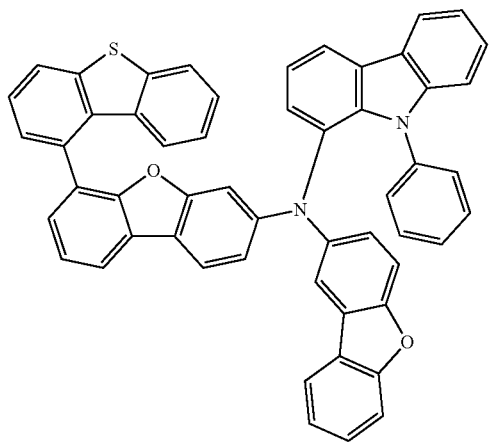
N-71
N-72
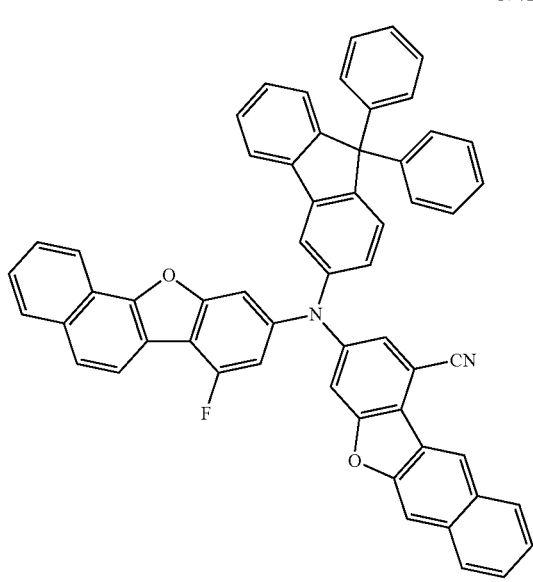

N-73
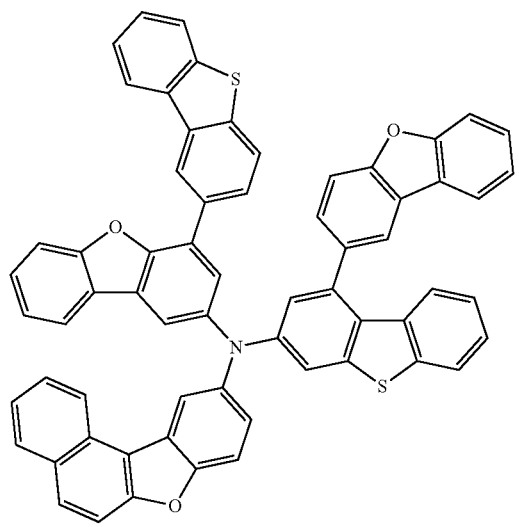
N-76
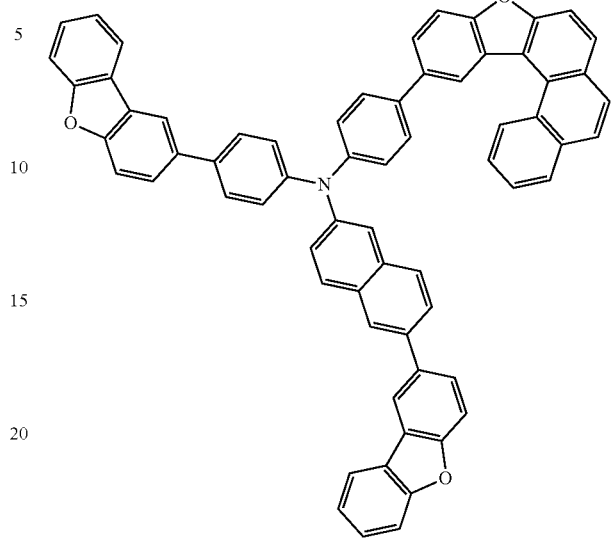
N-74
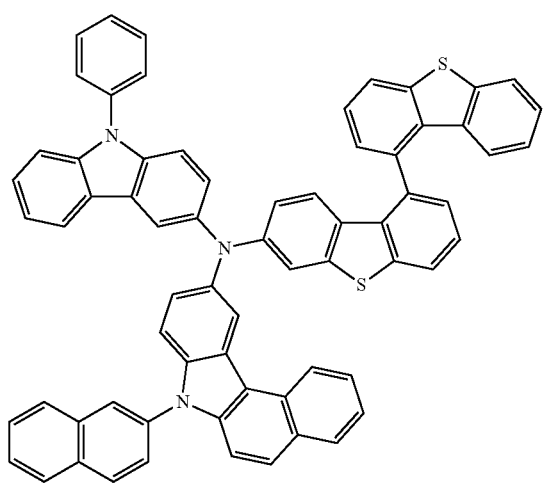
N-75
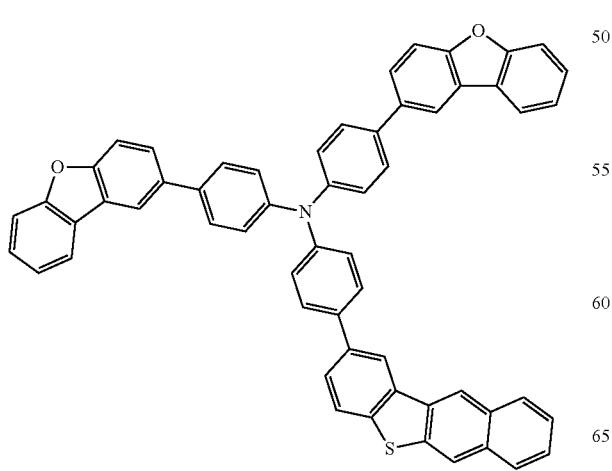
N-77
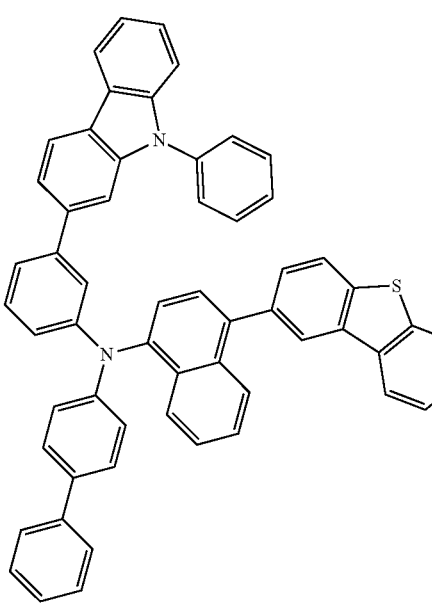

N-78
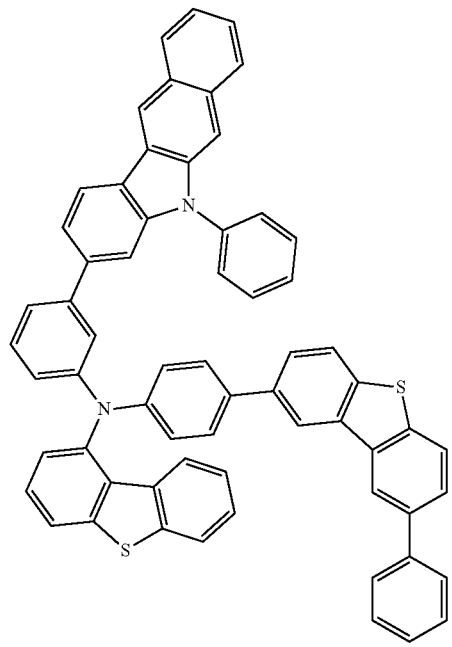
N-80
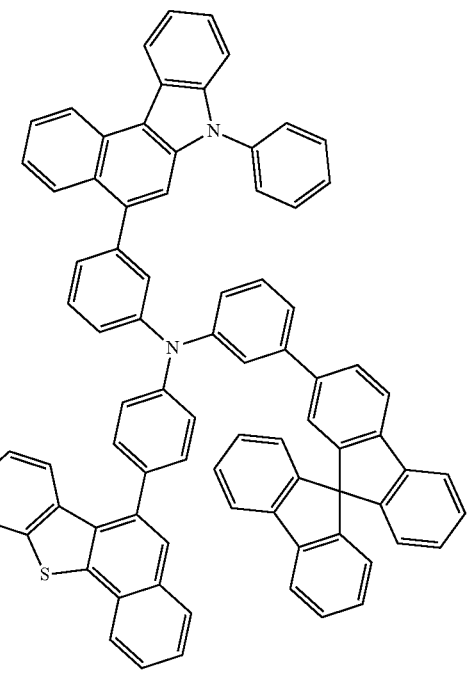
N-79
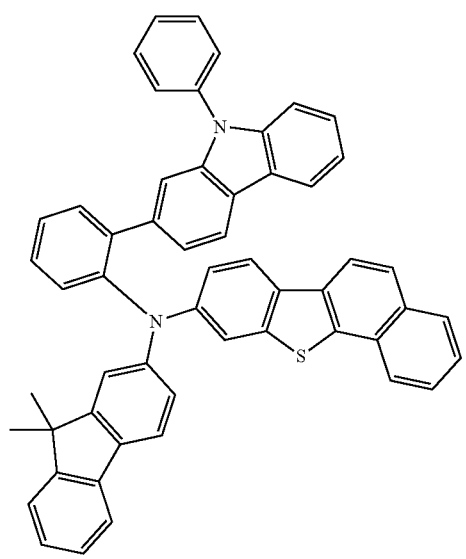
N-81
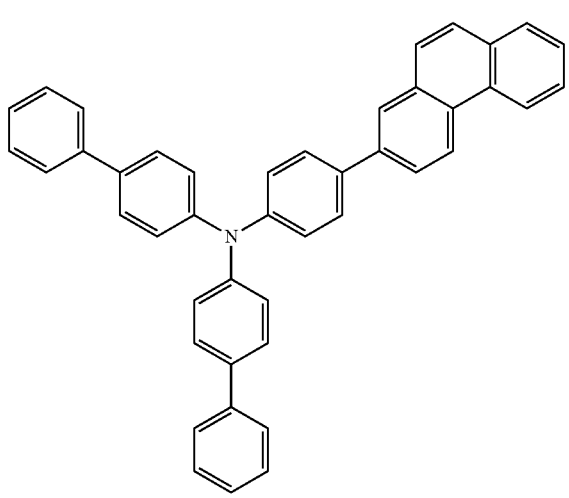

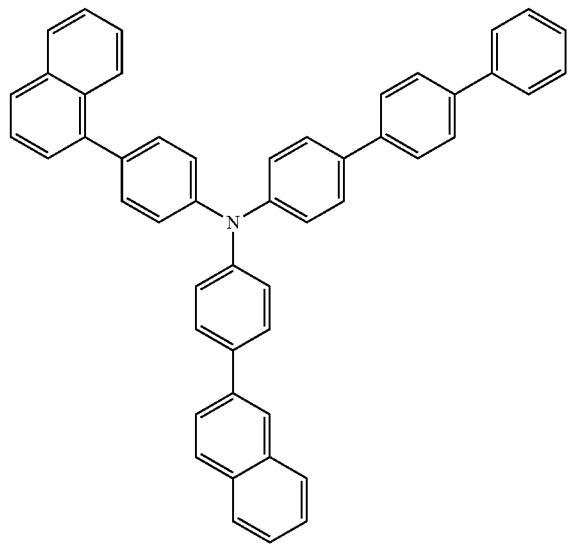
N-82
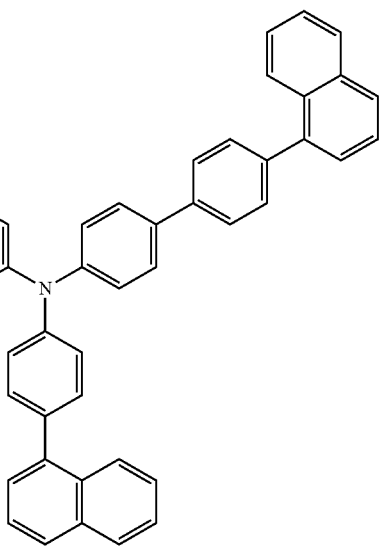
N-84
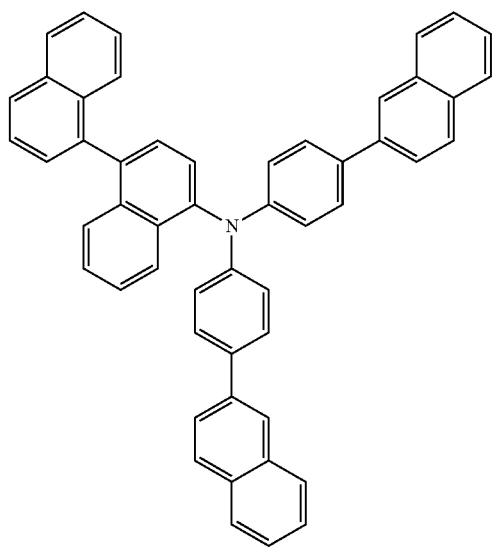
N-85
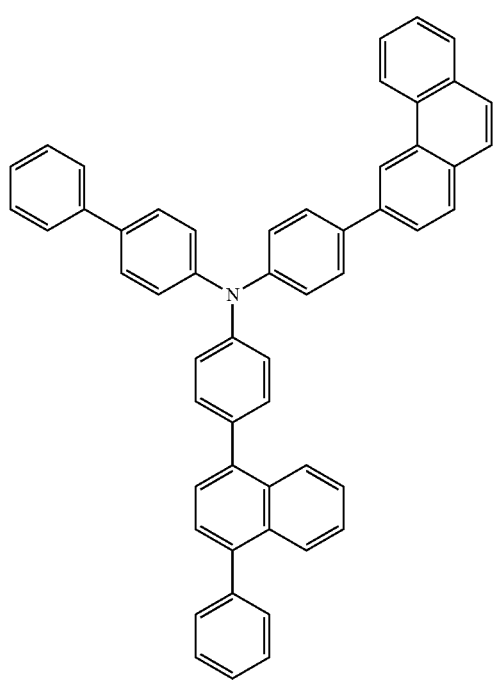
N-83
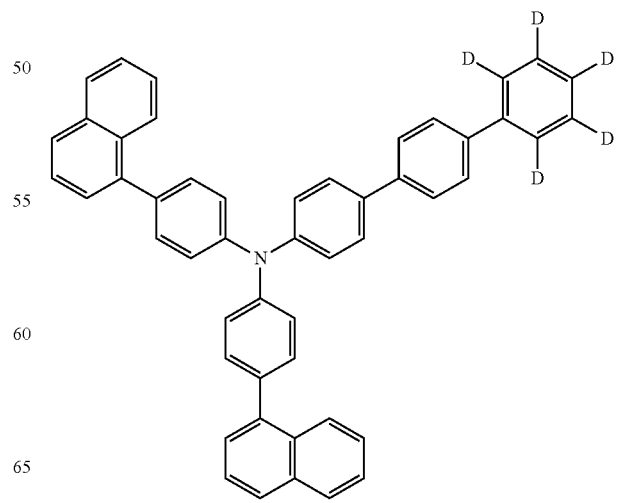
N-86

N-87
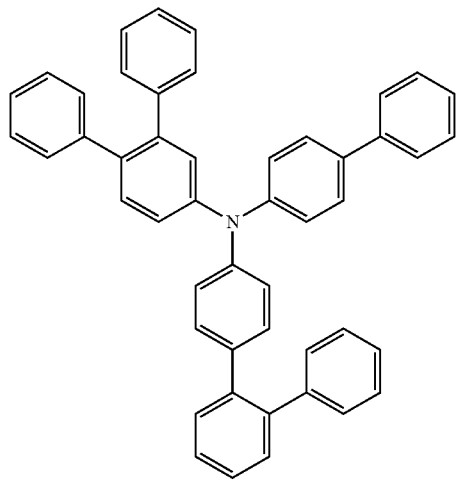
N-88
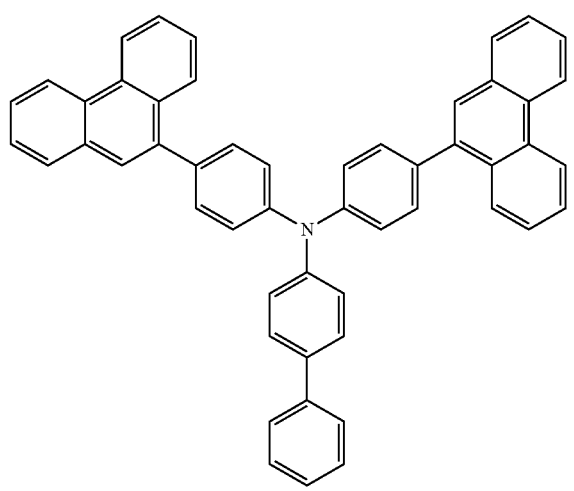
N-89
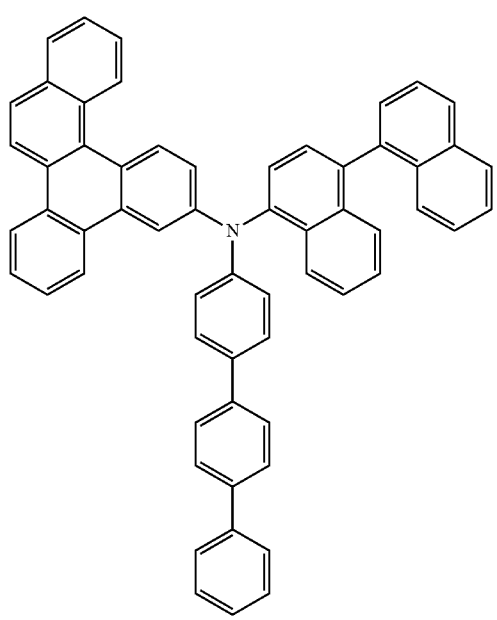
N-90
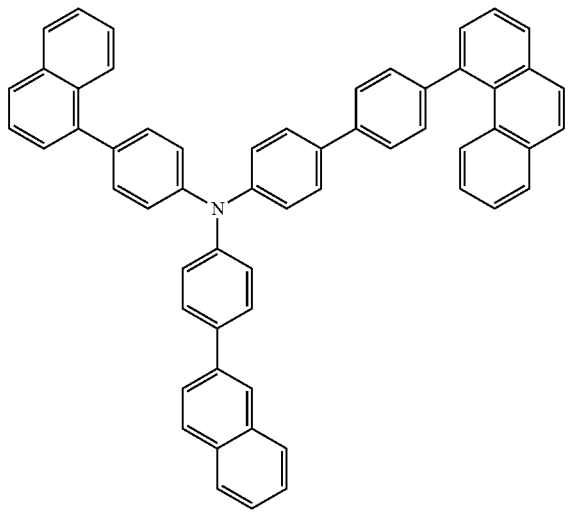
N-91
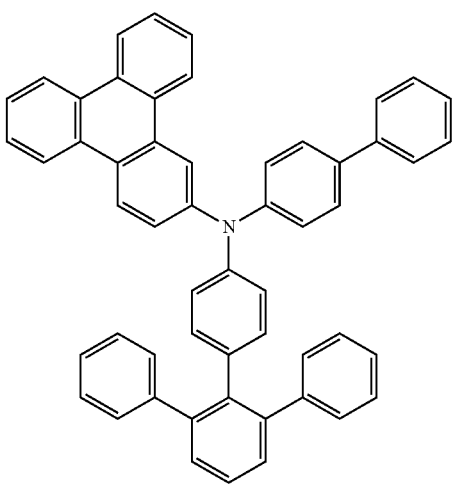
N-92
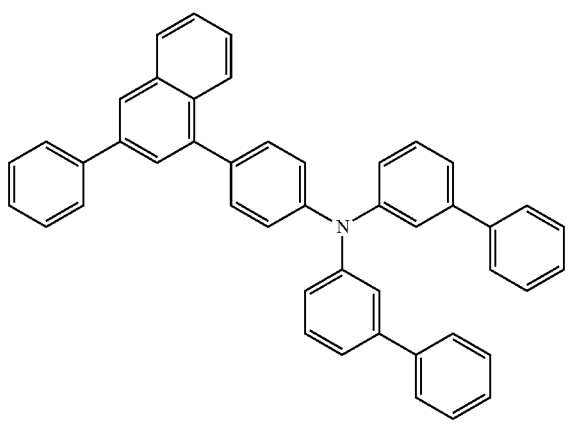

N-93
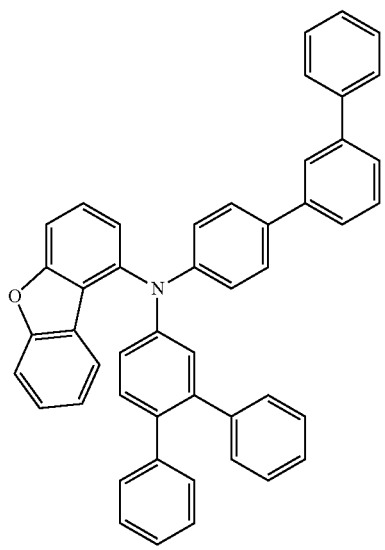
N-96
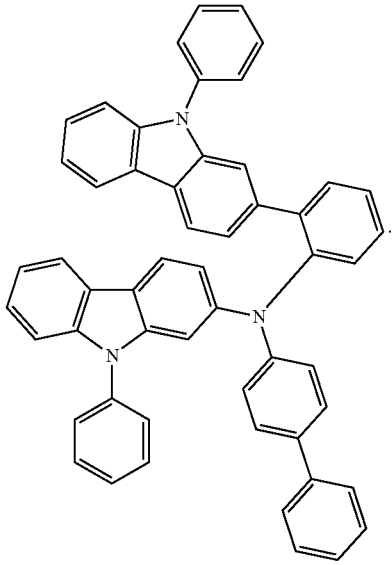
N-94
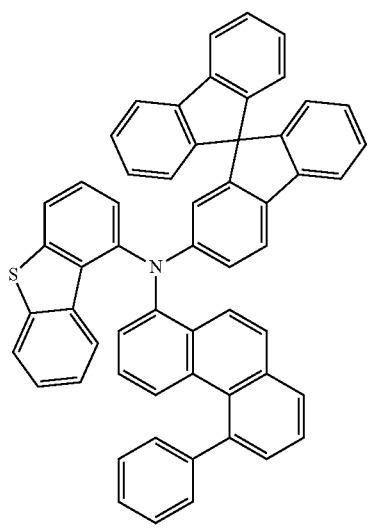
8. The organic electronic element of claim 6, wherein the compound represented by Formula 4 is any one of Compounds S-1 to S-108:
S-1
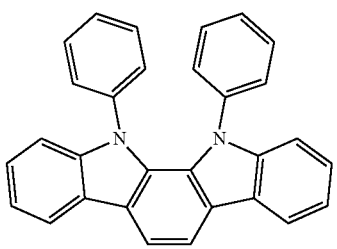
N-95
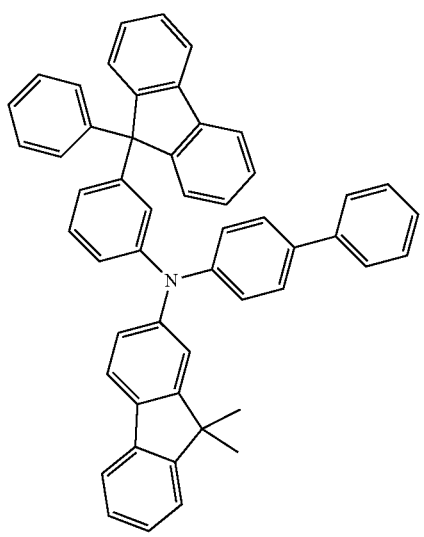
S-2
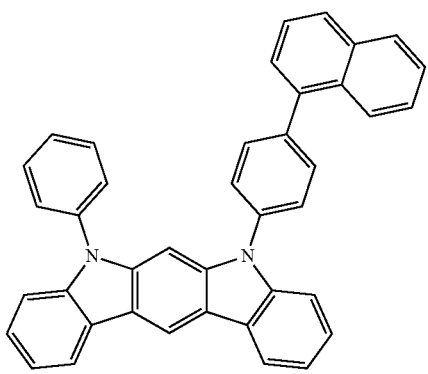

-continued
S-3
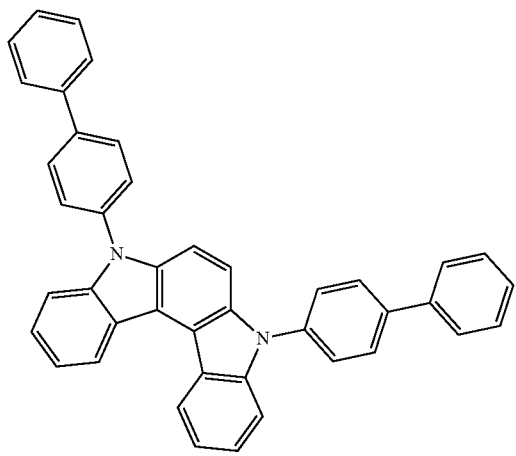
S-4
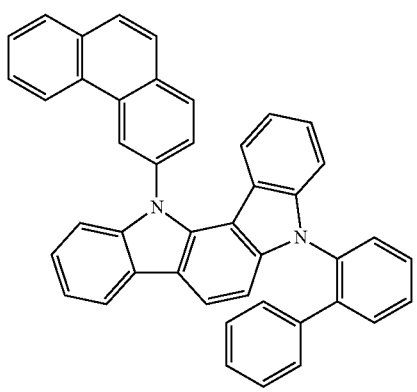
S-5
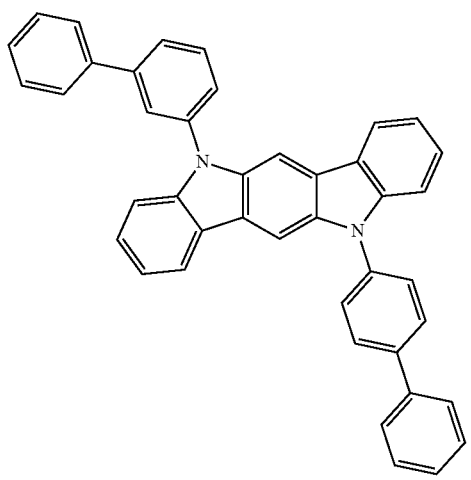
S-6
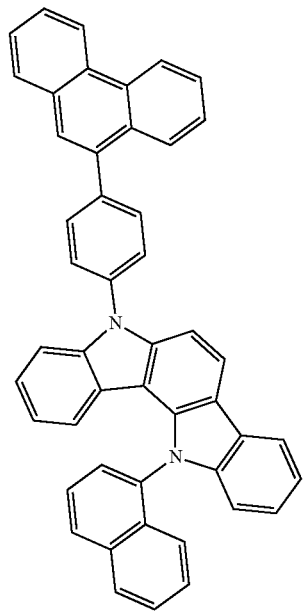
S-7
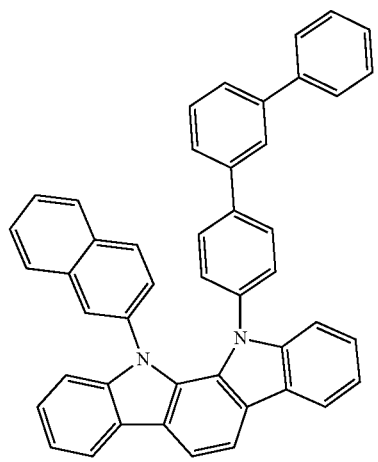
S-8
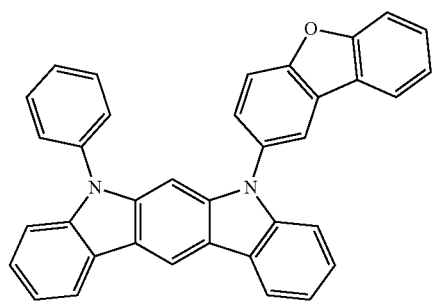

S-9
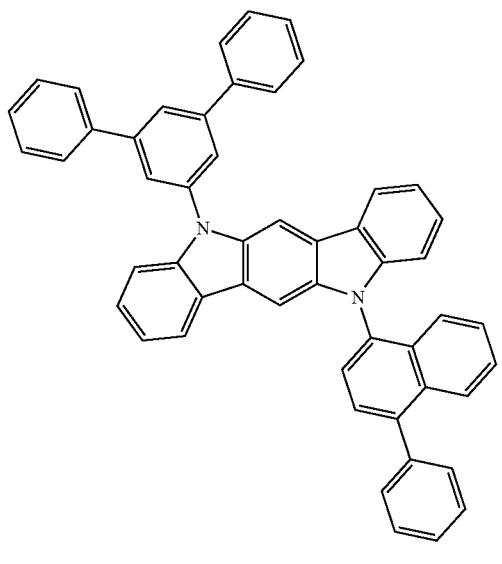
S-11
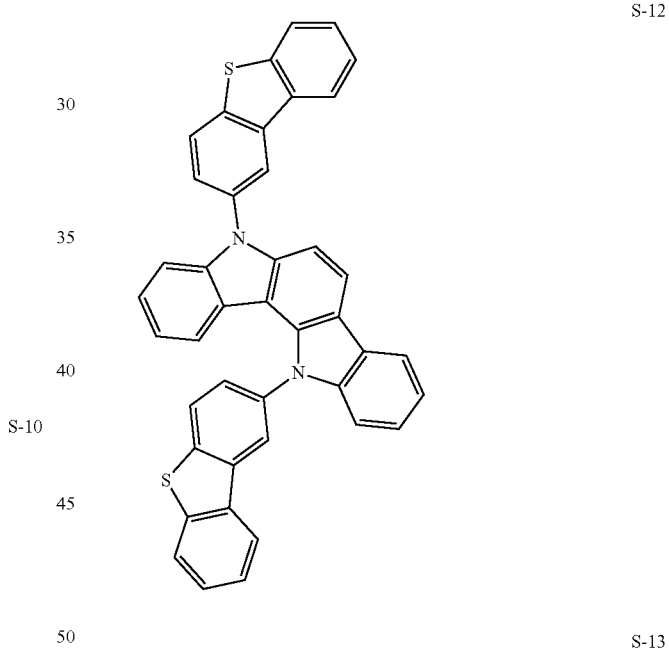
S-10
S-12
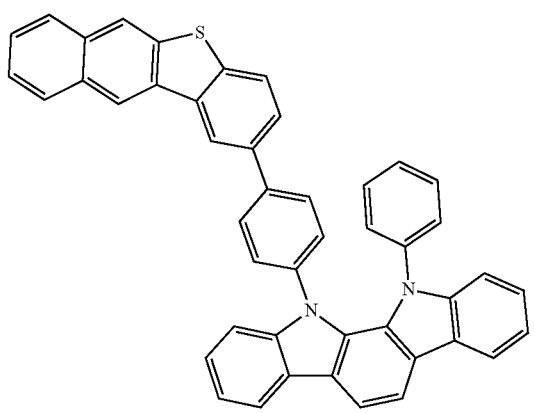
S-13

S-14
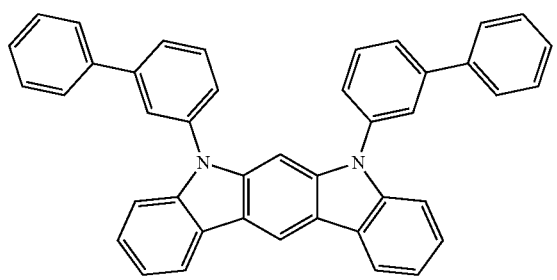
S-15
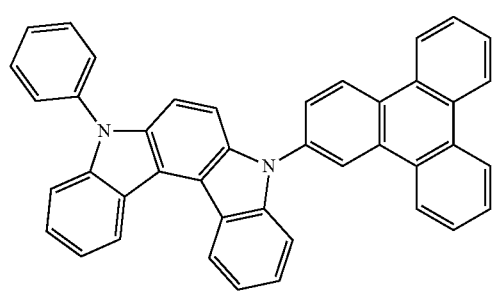
S-16
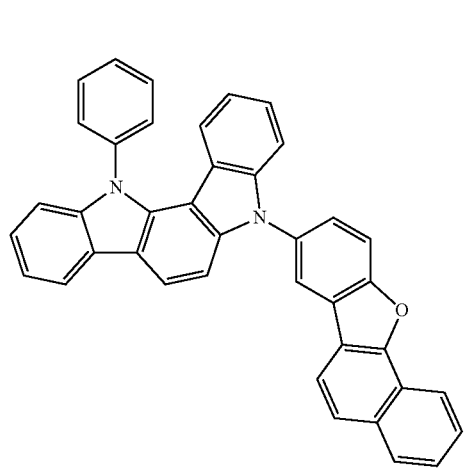
S-17
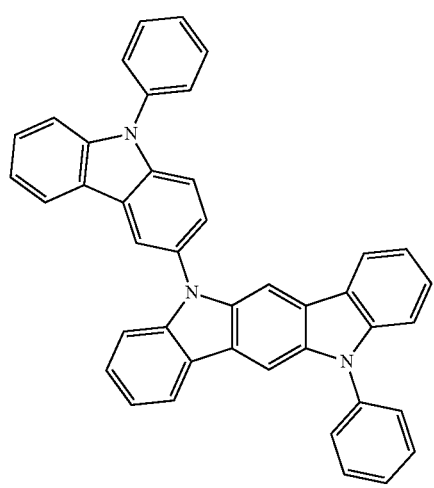
S-18
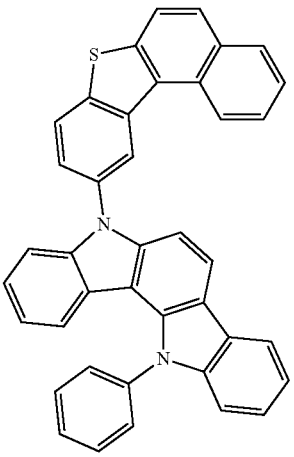
S-19
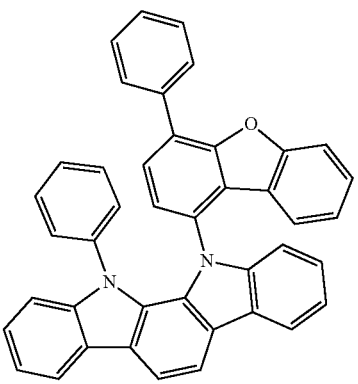
S-20
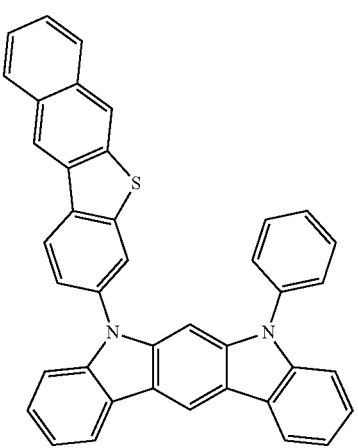

S-21
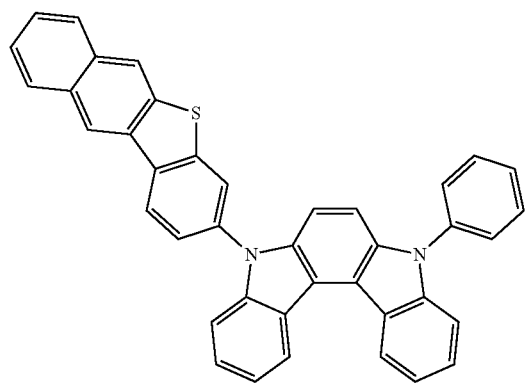
S-22
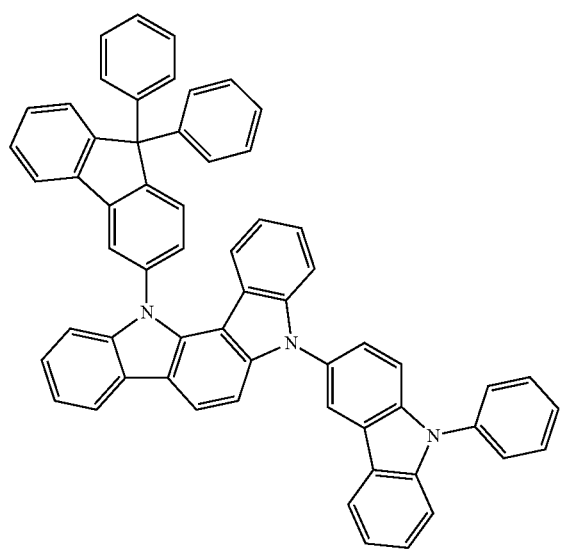
S-23
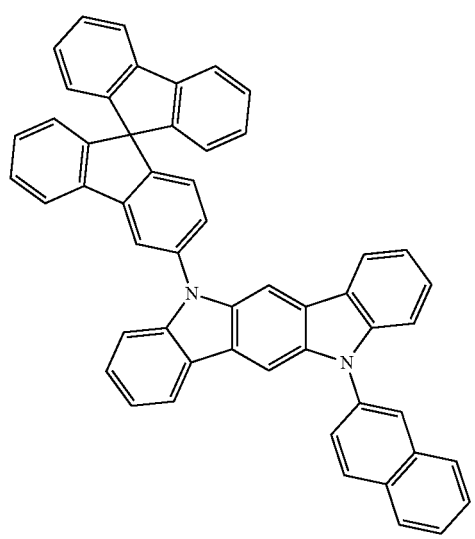
S-24
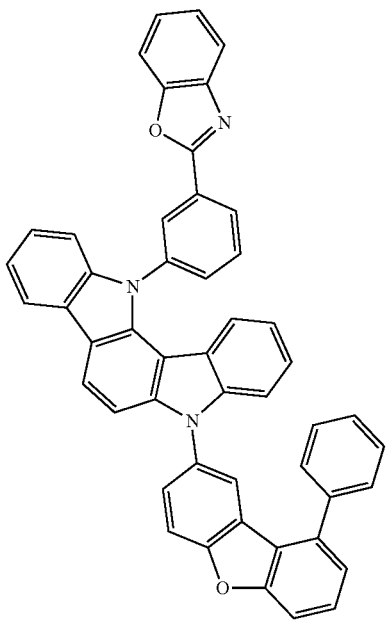
S-25
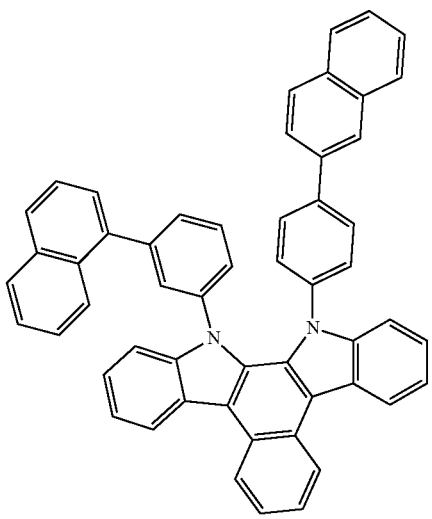
S-26
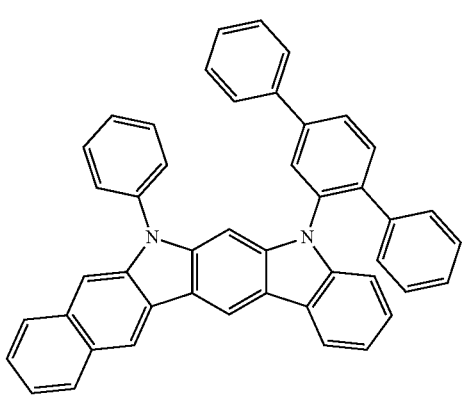

S-27
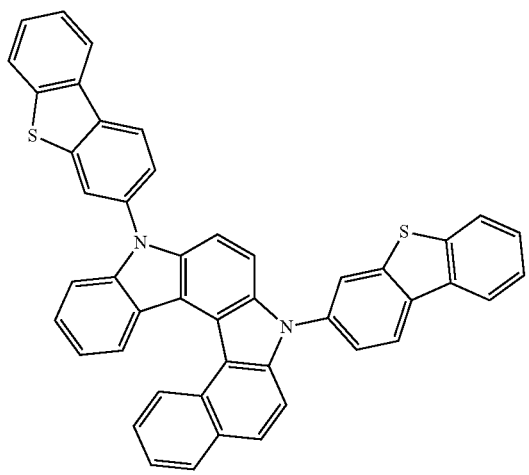
S-28
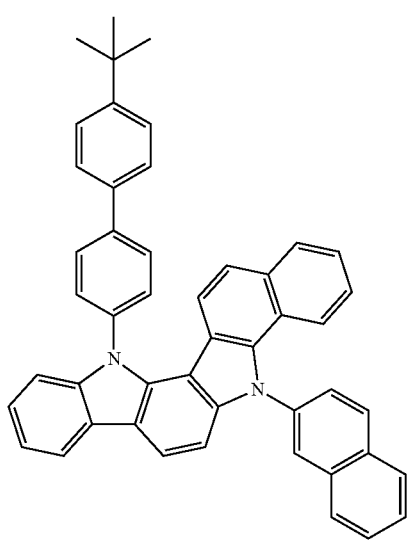
S-29
S-30
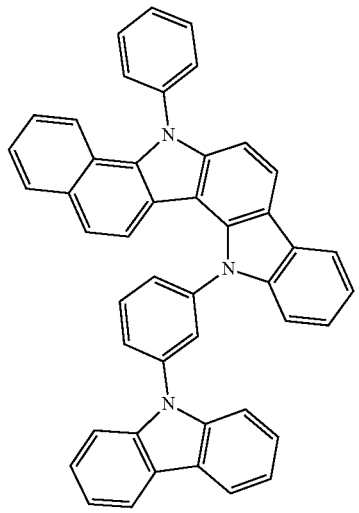
S-31
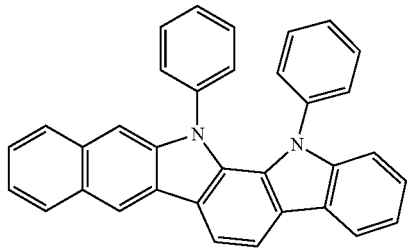
S-32
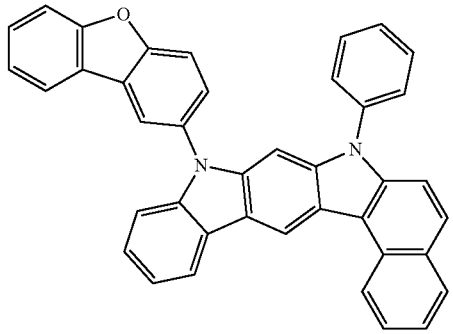
S-33
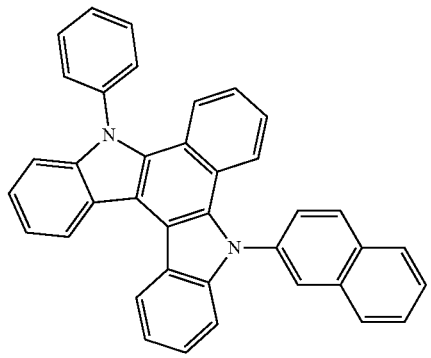

S-34 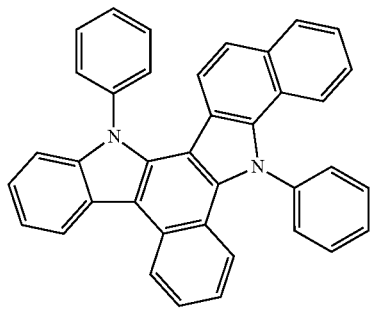
S-37 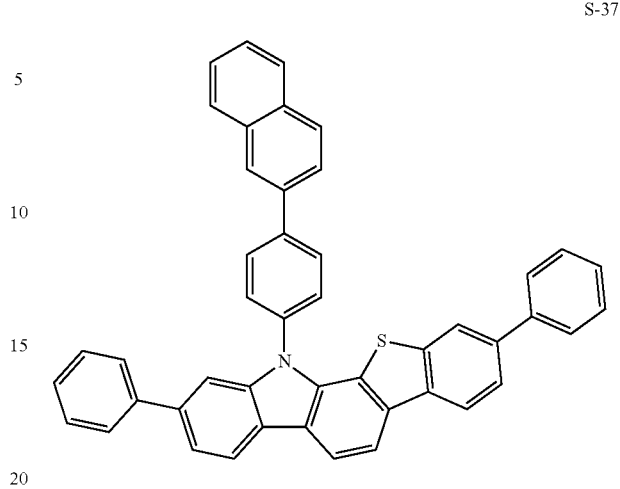
S-35 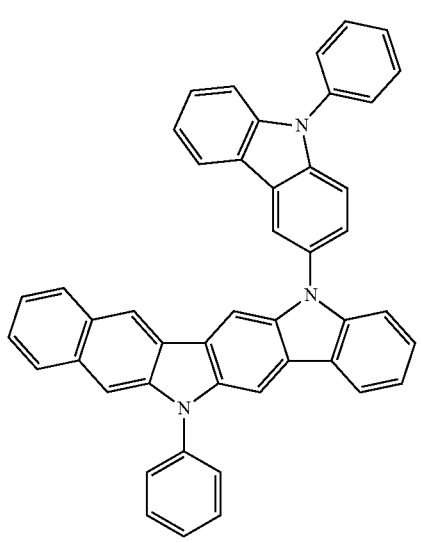
S-38 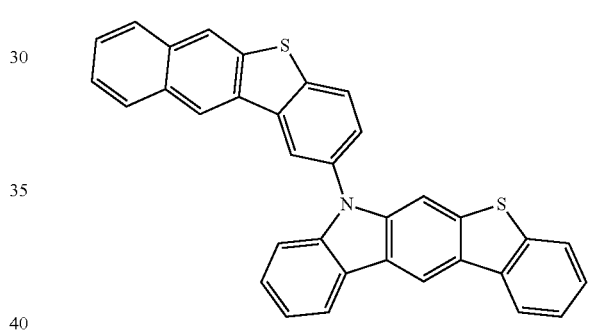
S-36 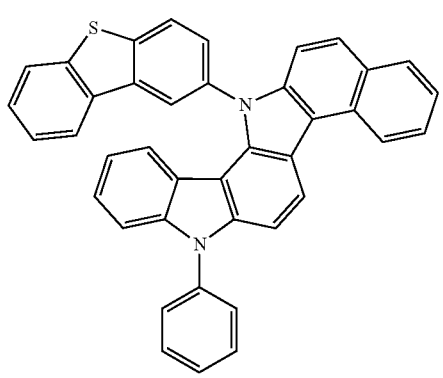
S-39 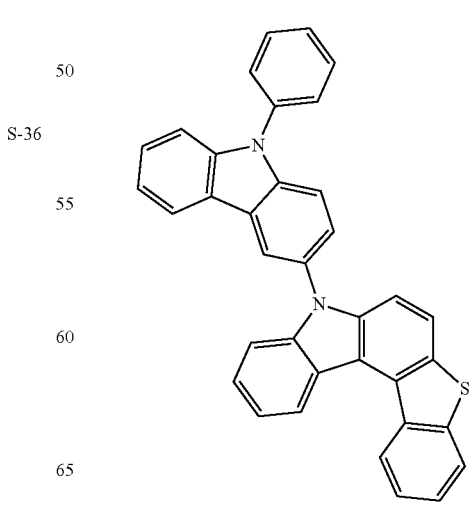

S-40
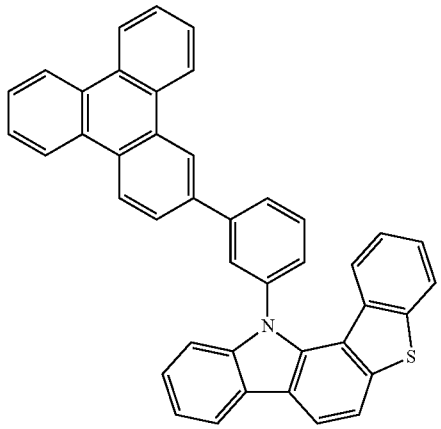
S-43
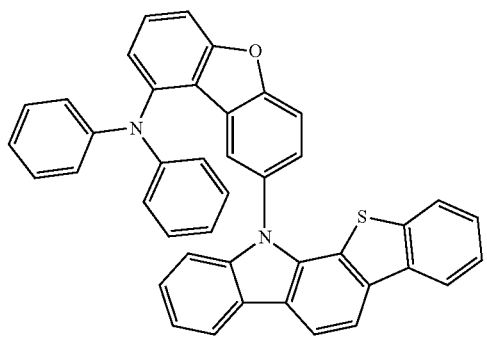
S-41
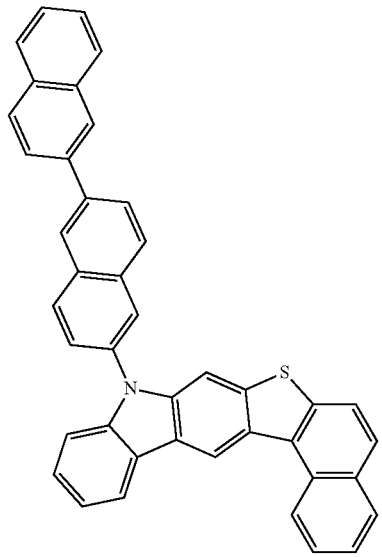
S-44
S-42
S-45
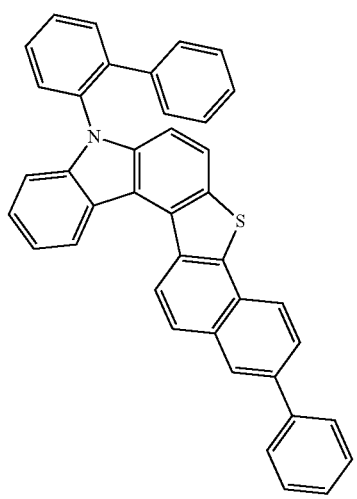

-continued
S-46
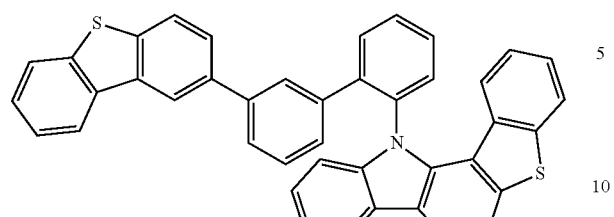
S-47
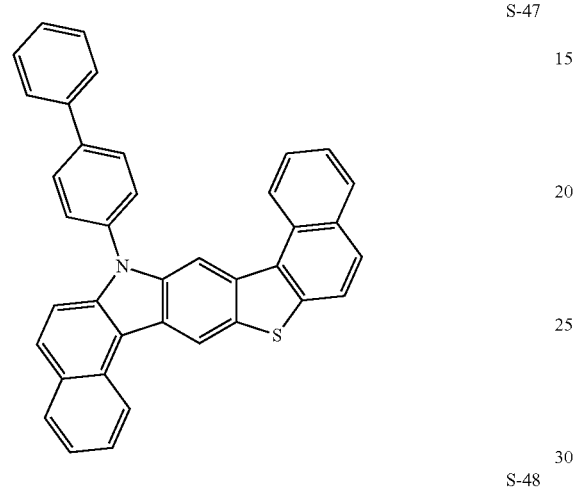
S-48
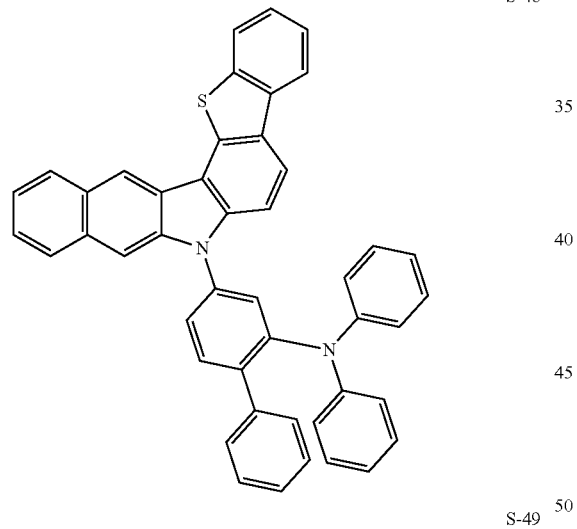
S-49
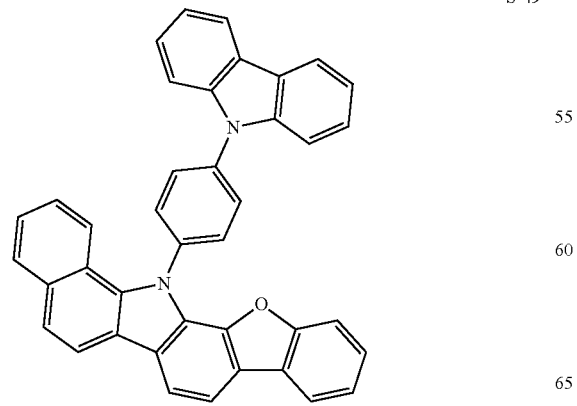
-continued
S-50
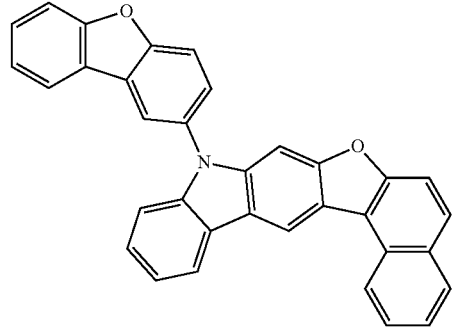
S-51
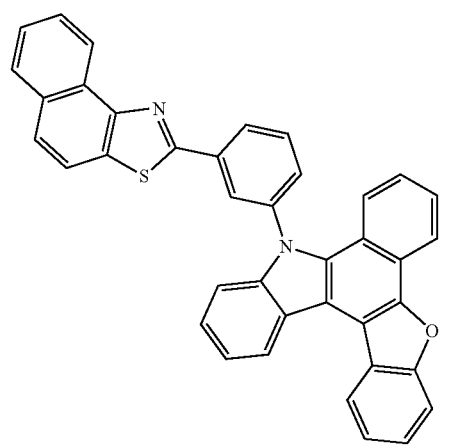
S-52
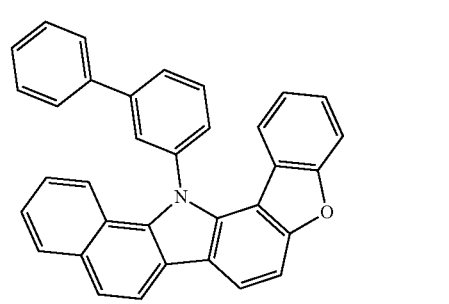
S-53
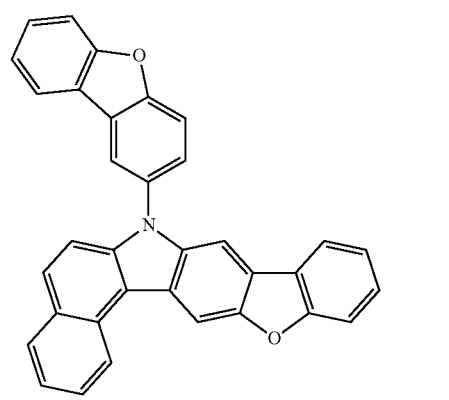

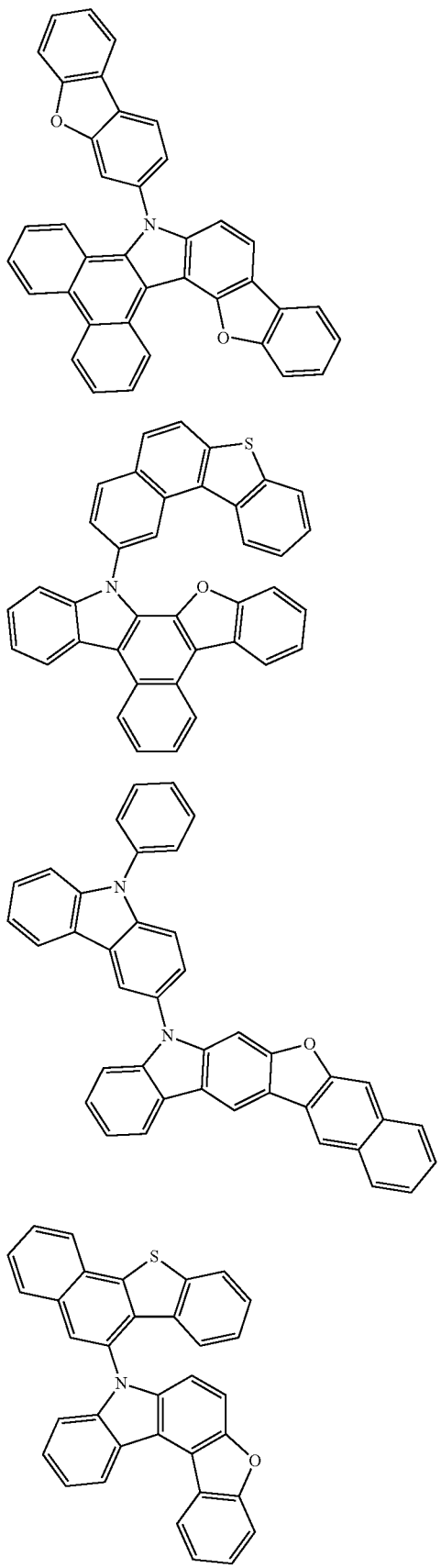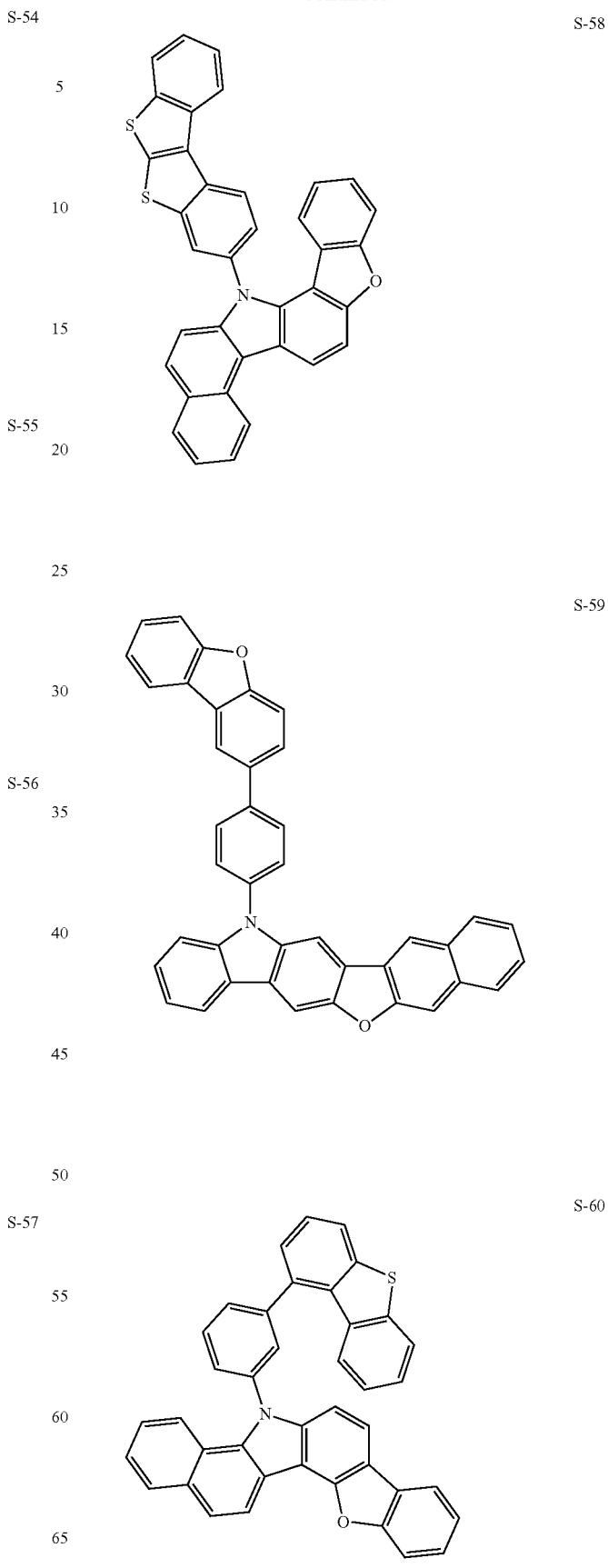

S-61
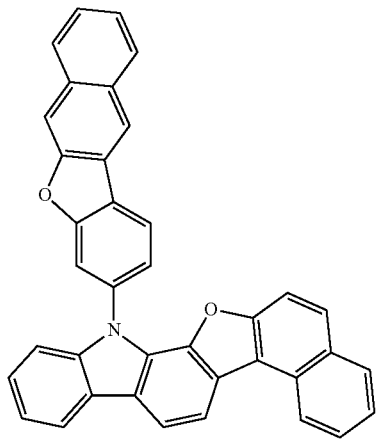
S-62
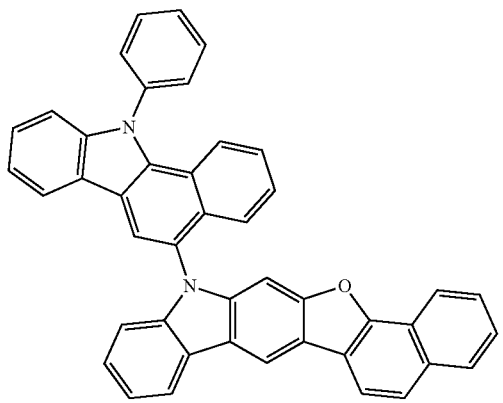
S-63
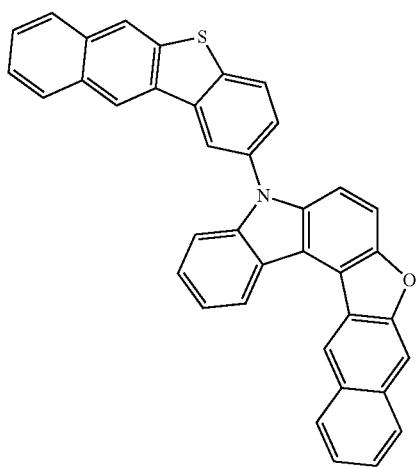
S-64
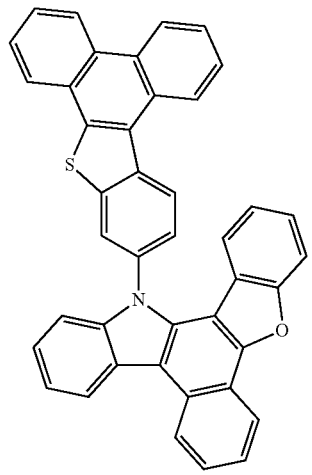
S-65
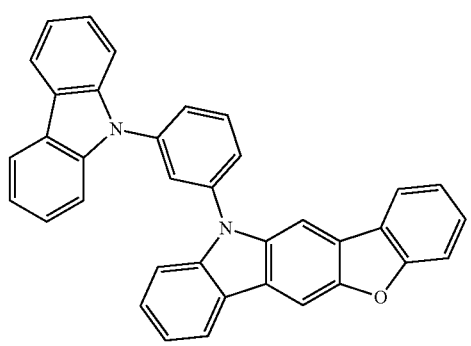
S-66
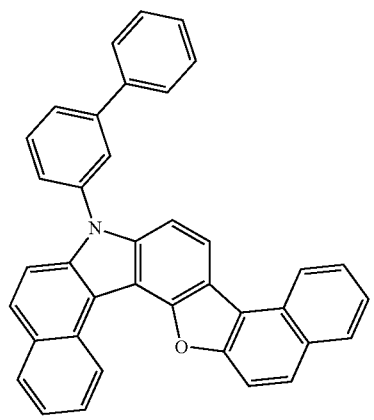
S-67
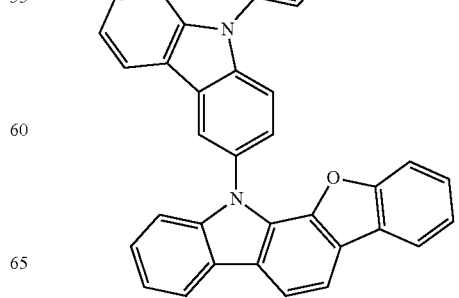

-continued
S-68
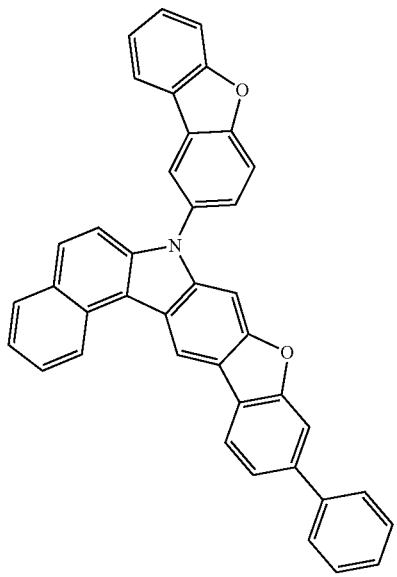
S-69
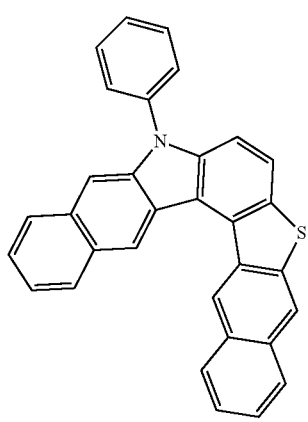
S-70
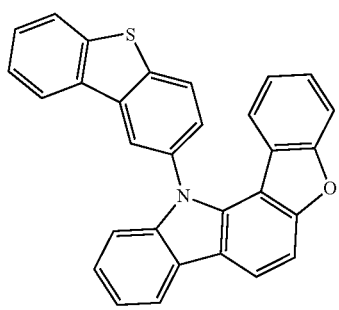
-continued
S-71
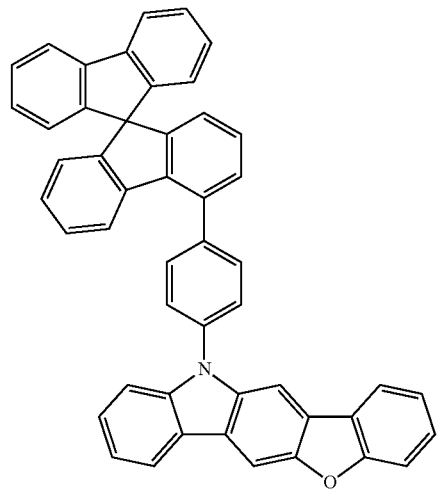
S-72
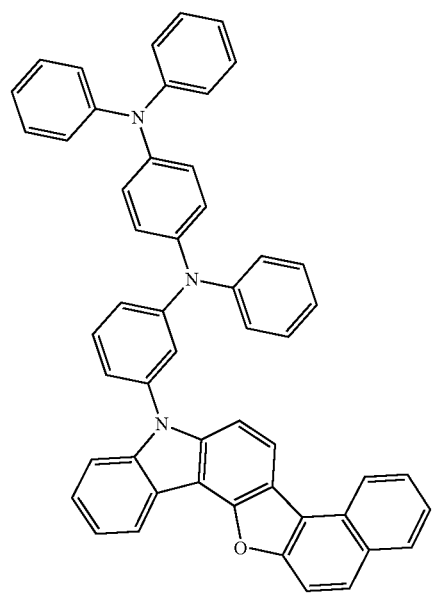
S-73
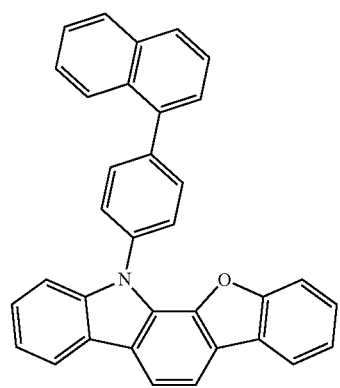

S-74
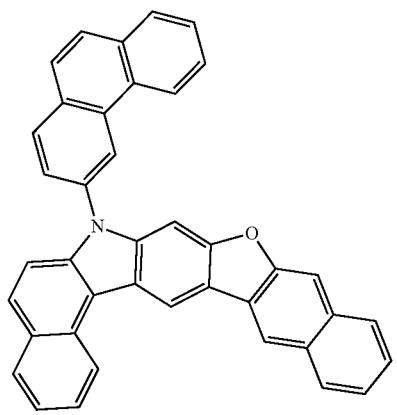
S-75
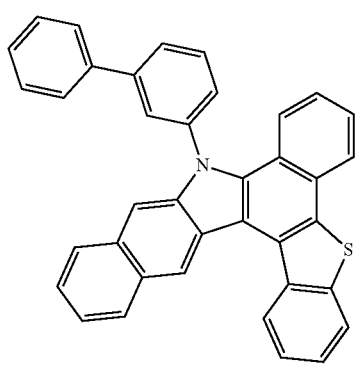
S-76
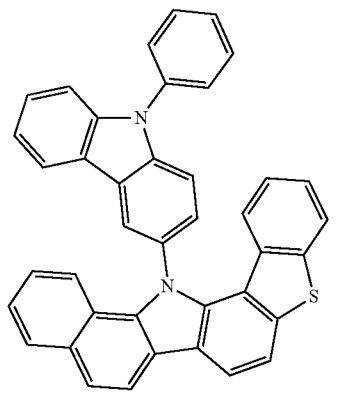
S-77
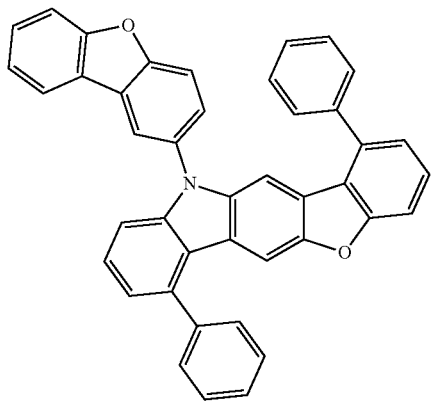
S-78
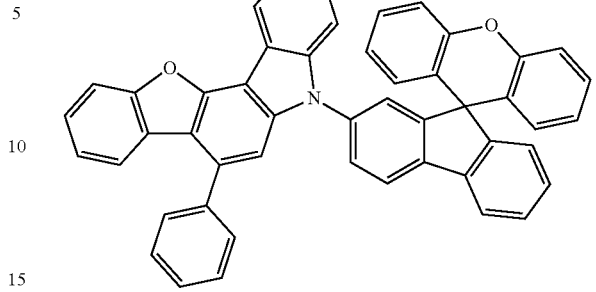
S-79
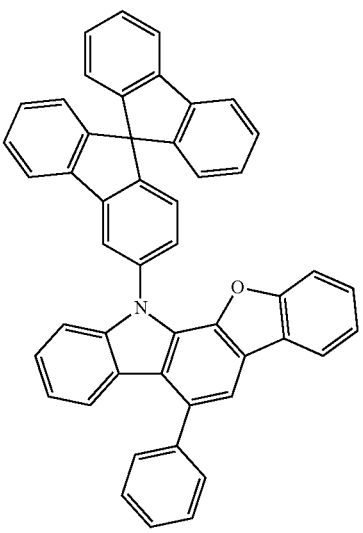
S-80
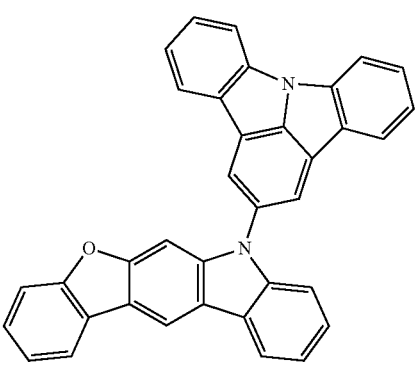
S-81
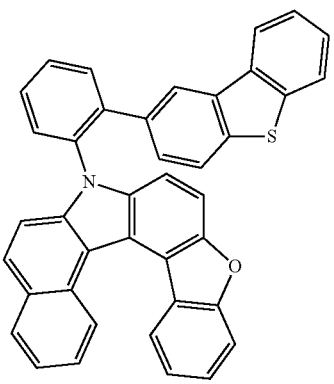

S-82
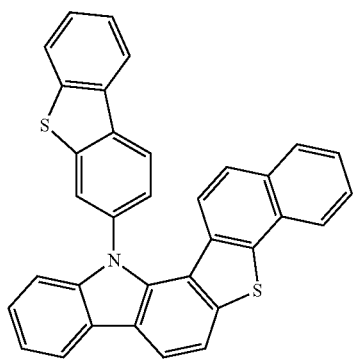
S-85
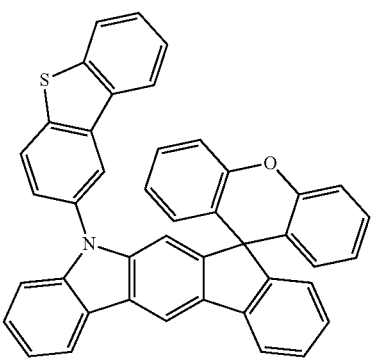
S-83
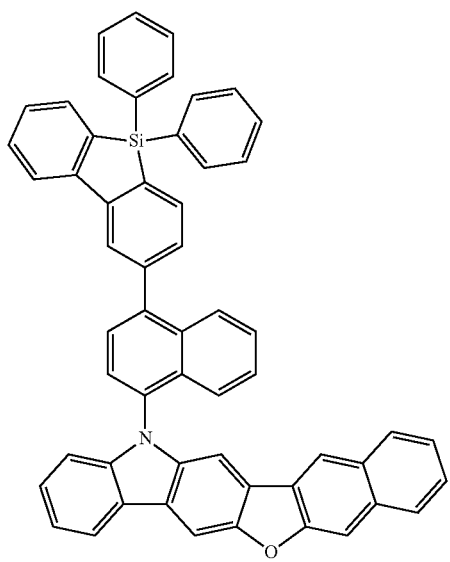
S-86
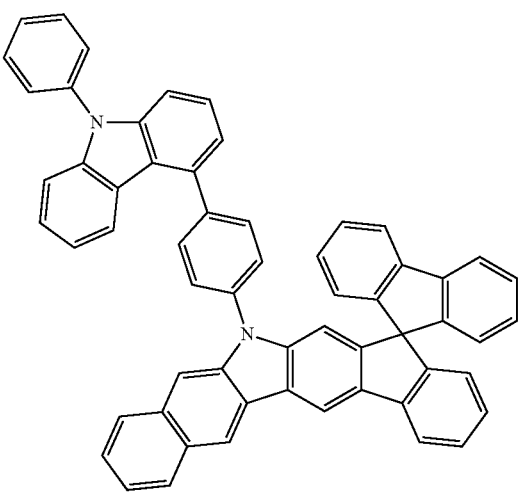
S-84
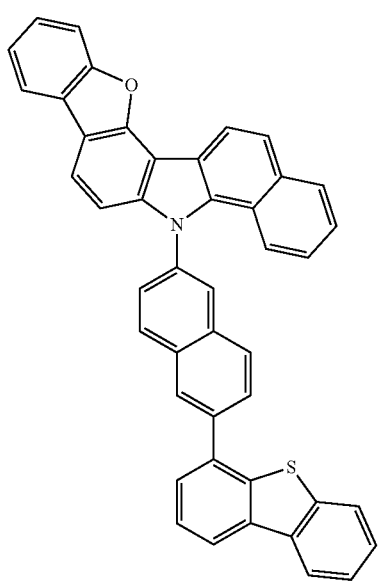
S-87
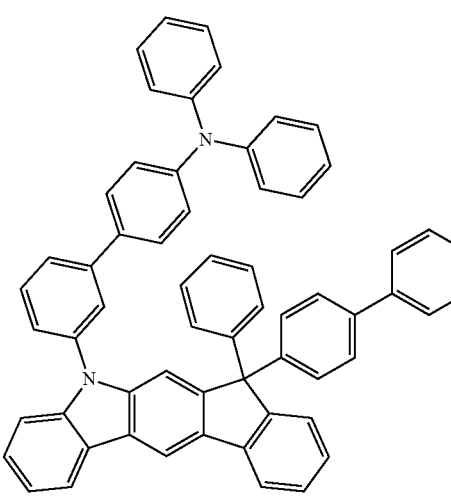

-continued
S-88
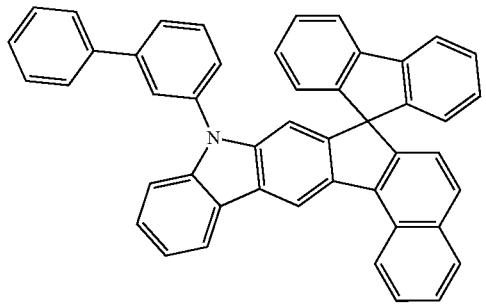
S-89
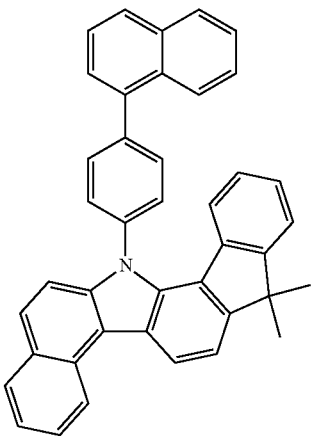
S-90
S-91
-continued
S-92
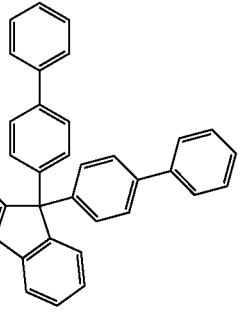
S-93
S-94
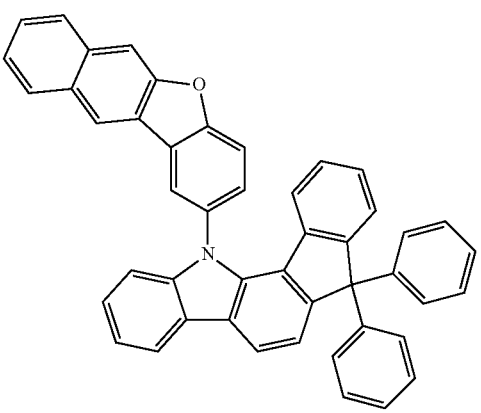
S-95
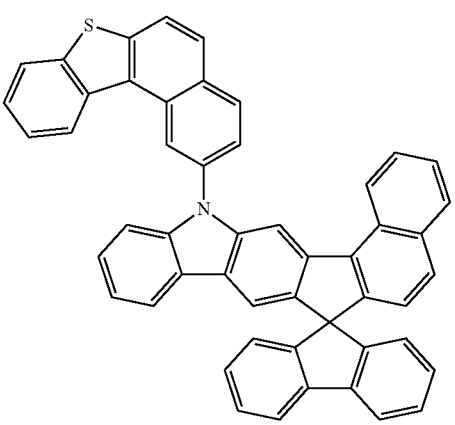

-continued
S-96
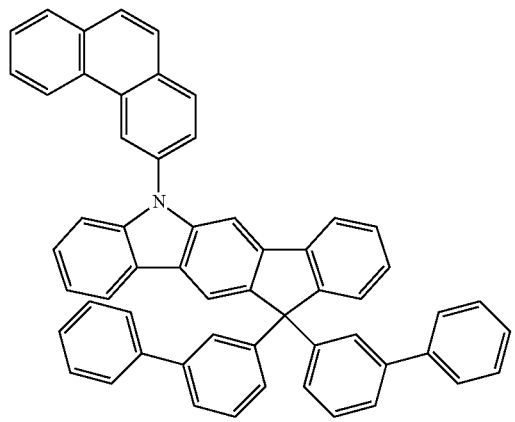
S-97
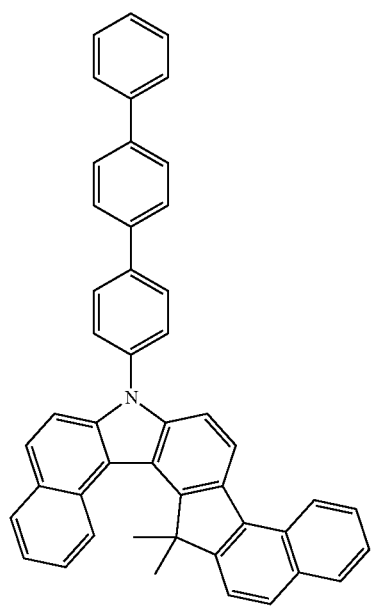
S-98
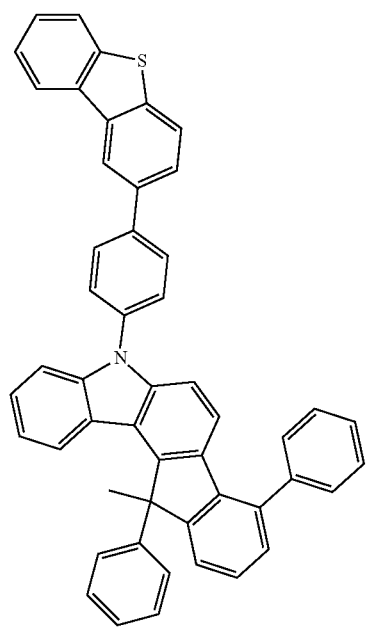
-continued
S-99
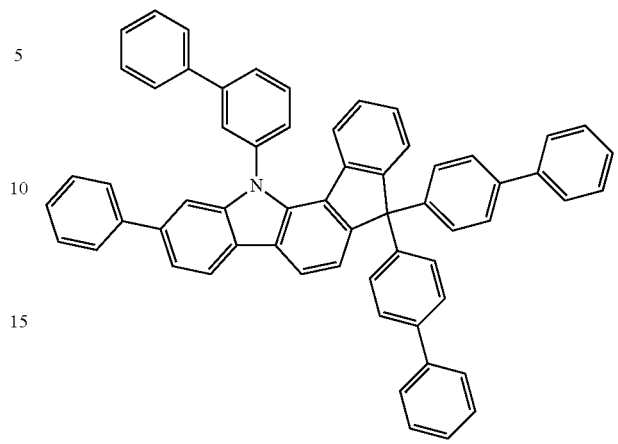
S-100
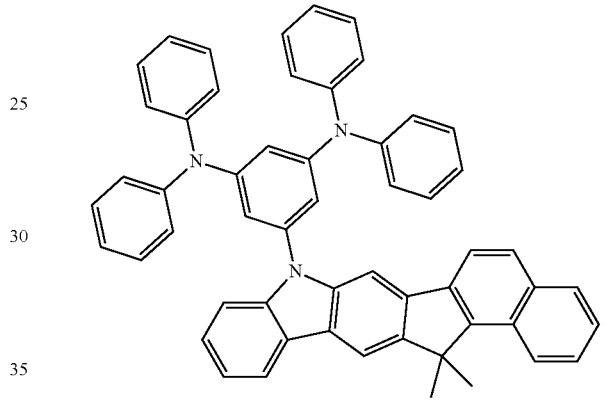
S-101
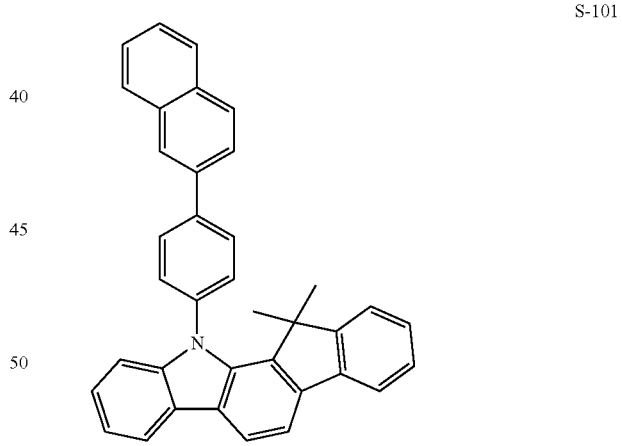
S-102
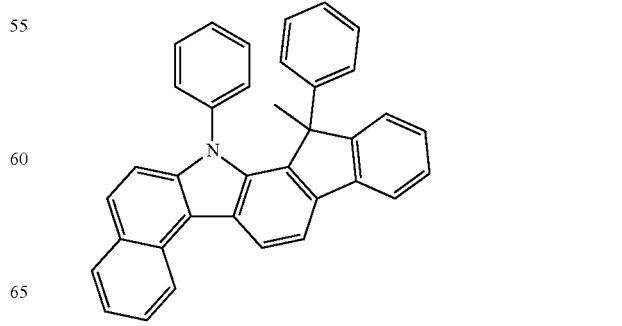

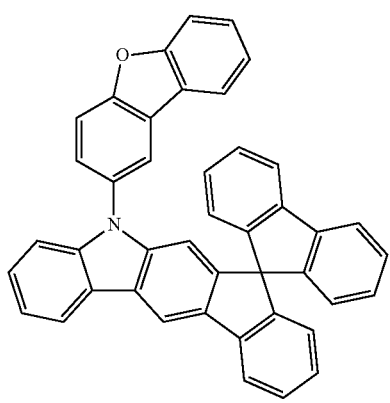
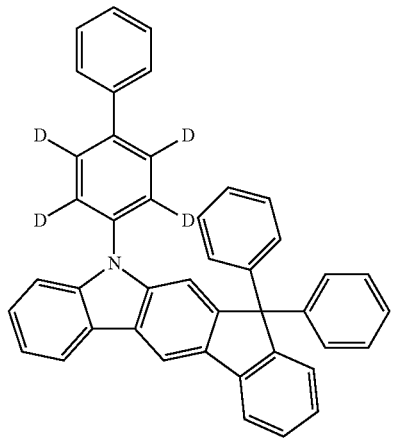
S-103
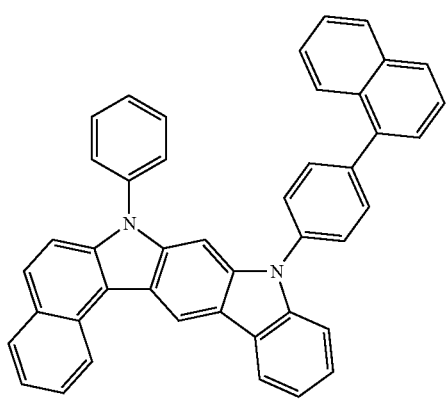
S-104
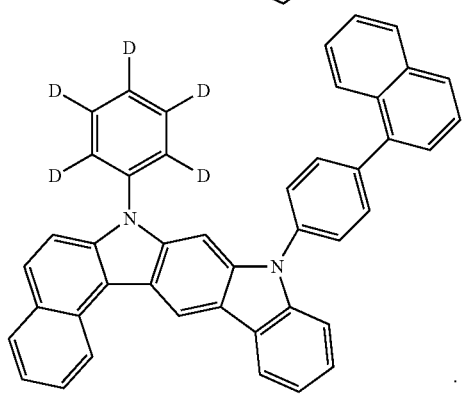
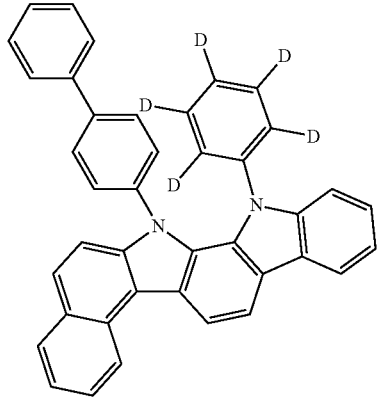
S-105
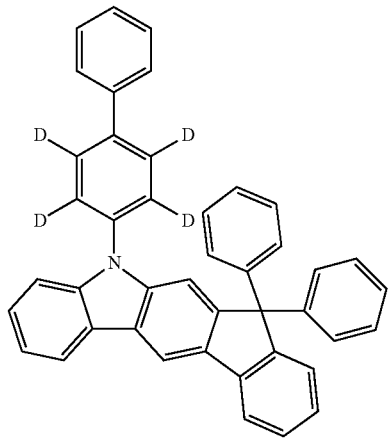
S-107
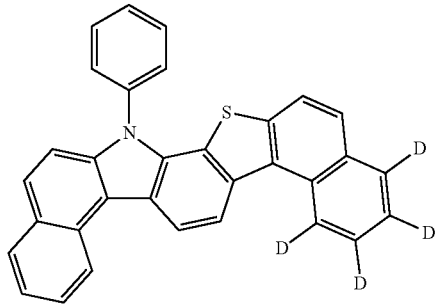
S-106
S-108

9. The organic electronic element of claim 6, wherein the organic electronic element further comprises a light efficiency enhancing layer formed on at least one surface of the first electrode and the second electrode, the surface being opposite to the organic material layer.

10. The organic electronic element of claim 6, wherein the organic material layer comprises 2 or more stacks comprising a hole transport layer, an emitting layer, and an electron transport layer sequentially formed on the first electrode.

11. The organic electronic element of claim 10, wherein the organic material layer further comprises a charge generation layer formed between the 2 or more stacks.

12. An electronic device comprising a display device comprising the organic electronic element of claim 6; and a control unit for driving the display device.

13. The electronic device of claim 12, wherein the organic electronic element is at least one of an OLED, an organic solar cell, an organic photo conductor (OPC), organic transistor (organic TFT) and an element for monochromic or white illumination.

14. A method for reusing the compound represented by Formula 1 of claim 1 comprising:
   a step of depositing an organic emitting material comprising the compound represented by Formula 1 of claim 1 in a manufacturing process of an organic light emitting device;
   a step of removing impurities from the crude organic light emitting material recovered from the deposition apparatus;
   a step of recovering the removed impurities; and
   a step of purifying the recovered impurities to a purity of 99.9% or higher.

* * * * *